United States Patent
Morshed et al.

(10) Patent No.: US 12,077,611 B2
(45) Date of Patent: *Sep. 3, 2024

(54) CYCLIC PEPTIDES MULTIMERS TARGETING α4β7 INTEGRIN

(71) Applicant: Zealand Pharma A/S, Søborg (DK)

(72) Inventors: Mohammed Monzur Morshed, Mississauga (CA); Sai Kumar Chakka, Dorval (CA); Jennifer L. Hickey, Toronto (CA); Manuel Perez Vazquez, Milton (CA); Andrew Roughton, Port Hope (CA); Adam Paul Kafal, Toronto (CA); Narendrakumar B. Patel, Brampton (CA)

(73) Assignee: Zealand Pharma A/S, Søborg (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/207,268

(22) Filed: Jun. 8, 2023

(65) Prior Publication Data

US 2023/0406884 A1    Dec. 21, 2023

Related U.S. Application Data

(63) Continuation of application No. 17/234,488, filed on Apr. 19, 2021, now Pat. No. 11,713,338, which is a continuation of application No. 16/348,103, filed as application No. PCT/CA2017/000244 on Nov. 10, 2017, now Pat. No. 11,111,273.

(60) Provisional application No. 62/421,117, filed on Nov. 11, 2016.

(51) Int. Cl.
| | |
|---|---|
| *A61P 37/06* | (2006.01) |
| *A61P 29/00* | (2006.01) |
| *C07K 5/12* | (2006.01) |
| *C07K 7/52* | (2006.01) |
| *A61K 38/00* | (2006.01) |

(52) U.S. Cl.
CPC ............... *C07K 7/52* (2013.01); *A61P 29/00* (2018.01); *A61P 37/06* (2018.01); *C07K 5/126* (2013.01); *A61K 38/00* (2013.01)

(58) Field of Classification Search
CPC . C07K 7/52; C07K 5/126; A61P 29/00; A61P 37/06; A61P 1/00; A61K 38/00; Y02A 50/30
See application file for complete search history.

(56) References Cited

U.S. PATENT DOCUMENTS

| | | | |
|---|---|---|---|
| 5,296,604 A | 3/1994 | Hanko et al. | |
| 5,693,325 A | 12/1997 | Kahn | |
| 5,693,612 A | 12/1997 | Jonczyk et al. | |
| 5,693,750 A | 12/1997 | Ohki et al. | |
| 5,696,084 A | 12/1997 | Lartey et al. | |
| 5,705,481 A | 1/1998 | Jonczyk et al. | |
| 5,731,286 A | 3/1998 | Harbeson et al. | |
| 6,034,056 A | 3/2000 | Dutta | |
| 6,492,553 B1 | 12/2002 | Hulme et al. | |
| 9,533,985 B2 | 1/2017 | Ueno et al. | |
| 10,981,921 B2 | 4/2021 | Vazquez et al. | |
| 11,046,695 B2 | 6/2021 | Vazquez et al. | |
| 11,072,616 B2 | 7/2021 | Vazquez et al. | |
| 11,111,273 B2 * | 9/2021 | Morshed ................ | C07K 7/52 |
| 11,713,338 B2 * | 8/2023 | Morshed ................ | A61P 1/00 |
| | | | 514/21.8 |
| 2008/0200398 A1 | 8/2008 | Smyth et al. | |
| 2010/0093612 A1 | 4/2010 | Casiraghi et al. | |
| 2011/0251247 A1 | 10/2011 | Chubb et al. | |
| 2014/0023700 A1 | 1/2014 | Knudsen et al. | |
| 2014/0193465 A1 | 7/2014 | Bhandari et al. | |
| 2016/0159862 A1 | 6/2016 | Bhandari et al. | |
| 2019/0077805 A1 | 3/2019 | Vazquez et al. | |
| 2020/0165300 A1 | 5/2020 | Vazquez et al. | |

FOREIGN PATENT DOCUMENTS

| | | |
|---|---|---|
| CA | 2427046 A1 | 11/2003 |
| CN | 1449385 A | 10/2003 |
| CN | 104144706 A | 11/2014 |
| CN | 105102470 A | 11/2015 |
| DE | 3219113 A1 | 11/1983 |
| JP | H10-508315 A | 8/1998 |
| WO | WO-96/00581 A1 | 1/1996 |
| WO | WO-96/20216 A1 | 7/1996 |
| WO | WO-97/02289 A1 | 1/1997 |
| WO | WO-97/03094 A1 | 1/1997 |
| WO | WO-2001/010799 A1 | 2/2001 |
| WO | WO-02/02556 A2 | 1/2002 |
| WO | WO-02/066500 A2 | 8/2002 |
| WO | WO-2008/046232 A1 | 4/2008 |
| WO | WO-2009/141687 A1 | 11/2009 |
| WO | WO-2010/105363 A1 | 9/2010 |
| WO | WO-2010/107832 A1 | 9/2010 |
| WO | WO-2013/110578 A1 | 8/2013 |
| WO | WO-2014/059213 A1 | 4/2014 |

(Continued)

OTHER PUBLICATIONS

Wang et al, Journal of Internal Medicine, 2015, 278, 369-395 (Year: 2015).*
Slack et al, Nat Rev Drug Discov., 2022, 21(1), 60-78 (Year: 2022).*
Banerjee et al, Frontiers in Cell and Developmental Biology, Mar. 2022, vol. 10, 1-28 (Year: 2022).*
Bruno et al, Ther Deliv, Nov. 2013, 4(11), 1443-1467 (Year: 2013).*
Achmatowicz et al., "The synthesis of L-proline derived hexaazamacrocyclic ligands of C3 symmetry via intramolecular methyl ester aminolysis," Tetrahedron: Asymmetry. 12(3):487-495 (2001).

(Continued)

*Primary Examiner* — Sudhakar Katakam
(74) *Attorney, Agent, or Firm* — Clark & Elbing LLP

(57) ABSTRACT

There is described herein, multimers comprising a plurality of compounds covalently linked together, the compounds independently being of formula (I).

19 Claims, 12 Drawing Sheets

Specification includes a Sequence Listing.

(56) References Cited

FOREIGN PATENT DOCUMENTS

| WO | WO-2015/176035 A1 | 11/2015 |
|---|---|---|
| WO | WO-2016/054411 A1 | 4/2016 |
| WO | WO-2016/054445 A1 | 4/2016 |
| WO | WO-2017/079820 A1 | 5/2017 |
| WO | WO-2017/079821 A1 | 5/2017 |
| WO | WO-2018/085921 A1 | 5/2018 |

OTHER PUBLICATIONS

Annex I: Summary of Product Characteristics for Entyvio, May 7, 2020 (93 pages).
Baktharaman et al., "Amino carbonyl compounds in organic synthesis," Aldrichimica Acta. 41(4):109-119 (2008).
Berezov et al., "Medicine," Biological chemistry, Moscow. p. 34, 59 (1998).
Boer et al., "Design and synthesis of potent and selective alpha(4)beta(7) integrin antagonists," J Med Chem. 44(16):2586-92 (2001).
Bova et al., "A label-free approach to identify inhibitors of alpha4beta7-mediated cell adhesion to MadCAM," J Biomol Screen. 16(5):536-44 (2011).
Burden et al., "Synthesis and biological activities of YkFA analogues: effects of position 4 substitutions and altered ring size on in vitro opioid activity," Bioorg Med Chem Lett. 12(2):213-6 (2002).
Chen et al., "Synthesis of 12-membered macrocyclic templates and library analogs for PPI," Tetrahedron Letters. 54(25):3298-301 (2013).
Chen et al., "Vedolizumab for prevention of graft-versus-host disease after allogeneic hematopoietic stem cell transplantation," Blood Adv. 3(23):4136-46 (2019).
Couturier et al., "Aziridinium from N,N-dibenzyl serine methyl ester: synthesis of enantiomerically pure beta-amino and alpha,beta-diamino esters," Org Lett. 8(10):2183-6 (2006).
Cushing et al., "Vedolizumab as a Novel Treatment for Refractory Collagenous Colitis: A Case Report," Am J Gastroenterol. 113(4):632-3 (2018).
Dörwald, F. Zaragoza. Side Reactions in Organic Synthesis: A Guide to Successful Synthesis Design, Weinheim: Wiley-VCH Verlag GmbH & Co. KGaA, 2005, Preface (6 pages).
Dutta et al., "Potent cyclic monomeric and dimeric peptide inhibitors of VLA-4 (alpha4beta1 integrin)-mediated cell adhesion based on the Ile-Leu-Asp-Val tetrapeptide," J Pept Sci. 6(7):321-41 (2000).
Dyson et al., Chemistry of synthetic medicines. *May's Chemistry of Synthetic Drugs, Fifth Edition.* Moscow: Mir. pp. 12-19 (1964).
Examination Report for Indian Application No. 201817021544, mailed May 18, 2020 (6 pages).
Extended European Search Report for European Application No. 16863253.7, dated Oct. 17, 2019 (6 pages).
Extended European Search Report for European Application No. 17870529.9, dated Jul. 28, 2020 (14 pages).
Extended European Search Report for European Application No. 18798999.1, dated Jun. 1, 2021 (14 pages).
Gorfu et al., "Role of betaz integrins in intestinal lymphocyte homing and retention," available in PMC Sep. 1, 2010, published in final edited form as: Curr Mol Med. 9(7):836-50 (2009) (24 pages).
Gottschling et al., "Synthesis and NMR structure of peptidomimetic alpha-4-beta-7-integrin antagonists," Chembiochem. 3(6):575-8 (2002).
Greene et al., "Preface to the Third Edition," *Protective Groups in Organic Synthesis*, Third Edition. John Wiley & Sons, Inc., v-vi (1999) (6 pages).
Hili et al., "Macrocyclization of linear peptides enabled by amphoteric molecules," J Am Chem Soc. 132(9):2889-91 (2010).
Hili et al., "Readily available unprotected amino aldehydes," J Am Chem Soc. 128(46):14772-3 (2006).
Hirose et al., "Total synthesis and determination of the absolute configuration of guadinomines B and C2," Chemistry. 14(27):8220-38 (2008).
International Search Report and Written Opinion Issued in Corresponding PCT Application No. PCT/CA2016/000274, mailed Dec. 19, 2016 (9 pages).
International Search Report and Written Opinion Issued in Corresponding PCT Application No. PCT/CA2016/000275, mailed Feb. 28, 2017 (15 pages).
International Search Report and Written Opinion Issued in Corresponding PCT Application No. PCT/CA2017/000244, mailed Feb. 8, 2018 (7 pages).
International Search Report and Written Opinion Issued in PCT Application No. PCT/CA2018/000087, mailed Aug. 7, 2018 (7 pages).
Jennings et al., "Vedolizumab-Induced Remission in 3 Patients With Refractory Microscopic Colitis: A Tertiary Care Center Case Series," Inflamm Bowel Dis. 25(8):e97 (Jul. 17, 2019).
Kim et al., "Vedolizumab Treatment May Reduce Steroid Burden and Improve Histology in Patients With Eosinophilic Gastroenteritis," available in PMC Dec. 1, 2019, published in final edited form as: Clin Gastroenterol Hepatol. 16(12):1992-1994, Epub Mar. 27, 2018 (Dec. 2018) (7 pages).
Li et al., "Abstract S12-085: Study on the Mechanism of Force Control and Hole Control Integrating the Interaction of alpha4, 7, and MAdCAM-1," Journal of Medical Biomechanics 33 Suppl.:334 (Aug. 2018).
Mohan et al., "Synthesis and biological activity of angiotensin II analogues containing a Val-His replacement, Val psi[CH(CONH2)NH]His," J Med Chem. 34(8):2402-10 (1991).
Murray et al., "The synthesis of cyclic tetrapeptoid analogues of the antiprotozoal natural product apicidin," Bioorg Med Chem Lett. 11(6):773-6 (2001).
Naveh et al., "Developing potent backbone cyclic peptides bearing the shared epitope sequence as rheumatoid arthritis drug-leads," Bioorg Med Chem Lett. 22(1):493-6 (2012).
Partial Supplementary European Search Report for European Application No. 17870529.9, mailed Apr. 23, 2020 (10 pages).
Partial Supplementary European Search Report for European Application No. 18798999.1, dated Feb. 2, 2021 (11 pages).
Patil et al., "Second generation, arginine-rich (R-X'-R)(4)-type cell-penetrating alpha-omega-alpha-peptides with constrained, chiral omega-amino acids (X') for enhanced cargo delivery into cells," Bioorg Med Chem Lett. 24(17):4198-202 (Sep. 1, 2014, Epub Jul. 19, 2014).
Pil et al., "Synthesis and electrophysiological characterization of cyclic morphiceptin analogues," Biochem Pharmacol. 67(10):1887-95 (2004).
Quartara et al., "Influence of lipophilicity on the biological activity of cyclic pseudopeptide NK-2 receptor antagonist," J Med Chem. 37(21):3630-8 (1994).
Ribaldone et al., "Vedolizumab for treatment of chronic refractory pouchitis: a systematic review with pool analysis," Rev Esp Enferm Dig. 112(1):59-63 (Jan. 2020).
Rotstein et al., "Synthesis of peptide macrocycles using unprotected amino aldehydes," Nat Protoc. 5(11):1813-22 (2010).
Roxin et al., "Conformational Modulation of in Vitro Activity of Cyclic RGD Peptides via Aziridine Aldehyde-Driven Macrocyclization Chemistry.", Bioconjug Chem 23(7), 1387-1395 (Jul. 2012) (9 pages).
Slama et al., "Convenient Synthesis of 1,2-Diamines from beta-Chloro Amines: Precursors of New Substituted Piperazin-2-ones" Synthetic Communications. 43(17):2286-2293 (2013).
Su, Youming, Dissertation: "The force-dependent mechanism of integrin alpha$_4$beta$_7$-MAdCAM-1 interaction," Master Degree, South China University of Technology, 2019 (English abstract included) (71 pages).
Suarez-Gea et al., "A General Method for the Synthesis of Carbamoylmethyleneamino Pseudopeptides" J Org Chem. 59(13):3600-3 (1994).
Supporting Information for Patil et al., "Second generation, arginine-rich (R-X'-R)(4)-type cell-penetrating alpha-omega-alpha-peptides with constrained, chiral omega-amino acids (X') for enhanced cargo delivery into cells," Bioorg Med Chem Lett. 24(17):4198-202 (Sep. 1, 2014, Epub Jul. 19, 2014).

(56) References Cited

OTHER PUBLICATIONS

Tal-Gan et al., "Backbone cyclic peptide inhibitors of protein kinase B (PKB/Akt)," J Med Chem. 54(14):5154-64 (2011).
Tamamura et al., "Stereoselective synthesis of [L-Arg-L/D-3-(2-naphthyl)alanine]-type (E)-alkene dipeptide isosteres and its application to the synthesis and biological evaluation of pseudopeptide analogues of the CXCR4 antagonist FC131," J Med Chem. 48(2):380-91 (2005).
Treder et al., "Solid-phase synthesis of piperazinones via disrupted Ugi condensation," Org Lett. 16(17):4674-7 (Sep. 5, 2014, Epub Aug. 25, 2014).
Vercillo et al., "Design and synthesis of cyclic RGD pentapeptoids by consecutive Ugi reactions," Org Lett. 10(2):205-8 (2008).
Verheijen et al., "An expeditious liquid-phase synthesis of cyclic peptide nucleic acids," Tetrahedron Letters. 41(20):3991-5 (2000).
Wagner et al., "New naturally occurring amino acids," Angew Chem Int Ed Engl. 22(11):816-28 (1983).
Wyant et al., "Development and validation of receptor occupancy pharmacodynamic assays used in the clinical development of the monoclonal antibody vedolizumab," Cytometry B Clin Cytom. 90(2):168-76 (Mar. 2016).
Yoosuf et al., "Evolving Therapy for Celiac Disease," Front Pediatr. 7:193 (May 14, 2019) (18 pages).
Yu et al., "Structural specializations of alpha$_4$beta$_7$, an integrin that mediates rolling adhesion," J Cell Biol. 196(1):131-46 (2012).
Yudin et al., "Overcoming the demons of protecting groups with amphoteric molecules," Chemistry 13(23):6538-42 (2007).

\* cited by examiner

|  | a4b7 IC50 (uM) |
|---|---|
| Thr | 0.026 |
| Ile | 0.036 |
| Thr(OBn) | 0.042 |
| Thr(OEt) | 0.063 |
| Thr(OMe) | 0.113 |
| Pen | 0.109 |
| Val | 0.262 |
| dCys-Me ether | 0.389 |
| cyclohexylGly | 0.475 |
| *allo*-Ile | 1.00 |
| Cys | 1.00 |
| Cys(Acm) | 1.00 |
| thio-dPro | 1.088 |
| tBu-Gly | 4.00 |
| Asn | 15 |
| Gln | 45.3 |
| His | 56.6 |
| 2-aza-dPhe | |

|  | a4b7 IC50 (uM) |
|---|---|
| Asp | 27.726 |
| Asp(alcohol) | 40 |
| Asp(OBn) | 50 (27 cell) |
| Asp(OEt) | |

|  | a4b7 IC50 (uM) |
|---|---|
| Leu | 0.375 |
| Cha | 0.609 |
| vinyl-Br-Leu | 0.785 |
| Nle | 1.703 |
| HomoLeu | 3.025 |
| cyclopropylAla | 3.358 |
| CF3-(d/l)Leu | 3.668 |
| Nle | 3.615 |
| (d/l)Leu | 3.896 |
| Cha | 30.00 |
| Phe | 40.00 |
| Trp | |

|  | a4b7 IC50 (uM) |
|---|---|
| "Tyr" | 0.005 |
| Met | 0.009 |
| Tyr(O-allyl) | 0.011 |
| Cycloleu | 0.016 |
| Aic | 0.019 |
| Pro | 0.021 |
| dTiq | 0.022 |
| dTic | 0.023 |
| dArg | 0.026 |
| 1Nal | 0.03 |
| 4-aza-dPhe | 0.03 |
| dHomoPro | 0.04 |
| 3-aza-dPhe | 0.035 |
| 4-amino-cPhe | 0.04 |
| Orn(ethylCarb) | 0.036 |
| dTyr(O-allyl) | 0.039 |
| Orn(Ac) | 0.04 |
| 2Nal | 0.042 |
| Phe | 0.046 |
| dTrp | 0.05 |
| dTyr(O-Bn) | 0.051 |
| Trp | 0.052 |
| 4-aminoMe-dPhe | 0.053 |
| benzthiophenhyl-dAla | 0.053 |
| Lys | 0.054 |
| 2,thiophen-yl-dAla | 0.057 |
| L-Disc | 0.057 |
| Tyr(4-CO2H diaryl ether) | 0.243 |
| Met-sulfoxide | 0.825 |
| P-Cl-10T | 0.873 |
| Dab | 0.963 |
| Gly | 0.995 |
| Ser(OBn) | 1.05 |
| Tic | 1.078 |
| Asn | 1.496 |
| Glu | 3.832 |
| Asp | 3.664 |
| D-Disc | 6.935 |
| Asp-acyl-methanesulfonamide | |

PYLDT / ET00696
a4b7 ELISA IC50 = 0.129 uM
a4b1 ELISA IC50 = 0.357 uM (2.8X)
RPMI 8866 cell IC50 = 11.782 uM

FIG. 2

| Asp | a4b7 IC50 (uM) |
|---|---|
| Leu | 0.054 |
| tertbutylAla | 0.719 |
| Nle | 0.83 |
| neopentylglycine | 1.04 |
| MeLeu | 1.443 |
| NorVal | 3.665 |
| HomocycloLeu | |

| no variants | a4b7 IC50 (uM) |
|---|---|
| Thr | 0.006 |
| Ile | 0.018 |
| Abu | 0.046 |
| alloThr | 0.192 |
| MeThr | 2.242 |
| HomoSer | 3.116 |
| dThr | 4.162 |
| Ser | |

| | a4b7 IC50 |
|---|---|
| "dHomoPro" | (uM) |
| dPic | 0.007 |
| dPro | 0.013 |
| cis-dHyp | 0.019 |
| trans-dHyp | 0.015 |
| Pro | 0.027 |
| dLys | 0.052 |
| Ala | 0.053 |
| dAla | 0.054 |
| Ser | 0.059 |
| dMeAla2 | 0.067 |
| Aze | 0.083 |
| dArg | 0.083 |
| dSer | 0.096 |
| trans-Hyp | 0.100 |
| Gly | 0.110 |
| dMeAla | 0.117 |
| cyclobLeu | 0.120 |
| dVal | 0.128 |
| dThr | 0.132 |
| dLys | 0.133 |
| dTaa | 0.215 |
| alphaMeAla | 0.219 |
| Cba | 0.222 |
| dTrp | 0.223 |
| BetaGly | 0.230 |
| dGln | 0.261 |
| Tyr | 0.274 |
| dOrn | 0.287 |
| His | 0.299 |
| Homocycloleu | 0.404 |
| Gln | 0.416 |
| Abz | 0.559 |
| Dab | 0.582 |
| Lys | 0.600 |
| Val | 0.677 |
| MeNle | 0.800 |
| Nle | 0.855 |
| dPhe | 0.951 |
| Met | 1.255 |
| Cit | 1.264 |
| thyronine | 1.517 |
| dMet | 1.575 |
| 2-Agl | 1.739 |
| (AcLys)x | 1.934 |
| dMeOrn | 2.291 |
| Ser | 2.656 |
| Thr | 2.980 |
| Asn | 3.061 |
| dCitr | 3.665 |
| nTyr | (2.058-cell) |
| 4-guanidino-Phe | (8.280-cell) |
| Tic | (24.080-cell) |

| | a4b7 IC50 (uM) |
|---|---|
| "Tyr" | |
| Tyr(O-allyl) | 0.013 |
| 2-(2-pyridyl)-4-thiazolyl-Ala | 0.013 |
| 2-(4-pyridyl)-4-thiazolyl-Ala | 0.013 |
| 2-iodo-Phe | 0.015 |
| 3-aminomethyl-Phe | 0.016 |
| 2-(3-pyridyl)-4-thiazolyl-Ala | 0.017 |
| 2-(amino-benzoyl)-4-thiazolyl-Ala | 0.018 |
| thiazolyl-Ala | 0.018 |
| Phe | 0.019 |
| 4-aminomethyl-Phe | 0.019 |
| 2,4-dichloro-Phe | 0.021 |
| 2-Phenyl-Phe | 0.023 |
| Bip | 0.024 |
| 2-(2-methoxy-Phenyl)-Phe | 0.024 |
| 3,4-di-methoxy-Phe | 0.025 |
| 3,4,5-tri-fluoro-Phe | 0.026 |
| cycloLeu | 0.027 |
| 2-(3-methoxy-Phenyl)-Phe | 0.032 |
| 2-(4-methoxy-Phenyl)-Phe | 0.033 |
| 1Nal | 0.033 |
| 2Nal | 0.043 |
| 3-aminomethyl-dPhe | 0.052 |
| 3-iodo-Phe | 0.059 |
| dTyr | 0.062 |
| 3,5-di-bromo-L-Tyr | 0.065 |
| 6-Phenyl-Ala | 0.077 |
| 2-aminomethyl-Phe | 0.083 |
| 3-phenyl-dPhe | 0.083 |
| MeTyr | 0.086 |
| Met | 0.135 |
| 4-iodo-Phe | 0.150 |
| Tic | 0.209 |
| 4-(2,6-diMethoxybenzene)-Phe | 0.234 |
| thyronine | 0.262 |
| Ala | 0.274 |
| Orn | 0.307 |
| 3-(4-Quinolinyl)-dPhe | 0.449 |
| dHomoPro | 1.058 |
| BnGly | 1.086 |
| dTic | 1.273 |
| dAla | 10 |
| 3-acetylamino-methyl-Phe | (0.616-cell) |
| 3-(5-Quinolinyl)-Phe | (1.411-cell) |
| 3-(7-Quinolinyl)-Phe | (23.142-cell) |
| 3-(6-Quinolinyl)-dPhe | (23.646-cell) |
| 3-(3-aminomethylphenyl)-dPhe | (25.690-cell) |

PY-dHomoPro-LDT / ET02272
a4b7 ELISA IC50 = 0.025 uM
a4b1 ELISA IC50 = 0.458 uM (18.4X)
RPMI 8866 cell IC50 = 1.925 uM

FIG. 3

CYCLIC PEPTIDES MULTIMERS TARGETING α4β7 INTEGRIN

SEQUENCE LISTING

The instant application contains a Sequence Listing which has been submitted electronically in XML format and is hereby incorporated by reference in its entirety. Said XML copy, created on Aug. 11, 2023, is named "50412-120004_SL" and is 664,716 bytes in size.

FIELD OF THE INVENTION

The invention relates to antagonists of α4β7 integrin, and more particularly to cyclic peptide antagonists.

BACKGROUND OF THE INVENTION

Integrins are transmembrane receptors that are the bridges for cell-cell and cell-extracellular matrix (ECM) interactions. When triggered, integrins trigger chemical pathways to the interior (signal transduction), such as the chemical composition and mechanical status of the ECM.

Integrins are obligate heterodimers, having two different chains: the α (alpha) and β (beta) subunits.

The α4β7 integrin is expressed on lymphocytes and is responsible for T-cell homing into gut-associated lymphoid tissues through its binding to mucosal addressin cell adhesion molecule (MAdCAM), which is present on high endothelial venules of mucosal lymphoid organs. Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

There is a need to develop improved α4β7 antagonists to prevent or treat inflammatory conditions and/or autoimmune diseases.

Certain methods of making cyclic peptides (nacellins) are described in Applicant's PCT Publication No. WO 2010/105363.

SUMMARY OF THE INVENTION

In an aspect, there is provided, a multimer comprising a plurality of compounds covalently linked together, the compounds independently being of formula (I):

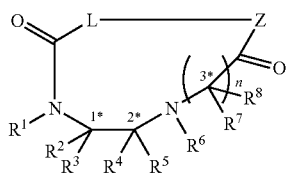

(I)

wherein
$R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid, provided that $R^2$ and $R^3$ may be covalently linked to each other to form a ring;

$R^4$ and $R^5$ are each independently H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; or —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^2$ or $R^3$ can be covalently linked to $R^1$ to form a cyclic secondary amine, and/or to $R^4$ or $R^5$ to form a ring, $R^4$ and $R^5$ may also be covalently linked to each other to form a ring;

$R^6$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; or —C(O)Rc; all of which are optionally substituted at one or more substitutable positions with one or more suitable substituents, or along with $R^7$ or $R^8$, a cyclic side chain of a proteinogenic or a non-proteinogenic amino acid having, the N-terminus thereof being the N—$R^6$, wherein the proteinogenic or a non-proteinogenic amino acid can be substituted with a suitable substituent;

$R^7$ and $R^8$ are independently selected from the amino acid side chains of a proteinogenic or a non-proteinogenic alpha-amino acid having the N-terminus thereof being the N—$R^6$, or may form a cyclic side chain with $R^6$;

stereocentres 1*, 2* and 3* are each independently selected from R and S;

n is 1, 2, 3, or 4 and where n is 2-4, each $R^7$ and each $R^8$ are independent of each other; and wherein Z is an amino terminus of an amino acid; —C═O— adjacent L is the carboxy terminus of an amino acid; and L along with Z and —C═O— is a peptide having the following formula:

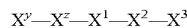

wherein $X^y$ and $X^z$ are each independently a proteinogenic or non-proteinogenic amino acid;
$X^1$ is Leucine or tert-butyl-Ala;
$X^2$ is Asp; and
$X^3$ is any amino acid listed under column $X^3$ of Table 1B.

In an aspect, there is provided a pharmaceutical composition comprising the multimer described herein along with the pharmaceutically acceptable carrier. The pharmaceutical composition may be formulated for any one of oral delivery, topical delivery and parenteral delivery.

In an aspect, there is provided, a method of treating inflammation or an autoimmune disease in a patient, comprising administering to the patient a therapeutically effective amount of the multimer described herein. Preferably the inflammation or an autoimmune disease is gastrointestinal.

In an aspect, there is provided, a method for treating a condition in a patient associated with a biological function of an α4β7 integrin, the method comprising administering to the patient a therapeutically effective amount of the multimer described herein.

In an aspect, there is provided, a method for treating a disease or condition in a patient comprising administering to the patient a therapeutically effective amount of the multimer described herein, wherein the disease or condition is a local or systemic infection of a virus or retrovirus.

In an aspect, there is provided, a method for treating a disease or condition in a patient comprising administering to the patient a therapeutically effective amount of the multimer described herein, wherein the hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, glycogen storage disease, hepatocellular carcinoma, liver cancer, primary biliary cholangitis, primary sclerosing cholangitis, primary biliary sclerosis, biliary tract disease, autoimmune hepatitis, or graft-versus-host disease.

BRIEF DESCRIPTION OF FIGURES AND TABLES

These and other features of the preferred embodiments of the invention will become more apparent in the following detailed description in which reference is made to the appended drawings and tables wherein:

FIG. 2 shows a representative 18-membered ring compound along with variations made at certain positions with corresponding α4β7 integrin ELISA IC50 binding values associated with those variations. Figure discloses SEQ ID NO: 3.

FIG. 3 shows a representative 21-membered ring compound along with variations made at certain positions with corresponding α4β7 integrin ELISA IC50 binding values associated with those variations. Figure discloses SEQ ID NO: 120.

Figure 1:
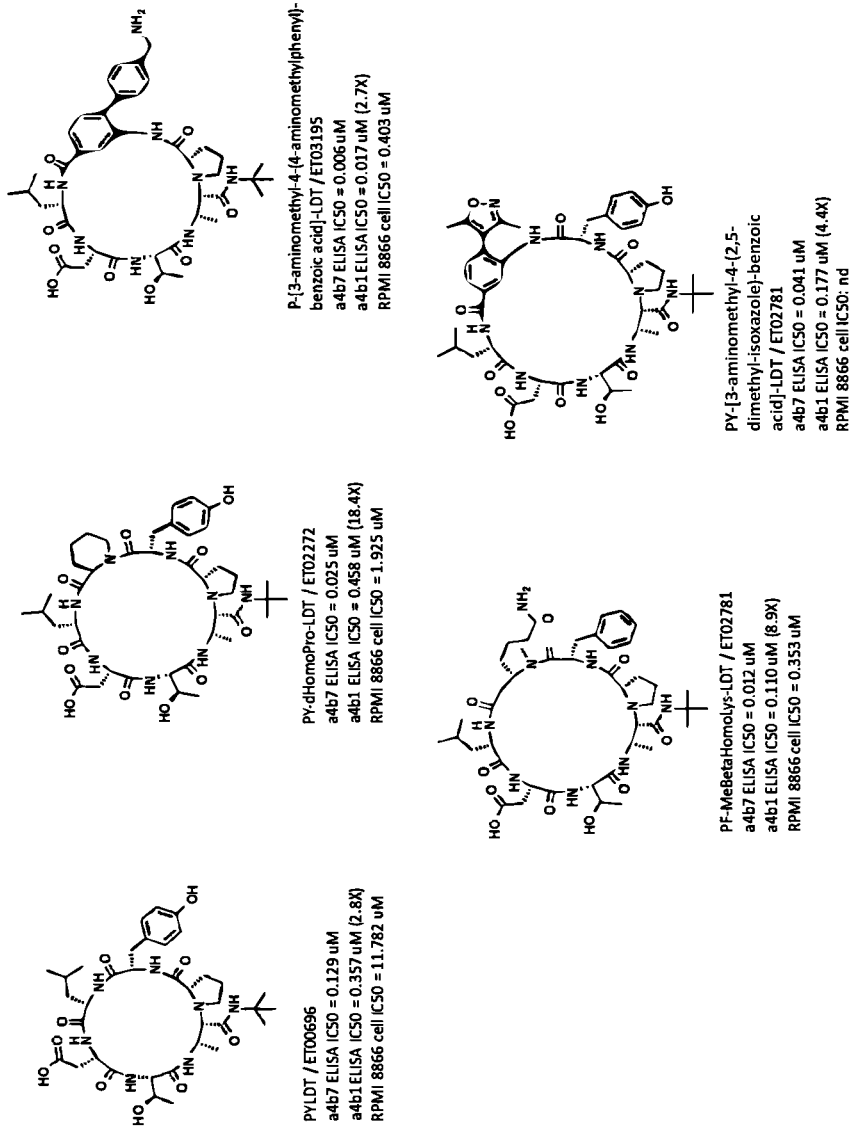
FIG. 1 shows representative compounds of the present application, namely from the following classes, 18-membered ring, 21-membered ring, 21-membered ring (non-canonical, i.e. having a delta amino acid), 22-membered ring, and 24-membered ring. Figure discloses SEQ ID NOS 3, 120, 375, 226, and 332, respectively, in order of appearance.
Figure 4:
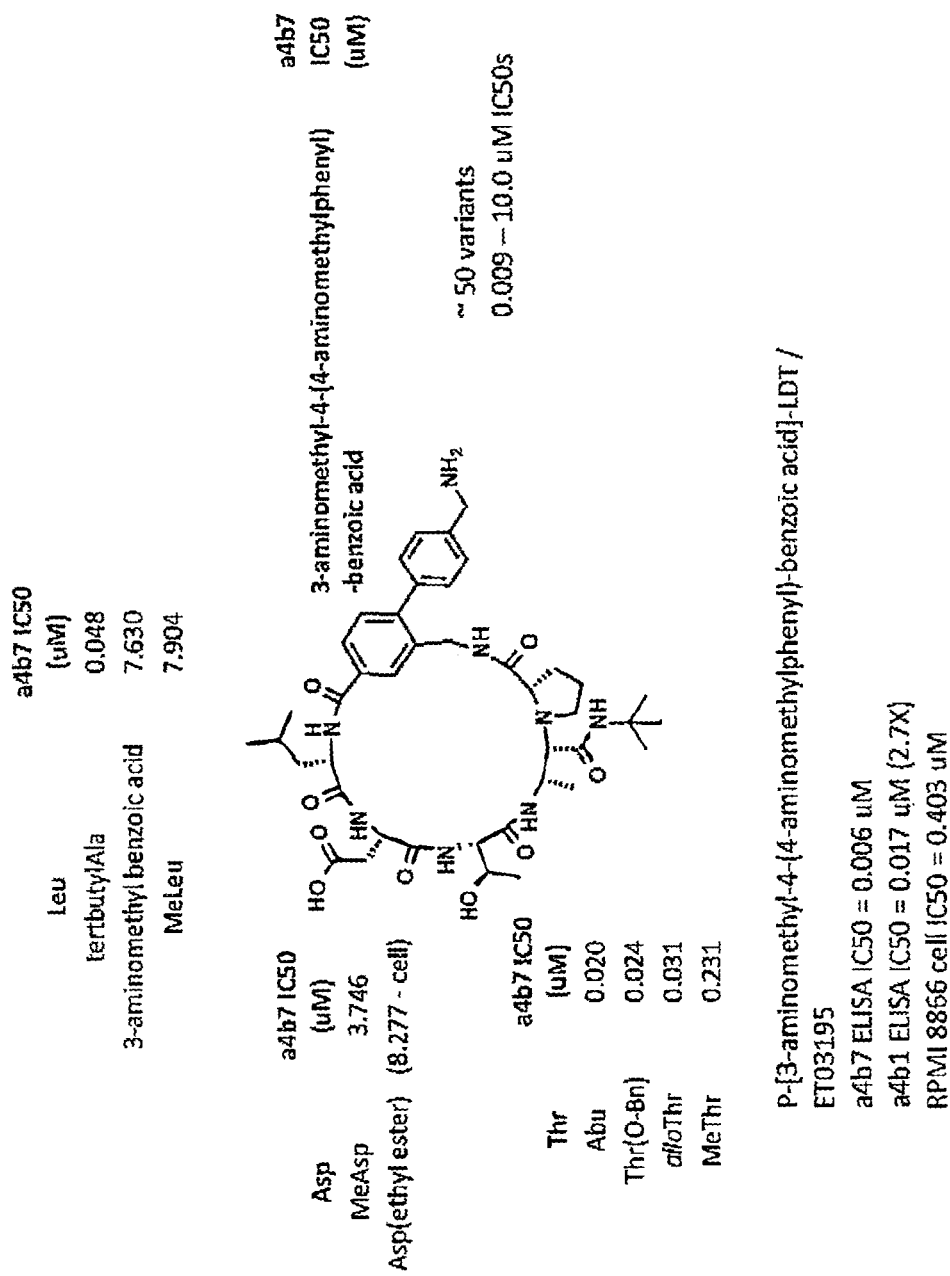
FIG. 4 shows a representative 21-membered ring (non-canonical, i.e. having a delta amino acid) compound along with variations made at certain positions with corresponding α4β7 integrin ELISA IC50 binding values associated with those variations. Figure discloses SEQ ID NO: 375.
Figure 5:
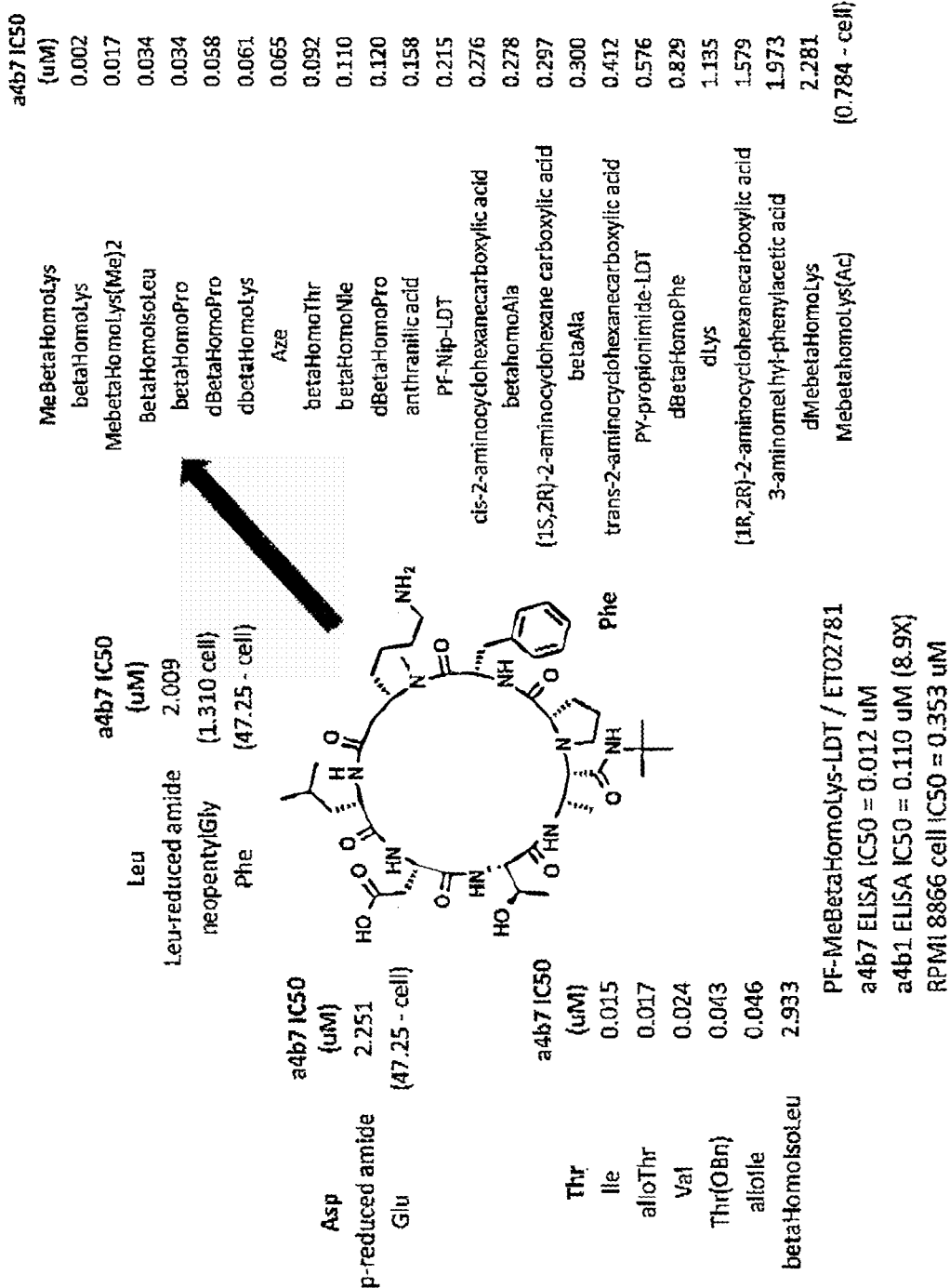
FIG. 5 shows a representative 22-membered ring compound along with variations made at certain positions with corresponding α4β7 integrin ELISA IC50 binding values associated with those variations. Figure discloses SEQ ID NO: 226.

Table 1 shows compounds exhibiting α4β7 integrin affinity, selectivity and/or activity; and specifically with respect to these compounds: (A) the structure of the linker portion; (B) the structure of the peptide portion; and (C) and (C') the affinity, selectivity and activity values.

To aid reading of the table, the following is noted:
Table 1A:
If R2 is H and R3 is CH3, the carbon atom bearing R2 and R3 has S-configuration.
If R2 is CH3 and R3 is H, the carbon atom bearing R2 and R3 has R-configuration.
If R2 is H and R3 is CH2-S-Ph, the carbon atom bearing R2 and R3 has S-configuration.
If R4 is H and R5 is C(O)—NH-tert-Butyl, the carbon atom bearing R4 and R5 has S-configuration.
If R4 is C(O)—NH-tert-Butyl and R5 is H, the carbon atom bearing R4 and R5 has R-configuration.
If R1 and R2 are both Pro-, the R1 and R2 substituents are covalently bound and form the pyrrolidine ring of Pro.

Table 1B
If R6 and R7 are both Pro, the R6 and R7 substituents are covalently bound and form the pyrrolidine ring of Pro.
If R6 and R8 are both dPro, the R6 and R8 substituents are covalently bound and form the pyrrolidine ring of dPro.
If R6 and R7 are both [(4S)-fluoro-Pro], the R6 and R7 substituents are covalently bound and form the pyrrolidine ring of [(4S)-fluoro-Pro].
If R7 is Nva and R8 is H, the carbon atom bearing R7 and R8 has S-configuration.
If R6 and R7 are both Hyp, the R6 and R7 substituents are covalently bound and form the pyrrolidine ring of Hyp.
If no entry exists under column Xz, the residue is absent.

Table 1C and 1C'
If no entry exists under any of the columns, no data was collected.

Table 1X is a correspondence table linking the compounds described herein with the synthesis protocols outlined in the methods and materials.

Table 2 shows multimeric compounds exhibiting α4β7 integrin affinity, selectivity and/or activity; and specifically with respect to these compounds: (A) the structure of the linker portion; (B) the structure of the peptide portion; and (C) the affinity, selectivity and activity values.

To aid reading of the table, the following is noted:
Table 2A
If R2 is H and R3 is CH3, the carbon atom bearing R2 and R3 has S-configuration.

Table 2B
If R6 and R7 are both Pro, the R6 and R7 substituents are covalently bound and form the pyrrolidine ring of Pro.

If R6 and R7 are both Hyp, the R6 and R7 substituents are covalently bound and form the pyrrolidine ring of Hyp.

If no entry exists under column Xz, the residue is absent.

Table 2X is a correspondence table linking the multimers described herein with the synthesis protocols outlined in the methods and materials. m/z is (M+2H/2) and additional information regarding the linker.

Table 3 is a table of the sequence listing

DETAILED DESCRIPTION

In the following description, numerous specific details are set forth to provide a thorough understanding of the invention. However, it is understood that the invention may be practiced without these specific details.

In an aspect, there is provided, a multimer comprising a plurality of compounds covalently linked together, the compounds independently being of formula (I):

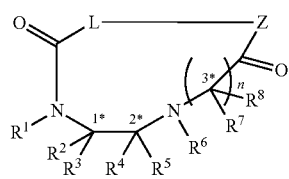

(I)

wherein $R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid,
provided that $R^2$ and $R^3$ may be covalently linked to each other to form a ring;

$R^4$ and $R^5$ are each independently H; lower alkyl; aryl; heteroaryl; alkenyl; heterocycle; acids of the formula —C(O)OH; esters of the formula —C(O)OR* wherein R* is selected from alkyl and aryl; amides of the formula —C(O)NRR*, wherein R and R* are independently selected from H, alkyl and aryl; —CH$_2$C(O)R, wherein R is selected from —OH, lower alkyl, aryl, -loweralkyl-aryl, or —NRaRb, where Ra and Rb are independently selected from H, lower alkyl, aryl or -loweralkyl-aryl; or —C(O)Rc, wherein Rc is selected from lower alkyl, aryl or -lower alkyl-aryl; or -lower alkyl-ORd, wherein Rd is a suitable protecting group or OH group; all of which are optionally substituted at one or more substitutable positions with one or more suitable substituents;

provided that $R^2$ or $R^3$ can be covalently linked to $R^1$ to form a cyclic secondary amine, and/or to $R^4$ or $R^5$ to form a ring, $R^4$ and $R^5$ may also be covalently linked to each other to form a ring;

$R^6$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH$_2$C(O)R; or —C(O)Rc; all of which are optionally substituted at one or more substitutable positions with one or more suitable substituents,
or along with $R^7$ or $R^8$, a cyclic side chain of a proteinogenic or a non-proteinogenic amino acid having, the N-terminus thereof being the N—$R^6$, wherein the proteinogenic or a non-proteinogenic amino acid can be substituted with a suitable substituent;

$R^7$ and $R^8$ are independently selected from the amino acid side chains of a proteinogenic or a non-proteinogenic alpha-amino acid having the N-terminus thereof being the N—$R^6$, or may form a cyclic side chain with $R^6$;

stereocentres 1*, 2* and 3* are each independently selected from R and S;

n is 1, 2, 3, or 4 and where n is 2-4, each $R^7$ and each $R^8$ are independent of each other; and wherein Z is an amino terminus of an amino acid; —C=O— adjacent L is the carboxy terminus of an amino acid; and L along with Z and —C=O— is a peptide having the following formula:

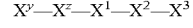

wherein $X^y$ and $X^z$ are each independently a proteinogenic or non-proteinogenic amino acid;

$X^1$ is Leucine or tert-butyl-Ala;

$X^2$ is Asp; and $X^3$ is any amino acid listed under column $X^3$ of Table 1B.

The compounds shown in Tables 1A, 1B and 1C (and 1C') exhibit antagonistic activity against α4β7 integrin and having selectivity over α4β1 integrin. A person skilled in the art would expect that substituents $R^1$-$R^8$ and amino acids $X^y$, $X^z$, $X^1$, $X^2$, and $X^3$ outlined in Tables 1 A and 1B with respect to different compounds could be combined in any manner and would likely result in a compound that would exhibit α4β7 integrin activity and selectivity. These compounds are further described in WO 2017/079820, the entirety of which is incorporated herein by reference.

Multimerized, specifically dimerized, versions of certain compounds described herein exhibited affinity, selectivity and activity, summarized in Tables 2A, 2B and 20.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta and gamma amino acids. Peptides are polymers of at least two amino acids and may include standard, non-standard, and unnatural amino acids. A peptide is a polymer of two or more amino acids.

The following abbreviations are used herein:

| Abbreviation | Description |
|---|---|
| 1,2-cis-ACHC | cis-2-aminocyclohexanecarboxylic acid |
| 1,2-trans-ACHC | trans-2-aminocyclohexanecarboxylic acid |
| 1Nal | 1-napthylalanine |
| 2Abz | anthranilic acid, 2-aminobenzoic acid |
| 2Igl | 2-indanylglycine |
| 2Nal | 2-napthylalanine |

| Abbreviation | Description |
| --- | --- |
| Abu | 2-aminobutyric acid |
| Aic | aminoindan-2-carboxylic acid |
| alloIle | allo-sioleucine, (2S,3R)-2-amino-3-methylpentanoic acid |
| alloThr | allo-threonine, (2S,3S)-2-amino-3-hydroxybutyric acid |
| alphaMePhe | α-methyl-phenylalanine, (S)-(−)-2-amino-2-methyl-3-phenylpropionic acid |
| Asp(ethyl ester) | aspartic acid β-ethyl ester |
| Atc | 2-aminotetraline-2-carboxylic acid |
| Aze | azetidine-2-carboxylic acid |
| BHT | butylated hydroxytoluene |
| Bip | biphenylalanine |
| C10 | sebacic acid |
| C12 | dodecanedioic |
| C7 | pimelic acid |
| C8 | suberic acid |
| C9 | azelaic acid |
| Cha | β-cyclohexyl alanine, (S)-2-amino-3-cyclohexylpropionic acid |
| Chg | cyclohexyl glycine |
| cis-dhyp | cis-D-4-Hydroxyproline, (2R,4R)-4-Hydroxypyrrolidine-2-carboxylic acid |
| cycloLeu | cyclo leucine, 1-Aminocyclopentane-1-carboxylic acid |
| cyclopropylAla | β-cyclopropyl alanine, (S)-2-amino-3-cyclopropyl-propionic acid |
| d2Igl | 2-indanyl-D-glycine |
| Dap(Cbz) | Nβ-2-2,3-diaminopropionic acid |
| DBU | 1,8-diazabicyclo[5.4.0]undec-7-ene |
| DEPBT | 3-(diethoxyphosphoryloxy)-1,2,3-benzotriazin-4(3H)-one |
| dHyp | trans-D-4-hydroxyproline, (2R,4S)-4-hydroxypyrrolidine-2-carboxylic acid |
| DIAD | diisopropyl azodicarboxylate |
| DIG | diglycolic acid |
| DIPEA | N,N-diisopropylethylamine |
| DMAP | 4-(Dimethylamino)pyridine |
| dMeArg | N-methyl-D-arginine |
| dMebetaHomoLys | N-methyl-D-β-homoLys |
| dMeLys | N-methyl-D-Lysine |
| DMF | N,N-dimethylformamide |
| DMSO | dimethyl sulfoxide |
| dNle | D-norleucine |
| dOrn | D-ornithine |
| dOrn(dimethyl) | Nδ-dimethyl-D-ornithine |
| dPip | D-pipecolic acid, D-homoPro |
| dSer(OBn) | O-benzyl-D-serine |
| dTic | (3R)-1,2,3,4-tetrahydroisoquinoline-3-carboxylic acid |
| dTiq | D-1,2,3,4-tetrahydroisoquinoline-1-carboxylic acid |
| dTyr(OAllyl) | O-allyl-D-tyrosine |
| dTyr(OBn) | O-benzyl-D-tyrosine |
| EDC | N-(3-Dimethylaminopropyl)-N'-ethylcarbodiimide hydrochloride |
| Fmoc | 9-fluorenylmethoxycarbonyl |
| HATU | O-(7-azabenzotriazol-1-yl)-N,N,N',N'-tetramethyluronium hexafluorophosphate |
| HCTU | 2-(6-chloro-1H-benzotriazole-1-yl)-1,1,3,3-tetramethylaminium hexafluorophosphate |
| HFIP | 1,1,1,3,3,3-hexafluoro-2-propanol |
| His(Bn) | Nτ-benzyl-histidine |
| HomocycloLeu | homocyclo leucine, 1-Aminocyclohexanecarboxylic acid |
| Hyp | trans-4-hydroxyproline, (2S,4R)-4-hydroxypyrrolidine-2-carboxylic acid |
| Hyp(OBn) | O-benzyl-trans-4-hydroxyproline |
| MeAsp | N-methyl aspartic acid |
| MebetaHomoLys | N-methyl β-homoLysine |
| MebetaHomoLys(Me)2 | Nα-methyl-Nε-dimethyl-β-homoLysine |
| MeLeu | N-methyl leucine |
| MeMet | N-methyl methionine |
| MePhe | N-methyl phenylalanine |
| metaY(Opr) | metaTyrosine |
| MeThr | N-methyl threonine |
| MeTyr | N-methyl tyrosine |
| NMP | N-methylpyrrolidone |
| Nosyl chloride | 2-nitrobenzenesulfonyl chloride |
| Nva | norvaline |
| Orn(acetamide) | Nδ-acetamide-ornithine |
| Orn(benzamide) | Nδ-benzamide-ornithine |
| Orn(ethylcarbamate) | Nδ-ethylcarbamate-ornithine |
| Orn(methanesulfonamide) | Nδ-methanesulfonamide-ornithine |
| Orn(pentyl amide) | Nδ-pentyl amide-ornithine |
| PDA | 1,4-phenyldiacetic acid |
| Pen | penicillamine, β,β-dimethyl-cysteine |
| Pip | pipecolic acid, homoPro |
| Sar | sarcosine, N-methyl glycine |
| tertbutylAla | β-tert-butyl alanine, neopentylglycine |
| TFA | trifluoroacetic acid |

-continued

| Abbreviation | Description |
| --- | --- |
| TFE | 2,2,2-Trifluoroethanol |
| THF | tetrahydrofuran |
| Thr(OBn) | O-benzyl-threonine |
| Thr(OEt) | O-ethyl-threonine |
| Thr(OMe) | O-methyl-threonine |
| Tic | (3S)-1,2,3,4-tetrahydroisoquinoline-3-carboxylic acid |
| TIS | triisopropylsilane |
| Tyr(2-methoxy diaryl ether) | O-2-methoxy-phenyl-tyrosine |
| Tyr(2-tolyl diaryl ether) | O-2-methyl-phenyl-tyrosine |
| Tyr(3,4-difluoro diaryl ether) | O-3,4-difluoro-phenyl-tyrosine |
| Tyr(3,4-dimethyl diaryl ether) | O-3,4-dimethyl-phenyl-tyrosine |
| Tyr(3-CO2Me diaryl ether) | O-3-methylester-phenyl-tyrosine |
| Tyr(3-fluoro diaryl ether) | O-3-fluoro-phenyl-tyrosine |
| Tyr(3-methoxy diaryl ether) | O-3-methoxy-phenyl-tyrosine |
| Tyr(3-methyl diaryl ether) | O-3-methyl-phenyl-tyrosine |
| Tyr(4-CF3 diaryl ether) | O-4-trifluoromethyl-phenyl-tyrosine |
| Tyr(4-CO2H diaryl ether) | O-4-carboxylate-phenyl-tyrosine |
| Tyr(4-CO2Me diaryl ether) | O-4-methylester-phenyl-tyrosine |
| Tyr(4-fluoro diaryl ether) | O-4-fluoro-phenyl-tyrosine |
| Tyr(4-methoxy diaryl ether) | O-4-methoxy-phenyl-tyrosine |
| Tyr(OAllyl) | O-allyl-tyrosine |
| Tyr(OPh) | O-phenyl-tyrosine |
| vinyl-Br-Leu | 2-amino-4-bromo-4-pentenoic acid |

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as C(O)—$C_6H_5$, and the like; ester such as —$C(O)OCH_3$ the like; ethers and thioethers, such as O-Bn and the like; thioalkoxy; phosphino; and —$NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic monocyclic system or an aromatic polycyclic system. For example, the term "aryl" includes a phenyl or a napthyl ring, and may also include larger aromatic polycyclic systems, such as fluorescent (eg. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-lower-alkyl- (eg. benzyl), -lower alkyl-alkenyl (eg. allyl), heteroaryl-alkyl-, and the like as used herein. For example, the term "aryl-alkyl-" means an alkyl radical, to which an aryl is bonded. Examples of aryl-alkyl- include, but are not limited to, benzyl (phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) cyclic compound containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—$(C_{1-n})$alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

A protecting group or protective group is a substituent introduced into a molecule to obtain chemoselectivity in a subsequent chemical reaction. Many protecting groups are known in the art and a skilled person would understand the kinds of protecting groups that would be incorporated and could be used in connection with the methods described herein. In "protecting group based peptide synthesis", typically solid phase peptide synthesis, the desired peptide is prepared by the step-wise addition of amino acid moieties to a building peptide chain. The two most widely used protocols, in solid-phase synthesis, employ tert-butyloxycarbonyl (Boc) or 9-fluorenylmethoxycarbonyl (Fmoc) as amino protecting groups. Amino protecting groups generally protect an amino group against undesirable reactions during synthetic procedures and which can later be removed to reveal the amine. Commonly used amino protecting groups are disclosed in Greene, T. W. et al., Protective Groups in Organic Synthesis, 3rd Edition, John Wiley & Sons (1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, .alpha.-, .alpha.-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

In some embodiments, $R^1$ is H.

In some embodiments, $R^2$ or $R^3$ is covalently linked to $R^1$ to form proline having $NR^1$ as the N-terminus.

In some embodiments, $R^2$ and $R^3$ are not both H.

In some embodiments, $R^2$ and $R^3$ are each independently selected from the group consisting of amino acid chains of a proteinogenic or a non-proteinogenic alpha-amino acids.

In some embodiments, $R^2$ and $R^3$ are H and $CH_3$ respectively or vice versa.

In some embodiments, $R^2$ or $R^3$ is —CH2-S—$R^s$, wherein $R^s$ is selected from lower alkyl; lower amino alkyl; aryl; heteroaryl; alkenyl; or heterocycle; all of which are optionally substituted at one or more substitutable positions with one or more suitable substituents; preferably $R^s$ is phenyl or phenyl substituted with lower alkyl, halogen; or lower amino alkyl.

In some embodiments, $R^4$ and $R^5$ are not both H.

In some embodiments, R and R* are not both H.

In some embodiments, $R^4$ and $R^5$ are each independently H, or C(O)—$NHR^t$, wherein $R^t$ is H or a lower alkyl. Preferably, $R^t$ is tert-butyl or H.

In some embodiments, $R^6$ is H.

In some embodiments, $R^6$ and either $R^8$ or $R^9$ form a ring resulting in a proline residue having N—$R^6$ as its N-terminus.

In some embodiments, n is 1.

In some embodiments, Z along with L and —C=O is any one of SEQ ID NOs. 1-380.

In some embodiments, $X^1$ is Leu.

In some embodiments, $X^2$ is Asp.

In some embodiments, $X^3$ is Thr.

In some embodiments, $X^3$ is Val.

In some embodiments, $X^3$ is Ile.

In some embodiments, $X^y$ and $X^z$ are each independently a proteinogenic or non-proteinogenic alpha-amino acid.

In some embodiments, $X^z$ is a proteinogenic or non-proteinogenic beta-amino acid.

In some embodiments, $X^z$ is betaHomoLys or MethylbetaHomoLys.

In some embodiments, $X^y$ and $X^z$ are each a primary amino acid.

In some embodiments, $X^y$ and $X^z$ are each any amino acid listed under column $X^y$ and column $X^z$ respectively of Table 1B.

In various embodiments, the compound is any one of compounds 1-389 and 456 or the multimer is any one of compounds 390-397 and 457-538.

In various embodiments, the multimer is a dimer, trimer, tetramer, or pentamer.

In some embodiments, the monomer compounds are linked by a linker.

In some embodiments, the compounds are linked together at a carbon, nitrogen, oxygen, sulphur or other atom associated with $R^2$, $R^3$, $R^4$, $R^5$, $R^6$, $R^7/R^8$, $X^z$, or $X^y$.

As person skilled in the art would understand that various linkers may be used to multimerize the macrocycles described herein, including esters, amides, amines or mixed amides/amines.

Additional linkages include, but are not limited to, ethers, thioethers, thioesters, disulphides, sulfoxides, sulfones, sulfonamides, sulfamates, sulfamides, carbamates, ureas, carbonates, phosphodiesters, phosphonamides, phosphoramidates, heterocycles such as triazoles from azide-alkyne cycloaddition ("Click" chemistry). Alternatively, monomeric macrocycles can be covalently attached to linkers via carbon-carbon single bond linkages, carbon-carbon double bond linkages or carbon-carbon triple bond linkages. Alternatively, monomeric macrocycles can be covalently attached directly to a second, third or fourth monomeric macrocycle via any of the above linkages; in this case no formal linker moiety is present.

In some embodiments, the multimer is a homo-multimer.

In some embodiments, the multimer is a hetero-multimer.

In certain embodiments, there is provided pharmaceutically acceptable salts of the compounds described herein. The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. In certain embodiments, any of the peptide compounds described herein are salt forms, e.g., acetate salts.

In an aspect, there is provided, a pharmaceutical composition comprising the multimer described herein along with the pharmaceutically acceptable carrier. The pharmaceutical composition may be formulated for any one of oral delivery, topical delivery and parenteral delivery.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

In an aspect, there is provided, a method of treating inflammation or an autoimmune disease in a patient, comprising administering to the patient a therapeutically effective amount of the multimer described herein. Preferably the inflammation or an autoimmune disease is gastrointestinal.

In an aspect, there is provided, a method for treating a condition in a patient associated with a biological function of an α4β7 integrin, the method comprising administering to the patient a therapeutically effective amount of the multimer described herein.

In some embodiments, the condition or disease is Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, radiotherapy, chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft versus host disease, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, and Wiskott-Aldrich Syndrome, or pouchitis resulting after proctocolectomy and ileoanal anastomosis and various forms of gastrointestinal cancer, osteoporosis, arthritis, multiple sclerosis, chronic pain, weight gain, and depression. In another embodiment, the condition is pancreatitis, insulin-dependent diabetes mellitus, mastitis, cholecystitis, cholangitis, pericholangitis, chronic bronchitis, chronic sinusitis, asthma or graft versus host disease.

In preferable embodiments, is an inflammatory bowel disease, such as ulcerative colitis or Crohn's disease.

In an aspect, there is provided, a method for treating a disease or condition in a patient comprising administering to the patient a therapeutically effective amount of the multimer described herein, wherein the disease or condition is a local or systemic infection of a virus or retrovirus.

In some embodiments, the a virus or retrovirus is echovirus 1 and 8, echovirus 9/Barty Strain, human papilloma viruses, hantaviruses, rotaviruses, adenoviruses, foot and mouth disease virus, coxsackievirus A9, human parechovirus 1 or human immunodeficiency virus type 1.

In an aspect, there is provided, a method for treating a disease or condition in a patient comprising administering to the patient a therapeutically effective amount of the multimer described herein, wherein the hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, glycogen storage disease, hepatocellular carcinoma, liver cancer, primary biliary cholangitis, primary sclerosing cholangitis, primary biliary sclerosis, biliary tract disease, autoimmune hepatitis, or graft-versus-host disease.

In some embodiments, the multimer inhibits binding of α4β7 integrin to MAdCAM. Preferably, the compound selectively inhibits binding of α4β7 integrin to MAdCAM.

In any embodiment, the patient is preferably a human.

As used herein, the terms "disease", "disorder", and "condition" may be used interchangeably.

As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, "prevent" or "prevention" includes (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In some embodiments, the compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In some embodiments, the compound is administered as an initial does followed by one or more subsequent doses and the minimum interval between any two doses is a period of less than 1 day, and wherein each of the doses comprises an effective amount of the compound.

In some embodiments, the effective amount of the compound is the amount sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In some embodiments, the compound is administered at an interval selected from the group consisting of around the clock, hourly, every four hours, once daily, twice daily, three times daily, four times daily, every other day, weekly, bi-weekly, and monthly.

The compounds described herein may be multimerized using methods and linkers that would be known to a person of skill in the art, for example, as described in WO2016/054411.

The advantages of the present invention are further illustrated by the following examples. The examples and their particular details set forth herein are presented for illustration only and should not be construed as a limitation on the claims of the present invention.

Examples

Methods and Materials
Synthesis

Methods applicable for making the cyclic peptides described herein can be found generally in Applicant's PCT Publication No. WO 2010/105363 and in U.S. patent application Ser. No. 15/775,319 claiming priority to U.S. Provisional Application No. 62/254,003 filed on Nov. 11, 2015.

More specifically, the below protocols were used to synthesize each of the compounds as indicated in Table 1X. Multimer of the compounds were also synthesized as indicated in Table 2X.

Protocol A: General Nacellin Synthesis

1. Preparation of resin: Fmoc amino acid (1.1 eq. with respect to resin) was dissolved in $CH_2Cl_2$ (10 mL/g of resin). If the amino acid did not dissolve completely, DMF was added slowly dropwise until a homogeneous mixture persisted upon stirring/sonication. The 2-chlorotrityl resin was allowed to swell in $CH_2Cl_2$ (5 mL/g of resin) for 15 minutes. The $CH_2Cl_2$ was then drained and the Fmoc amino acid solution was added to the vessel containing the 2-Cl Trt resin. DIPEA was added (2 eq. with respect to the amino acid) and the vessel was agitated for five minutes. Another 2 eq. of DIPEA was then added and the vessel was left to agitate for an additional 60 minutes. The resin was then treated with methanol (1 mL/g of resin) to endcap any remaining reactive 2-Cl Trt groups. The solution was mixed for 15 minutes, drained and then rinsed with $CH_2Cl_2$ (×3), DMF (×3), $CH_2Cl_2$ (×2), and MeOH (×3). The resin was then dried under vacuum and weighed to determine the estimated loading of Fmoc amino acid.

2. Preparation of linear peptide sequence via manual or automated synthesis: Fully protected resin-bound peptides were synthesized via standard Fmoc solid-phase peptide chemistry manually or using an automated peptide synthesizer. All N-Fmoc amino acids were employed.

a. Fmoc deprotection: the resin was treated with 20% piperidine in NMP or DMF twice, for 5 and 10 minutes respectively, with consecutive DMF and NMP washes after each addition.

b. Fmoc amino acid coupling: the resin was treated with 3 eq. of Fmoc amino acid, 3 eq. of HATU and 6 eq. of DIPEA in NMP for 60 minutes. For difficult couplings, a second treatment with 3 eq. of Fmoc amino acid, 3 eq. of HATU and 6 eq. of DIPEA in NMP for 40 minutes was employed.

3. General cleavage with retention of protecting groups: Once the desired linear sequence was synthesized, the resin was treated with either 1.) 1:3, HFIP:$CH_2Cl_2$ or 2.) 5% TFA in $CH_2Cl_2$, twice for 30 minutes each, to afford cleavage from the solid support. The solvent was then removed, followed by trituration twice with chilled tert-butyl methyl ether (or diethyl ether/hexanes) to give the desired product. The purity was then analyzed by reverse-phase LCMS.

Protocol B: Preparation of N-Alkylated Fmoc Amino Acid Building Blocks

1. Resin prep: see protocol A, step 1
2. Fmoc deprotection: see protocol A, step 2a
3. Nosyl protection: The deprotected resin was stirred in $CH_2Cl_2$ (5 mL/mmol of resin) and DIPEA (6.5 eq.). A solution of Nosyl chloride (4.0 eq.) was added slowly, dropwise, over 30 minutes, to avoid a rapid exothermic reaction. After the addition was complete, stirring was continued at room temperature for three hours. The resulting nosyl-protected resin was filtered and washed with $CH_2Cl_2$, MeOH, $CH_2Cl_2$, and THF.

4. N-Methylation: To a suspension of resin in THF (10 mL/mmol of resin) was added a solution of triphenylphosphine (5 eq.) in THF (2 M) and MeOH (10 eq.). The stirring suspension was cooled in an ice bath. A solution of DIAD (5 eq.) in THF (1 M) was added dropwise, via addition funnel. After addition was complete the bath was removed and the reaction was stirred at room temperature for an additional 90 minutes. The resin was filtered, washed with THF (×4), $CH_2Cl_2$ (×3), and THF (×2).

5. Nosyl-deprotection: To a suspension of resin in NMP (10 mL/mmol of resin) was added 2-mercaptoethanol (10.1 eq.) and DBU (5.0 eq.). The solution became a dark green colour. After five minutes, the resin was filtered, washed with DMF until washes ran colourless. This procedure was repeated a second time, and the resin was then washed a final time with $CH_2Cl_2$.

6. Fmoc protection: To a suspension of resin in $CH_2Cl_2$ (7 mL/mmol of resin) was added a solution of Fmoc-Cl (4 eq.) in $CH_2Cl_2$ (7 mL), and DIPEA (6.1 eq.). The suspension was stirred at room temperature for four hours then filtered and washed with $CH_2Cl_2$ (×2), MeOH (×2), $CH_2Cl_2$ (×2), and $Et_2O$ (×2).

7. Cleavage from resin: see protocol A, step 3

Protocol C: Reductive Amination

1. Fmoc Weinreb amide formation: a mixture of Fmoc amino acid (1 mmol), N,O-dimethylhydroxylamine-HCl (1.2 eq.), and HCTU (1.2 eq.) in $CH_2Cl_2$ (6.5 mL), was cooled to 0° C. DIPEA (3 eq.) was then slowly added to the stirring mixture. The cooling bath was removed and the reaction was stirred at room temperature for 16 h. A 10% solution of HCl (4 mL) was added resulting in the formation of a precipitate, which was removed through filtration. The filtrate was washed with 10% HCl (3×4 mL) and brine (2×4 mL). The organic phase was then dried over $Na_2SO_4$. The solvent was removed under reduced pressure to give crude Fmoc Weinreb amide, which was used in the next reaction without purification.

2. a) Fmoc amino aldehyde formation: lithium aluminum hydride powder (1.5 eq) was placed in a dry flask. THF (Sigma-Aldrich, 250 ppm of BHT, ACS reagent >99.0%, 6.5 mL) was added, and the resulting slurry was cooled to −78° C., with stirring. To the slurry was added a solution of the Fmoc Weinreb amide in THF (10 mL). The reaction vessel was transferred to an ice/water bath, and maintained at 0° C. for 1 h. To the reaction at 0° C., was added dropwise acetone (1.5 mL), then $H_2O$ (0.25 mL) and then the reaction was left to stir for an additional hour at room temperature. The mixture was filtered through Celite, washed with EtOAc (10 mL) and MeOH (10 mL), and the filtrate was concentrated. The crude material was dissolved in $CHCl_3$ (6.5 mL) and washed with brine (2×3 mL) and the organic phase was then dried over $Na_2SO_4$, filtered and concentrated to give the Fmoc amino aldehyde.

Alternatively, b) Under argon atmosphere a Lithium Aluminum Hydride 1.0 M solution in THF (Sigma-Aldrich, 157.81 mL, 157.82 mmol, 1 eq.) was slowly added over a solution of the Weinreb amide (157.82 mmol) in THF (Sigma-Aldrich, 250 ppm of BHT, ACS reagent >99.0%, 1 L) at 0° C. and then stirred for 1 h. The reaction at 0° C., was diluted with $Et_2O$ (500 mL) and the resultant solution was washed with 10% $NaHSO_4$ (10×300 mL), 10% $KHSO_4$ (10×300 mL) and HCl (10×300 mL). The organic phase was then dried over $Na_2SO_4$, filtered and concentrated to afford the crude Fmoc amino aldehyde.

3. Reductive amination on-resin: the linear peptide on-resin was placed in a solid-phase peptide synthesis reaction vessel and diluted with DMF (22 mL/g of resin). The Fmoc aldehyde (4.0 eq.) was added and the reaction was left to shake overnight. The solution was then drained and the resin was washed with $CH_2Cl_2$ (×3) and DMF (×3). The resin was then diluted with a mixture of MeOH/$CH_2Cl_2$ (22 mL/g of resin, 1:3 ratio) and $NaBH_4$ (7 eq.) was subsequently added. The mixture was left to shake for four hours, then the solution was drained and the resin was washed with $CH_2Cl_2$ (×3) and DMF (×3).

Protocol D: Fragment-Based Macrocyclization a) In a two-dram vial, 0.1 mmol of the linear peptide and DEPBT (1.5 eq.) were dissolved in 5 mL of freshly distilled THF (0.02 M). DIPEA (3 eq.) was then added and the reaction mixture was left to stir overnight at room temperature (16 h). Tetraalkylammonium carbonate resin (Biotage®, 6 eq.) was then added to the reaction mixture and stirring was continued for an additional 24 h. The reaction was then filtered through a solid-phase extraction vessel and rinsed with $CH_2Cl_2$ (2 mL). The filtrate and washes were combined and the solvent was removed under reduced pressure.

Alternatively, b) In a two-dram vial, 0.1 mmol of the linear peptide and HATU (2.0 eq.) were dissolved in 80 mL of $CH_2Cl_2$ (1.25 mM). DIPEA (6 eq.) was then added and the reaction mixture was left to stir overnight at room temperature (16 h). The solvent was removed under reduced pressure.

Protocol E: Aziridine Aldehyde-Based Macrocyclization

The linear peptide was dissolved in TFE (if solubility problems were encountered, a 50:50 mixture of TFE:$CH_2Cl_2$ was used for the cyclization). Then 0.6 eq. of (S)-aziridine-2-carboxaldehyde dimer (prepared as per literature protocol: *J. Am. Chem. Soc.* 2006, 128 (46), 14772-14773 and *Nat. Protoc.* 2010, 5 (11), 1813-1822) as a TFE stock solution (0.2 M) was added, giving a final reaction mixture concentration of 0.1 M. tert-Butyl isocyanide (1.2 eq.) was then added and the reaction mixture was stirred for four hours. Progress was analyzed along the way via LC-MS.

Protocol F: Nucleophilic Ring-Opening of Acyl Aziridine, Post Macrocyclization a) Thioacetic acid/thiobenzoic acid: the corresponding thio acid (4 eq.) was added to the crude reaction mixture. Reaction progress was monitored by LC-MS, and was generally complete after 1-2 hours.

Alternatively, b) Thiophenol: Thiophenol (4 eq.) and DIPEA (4 eq.) were added to the crude cyclization mixture. Reaction progress was monitored by LC-MS, and was generally complete after 1-2 hours. Solvent was removed under reduced pressure and dried under vacuum. Crude material was either triturated with $Et_2O$/hexanes or TBME, or alternatively, diluted with $H_2O$, frozen and lyophilized.

Protocol G: Suzuki Coupling, Post Macrocyclization a) As a general example, an iodo-Phe-containing macrocycle (0.1 mmol), $Na_2CO_3$ (2 eq.), substituted boronic acid (1.1 eq.) and 4 mL of water:acetonitrile (1:1 ratio) were combined in a microwave vial. The mixture was treated with $N_2$ gas flow for 10 minutes. While under $N_2$, silicon based Pd-catalyst (Siliacat-DPP Pd heterogenous catalyst, 0.05 eq.) was added. The microwave vial was sealed and placed in the microwave for 10 minutes at 120° C. (reaction time and temperature were increased to 30 min. and 150° C., depending on the substrate) or thermally heated at 90° C. for 1 h. Reaction progress was monitored by LCMS. Once complete, the reaction was filtered through a Celite plug and the solvent was removed under reduced pressure.

Alternatively, b) as a specific example, Suzuki couplings with macrocycles that were prepared using 3-(((((9H-fluoren-9-yl)methoxy)carbonyl)amino)methyl)-4-bromobenzoic acid were conducted as follows: A mixture of crude macrocyclic Compound 340 that had been orthogonally protected as the p-tert-butyl ester of the Asp residue and the tert-butyl ether of the Thr residue (200 mg, 0.22 mmol) and 4-(4-Boc-piperazino) phenylboronic acid pinacol ester (171 mg, 0.44 mmol) were dissolved in a 1,2-dimethoxyethane (5.4 mL) and Ethanol (1.2 mL) at room temperature. Water (1.2 mL) was added to the solution, followed by $Na_2CO_3$(35 mg, 0.33 mmol). The reaction flask was flushed for at least 5 to 10 min under nitrogen gas and then catalyst SiliaCat-DPP Pd (88 mg, 10 mol %, 0.25 mmol/gm) was added. The reaction mixture was heated with stirring under nitrogen at 90° C. for 1 hr. LCMS after 1 hour showed complete consumption of substrate and ~ 5% de-bromination compound; the desired Suzuki cross-coupled product represented ~ 84% yield after taking into account the excess of boronate ester by UV. The reaction mixture was cooled to room temperature and filtered over a celite pad to remove catalyst SiliaCat-DPP Pd. The celite pad was washed with a little DCM and the solvents were removed under vacuum to give pale yellow crude solid as the Suzuki coupling product. Reagent 3-(((((9H-fluoren-9-yl)methoxy)carbonyl)amino) methyl)-4-bromobenzoic acid was itself prepared from methyl 3-(aminomethyl)-4-bromobenzoate (US2011251247) via saponification of the methyl ester and protection of the amine as the Fmoc carbamate, as follows: to a solution of methyl 3-(aminomethyl)-4-bromobenzoate (1.36 g, 5.57 mmol) in Dioxane (33 ml) and Water (9 ml) was added lithium hydroxide (6.13 ml, 6.13 mmol). The mixture was stirred for 3 hrs at room temperature. TLC showed the hydrolysis reaction was complete. Dioxane (16 ml) was added. The mixture was neutralized by the addition of 1 N HCl (aq) (6.17 mL). Sodium bicarbonate (0.468 g, 5.57 mmol) was added, followed by (9H-fluoren-9-yl) methyl carbonochloridate (2.162 g, 8.36 mmol). The mixture was stirred for 2 hrs at room temperature and was acidified to pH 3 by the addition of 1 N HCl (aq) (6.2 mL). Water (40 ml) was added, extracted with AcOEt (4×150 mL). The combined organic layers were dried over sodium sulfate and the solvent was evaporated to ~50 ml. Precipitation began to occur and was allowed to slowly continue overnight at room temperature. White solid was then collected by filtration, washed with hexane and dried under high vacuum to afford 3-(((((9H-fluoren-9-yl)methoxy)carbonyl)amino)methyl)-4-bromobenzoic acid (2.0 g, 4.42 mmol, 79% yield).

Protocol H: General Ulmann Coupling, Post Macrocyclization

Under inert atmosphere, the peptide macrocycle (0.018 mmol) was placed in a 2-dram vial containing 2 mL of dry $CH_2Cl_2$. $Cu(OAc)_2$ (1 eq.), benzene boronic acid (2 eq.) and 4 Å (oven-dried) molecular sieves were then added to the vial followed by DIPEA (4 eq.). The contents of the vial were stirred at room temperature overnight. The reaction progress was assessed by LCMS. Once the reaction was deemed complete, the mixture was filtered through a Celite plug and the solvent was removed under reduced pressure.

Protocol I: General Global Deprotection and Cleavage

Deprotection of the side chain protecting groups was achieved by dissolving the peptides in 2 mL of a cleavage cocktail consisting of TFA:$H_2O$:TIS (95:2.5:2.5) for two hours (for sensitive peptides the mixture of TFA:$H_2O$:TIS (95:2.5:2.5) may be substituted for a mixture of TFA: $CH_2Cl_2$ (50:50)). Subsequently, the cleavage mixture was evaporated under reduced pressure and the peptides were precipitated twice from chilled diethyl ether/hexanes (or tert-butyl methyl ether).

Protocol J: General Cleavage of Reductively-Labile Protecting Groups a) Pd/C and formic acid debenzylation: the benzyl protected macrocycle (0.35 mmol) was dissolved in MeOH (8 mL) with 10% formic acid, 10% wt. Pd/C (Sigma-Aldrich, 37 mg, 0.1 Eq) and heated to 55° C. for 1 h to 4 h. Once the reaction was deemed complete, the mixture was filtered through a Celite plug, washed with MeOH and the solvent was removed under reduced pressure.

Or alternatively, b) Raney Ni desulfurization/debenzylation: Raney Ni slurry (1-2 mL) was added directly to the cyclization reaction mixture and stirred vigorously overnight. The vial was then centrifuged and the liquid was transferred using a pipette to a tared vial. MeOH was added to the vial containing Raney Ni. The vial was then sonicated, vortexed, and centrifuged. Again, the liquid was transferred to a tared vial. This process was repeated with EtOAc and then a final time with MeOH. The combined washes were then removed under reduced pressure and the residue dried under vacuum.

Protocol K: Amidation of Side Chain, Post Macrocyclization

Macrocycle (0.021 mmol) was dissolved in 1 mL of $CH_3CN$. $K_2CO_3$ (5 eq.) and the corresponding acid chloride (2 eq.) were then added and the reaction mixture was left to stir at room temperature overnight. Reaction progress was checked by LC-MS in the morning. Upon completion, the solvent was removed by reduced pressure.

Protocol L: Fluorescent Dye Attachment

The macrocycle (4 μmol) was dissolved in DMSO (200 μL). DIPEA (5 eq.) was then added. In a separate vial, 5 mg of fluorescent dye as the NHS ester was dissolved in 200 μL of DMSO. The macrocycle solution was then added to the solution of the fluorescent label. The reaction mixture was stirred overnight. Reaction progress was checked by LC-MS in the morning and then the solvent was removed by lyophilization.

Protocol M: Purification Methods

All macrocycles were purified using reverse-phase flash column chromatography using a 30 g RediSep C18 Gold Column. The gradient consisted of eluents A (0.1% formic acid in double distilled water) and B (0.1% formic acid in HPLC-grade acetonitrile) at a flow rate of 35 mL/min.

Multimerization Protocols

Protocol N: Linker Synthesis for Multimerization a) Preparation of Acyl chloride linkers: Di-, tri- or tetracarboxylic acids (1 eq.) and $CH_2Cl_2$ (0.114 M concentration) were added to a two-dram vial. $SOCl_2$ (15 eq. per carboxylic acid) was then added and the reaction mixture was left to stir for four hours at room temperature (some substrates required heating at 70° C. overnight for full solution and/or conversion). The solvent was removed via $N_2$ flow. The residue was dissolved in 3 mL of dry $CH_2Cl_2$ which was then removed under $N_2$ flow. This process was performed two additional times in an attempt to remove any free HCl from the sample. The resulting residue was then used without purification in the dimerization reaction.

b) Preparation of Benzotriazole linkers, Method A: Thionyl chloride (2 eq. per carboxylic acid) was added to a solution of benzotriazole (10 eq. per carboxylic acid) in dichloromethane (20 mL per mmol of starting linker) and the solution was stirred at room temperature for 20 min. The di-, tri- or tetra-carboxylic acids (1 eq.) were added to each mixture, which were then stirred at room temperature for 24 h (a change in order of addition did not materially alter the outcome). The reaction was quenched with $NaHCO_3$ (10%, 100 mL) and the layers were separated. The organic layer was washed with HCl (10%, 2×100 mL) and $NaHCO_3$ (10%, 2×100 mL), dried over anhydrous sodium sulfate, filtered and evaporated under vacuum to give the desired Benzotriazole-activated carboxylic acids.

c) Preparation of Benzotriazole linkers, Method B: To a suspension of HATU (1.5 eq. per carboxylic acid), Benzotriazole (2 eq. per carboxylic acid) and the di-, tri- or tetra-carboxylic acids (1 eq.) in dichloromethane (20 mL per mmol of starting linker) was added DIPEA (3 eq. per carboxylic acid) and the resultant yellow solution was stirred at room temperature for 16 h. The reaction was quenched with $NaHCO_3$ (10%, 100 mL) and the layers were separated. The organic layer was washed with HCl (10%, 2×100 mL) and $NaHCO_3$ (10%, 2×100 mL), dried over anhydrous sodium sulfate, filtered and evaporated under vacuum to give the desired Benzotriazole-activated carboxylic acids d) Preparation of Lys(CBz)-Pimelic acid-Lys(CBz) linker: Pimelic acid was converted to the bis-Benzotriazole-activated moiety using Protocol Nb. Commercial $N^\alpha$—Z-L-lysine methyl ester hydrochloride (2 eq.; Chemlmpex) was treated with bis-Benzotriazole-activated Pimelic acid (1 eq.) in $CH_3CN$ (0.011 M) containing DIPEA (10 eq.). The reaction mixture was stirred for 16 h (monitored by LC-MS). The solvent was removed by rotoevaporation and the crude material was submitted to reverse-phase silica chromatography (Biotage) to obtain the purified bis-methyl ester of Lys(CBz)-Pimelic acid-Lys(CBz) as an intermediate. To a solution of the bis-methyl ester (1.5 mmol, 1.0 eq.) in THF (10 mL) were added LiCl (3.0 mmol, 2.0 eq.) and LiOH—$H_2O$ (3.0 mmol, 2.0 eq.), followed by $H_2O$ (250 uL) to help solubilize the salts. The reaction was stirred at room temperature overnight. Upon completion of the hydrolysis, as assessed by LC-MS monitor, formic acid was added dropwise to neutralize the basic solution. The solvent was removed by rotoevaporation and the crude material was submitted to reverse-phase chromatography (Biotage) to obtain the purified di-acid linker.

e) Preparation of PEG2-Diglycolic acid-PEG2 linker: Diglycolyl chloride (0.35 mmol; 1 eq.; Sigma Aldrich cat. No. 378151) in anhydrous $CH_2Cl_2$ (5 mL) was treated with $NH_2$—PEG2-$CH_2CH_2COOtBu$ (2 eq.; Biochempeg Cat. No. MD005067-2), followed by dropwise addition of DIPEA (3.5 mmol, 10.0 eq); NB—this order of addition proved to be very important. The reaction was monitored by LC-MS. After 30 min., the reaction was complete, and longer stirring times did not affect the product ratio. The solvents were removed in vacuo and the crude material was submitted to reverse-phase chromatography (Biotage) to obtain the purified di-tert-butyl ester intermediate. Removal of the tert-butyl ester groups was effected by Protocol I. The diacid linker was isolated as a crude and used as such multimerization reactions without further manipulation.

f) Preparation of PEG2-Diphenic acid-PEG2 linker: Diphenic acid was converted to the bis-Benzotriazole-activated moiety using Protocol Nb. Commercial $NH_2$—PEG2-$CH_2CH_2COOtBu$ (2 eq.; Biochempeg Cat. No. MD005067-2) was treated with bis-Benzotriazole-activated Diphenic acid (1 eq.) in $CH_3CN$ (0.011 M) containing DIPEA (10 eq.). The reaction mixture was stirred for 16 h (monitored by LC-MS). The solvent was removed by rotoevaporation and the crude material was submitted to reverse-phase silica chromatography (Biotage) to obtain the purified di-tert-butyl ester intermediate. Removal of the tert-butyl ester groups was effected by Protocol I. The diacid linker was isolated as a crude and used as such in multimerization reactions without further manipulation.

g) Preparation of PEG2-Pimelic acid-PEG2 linker: Pimelic acid was converted to the bis-Benzotriazole-activated moiety using Protocol Nb. Commercial $NH_2$—PEG2-$CH_2CH_2COOtBu$ (2 eq.; Biochempeg Cat. No. MD005067-2) was treated with bis-Benzotriazole-activated Pimelic acid (1 eq.) in $CH_3CN$ (0.011 M) containing DIPEA (10 eq.). The reaction mixture was stirred for 16 h (monitored by LC-MS). The solvent was removed by rotoevaporation and the crude material was submitted to reverse-phase silica chromatography (Biotage) to obtain the purified di-tert-butyl ester intermediate. Removal of the tert-butyl ester groups was effected by Protocol I. The diacid linker was isolated as a crude and used as such in multimerization reactions without further manipulation.

Protocol O: Nacellin Multimerization a) Multimerization of amine-containing monomeric macrocycles using bis- or tris-acyl chloride-activated linkers: The corresponding acyl chloride (0.35 mmol, 1.0 eq.), freshly prepared and under Argon atmosphere, was dissolved in anhydrous $CH_2Cl_2$ (5 mL; note that larger scale reactions required more-concentrated solution to produce higher-yielding dimerizations). Monomeric macrocycle (2, 3 or 4 eq. for bis-, tris-, or tetra-acyl chlorides), optimally supplied as the free-base/non-salted form of the reacting amine center, was added to the flask, followed by dropwise addition of DIPEA (3.5 mmol, 10.0 eq); NB—this order of addition proved to be very important. The reaction was monitored by LC-MS. After 30 min., the reaction was complete, and longer stirring times did not affect the product ratio. The solvents were removed in vacuo and the crude material was submitted to reverse-phase chromatography (Biotage) to obtain the purified product.

b) Multimerization of amine-containing monomeric macrocycles using Benzotriazole-activated linkers: To a solution of monomeric macrocycle (2, 3 or 4 eq.), optimally supplied as the free-base/non-salted form of the reacting amine center, and the corresponding Benzotriazole-activated linker, previously prepared but not longer than 1 week prior to multimerization, (0.011 mmol, 1 eq.) in $CH_3CN$ (1 mL) in the presence of DIPEA (0.02 mL, 0.114 mmol, 10 eq). The reaction mixture was stirred for 16 h (monitored by LC-MS). The solvent was removed by rotoevaporation and the crude material was submitted to reverse-phase silica chromatography (Biotage) to obtain the purified product.

c) Dimerization of amine-containing monomeric macrocycles using 2-Chloroacetyl chloride: To a solution of the monomeric macrocycle (0.0571 mmol, 2 eq.), optimally supplied as the free-base/non-salted form of the reacting amine center, in distilled THF (1.0 mL), were added 2-chloroacetyl chloride (3.19 mg, 0.029 mmol, 1 eq.) followed by DIPEA (25 uL, 0.17 mmol, 6.0 eq.). The reaction mixture was stirred for 16 h (monitored by LC-MS). NaI (8.5 mg, 0.05708 mmol, 2 eq) was then added and the reaction mixture was heated at 50° C. for 2 h. The solvent was removed in vacuo and the crude material was submitted to reverse-phase silica chromatography (Biotage) to obtain the purified product.

d) Dimerization of amine-containing monomeric macrocycles using Acryloyl chloride: To a solution of the monomeric macrocycle (0.0571 mmol, 2 eq.), optimally supplied as the free-base/non-salted form of the reacting amine center, in distilled THF (1.0 mL), were added Acryloyl chloride (2.6 mg, 0.029 mmol, 1 eq.) and then DIPEA (25 uL, 0.17 mmol, 6.0 eq.). The reaction mixture was stirred for 16 h (monitored by LC-MS). DBU (8.5 uL, 0.057 mmol, 2 eq) was then added and the reaction was heated at 50° C. for 5 h. The solvent was removed in vacuo and the crude material was submitted to reverse-phase silica chromatography (Biotage) to obtain the purified product.

e) Multimerization of hydoxyl-containing monomeric macrocycles: Di-, tri- or tetra-carboxylic acid linker (4.3 μmol), monomeric macrocycle (2, 3 or 4 eq.), DMAP (2, 3 or 4 eq.), and EDC-HCl (4, 8 or 12 eq.) were dissolved in DCM (500-1000 μL). The reaction mixture was left to stir at room temperature overnight. Reaction progress was assessed by LC-MS. Upon completion, the solvent was removed under reduced pressure and the crude was submitted to reverse-phase silica chromatography (Biotage) to obtain the purified product.

f) Dimerization of amine-containing monomeric macrocycles using 2,4-dichloro-5-nitropyrimidine: To a solution of 2,4-dichloro-5-nitropyrimidine (2.0 mg, 0.010 mmol, 1.0 equiv) and monomeric macrocycle (0.021 mmol, 2.1 eq.), optimally supplied as the free-base/non-salted form of the reacting amine center, in chloroform (1 mL), in a 1-dram vial, was added DIPEA (0.02 mL, 0.11 mmol, 11.0 equiv); the reaction mixture immediately turned yellow. Stirring was continued at room temperature overnight, at which point LC-MS analysis exhibited almost full conversion to desired dimer. An additional 24 h of reaction time did not lead to any further conversion. Solvent was rotoevaporated to dryness, and the crude residue was submitted to reverse-phase chromatography to afford the purified material in 76% isolated yield.

g) Multimerization of amine-containing monomeric macrocycles using HATU-activated linkers: To a solution of the monomeric macrocycle (2, 3 or 4 eq.), optimally supplied as the free-base/non-salted form of the reacting amine center, in 1 mL dry DCM, was added the di-, tri- or tetra-substituted carboxylic acid (1 eq.) under inert atmosphere at room temperature. HATU (3, 6 or 9 eq.) was added to the solution, followed by the addition of DIPEA (3, 6 or 9 eq.). The reaction mixture was left to stir overnight. Assessment of reaction progress by LC-MS after 14 h indicated completion. The reaction mixture was rotoevaporated to near-dryness, then placed under high vacuum. If no orthogonal protecting groups required removal (for example, amines protected as the CBz carbamate), the crude material was submitted to reverse-phase chromatography to afford the purified material.

h) Multimerization of amine-containing monomeric macrocycles using halide-activated linkers: To a solution of monomeric macrocycle (3.0 eq. if used with a dihalide, 4.5 eq. if used with a trihalide) and the corresponding di or tri-halide linker (1.0 eq) in CH$_3$CN (2 mL) was added DIPEA (~ 30 eq.). The reaction mixture was stirred for 16 h (monitored by LC-MS). The solvent was removed, and crude was submitted to reverse-phase chromatography to afford the purified material.

Integrin α4β7-MAdCAM-1 ELISA Competition Assay

A 96-well Microlon plate (Greiner, 655001) was coated with 100 μl per well of a solution of 1 μg/ml recombinant integrin α4β7 (R&D Systems, 5397-A3-050) in carbonate buffer (50 mM, pH 9.6). The plate was incubated at 4° C. overnight. The solution was removed and 250 μl blocking buffer (50 mM Tris, 150 mM NaCl, 1 mM MnCl$_2$, 1% BSA, 0.05% Tween) was added per well. The plate was then incubated for 1 hour at room temperature. The plate was washed three times with wash buffer (50 mM Tris, 100 mM NaCl, 1 mM MnCl$_2$, 0.05% Tween). To each well, 50 μl of compound diluted in assay buffer was added by transfer from a compound serial dilution plate. 50 μl recombinant MAdCAM-Fc (R&D systems, 6056-MC-050) at a concentration of 0.1 μg/ml in assay buffer (50 mM Tris, 150 mM NaCl, 1 mM MnCl$_2$, 0.1% BSA, 0.05% Tween) was added to each well. The plate was incubated at room temperature with shaking (300 rpm) for 2 hours to reach binding equilibrium. Then the plate was washed three times in wash buffer and 100 μl anti-human IgG Fc specific-HRP (Abcam, Ab97225) diluted at 1:2000 in assay buffer was added to each well. The plate was incubated at room temperature for 1 hour under agitation. The plate was then washed three times and 100 μl of 1,3',5,5'-Tetramethylbenxidie (TMB, KPL 5120-0083) was then added to each well. The reaction was stopped after 2 minute-incubation by adding 50 μl of 1 M H$_2$SO$_4$ and optical absorbance was read at 450 nM.

Integrin α4β1-VCAM-1 Competition ELISA

A 96-well Microlon plate (Greiner, 655001) was coated with 100 μl per well of a solution of 0.5 μg/ml recombinant integrin α4β1 (R&D Systems, 5397-A3-050) in carbonate buffer (50 mM, pH 9.6). The plate was incubated at 4° C. overnight. The solution was removed and 250 μl blocking buffer (50 mM Tris, 150 mM NaCl, 1 mM MnCl$_2$, 1% BSA, 0.05% Tween) was added per well. The plate was then incubated for 1 hour at room temperature. The plate was washed three times with wash buffer (50 mM Tris, 100 mM NaCl, 1 mM MnCl$_2$, 0.05% Tween). To each well, 50 μl of compound diluted in assay buffer was added by transfer from a compound serial dilution plate. 50 μl recombinant VCAM-Fc (R&D systems, 862-VC-100) at a concentration of 0.1 μg/ml in assay buffer (50 mM Tris, 150 mM NaCl, 1 mM MnCl$_2$, 0.1% BSA, 0.05% Tween) was added to each well. The plate was incubated at room temperature with shaking (300 rpm) for 2 hours to reach binding equilibrium. Then the plate was washed three times in wash buffer and 100 μl anti-human IgG Fc specific-HRP (Abcam, Ab97225) diluted at 1:2000 in assay buffer was added to each well. The plate was incubated at room temperature for 1 hour under agitation. The plate was then washed three times and 100 μl of 1,3',5,5'-Tetramethylbenxidie (TMB, (TMB, KPL 5120-0083) was then added to each well. The reaction was stopped after 2 minute-incubation by adding 50 Pl of 1 M H$_2$SO$_4$ and optical absorbance was read at 450 nM.

Integrin α4β7-MAdCAM Cell Adhesion Assay

RPM18866 human cells (Sigma #95041316) were cultured in RPMI 1640 medium (HyClone SH30027.1) supplemented with 10% FBS (Seradigm) and 1% Penicillin-Streptomycin. A 96-well plate (Costar, 3603) was coated with 100 ml/well of human recombinant MAdCAM-1 Fc Chimera (R&D Systems, 6056-MC-050) solution at 0.25 μg/ml in coating buffer (50 mM sodium carbonate, pH 9.6). The plate was incubated overnight at 4° C. and washed twice with 150 μl per well wash buffer (0.05% Tween 20 in PBS), blocked with 250 μl per well blocking buffer (1% non-fat dry milk in PBS), and incubated for 2 hours at room temperature. RPM18866 cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/ml. Compounds were diluted by serial dilution in binding buffer (1.5 mM CaCl$_2$, 0.5 mM MnCl$_2$, 50 mM Tris-HCl, pH 7.5) to a final volume of 50 μl per well at 2× concentration. The plate was washed once with 300 □l of PBS, 50 μl of compound and 50 μl of cells (100,000 cells) were transferred to each well and the plate was incubated in the dark at 37° C., 5% CO$_2$ for 45 min to allow cell adhesion.

The plate was emptied by inverting and blotting on paper towels and washed manually twice with PBS. 100 µl PBS was then added to each well. The fluorescence was read ($Ex_{495}/Em_{515}$) using a plate reader (Tecan Infinite 1000). To calculate the dose response, the fluorescence value of control wells not containing cells was subtracted from each test well.

Integrin α4β1-VCAM Cell Adhesion Assay

RAMOS human cells (ATCC CRL-1596) were cultured in RPMI 1640 medium (HyClone SH30027.1) supplemented with 10% FBS (Seradigm) and 1% Penicillin-Streptomycin. A 96-well plate (Costar, 3603) was coated with 100 ml/well of recombinant human VCAM-1 Fc Chimera (R&D systems, 862-VC-100) solution at 0.25 µg/ml in coating buffer (50 mM sodium carbonate, pH 9.6). The plate was incubated overnight at 4° C. and washed twice with 150 µl per well wash buffer (0.05% Tween 20 in PBS), blocked with 250 µl per well blocking buffer (1% non-fat dry milk in PBS), for 1 hour at room temperature. During blocking step, RAMOS cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/ml. Compounds were diluted by serial dilution in binding buffer (1.5 mM $CaCl_2$, 0.5 mM $MnCl_2$, 50 mM Tris-HCl, pH 7.5) to a final volume of 50 µl per well at 2× concentration. The plate was washed once with 300 µl of PBS, 50 µl of compound and 50 µl of cells (100,000 cells) were transferred to each well and the plate was incubated in the dark at 37° C., 5% $CO_2$ for 45 min to allow cell adhesion. The plate was emptied by inverting and blotting on paper towels and washed manually twice with PBS. After last wash, 100 µL of PBS was added to wells and the fluorescence was read ($Ex_{495}/Em_{515}$) using a plate reader (Tecan Infinite 1000). To calculate the dose response, the fluorescence value of control wells not containing cells was subtracted from each test well.

Analyte Competition Assay in CD4+ Integrin $α_4+β_7$-Lo Memory T Cells

Receptor occupancy in primary cells was determined by measuring the amount of biotinylated human recombinant MAdCAM-1-FC or human recombinant VCAM-1-Fc bound to selected cell populations using flow cytometry. Human recombinant MAdCAM-1-FC or human recombinant VCAM-1-FC (R&D systems) were biotinylated using commercially available reagents and protocol (Pierce).

Whole blood was collected from human donors in sodium heparin tubes. A volume of 100 microL of blood was incubated with compound and 4 mM $MnCL_2$ for 1 hour at room temperature. Cells were washed twice with 1 mL of 1×DPBS calcium magnesium free (CMF) (ThermoFisher Scientific) and resuspended in 100 microL of DPBS CMF.

Biotinylated human recombinant MAdCAM-1-Fc or VCAM-1-Fc were added at saturating concentration and incubated at room temperature for 1 hour. A volume of 2 mL of 1×BD FACS Lyse (BD Biosciences) was then added and the mixture was incubated for 8-12 minutes at room temperature in the dark to lyse red blood cells. Cells were washed with 1 mL stain buffer-FBS (BD Biosciences) and resuspended in 100 µl stain Buffer-FBS (BD Biosciences) containing 4 mM $MnCl_2$. Biotinylated-rhMAdCAM-1 was applied at a saturating concentration of 1200 ng/mL to compete with test article binding and incubated at room temperature for 1 hour. Cells were then washed with 1 mL stain buffer-FBS and resuspended in 100 µl stain buffer-FBS. The cells were incubated in the dark for 30 minutes at room temperature with 1 ul Streptavidin APC (Biolegend 0.2 mg/ml) and a panel of antibodies for the detection of memory T helper a4b7-positive cells subset. And amount of 5.0 ul each of the following antibodies were used; CD45 FITC (BioLegend 200 ug/ml), CD29 APC Cy7 (BioLegend 100 ug/ml), Integrin beta7 PE, (BioLegend concentration 50 µg/mL), CD49d V421 (BioLegend 50 µg/mL), CD3 V510 (BioLegend 30 µg/mL), CD4 PECy7 (BioLegend 100 µg/mL), CD45RO PerCP, BioLegend 200 µg/mL). The cells were then washed with stain-buffer-FBS and resuspended in 150 microL stain buffer-FBS for acquisition on the flow cytometer (BD FACSCanto™ flow cytometer and BDFACSDiva™ software). FACS data was acquire by electronic gating on the basis of forward versus side scatter, The cytometer was set to collect 20,000 events in each tube. Cell population were determined using the following markers, CD45+, CD3+, CD4+, CD45RO+, CD49d+, integrin b7, biotinylated ligands.

Compound receptor occupancy was defined as the decrease in the number of integrin $β_7$+ or integrin $β_7$-lo cells binding biotinylated rhMAdCAM-1 or rhVCAM-1, respectively.

Receptor occupancy was calculated with the following equation: 100−((% ligand-positive cells with compound/% ligand-positive cells DMSO)*100)

In vivo T lymphocyte trafficking analysis in mouse model of colitis

Animal care: The animal care facility employed is accredited by the Canadian Council on Animal Care (CCAC). This study was approved by a certified Animal Care Committee and complied with CACC standards and regulations governing the use of animals for research. The animals were housed under standardized environmental conditions. A standard certified commercial rodent diet was provided ad libitum. Tap water was provided ad libitum at all times.

Dextran sulfate sodium (DSS) was administered to C57Bl/6 female mice for five days through addition to their drinking water at 3%. Body weight and disease activity index ("DAI") were measured on Day 5 in order to distribute DSS-treated animals in uniform groups prior to dosing. DAI was scored based on the severity three specific symptoms associated with colitis: 1—blood in stool (negative hemoccult, positive hemoccult, blood traces in stool visible, rectal bleeding); 2—stool consistency (normal, soft but still formed, very soft, diarrhea); 3—body weight loss.

From Day 6 to day 9, Compound No. 517 (ET03764) or the vehicle were administered orally daily at 5 ml/kg. On day 9, four hours after dosing, the animals were euthanized by cardiac puncture under general anesthesias. Mesenteric lymph nodes (MLN) were collected, triturated, and washed in HBSS-FCS. The cells were incubated for 15 minutes in BD mouse FcBlock followed by 30-minute incubation with specific antibodies. After washes, cells were either fixed using BD fix solution or immediately process for cell surface marker staining. The antibodies used were as followed: CD4 PE (BD Bioscience), CD44 FITC (BD Biosciences), CD45RB PerCy 5.5 (BD Biosciences), α4b7 PE (eBiosciences). Cell populations were then analyzed using FACSCanto cytometer and gating on CD4+, $CD44^{hi}$, $CD45RB^{low}$, α4β7+.

Statistical analysis was performed using GraphPad Prism. Differences among groups were evaluated by two-way ANOVA, with a 95% confidence interval.

Results and Discussion

Figure 6A:
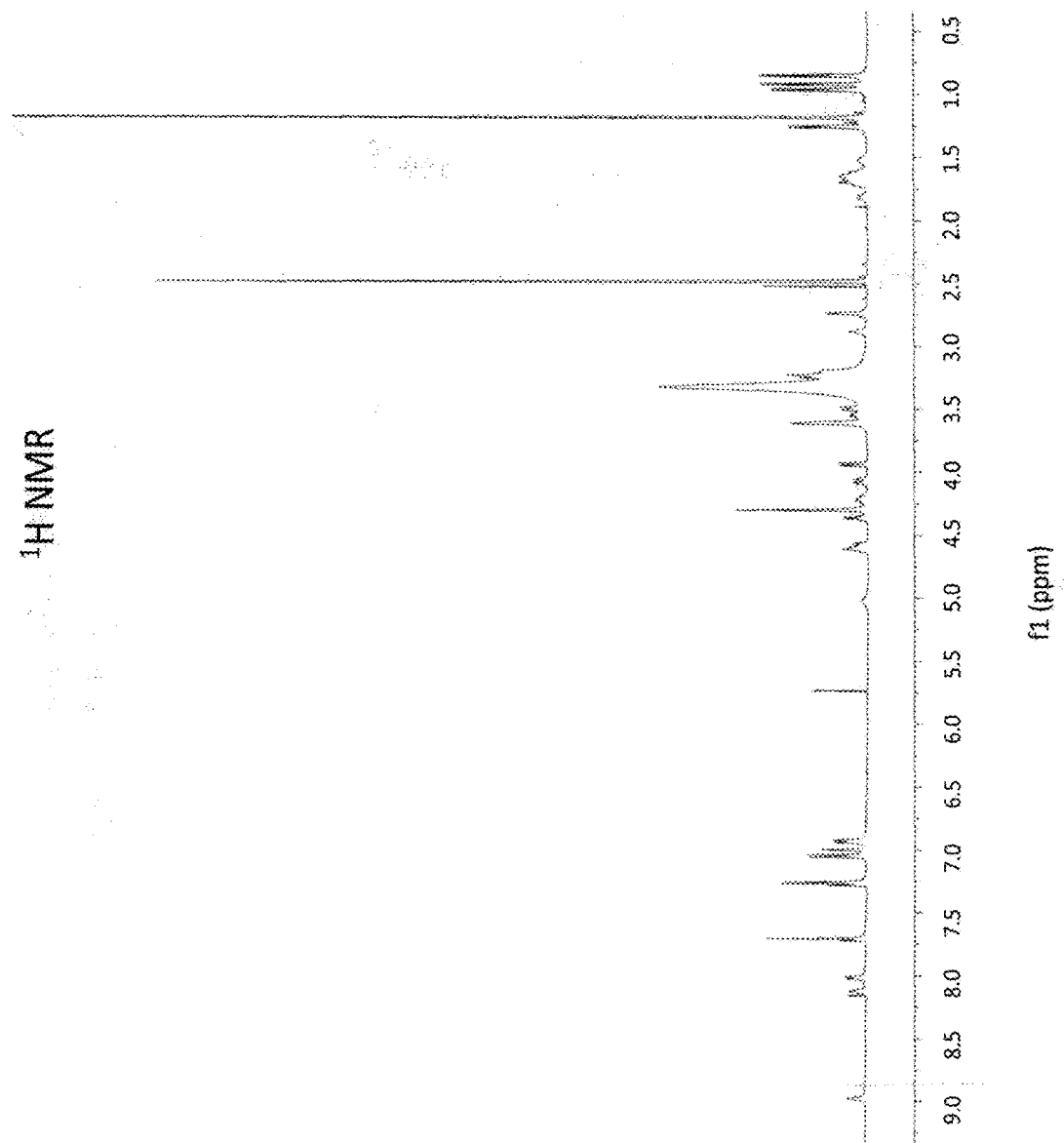
FIGS. 6A and 6B show representative NMR data for a multimeric molecule, Compound No. 390, with $^1$H- and $^1$H-$^1$H TOCSY NMR spectra recorded at 25° C.
Figure 6B:
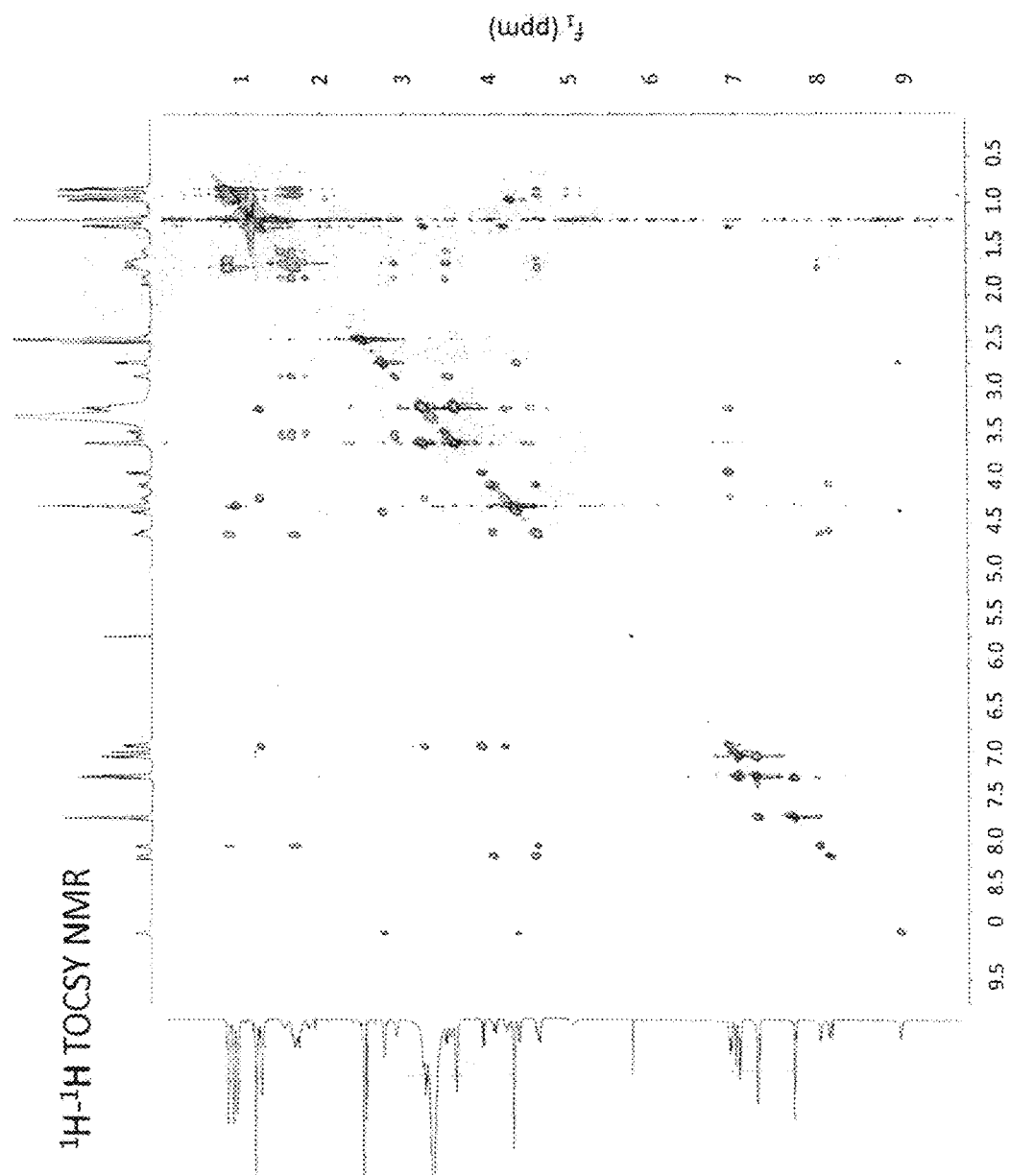

Compounds were synthesized in accordance with the above-noted methods. A selection of compounds was characterized using NMR (not all data shown). A subset of NMR data is provided in FIG. 6 for Compound No. 390.

Binding Affinity and Selectivity of Compounds for Integrin α4β7 and α4β1

We measured binding potency for monomeric and dimeric compounds to α4β7-integrin using a battery of biochemical, cell-based and ex-vivo assays. Multimeric compounds were generally more potent in cellular assays.

We measured the ability of test articles to prevent the adhesion of RMP18866 cells, which express integrin α4β7, to plates coated with MAdCAM-1. Multimeric compounds were generally more potent in their ability to inhibit cell adhesion than their constituent monomers. For example Compound No. 340 (ET2451) and Compound No. 456 (ET4062) had IC50 of 175 and 199 nM respectively in the RPM18866 cell adhesion assays (Table 1C and 1C'). Multimeric compounds with over 10-fold greater potency than their constituent monomeric compounds were generated. For example, Compound No. 517 (ET3764), a homodimer of Compound No. 340 (ET2451), had an IC50 of 9.9 nM in the RPM18866 cell adhesion assay. Compound multimers generated from monomeric Compound 456 (ET4062) also showed higher binding affinity (Table 2C).

Figure 7:
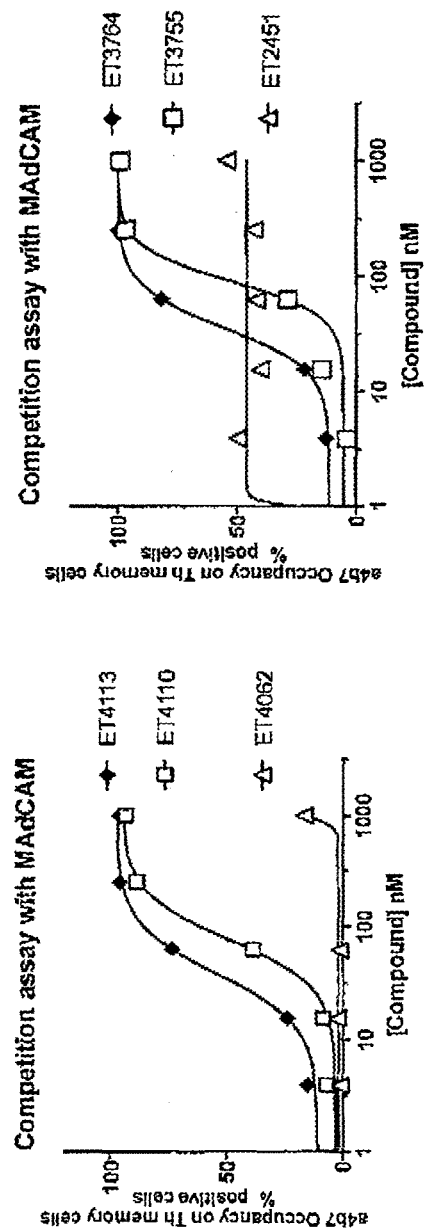
FIG. 7 shows the binding to α4β7 integrin measured as a MADCAM-1 competition assay in human whole blood for: a) representative monomeric Compound 456 (ET4062) and multimeric Compound No.s 534 (ET4113) and 535 (ET4110), derived from Compound 456, and; b) representative monomeric Compound 340 (ET2451) and multimeric Compound No.s 390 (ET3755) and 517 (ET3764), derived from Compound 340.

Similar results were obtained in a ligand competition assay for binding to integrin α4β7 in human whole blood. Receptor occupancy of nacellins was determined by measuring the proportion of α4β7+ memory T helper cells able to bind biotinylated rhMAdCAM-1 using flow cytometry (FIG. 7). Multimeric compounds were able to compete with MadCAM-1 on α4β7-positive primary cells with greater potency than monomeric compounds. Two general monomeric chemotypes were shown to compete more effectively, with increased potency for binding to integrin α4β7 when multimerized using a variety of linkers. For example, Dimeric Compound No.s 534 (ET4113) and 535 (ET4110) demonstrated IC50 of 38 and 76 nM respectively while the corresponding parent monomeric Compound No. 456 (ET4062) only reached 15% receptor occupancy at the maximum concentration of 1000 nM. Similarly, the dimeric Compound No.s 517 (ET3764) and 390 (ET3755) competed with a saturating amount of MAdCAM, with EC50 of 38 and 90 nM respectively within the same study. The corresponding monomeric Compound 340 (ET2451) reached 50% receptor occupancy at low concentrations but no concentration-response curve could be obtained. This could be the result of non-specific binding of the monomeric compound to the cell.

Interestingly, differences in binding affinity between monomeric and multimeric compounds were not as pronounced in ELISA binding assays. It is possible that avidity enhances the binding potency of multimeric compounds in cells.

Multimeric compounds showed enhanced selectivity for integrin α4β7 over integrin α4β1. In order to determine the selectivity of the compounds in cell assays, we measured the adhesion of Ramos cells, which express integrin α4β1 to VCAM-coated plates. Multimeric compounds had generally higher selectivity for integrin α4β7 over integrin α4β1 than their monomeric constituents. For example, monomeric Compound No.s 340 (ET2451) and 456 (ET4062) showed 16- and 45-fold selectivity, respectively, when comparing α4β7 versus α4β1 cell adhesion assays. In contrast, multimeric compounds based on monomeric Compound No. 340 (ET2451) exhibited 20- to 100-fold selectivity in favor of integrin α4β7, and multimeric compounds based on monomeric Compound No. 456 (ET4062) exhibited no measurable effect on the adhesion of α4β11-expressing Ramos cells to VCAM (Table 2C).

In Vivo T Lymphocyte Trafficking Analyses

The ability of several integrin alpha-4-beta-7-inhibiting compounds to attenuate the trafficking of integrin alpha-4-beta-7-expressing T lymphocytes was demonstrated in in vivo pharmacodynamics studies in DSS-treated mice. Dextran Sodium Sulfate (DSS) induces chronic colitis in experimental animals when given orally in drinking water for five days followed by no DSS in drinking water. Chronic inflammation is associated with the infiltration of leucocytes from the blood to intestinal tissues. The interaction between integrin α4β7 and MAdCAM-1 on the endothelium of the gut allows adhesion and trafficking of T cells to the gut. The ability of several integrin alpha-4-beta-7-inhibiting nacellins to attenuate the trafficking of integrin alpha-4-beta-7-expressing T lymphocytes was demonstrated in in vivo pharmacodynamics studies in DSS-treated mice.

Figure 8:
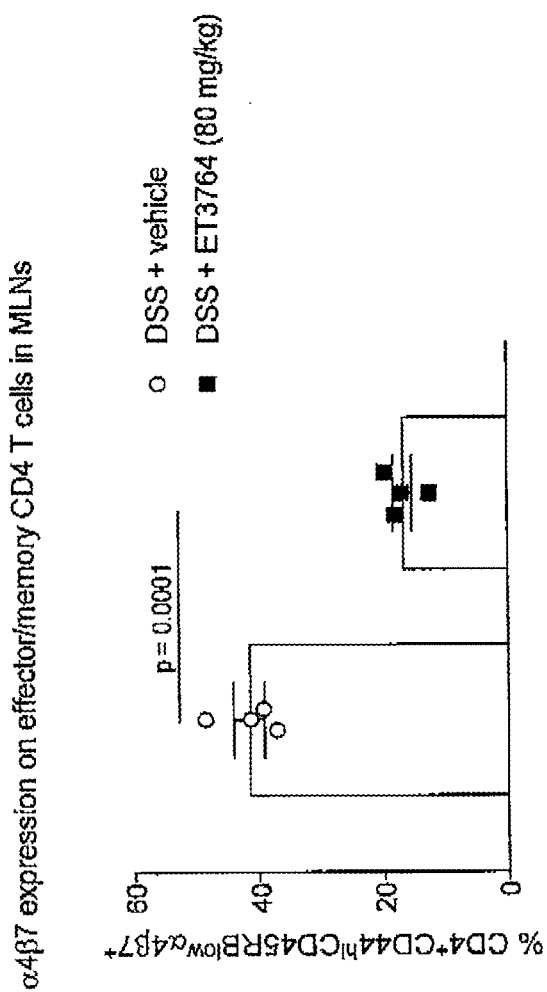
FIG. 8 Shows the detection of α4β7+ Th memory cells trafficking in the mesenteric lymph nodes in mice suffering from DSS-induced colitis treated for 4 days with Compound No. 517 (ET3764) or vehicle.

A study was conducted in which mice were exposed for 5 days to dextran sulfate in their drinking water. On days 6 to 9, compounds or vehicle were administered orally daily. Mesenteric lymph nodes were collected 4 hours following the last dose and assessed. As shown in FIG. 8, Compound No. 517 (ET3764) reduced the detection of integrin □4□7+ T helper memory lymphocytes in the mesenteric lymph nodes (MLN). Compound No. 517, administered at a dose of 80 mg/kg, reduced the number of α4β7+ positive lymphocytes by 60%.

Figure 9:
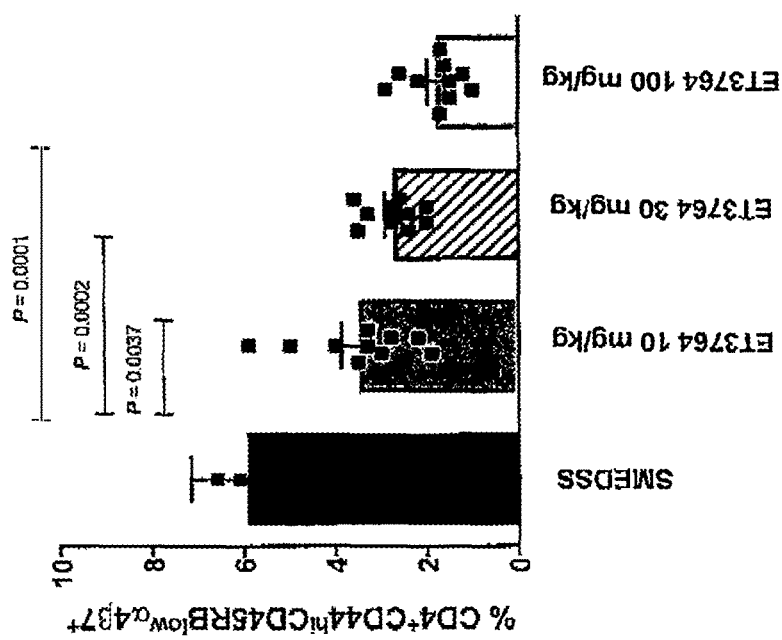
FIG. 9 shows the α4β7+ Th memory lymphocyte content in mesenteric lymph nodes taken from mice exposed to DSS irritant and treated for 4 days with various concentrations of Compound No. 517 (ET3764) or control (SMEDDS vehicle).

We determined that the level of reduction in α4β7+ T helper memory lymphocytes detected in the mesenteric lymph nodes of DSS treated mice was dependent on the dose of Compound No. 517 administered. FIG. 9 shows the dose-dependent reduction in α4β7+ T cells present in the mesenteric lymph nodes.

Figure 10:
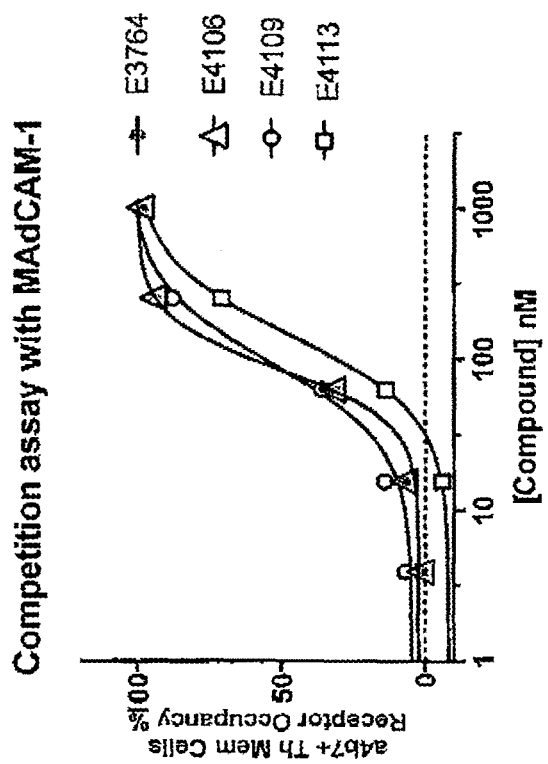
FIG. 10 shows the receptor occupancy of representative multimeric compounds on α4β7-positive T helper memory cells as measured in a MADCAM-1 competition assay in human whole blood.
Figure 11:
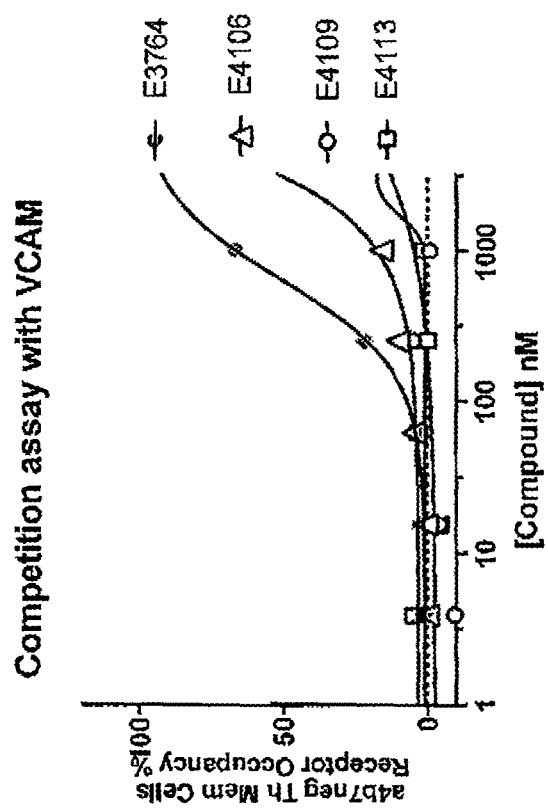
FIG. 11 shows the receptor occupancy of representative nacellin dimers on α4β7-negative Th memory cells as measured in a VCAM-1 competition assay in human whole blood.

We compared the ability of compounds to inhibit the binding of labeled human recombinant MADCAM-1 or VCAM to α4β7-positive or α4β7-negative Th memory cells respectively. Whole blood from a single donor was incubated with compounds and saturated amounts of recombinant ligands. The inhibition of MAdCAM or VCAM binding was measured on T cell subsets using FACS analysis. As shown in FIG. 10, representative multimeric Compound No.s 517, 482, 530 and 534 inhibited MAdCAM-1 binding to primary cells with IC50 values ranging from 87 to 141 nM. The same representative compounds bound to VCAM with lower affinity, with IC50 values ranging from 600 nM to undetectable binding at 4000 nM (FIG. 11).

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1A

| Compound No. | $R^1$ | $R^2$ | $R^3$ | $R^4$ | $R^5$ |
|---|---|---|---|---|---|
| 1 | H | H | CH2—S—Ph | H | C(O)NH-tert-Butyl |
| 2 | H | H | CH2—S—Ph | H | C(O)—NH-tert-Butyl |

TABLE 1A-continued

| Compound No. | R¹ | R² | R³ | R⁴ | R⁵ |
|---|---|---|---|---|---|
| 3 | H | H | CH2—S—Ph | H | C(O)—NH-tert-Butyl |
| 4 | H | H | CH$_3$ | H | C(O)—NH-tert-Butyl |
| 5 | H | H | CH$_3$ | H | C(O)—NH-tert-Butyl |
| 6 | H | H | CH$_3$ | H | C(O)—NH-tert-Butyl |
| 7 | H | H | CH$_3$ | H | C(O)—NH-tert-Butyl |
| 8 | H | H | CH$_3$ | H | C(O)—NH-tert-Butyl |
| 9 | H | H | CH$_3$ | H | C(O)—NH-tert-Butyl |
| 10 | H | H | CH$_3$ | H | C(O)—NH-tert-Butyl |
| 11 | H | H | CH$_3$ | H | C(O)—NH-tert-Butyl |
| 12 | H | H | CH$_3$ | H | C(O)—NH-tert-Butyl |
| 13 | H | H | CH$_3$ | H | C(O)—NH-tert-Butyl |
| 14 | H | H | CH$_3$ | H | C(O)—NH-tert-Butyl |
| 15 | H | H | CH$_3$ | H | C(O)—NH-tert-Butyl |
| 16 | H | H | CH$_3$ | H | C(O)—NH-tert-Butyl |
| 17 | H | H | CH$_3$ | H | C(O)—NH-tert-Butyl |
| 18 | H | H | CH$_3$ | H | C(O)—NH-tert-Butyl |
| 19 | H | H | CH$_3$ | H | C(O)—NH-tert-Butyl |
| 20 | H | H | CH$_3$ | H | C(O)—NH-tert-Butyl |
| 21 | H | H | CH$_3$ | H | C(O)—NH-tert-Butyl |
| 22 | H | H | CH$_3$ | H | C(O)—NH-tert-Butyl |
| 23 | H | H | CH$_3$ | H | C(O)—NH-tert-Butyl |
| 24 | H | H | CH$_3$ | H | C(O)—NH-tert-Butyl |
| 25 | H | H | CH$_3$ | H | C(O)—NH-tert-Butyl |
| 26 | H | H | CH$_3$ | H | C(O)—NH-tert-Butyl |
| 27 | H | H | CH$_3$ | H | C(O)—NH-tert-Butyl |
| 28 | H | H | CH$_3$ | H | C(O)—NH-tert-Butyl |
| 29 | H | H | CH$_3$ | H | C(O)—NH-tert-Butyl |
| 30 | H | H | CH$_3$ | H | C(O)—NH-tert-Butyl |
| 31 | H | H | CH$_3$ | H | C(O)—NH-tert-Butyl |
| 32 | H | H | CH$_3$ | H | C(O)—NH-tert-Butyl |
| 33 | H | H | CH$_3$ | H | C(O)—NH-tert-Butyl |
| 34 | H | H | CH$_3$ | H | C(O)—NH-tert-Butyl |
| 35 | H | H | CH$_3$ | H | C(O)—NH-tert-Butyl |
| 36 | H | H | CH$_3$ | H | C(O)—NH-tert-Butyl |
| 37 | H | H | CH$_3$ | H | C(O)—NH-tert-Butyl |
| 38 | H | H | CH$_3$ | H | C(O)—NH-tert-Butyl |
| 39 | H | H | CH$_3$ | H | C(O)—NH-tert-Butyl |
| 40 | H | H | CH$_3$ | H | C(O)—NH-tert-Butyl |
| 41 | H | H | CH$_3$ | H | C(O)—NH-tert-Butyl |
| 42 | H | H | CH$_3$ | H | C(O)—NH-tert-Butyl |
| 43 | H | CH$_3$ | H | H | C(O)—NH-tert-Butyl |
| 44 | H | H | CH$_3$ | H | C(O)—NH-tert-Butyl |
| 45 | H | H | CH$_3$ | H | C(O)—NH-tert-Butyl |
| 46 | H | H | CH$_3$ | H | C(O)—NH-tert-Butyl |
| 47 | H | H | CH$_3$ | H | C(O)—NH-tert-Butyl |
| 48 | H | H | CH$_3$ | H | C(O)—NH-tert-Butyl |
| 49 | H | H | CH$_3$ | H | C(O)—NH-tert-Butyl |
| 50 | H | H | CH$_3$ | H | C(O)—NH-tert-Butyl |
| 51 | H | H | CH$_3$ | H | C(O)—NH-tert-Butyl |
| 52 | H | H | CH$_3$ | H | C(O)—NH-tert-Butyl |
| 53 | H | H | CH$_3$ | H | C(O)—NH-tert-Butyl |
| 54 | H | H | CH$_3$ | H | C(O)—NH-tert-Butyl |
| 55 | H | H | CH$_3$ | H | C(O)—NH-tert-Butyl |
| 56 | H | H | CH$_3$ | H | C(O)—NH-tert-Butyl |
| 57 | H | H | CH$_3$ | H | C(O)—NH-tert-Butyl |
| 58 | H | H | CH$_3$ | H | C(O)—NH-tert-Butyl |
| 59 | H | H | CH$_3$ | H | C(O)—NH-tert-Butyl |
| 60 | H | H | CH$_3$ | H | C(O)—NH-tert-Butyl |
| 61 | H | H | CH$_3$ | H | C(O)—NH-tert-Butyl |
| 62 | H | H | CH$_3$ | H | C(O)—NH-tert-Butyl |
| 63 | H | H | CH$_3$ | H | C(O)—NH-tert-Butyl |
| 64 | H | H | CH$_3$ | H | C(O)—NH-tert-Butyl |
| 65 | H | H | CH$_3$ | H | C(O)—NH-tert-Butyl |
| 66 | H | H | CH$_3$ | H | C(O)—NH-tert-Butyl |
| 67 | H | H | CH$_3$ | H | C(O)—NH-tert-Butyl |
| 68 | H | H | CH$_3$ | H | C(O)—NH-tert-Butyl |
| 69 | H | H | CH$_3$ | H | C(O)—NH-tert-Butyl |
| 70 | H | H | CH$_3$ | H | C(O)—NH-tert-Butyl |
| 71 | H | H | CH$_3$ | H | C(O)—NH-tert-Butyl |
| 72 | H | H | CH$_3$ | H | C(O)—NH-tert-Butyl |
| 73 | H | H | CH$_3$ | H | C(O)—NH-tert-Butyl |
| 74 | H | H | CH$_3$ | H | C(O)—NH-tert-Butyl |
| 75 | H | H | CH$_3$ | H | C(O)—NH-tert-Butyl |
| 76 | H | H | CH$_3$ | H | C(O)—NH-tert-Butyl |
| 77 | H | H | CH$_3$ | H | C(O)—NH-tert-Butyl |
| 78 | H | H | CH$_3$ | H | C(O)—NH-tert-Butyl |
| 79 | H | H | CH$_3$ | H | C(O)—NH-tert-Butyl |

TABLE 1A-continued

| Compound No. | R¹ | R² | R³ | R⁴ | R⁵ |
|---|---|---|---|---|---|
| 80 | H | H | CH₃ | H | C(O)—NH-tert-Butyl |
| 81 | H | H | CH₃ | H | C(O)—NH-tert-Butyl |
| 82 | H | H | CH₃ | H | C(O)—NH-tert-Butyl |
| 83 | H | H | CH₃ | H | C(O)—NH-tert-Butyl |
| 84 | H | H | CH₃ | H | C(O)—NH-tert-Butyl |
| 85 | H | H | CH₃ | H | C(O)—NH-tert-Butyl |
| 86 | H | H | CH₃ | H | C(O)—NH-tert-Butyl |
| 87 | H | H | CH₃ | H | C(O)—NH-tert-Butyl |
| 88 | H | H | CH₃ | H | C(O)—NH-tert-Butyl |
| 89 | H | H | CH₃ | H | C(O)—NH-tert-Butyl |
| 90 | H | H | CH₃ | H | C(O)—NH-tert-Butyl |
| 91 | H | H | CH₃ | H | C(O)—NH-tert-Butyl |
| 92 | H | H | CH₃ | H | C(O)—NH-tert-Butyl |
| 93 | H | H | CH₃ | H | C(O)—NH-tert-Butyl |
| 94 | H | H | CH₃ | H | C(O)—NH-tert-Butyl |
| 95 | H | H | CH₃ | H | C(O)—NH-tert-Butyl |
| 96 | H | H | CH₃ | H | C(O)—NH-tert-Butyl |
| 97 | H | H | CH₃ | H | C(O)—NH-tert-Butyl |
| 98 | H | H | CH₃ | H | C(O)—NH-tert-Butyl |
| 99 | H | H | CH₃ | H | C(O)—NH-tert-Butyl |
| 100 | H | H | CH₃ | H | C(O)—NH-tert-Butyl |
| 101 | H | H | CH₃ | H | C(O)—NH-tert-Butyl |
| 102 | H | H | CH₃ | H | C(O)—NH-tert-Butyl |
| 103 | H | CH₃ | H | H | C(O)—NH-tert-Butyl |
| 104 | H | H | CH₃ | H | C(O)—NH-tert-Butyl |
| 105 | H | H | CH₃ | H | C(O)—NH-tert-Butyl |
| 106 | H | H | CH₃ | H | C(O)—NH-tert-Butyl |
| 107 | H | H | CH₃ | H | C(O)—NH-tert-Butyl |
| 108 | H | H | CH₃ | H | C(O)—NH-tert-Butyl |
| 109 | H | H | CH₃ | H | C(O)—NH-tert-Butyl |
| 110 | H | H | CH₃ | H | C(O)—NH-tert-Butyl |
| 111 | H | H | CH₃ | H | C(O)—NH-tert-Butyl |
| 112 | H | H | CH₃ | H | C(O)—NH-tert-Butyl |
| 113 | H | H | CH₃ | H | C(O)—NH-tert-Butyl |
| 114 | H | H | CH₃ | H | C(O)—NH-tert-Butyl |
| 115 | H | H | CH₃ | H | C(O)—NH-tert-Butyl |
| 116 | H | H | CH₃ | H | C(O)—NH-tert-Butyl |
| 117 | H | H | CH₃ | H | C(O)—NH-tert-Butyl |
| 118 | H | H | CH₃ | H | C(O)—NH-tert-Butyl |
| 119 | H | H | CH₃ | H | C(O)—NH-tert-Butyl |
| 120 | H | H | CH₃ | H | C(O)—NH-tert-Butyl |
| 121 | H | H | CH₃ | H | C(O)—NH-tert-Butyl |
| 122 | H | H | CH₃ | H | C(O)—NH-tert-Butyl |
| 123 | H | H | CH₃ | H | C(O)—NH-tert-Butyl |
| 124 | H | CH₃ | H | H | C(O)—NH-tert-Butyl |
| 125 | H | H | CH₃ | H | C(O)—NH-tert-Butyl |
| 126 | H | H | CH₃ | H | C(O)—NH-tert-Butyl |
| 127 | H | H | CH₃ | H | C(O)—NH-tert-Butyl |
| 128 | H | H | CH₃ | H | C(O)—NH-tert-Butyl |
| 129 | H | H | CH₃ | H | C(O)—NH-tert-Butyl |
| 130 | H | H | CH₃ | H | C(O)—NH-tert-Butyl |
| 131 | H | H | CH₃ | H | C(O)—NH-tert-Butyl |
| 132 | H | H | CH₃ | H | C(O)—NH-tert-Butyl |
| 133 | H | H | CH₃ | H | C(O)—NH-tert-Butyl |
| 134 | H | H | CH₃ | H | C(O)—NH-tert-Butyl |
| 135 | H | H | CH₃ | H | C(O)—NH-tert-Butyl |
| 136 | H | H | CH₃ | H | C(O)—NH-tert-Butyl |
| 137 | H | H | CH₃ | H | C(O)—NH-tert-Butyl |
| 138 | H | H | CH₃ | H | C(O)—NH-tert-Butyl |
| 139 | H | H | CH₃ | H | C(O)—NH-tert-Butyl |
| 140 | H | H | CH₃ | H | C(O)—NH-tert-Butyl |
| 141 | H | H | CH₃ | H | C(O)—NH-tert-Butyl |
| 142 | H | CH₃ | H | C(O)—NH-tert-Butyl | C(O)—NH-tert-Butyl |
| 143 | H | H | CH₃ | H | C(O)—NH-tert-Butyl |
| 144 | H | H | CH₃ | H | C(O)—NH-tert-Butyl |
| 145 | H | H | CH₃ | H | C(O)—NH-tert-Butyl |
| 146 | H | H | CH₃ | H | C(O)—NH-tert-Butyl |
| 147 | H | H | CH₃ | H | C(O)—NH-tert-Butyl |
| 148 | H | H | CH₃ | H | C(O)—NH-tert-Butyl |
| 149 | H | H | CH₃ | H | C(O)—NH-tert-Butyl |
| 150 | H | H | CH₃ | H | C(O)—NH-tert-Butyl |
| 151 | H | H | CH₃ | H | C(O)—NH-tert-Butyl |
| 152 | H | H | CH₃ | H | C(O)—NH-tert-Butyl |
| 153 | H | H | CH₃ | H | C(O)—NH-tert-Butyl |
| 154 | H | H | CH₃ | H | C(O)—NH-tert-Butyl |
| 155 | H | H | CH₃ | H | C(O)—NH-tert-Butyl |
| 156 | H | H | CH₃ | H | C(O)—NH-tert-Butyl |

TABLE 1A-continued

| Compound No. | $R^1$ | $R^2$ | $R^3$ | $R^4$ | $R^5$ |
| --- | --- | --- | --- | --- | --- |
| 157 | H | H | $CH_3$ | H | C(O)—NH-tert-Butyl |
| 158 | H | H | $CH_3$ | H | C(O)—NH-tert-Butyl |
| 159 | H | H | $CH_3$ | H | C(O)—NH-tert-Butyl |
| 160 | H | H | $CH_3$ | H | C(O)—NH-tert-Butyl |
| 161 | H | H | $CH_3$ | H | C(O)—NH-tert-Butyl |
| 162 | H | H | $CH_3$ | H | C(O)—NH-tert-Butyl |
| 163 | H | H | $CH_3$ | H | C(O)—NH-tert-Butyl |
| 164 | H | H | $CH_3$ | H | C(O)—NH-tert-Butyl |
| 165 | H | H | $CH_3$ | H | C(O)—NH-tert-Butyl |
| 166 | H | H | $CH_3$ | H | C(O)—NH-tert-Butyl |
| 167 | H | H | $CH_3$ | H | C(O)—NH-tert-Butyl |
| 168 | H | H | $CH_3$ | H | C(O)—NH-tert-Butyl |
| 169 | H | H | $CH_3$ | H | C(O)—NH-tert-Butyl |
| 170 | H | H | $CH_3$ | H | C(O)—NH-tert-Butyl |
| 171 | H | H | $CH_3$ | H | C(O)—NH-tert-Butyl |
| 172 | H | H | $CH_3$ | H | C(O)—NH-tert-Butyl |
| 173 | H | H | $CH_3$ | H | C(O)—NH-tert-Butyl |
| 174 | H | H | $CH_3$ | H | C(O)—NH-tert-Butyl |
| 175 | H | H | $CH_3$ | H | C(O)—NH-tert-Butyl |
| 176 | H | H | $CH_3$ | H | C(O)—NH-tert-Butyl |
| 177 | H | H | $CH_3$ | H | C(O)—NH-tert-Butyl |
| 178 | H | H | $CH_3$ | H | C(O)—NH-tert-Butyl |
| 179 | H | H | $CH_3$ | H | C(O)—NH-tert-Butyl |
| 180 | H | H | $CH_3$ | H | C(O)—NH-tert-Butyl |
| 181 | H | H | $CH_3$ | H | C(O)—NH-tert-Butyl |
| 182 | H | H | $CH_3$ | H | C(O)—NH-tert-Butyl |
| 183 | H | H | $CH_3$ | H | C(O)—NH-tert-Butyl |
| 184 | H | H | $CH_3$ | H | C(O)—NH-tert-Butyl |
| 185 | H | H | $CH_3$ | H | C(O)—NH-tert-Butyl |
| 186 | H | H | $CH_3$ | H | C(O)—NH-tert-Butyl |
| 187 | H | H | $CH_3$ | H | C(O)—NH-tert-Butyl |
| 188 | H | H | $CH_3$ | H | C(O)—NH-tert-Butyl |
| 189 | H | H | $CH_3$ | H | C(O)—NH-tert-Butyl |
| 190 | H | H | $CH_3$ | H | C(O)—NH-tert-Butyl |
| 191 | H | H | $CH_3$ | H | C(O)—NH-tert-Butyl |
| 192 | H | H | $CH_3$ | H | C(O)—NH-tert-Butyl |
| 193 | H | H | $CH_3$ | H | C(O)—NH-tert-Butyl |
| 194 | H | H | $CH_3$ | H | C(O)—NH-tert-Butyl |
| 195 | H | H | $CH_3$ | H | C(O)—NH-tert-Butyl |
| 196 | H | H | $CH_3$ | H | C(O)—NH-tert-Butyl |
| 197 | H | H | $CH_3$ | H | C(O)—NH-tert-Butyl |
| 198 | H | H | $CH_3$ | H | C(O)—NH-tert-Butyl |
| 199 | H | H | $CH_3$ | H | C(O)—NH-tert-Butyl |
| 200 | H | H | $CH_3$ | H | C(O)—NH-tert-Butyl |
| 201 | H | H | $CH_3$ | H | C(O)—NH-tert-Butyl |
| 202 | H | H | $CH_3$ | H | C(O)—NH-tert-Butyl |
| 203 | H | H | $CH_3$ | H | C(O)—NH-tert-Butyl |
| 204 | H | H | $CH_3$ | H | C(O)—NH-tert-Butyl |
| 205 | H | H | $CH_3$ | H | C(O)—NH-tert-Butyl |
| 206 | H | H | $CH_3$ | H | C(O)—NH-tert-Butyl |
| 207 | H | H | $CH_3$ | H | C(O)—NH-tert-Butyl |
| 208 | H | H | $CH_3$ | H | C(O)—NH-tert-Butyl |
| 209 | H | H | $CH_3$ | H | C(O)—NH-tert-Butyl |
| 210 | H | H | $CH_3$ | H | C(O)—NH-tert-Butyl |
| 211 | H | H | $CH_3$ | H | C(O)—NH-tert-Butyl |
| 212 | H | H | $CH_3$ | H | C(O)—NH-tert-Butyl |
| 213 | H | H | $CH_3$ | H | C(O)—NH-tert-Butyl |
| 214 | H | H | $CH_3$ | H | C(O)—NH-tert-Butyl |
| 215 | H | H | $CH_3$ | H | C(O)—NH-tert-Butyl |
| 216 | H | H | $CH_3$ | H | C(O)—NH-tert-Butyl |
| 217 | H | H | $CH_3$ | H | C(O)—NH-tert-Butyl |
| 218 | H | H | $CH_3$ | H | C(O)—NH-tert-Butyl |
| 219 | H | H | $CH_3$ | H | C(O)—NH-tert-Butyl |
| 220 | H | H | $CH_3$ | H | C(O)—NH-tert-Butyl |
| 221 | H | H | $CH_3$ | H | C(O)—NH-tert-Butyl |
| 222 | H | H | $CH_3$ | H | C(O)—NH-tert-Butyl |
| 223 | H | H | $CH_3$ | H | C(O)—NH-tert-Butyl |
| 224 | H | H | $CH_3$ | H | C(O)—NH-tert-Butyl |
| 225 | H | H | $CH_3$ | H | C(O)—NH-tert-Butyl |
| 226 | H | H | $CH_3$ | H | C(O)—NH-tert-Butyl |
| 227 | H | H | $CH_3$ | H | C(O)—NH-tert-Butyl |
| 228 | H | H | $CH_3$ | H | C(O)—NH-tert-Butyl |
| 229 | H | H | $CH_3$ | H | C(O)—NH-tert-Butyl |
| 230 | H | H | $CH_3$ | H | C(O)—NH-tert-Butyl |
| 231 | H | H | $CH_3$ | H | C(O)—NH-tert-Butyl |
| 232 | H | H | $CH_3$ | H | C(O)—NH-tert-Butyl |
| 233 | H | H | $CH_3$ | H | C(O)—NH-tert-Butyl |

TABLE 1A-continued

| Compound No. | $R^1$ | $R^2$ | $R^3$ | $R^4$ | $R^5$ |
|---|---|---|---|---|---|
| 234 | H | H | $CH_3$ | H | C(O)—NH-tert-Butyl |
| 235 | H | H | $CH_3$ | H | C(O)—NH-tert-Butyl |
| 236 | H | H | $CH_3$ | H | C(O)—NH-tert-Butyl |
| 237 | H | H | $CH_3$ | H | C(O)—NH-tert-Butyl |
| 238 | H | H | $CH_3$ | H | C(O)—NH-tert-Butyl |
| 239 | H | H | $CH_3$ | H | C(O)—NH-tert-Butyl |
| 240 | H | H | $CH_3$ | H | C(O)—NH-tert-Butyl |
| 241 | H | H | $CH_3$ | H | C(O)—NH-tert-Butyl |
| 242 | H | H | $CH_3$ | H | C(O)—NH-tert-Butyl |
| 243 | H | H | $CH_3$ | H | C(O)—NH-tert-Butyl |
| 244 | H | H | $CH_3$ | H | C(O)—NH-tert-Butyl |
| 245 | H | H | $CH_3$ | H | C(O)—NH-tert-Butyl |
| 246 | H | H | $CH_3$ | H | C(O)—NH-tert-Butyl |
| 247 | H | H | $CH_3$ | H | C(O)—NH-tert-Butyl |
| 248 | H | H | $CH_3$ | H | C(O)—NH-tert-Butyl |
| 249 | H | H | $CH_3$ | H | C(O)—NH-tert-Butyl |
| 250 | H | H | $CH_3$ | H | C(O)—NH-tert-Butyl |
| 251 | H | H | $CH_3$ | H | C(O)—NH-tert-Butyl |
| 252 | H | H | $CH_3$ | H | C(O)—NH-tert-Butyl |
| 253 | H | H | $CH_3$ | H | C(O)—NH-tert-Butyl |
| 254 | H | H | $CH_3$ | H | C(O)—NH-tert-Butyl |
| 255 | H | H | $CH_3$ | H | C(O)—NH-tert-Butyl |
| 256 | H | H | $CH_3$ | H | C(O)—NH-tert-Butyl |
| 257 | H | H | $CH_3$ | H | C(O)—NH-tert-Butyl |
| 258 | H | H | $CH_3$ | H | C(O)—NH-tert-Butyl |
| 259 | H | H | $CH_3$ | H | C(O)—NH-tert-Butyl |
| 260 | H | H | $CH_3$ | H | C(O)—NH-tert-Butyl |
| 261 | H | H | $CH_3$ | H | C(O)—NH-tert-Butyl |
| 262 | H | H | $CH_3$ | H | C(O)—NH-tert-Butyl |
| 263 | H | H | $CH_3$ | H | C(O)—NH-tert-Butyl |
| 264 | H | H | $CH_3$ | H | C(O)—NH-tert-Butyl |
| 265 | H | H | $CH_3$ | H | C(O)—NH-tert-Butyl |
| 266 | H | H | $CH_3$ | H | C(O)—NH-tert-Butyl |
| 267 | H | H | $CH_3$ | H | C(O)—NH-tert-Butyl |
| 268 | H | H | $CH_3$ | H | C(O)—NH-tert-Butyl |
| 269 | H | H | $CH_3$ | H | C(O)—NH-tert-Butyl |
| 270 | H | H | $CH_3$ | H | C(O)—NH-tert-Butyl |
| 271 | H | H | $CH_3$ | H | C(O)—NH-tert-Butyl |
| 272 | H | H | $CH_3$ | H | C(O)—NH-tert-Butyl |
| 273 | H | H | $CH_3$ | H | C(O)—NH-tert-Butyl |
| 274 | H | H | $CH_3$ | H | C(O)—NH-tert-Butyl |
| 275 | H | H | $CH_3$ | H | C(O)—NH-tert-Butyl |
| 276 | H | H | $CH_3$ | H | C(O)—NH-tert-Butyl |
| 277 | H | H | $CH_3$ | H | C(O)—NH-tert-Butyl |
| 278 | H | H | $CH_3$ | H | C(O)—NH-tert-Butyl |
| 279 | H | H | $CH_3$ | H | C(O)—NH-tert-Butyl |
| 280 | H | H | $CH_3$ | H | C(O)—NH-tert-Butyl |
| 281 | H | H | $CH_3$ | H | C(O)—NH-tert-Butyl |
| 282 | H | H | $CH_3$ | H | C(O)—NH-tert-Butyl |
| 283 | H | H | $CH_3$ | H | C(O)—NH-tert-Butyl |
| 284 | H | H | $CH_3$ | H | C(O)—NH-tert-Butyl |
| 285 | H | H | $CH_3$ | H | C(O)—NH-tert-Butyl |
| 286 | H | H | $CH_3$ | H | C(O)—NH-tert-Butyl |
| 287 | H | H | $CH_3$ | H | C(O)—NH-tert-Butyl |
| 288 | H | H | $CH_3$ | H | C(O)—NH-tert-Butyl |
| 289 | H | H | $CH_3$ | H | C(O)—NH-tert-Butyl |
| 290 | H | H | $CH_3$ | H | C(O)—NH-tert-Butyl |
| 291 | H | H | $CH_3$ | H | C(O)—NH-tert-Butyl |
| 292 | H | H | $CH_3$ | H | C(O)—NH-tert-Butyl |
| 293 | H | H | $CH_3$ | H | C(O)—NH-tert-Butyl |
| 294 | H | H | $CH_3$ | H | C(O)—NH-tert-Butyl |
| 295 | PRO- | PRO- | H | H | C(O)—NH-tert-Butyl |
| 296 | H | H | $CH_3$ | H | C(O)—NH-tert-Butyl |
| 297 | H | H | $CH_3$ | H | C(O)—NH-tert-Butyl |
| 298 | H | H | $CH_3$ | H | C(O)—NH-tert-Butyl |
| 299 | H | H | $CH_3$ | H | C(O)—NH-tert-Butyl |
| 300 | H | H | $CH_3$ | H | C(O)—NH-tert-Butyl |
| 301 | H | H | $CH_3$ | H | C(O)—NH-tert-Butyl |
| 302 | H | H | $CH_3$ | H | C(O)—NH-tert-Butyl |
| 303 | H | H | $CH_3$ | H | C(O)—NH-tert-Butyl |
| 304 | H | H | $CH_3$ | H | C(O)—NH-tert-Butyl |
| 305 | H | H | $CH_3$ | H | C(O)—NH-tert-Butyl |
| 306 | H | H | $CH_3$ | H | C(O)—NH-tert-Butyl |
| 307 | H | H | $CH_3$ | H | C(O)—NH-tert-Butyl |
| 308 | H | H | $CH_3$ | H | C(O)—NH-tert-Butyl |
| 309 | H | H | $CH_3$ | H | C(O)—NH-tert-Butyl |
| 310 | H | H | $CH_3$ | H | C(O)—NH-tert-Butyl |

TABLE 1A-continued

| Compound No. | R¹ | R² | R³ | R⁴ | R⁵ |
|---|---|---|---|---|---|
| 311 | H | H | CH₃ | H | C(O)—NH-tert-Butyl |
| 312 | H | H | CH₃ | H | C(O)—NH-tert-Butyl |
| 313 | H | H | CH₃ | H | C(O)—NH-tert-Butyl |
| 314 | H | H | CH₃ | H | C(O)—NH-tert-Butyl |
| 315 | H | H | CH₃ | H | C(O)—NH-tert-Butyl |
| 316 | H | H | CH₃ | H | C(O)—NH-tert-Butyl |
| 317 | H | H | CH₃ | H | C(O)—NH-tert-Butyl |
| 318 | H | H | CH₃ | H | C(O)—NH-tert-Butyl |
| 319 | H | H | CH₃ | H | C(O)—NH-tert-Butyl |
| 320 | H | H | CH₃ | H | C(O)—NH-tert-Butyl |
| 321 | H | H | CH₃ | H | C(O)—NH-tert-Butyl |
| 322 | H | H | CH₃ | H | C(O)—NH-tert-Butyl |
| 323 | H | H | CH₃ | H | C(O)—NH-tert-Butyl |
| 324 | H | H | CH₃ | H | C(O)—NH-tert-Butyl |
| 325 | H | H | CH₃ | H | C(O)—NH-tert-Butyl |
| 326 | H | H | CH₃ | H | C(O)—NH-tert-Butyl |
| 327 | H | H | CH₃ | H | C(O)—NH-tert-Butyl |
| 328 | H | H | CH₃ | H | C(O)—NH-tert-Butyl |
| 329 | H | H | CH₃ | H | C(O)—NH-tert-Butyl |
| 330 | H | H | CH₃ | H | C(O)—NH-tert-Butyl |
| 331 | H | H | CH₃ | H | C(O)—NH-tert-Butyl |
| 332 | H | H | CH₃ | H | C(O)—NH-tert-Butyl |
| 333 | H | H | CH₃ | H | C(O)—NH-tert-Butyl |
| 334 | H | H | CH₃ | H | C(O)—NH-tert-Butyl |
| 335 | H | H | CH₃ | H | C(O)—NH-tert-Butyl |
| 336 | H | H | CH₃ | H | C(O)—NH-tert-Butyl |
| 337 | H | H | CH₃ | H | C(O)—NH-tert-Butyl |
| 338 | H | H | CH₃ | H | C(O)—NH-tert-Butyl |
| 339 | H | H | CH₃ | H | C(O)—NH-tert-Butyl |
| 340 | H | H | CH₃ | H | C(O)—NH-tert-Butyl |
| 341 | H | H | CH₃ | H | C(O)—NH-tert-Butyl |
| 342 | H | H | CH₃ | H | C(O)—NH-tert-Butyl |
| 343 | H | H | CH₃ | H | C(O)—NH-tert-Butyl |
| 344 | H | CH₃ | H | C(O)—NH-tert-Butyl | H |
| 345 | H | H | CH₃ | H | C(O)—NH-tert-Butyl |
| 346 | H | H | CH₃ | H | C(O)—NH-tert-Butyl |
| 347 | H | H | CH₃ | H | C(O)—NH-tert-Butyl |
| 348 | H | H | CH₃ | H | C(O)—NH-tert-Butyl |
| 349 | H | H | CH₃ | H | C(O)—NH-tert-Butyl |
| 350 | H | H | CH₃ | H | C(O)—NH-tert-Butyl |
| 351 | H | H | CH₃ | C(O)—NH-tert-Butyl | H |
| 352 | H | H | CH₃ | H | C(O)—NH-tert-Butyl |
| 353 | H | H | CH₃ | H | C(O)—NH-tert-Butyl |
| 354 | H | H | CH₃ | H | C(O)—NH-tert-Butyl |
| 355 | H | H | CH₃ | H | C(O)—NH-tert-Butyl |
| 356 | H | H | CH₃ | H | C(O)—NH-tert-Butyl |
| 357 | H | H | CH₃ | H | C(O)—NH-tert-Butyl |
| 358 | H | H | CH₃ | H | C(O)—NH-tert-Butyl |
| 359 | H | H | CH₃ | H | C(O)—NH-tert-Butyl |
| 360 | H | H | CH₃ | H | C(O)—NH-tert-Butyl |
| 361 | H | H | CH₃ | H | C(O)—NH-tert-Butyl |
| 362 | H | H | CH₃ | H | C(O)—NH-tert-Butyl |
| 363 | H | H | CH₃ | H | C(O)—NH-tert-Butyl |
| 364 | H | H | CH₃ | H | C(O)—NH-tert-Butyl |
| 365 | H | H | CH₃ | H | C(O)—NH-tert-Butyl |
| 366 | H | H | CH₃ | H | C(O)—NH-tert-Butyl |
| 367 | H | H | CH₃ | H | C(O)—NH-tert-Butyl |
| 368 | H | H | CH₃ | H | C(O)—NH-tert-Butyl |
| 369 | H | H | CH₃ | H | C(O)—NH-tert-Butyl |
| 370 | H | H | CH₃ | H | C(O)—NH-tert-Butyl |
| 371 | H | H | CH₃ | H | C(O)—NH-tert-Butyl |
| 372 | H | H | CH₃ | H | C(O)—NH-tert-Butyl |
| 373 | H | H | CH₃ | H | C(O)—NH-tert-Butyl |
| 374 | H | H | CH₃ | H | C(O)—NH-tert-Butyl |
| 375 | H | H | CH₃ | H | C(O)—NH-tert-Butyl |
| 376 | H | H | CH₃ | H | C(O)—NH-tert-Butyl |
| 377 | H | H | CH₃ | H | C(O)—NH-tert-Butyl |
| 378 | H | H | CH₃ | H | C(O)—NH-tert-Butyl |
| 379 | H | H | CH₃ | H | C(O)—NH-tert-Butyl |
| 380 | H | H | CH₃ | H | C(O)—NH-tert-Butyl |
| 381 | H | H | CH₃ | H | C(O)—NH-tert-Butyl |
| 382 | H | H | CH₃ | H | C(O)—NH-tert-Butyl |
| 383 | H | H | CH₃ | H | C(O)—NH-tert-Butyl |
| 384 | H | H | CH₃ | H | C(O)—NH-tert-Butyl |
| 385 | H | H | CH₃ | H | C(O)—NH-tert-Butyl |
| 386 | H | H | CH₃ | H | C(O)—NH-tert-Butyl |
| 387 | H | H | CH₃ | H | C(O)—NH-tert-Butyl |

TABLE 1A-continued

| Compound No. | R¹ | R² | R³ | R⁴ | R⁵ |
|---|---|---|---|---|---|
| 388 | H | H | CH₃ | H | C(O)—NH-tert-Butyl |
| 389 | H | H | CH₃ | H | C(O)—NH-tert-Butyl |
| 456 | H | H | CH₃ | H | C(O)—NH-tert-Butyl |

TABLE 1B

| Compound No. | Seq. ID. No. | R⁶ | R⁷ | R⁸ | Xʸ | Xᶻ | X¹ | X² | X³ |
|---|---|---|---|---|---|---|---|---|---|
| 1 | 1 | PRO | PRO | H | Y | | L | D | V |
| 2 | 2 | PRO | PRO | H | H | | L | D | V |
| 3 | 3 | PRO | PRO | H | Y | | L | D | T |
| 4 | 3 | PRO | PRO | H | Y | | L | D | T |
| 5 | 4 | PRO | PRO | H | F | | L | D | T |
| 6 | 5 | PRO | PRO | H | HomoPhe | | L | D | T |
| 7 | 6 | PRO | PRO | H | Cha | | L | D | T |
| 8 | 7 | PRO | PRO | H | W | | L | D | I |
| 9 | 8 | PRO | PRO | H | 1Nal | | L | D | T |
| 10 | 9 | PRO | PRO | H | 2Nal | | L | D | T |
| 11 | 10 | PRO | PRO | H | W | | L | D | Thr(OBn) |
| 12 | 11 | PRO | PRO | H | Bip | | L | D | T |
| 13 | 12 | PRO | PRO | H | Tyr(OPh) | | L | D | T |
| 14 | 13 | PRO | PRO | H | 1Nal | | L | D | I |
| 15 | 14 | PRO | PRO | H | 2Nal | | L | D | I |
| 16 | 15 | PRO | PRO | H | 2Nal | | L | D | Thr(OBn) |
| 17 | 16 | [(4S)-fluoro-Pro] | [(4S)-fluoro-Pro] | H | W | | L | D | T |
| 18 | 17 | PRO | PRO | H | Bip | | L | D | Thr(OBn) |
| 19 | 18 | PRO | PRO | H | Tyr(2-tolyl diaryl ether) | | L | D | T |
| 20 | 19 | PRO | PRO | H | Tyr(4-CF3 diaryl ether) | | L | D | T |
| 21 | 20 | PRO | PRO | H | Tyr(4-methoxy diaryl ether) | | L | D | T |
| 22 | 21 | PRO | PRO | H | Tyr(4-fluoro diaryl ether) | | L | D | T |
| 23 | 22 | PRO | PRO | H | Tyr(2-methoxy diaryl ether) | | L | D | T |
| 24 | 23 | PRO | PRO | H | Tyr(3-methoxy diaryl ether) | | L | D | T |
| 25 | 24 | PRO | PRO | H | Tyr(3-fluoro diaryl ether) | | L | D | T |
| 26 | 25 | PRO | PRO | H | Tyr(3,4-difluoro diaryl ether) | | L | D | T |
| 27 | 26 | PRO | PRO | H | Tyr(3-methyl diaryl ether) | | L | D | T |
| 28 | 27 | PRO | PRO | H | Tyr(3,4-dimethyl diaryl ether) | | L | D | T |
| 29 | 28 | PRO | PRO | H | Tyr(4-CO2Me diaryl ether) | | L | D | T |
| 30 | 29 | PRO | PRO | H | Tyr(3-CO2Me diaryl ether) | | L | D | T |
| 31 | 30 | PRO | PRO | H | Tyr(4-CO2H diaryl ether) | | L | D | T |
| 32 | 31 | HYP | HYP | H | F | | L | D | T |
| 393 | 31 | HYP | HYP | H | F | | L | D | T |
| 394 | 31 | HYP | HYP | H | F | | L | D | T |
| 395 | 31 | HYP | HYP | H | F | | L | D | T |
| 396 | 31 | HYP | HYP | H | F | | L | D | T |
| 397 | 31 | HYP | HYP | H | F | | L | D | T |
| 33 | 32 | PRO | PRO | H | metaY(Opr) | | L | D | T |
| 34 | 33 | PRO | PRO | H | Orn(benzamide) | | L | D | Thr(OBn) |
| 35 | 34 | PRO | PRO | H | Orn(acetamide) | | L | D | Thr(OBn) |
| 36 | 35 | PRO | PRO | H | Orn(methanesulfonamide) | | L | D | Thr(OBn) |
| 37 | 36 | PRO | PRO | H | Orn(ethylcarbamate) | | L | D | Thr(OBn) |
| 38 | 37 | PRO | PRO | H | Orn(pentyl amide) | | L | D | Thr(OBn) |
| 39 | 38 | PRO | PRO | H | R | | L | D | T |
| 40 | 39 | PRO | PRO | H | F | | L | D | Thr(OMe) |
| 41 | 40 | PRO | PRO | H | F | | L | D | Thr(OEt) |
| 42 | 41 | PRO | PRO | H | dTyr | | L | D | T |
| 43 | 42 | PRO | PRO | H | dTic | | L | D | T |
| 69 | 42 | PRO | PRO | H | dTic | | L | D | T |
| 44 | 43 | HYP | HYP | H | [3-(3'-pyridyl)-Ala] | | L | D | T |
| 45 | 44 | [(4R)-fluoro-Pro] | [(4R)-fluoro-Pro] | H | F | | L | D | T |
| 46 | 45 | [(4R)-fluoro-Pro] | [(4R)-fluoro-Pro] | H | Bip | | L | D | T |
| 47 | 46 | [(4R)-fluoro-Pro] | [(4R)-fluoro-Pro] | H | [3-(3'-pyridyl)-Ala] | | L | D | T |
| 48 | 47 | [(4R)-fluoro-Pro] | [(4R)-fluoro-Pro] | H | Y | | L | D | T |

TABLE 1B-continued

| Compound No. | Seq. ID. No. | R6 | R7 | R8 | Xy | Xz | X1 | X2 | X3 |
|---|---|---|---|---|---|---|---|---|---|
| 49 | 48 | [(4S)-fluoro-Pro] | [(4S)-fluoro-Pro] | H | Y | | L | D | T |
| 50 | 49 | PRO | PRO | H | dArg | | L | D | T |
| 51 | 50 | PRO | PRO | H | dPip | | L | D | T |
| 52 | 51 | PRO | PRO | H | [3-(4-thiazolyl)-Ala] | | L | D | T |
| 53 | 52 | PRO | PRO | H | Y | | L | D | I |
| 54 | 53 | PRO | PRO | H | (4-aza-Phe) | | L | D | T |
| 55 | 54 | PRO | PRO | H | Y | | L | D | Pen |
| 56 | 55 | PRO | PRO | H | (vinyl-Br-Leu) | | L | D | T |
| 57 | 56 | PRO | PRO | H | Hyp(OBn) | | L | D | T |
| 58 | 56 | PRO | PRO | H | Hyp(OBn) | | L | D | T |
| 59 | 57 | PRO | PRO | H | Dap(Cbz) | | L | D | T |
| 60 | 58 | PRO | PRO | H | His(Bn) | | L | D | T |
| 61 | 59 | PRO | PRO | H | (4-amino-Phe) | | L | D | T |
| 62 | 60 | PRO | PRO | H | (4-aza-dPhe) | | L | D | T |
| 63 | 61 | PRO | PRO | H | Hyp | | L | D | T |
| 64 | 62 | PRO | PRO | H | dTrp | | L | D | T |
| 65 | 63 | PRO | PRO | H | M | | L | D | T |
| 66 | 64 | PRO | PRO | H | dMet | | L | D | T |
| 67 | 65 | PRO | PRO | H | (4-guanidino-Phe) | | L | D | T |
| 68 | 66 | PRO | PRO | H | (3-aza-Phe) | | L | D | T |
| 70 | 67 | PRO | PRO | H | (3-aza-dPhe) | | L | D | T |
| 71 | 68 | PRO | PRO | H | Nva | | L | D | T |
| 72 | 69 | PRO | PRO | H | dNle | | L | D | T |
| 73 | 70 | PRO | PRO | H | dLys | | L | D | T |
| 74 | 71 | PRO | PRO | H | dPro | | L | D | T |
| 75 | 72 | PRO | PRO | H | dOrn | | L | D | T |
| 76 | 73 | PRO | PRO | H | (3-benzothienyl-Ala) | | L | D | T |
| 77 | 74 | PRO | PRO | H | dTyr(OAllyl) | | L | D | T |
| 78 | 75 | PRO | PRO | H | dSer(OBn) | | L | D | T |
| 79 | 76 | PRO | PRO | H | [3-(4-thiazolyl)-dAla] | | L | D | T |
| 80 | 77 | PRO | PRO | H | (3-benzothienyl-dAla) | | L | D | T |
| 81 | 78 | PRO | PRO | H | [3-(2-thienyl)-dAla] | | L | D | T |
| 82 | 79 | PRO | PRO | H | (4-aminomethyl-Phe) | | L | D | T |
| 83 | 80 | PRO | PRO | H | dOrn(dimethyl) | | L | D | T |
| 84 | 81 | PRO | PRO | H | (4-amino-dPhe) | | L | D | T |
| 85 | 82 | PRO | PRO | H | (4-aminomethyl-dPhe) | | L | D | T |
| 86 | 83 | PRO | PRO | H | dTyr(OBn) | | L | D | T |
| 87 | 84 | PRO | PRO | H | P | | L | D | T |
| 88 | 85 | PRO | PRO | H | cycloLeu | | L | D | T |
| 89 | 86 | PRO | PRO | H | Aic | | L | D | T |
| 90 | 87 | PRO | PRO | H | Tyr(OAllyl) | | L | D | T |
| 91 | 88 | PRO | PRO | H | Chg | | L | D | T |
| 92 | 89 | PRO | PRO | H | K | | L | D | T |
| 93 | 90 | PRO | PRO | H | (2-aza-dPhe) | | L | D | T |
| 94 | 91 | PRO | PRO | H | (2-aza-Phe) | | L | D | T |
| 95 | 92 | PRO | PRO | H | [2-(2-pyridyl)-4-thiazolyl-Ala] | | L | D | T |
| 96 | 93 | PRO | PRO | H | [2-(3-pyridyl)-4-thiazolyl-Ala] | | L | D | T |
| 97 | 94 | PRO | PRO | H | [2-(4-pyridyl)-4-thiazolyl-Ala] | | L | D | T |
| 98 | 95 | PRO | PRO | H | dTiq | | L | D | T |
| 99 | 96 | PRO | PRO | H | [1-(S)-isoindoline-carboxylic acid] | | L | D | T |
| 100 | 97 | PRO | PRO | H | Y | dThr | L | D | T |
| 101 | 98 | PRO | PRO | H | Y | P | L | D | T |
| 102 | 99 | PRO | PRO | H | Y | dPro | L | D | T |
| 124 | 99 | PRO | PRO | H | Y | dPro | L | D | T |
| 103 | 100 | PRO | PRO | H | Y | Sar | L | D | T |
| 105 | 100 | PRO | PRO | H | Y | Sar | L | D | T |
| 104 | 101 | PRO | PRO | H | Y | cycloLeu | L | D | T |
| 106 | 102 | PRO | PRO | H | (3-iodo-Phe) | Sar | L | D | T |
| 107 | 103 | PRO | PRO | H | (4-iodo-Phe) | Sar | L | D | T |
| 108 | 104 | PRO | PRO | H | (3,3-diphenyl-Ala) | Sar | L | D | T |
| 109 | 105 | PRO | PRO | H | F | dLys | L | D | T |
| 110 | 106 | PRO | PRO | H | Bip | dLys | L | D | T |
| 111 | 107 | PRO | PRO | H | [3-(4-thiazolyl)-Ala] | dLys | L | D | T |
| 112 | 108 | PRO | PRO | H | (3,3-diphenyl-Ala) | dLys | L | D | T |
| 113 | 109 | PRO | PRO | H | Y | dLys | L | D | I |
| 114 | 110 | PRO | PRO | H | Y | dArg | L | D | T |
| 115 | 111 | PRO | PRO | H | Y | dSer | L | D | T |
| 116 | 112 | PRO | PRO | H | Bip | Sar | L | D | T |
| 117 | 113 | PRO | PRO | H | 1Nal | Sar | L | D | T |
| 118 | 114 | PRO | PRO | H | Y | Pip | L | D | T |
| 119 | 115 | PRO | PRO | H | (2-iodo-Phe) | Sar | L | D | T |
| 120 | 116 | PRO | PRO | H | 1Nal | dLys | L | D | T |
| 121 | 117 | PRO | PRO | H | Y | dLys | L | D | MeThr |
| 122 | 118 | PRO | PRO | H | F | Sar | L | D | T |

TABLE 1B-continued

| Compound No. | Seq. ID. No. | R⁶ | R⁷ | R⁸ | Xʸ | Xᶻ | X¹ | X² | X³ |
|---|---|---|---|---|---|---|---|---|---|
| 123 | 119 | PRO | PRO | H | Y | dTic | L | D | T |
| 125 | 120 | PRO | PRO | H | Y | dPip | L | D | T |
| 126 | 121 | PRO | PRO | H | F | dPro | L | D | T |
| 127 | 122 | PRO | PRO | H | (3,4-dimethoxy-Phe) | dPro | L | D | T |
| 128 | 123 | PRO | PRO | H | (3,4,5-trifluoro-Phe) | dPro | L | D | T |
| 129 | 124 | PRO | PRO | H | (3,5-dibromo-Tyr) | dPro | L | D | T |
| 130 | 125 | PRO | PRO | H | F | dPip | L | D | T |
| 131 | 126 | PRO | PRO | H | [3-(4-thiazolyl)-Ala] | dPip | L | D | T |
| 132 | 127 | PRO | PRO | H | (4-aminomethyl-Phe) | dPip | L | D | T |
| 133 | 128 | PRO | PRO | H | [2-iodo-Phe] | dPip | L | D | T |
| 134 | 129 | PRO | PRO | H | (2-phenyl-Phe) | dPip | L | D | T |
| 135 | 130 | PRO | PRO | H | [2-(2-methoxy-phenyl)-Phe] | dPip | L | D | T |
| 136 | 131 | PRO | PRO | H | [2-(3-methoxy-phenyl)-Phe] | dPip | L | D | T |
| 137 | 132 | PRO | PRO | H | [2-(4-methoxy-phenyl)-Phe] | dPip | L | D | T |
| 138 | 133 | PRO | PRO | H | Bip | dPip | L | D | T |
| 139 | 134 | PRO | PRO | H | Y | Hyp | L | D | T |
| 140 | 135 | PRO | PRO | H | Y | dHyp | L | D | T |
| 141 | 136 | PRO | PRO | H | Y | (cis-dHyp) | L | D | T |
| 142 | 137 | dPRO | H | dPRO | dTyr | dPip | L | D | T |
| 143 | 138 | PRO | PRO | H | 1Nal | dPip | L | D | T |
| 144 | 139 | PRO | PRO | H | 2Nal | dPip | L | D | T |
| 145 | 140 | PRO | PRO | H | (4-aminomethyl-Phe) | dTic | L | D | T |
| 146 | 141 | PRO | PRO | H | (3-aminomethyl-Phe) | dTic | L | D | T |
| 147 | 142 | PRO | PRO | H | (3-aminomethyl-dPhe) | dTic | L | D | T |
| 148 | 143 | PRO | PRO | H | MeTyr | dPip | L | D | T |
| 149 | 144 | PRO | PRO | H | Y | dPip | L | D | alloThr |
| 150 | 145 | PRO | PRO | H | Y | dPip | tertbutylAla | D | T |
| 151 | 146 | PRO | PRO | H | [3-(4-thiazolyl)-Ala] | dHyp | L | D | T |
| 152 | 147 | PRO | PRO | H | (4-aminomethyl-Phe) | dHyp | L | D | T |
| 153 | 148 | PRO | PRO | H | Y | dPip | L | D | I |
| 154 | 149 | PRO | PRO | H | Y | dMeLys | L | D | I |
| 155 | 150 | PRO | PRO | H | Y | dNle | L | D | T |
| 156 | 151 | PRO | PRO | H | F | dHyp | L | D | T |
| 157 | 152 | PRO | PRO | H | Y | dMeArg | L | D | T |
| 158 | 153 | PRO | PRO | H | Y | G | L | D | T |
| 159 | 154 | PRO | PRO | H | Y | A | L | D | T |
| 160 | 155 | PRO | PRO | H | Y | dAla | L | D | T |
| 161 | 156 | PRO | PRO | H | M | G | L | D | T |
| 162 | 157 | PRO | PRO | H | Tyr(OAllyl) | Sar | L | D | T |
| 163 | 158 | PRO | PRO | H | Tyr(OAllyl) | G | L | D | T |
| 164 | 159 | PRO | PRO | H | [3-(4-thiazolyl)-Ala] | Sar | L | D | T |
| 165 | 160 | PRO | PRO | H | (4-aminomethyl-Phe) | G | L | D | T |
| 166 | 161 | PRO | PRO | H | Tyr(OAllyl) | dVal | L | D | T |
| 167 | 162 | PRO | PRO | H | Tyr(OAllyl) | dSer | L | D | T |
| 168 | 163 | PRO | PRO | H | Tyr(OAllyl) | dAla | L | D | T |
| 169 | 164 | PRO | PRO | H | Tyr(OAllyl) | P | L | D | T |
| 170 | 165 | PRO | PRO | H | Tyr(OAllyl) | dPro | L | D | T |
| 171 | 166 | PRO | PRO | H | [3-(4-thiazolyl)-Ala] | dVal | L | D | T |
| 172 | 167 | PRO | PRO | H | [3-(4-thiazolyl)-Ala] | dSer | L | D | T |
| 173 | 168 | PRO | PRO | H | [3-(4-thiazolyl)-Ala] | dAla | L | D | T |
| 174 | 169 | PRO | PRO | H | [3-(4-thiazolyl)-Ala] | P | L | D | T |
| 175 | 170 | PRO | PRO | H | [3-(4-thiazolyl)-Ala] | dPro | L | D | T |
| 176 | 171 | PRO | PRO | H | (4-aminomethyl-Phe) | P | L | D | T |
| 177 | 172 | PRO | PRO | H | (4-aminomethyl-Phe) | dPro | L | D | T |
| 178 | 173 | PRO | PRO | H | cycloLeu | P | L | D | T |
| 179 | 174 | PRO | PRO | H | [2-(2-pyridyl)-4-thiazolyl-Ala] | Sar | L | D | T |
| 180 | 175 | PRO | PRO | H | [2-(2-pyridyl)-4-thiazolyl-Ala] | dPro | L | D | T |
| 181 | 176 | PRO | PRO | H | [2-(3-pyridyl)-4-thiazolyl-Ala] | Sar | L | D | T |
| 182 | 177 | PRO | PRO | H | [2-(3-pyridyl)-4-thiazolyl-Ala] | dPro | L | D | T |
| 183 | 178 | PRO | PRO | H | [2-(4-pyridyl)-4-thiazolyl-Ala] | dPro | L | D | T |
| 184 | 179 | PRO | PRO | H | [3-(2-aminobenzyl-4-thiazolyl)-Ala] | Sar | L | D | T |
| 185 | 180 | PRO | PRO | H | [2-(amino-benzyl)-4-thiazolyl-Ala] | dPro | L | D | T |
| 186 | 181 | PRO | PRO | H | dTyr | dPip | L | D | I |
| 187 | 182 | PRO | PRO | H | (2-aminomethyl-Phe) | Aze | L | D | T |
| 188 | 183 | PRO | PRO | H | Y | dPip | L | D | Abu |
| 189 | 184 | PRO | PRO | H | (3-aminomethyl-Phe) | dTic | L | D | Abu |
| 190 | 185 | PRO | PRO | H | (2,4-dichloro-Phe) | dPip | L | D | T |
| 191 | 186 | PRO | PRO | H | (3-phenyl-dPhe) | dPip | L | D | T |
| 192 | 187 | PRO | PRO | H | [3-(5-quinolinyl)-dPhe] | dPip | L | D | T |
| 193 | 188 | PRO | PRO | H | Y | betaHomoLys | L | D | T |
| 194 | 189 | PRO | PRO | H | Y | betaHomoPro | L | D | T |
| 195 | 190 | PRO | PRO | H | Y | betaHomoLys | L | D | T |
| 196 | 191 | PRO | PRO | H | Y | 2Abz | L | D | T |
| 197 | 192 | PRO | PRO | H | F | betaHomoLys | L | D | T |
| 198 | 193 | PRO | PRO | H | [3-(4-thiazolyl)-Ala] | betaHomoLys | L | D | T |
| 199 | 194 | PRO | PRO | H | (4-aminomethyl-Phe) | betaHomoLys | L | D | T |

TABLE 1B-continued

| Compound No. | Seq. ID. No. | R⁶ | R⁷ | R⁸ | Xʸ | Xᶻ | X¹ | X² | X³ |
|---|---|---|---|---|---|---|---|---|---|
| 200 | 195 | PRO | PRO | H | Y | betaHomoLys | L | D | Thr(OBn) |
| 201 | 196 | PRO | PRO | H | MeTyr | dbetaHomoLys | L | D | T |
| 202 | 197 | PRO | PRO | H | 1Nal | betaHomoLys | L | D | T |
| 203 | 198 | PRO | PRO | H | 2Nal | betaHomoLys | L | D | T |
| 204 | 199 | PRO | PRO | H | Bip | betaHomoLys | L | D | T |
| 205 | 200 | PRO | PRO | H | (2-iodo-Phe) | betaHomoLys | L | D | T |
| 206 | 201 | PRO | PRO | H | [2-(2,5-dimethyl-isoxazole)-Phe] | betaHomoLys | L | D | T |
| 207 | 202 | PRO | PRO | H | (2-phenyl-Phe) | betaHomoLys | L | D | T |
| 208 | 202 | PRO | PRO | H | (2-phenyl-Phe) | betaHomoLys | L | D | T |
| 209 | 203 | PRO | PRO | H | [(2-piperazinyl-2-Phenyl)-Phe] | betaHomoLys | L | D | T |
| 210 | 204 | PRO | PRO | H | Cha | betaHomoLys | L | D | T |
| 211 | 205 | PRO | PRO | H | W | betaHomoLys | L | D | T |
| 212 | 206 | PRO | PRO | H | dTrp | betaHomoLys | L | D | T |
| 213 | 207 | PRO | PRO | H | (3-aminomethyl-Phe) | betaHomoLys | L | D | T |
| 214 | 208 | PRO | PRO | H | (4-aminomethyl-dPhe) | betaHomoLys | L | D | T |
| 215 | 209 | PRO | PRO | H | (4-aminomethyl-Phe) | betaHomoLys | L | D | I |
| 216 | 210 | PRO | PRO | H | Y | dbetaHomoLys | L | D | I |
| 217 | 211 | PRO | PRO | H | dArg | betaHomoLys | L | D | T |
| 218 | 212 | PRO | PRO | H | (4-aminomethyl-Phe)-reduced | betaHomoLys | L | D | T |
| 219 | 213 | PRO | PRO | H | [3-(4-thiazolyl)-Ala] | dbetaHomoLys | L | D | I |
| 220 | 214 | PRO | PRO | H | F | dbetaHomoLys | L | D | I |
| 221 | 215 | PRO | PRO | H | [3-(4-thiazolyl)-Ala] | MebetaHomoLys | L | D | T |
| 222 | 216 | PRO | PRO | H | (4-aminomethyl-Phe) | MebetaHomoLys | L | D | T |
| 223 | 217 | PRO | PRO | H | [3-(4-thiazolyl)-Ala] | betaHomoLys | L | D | I |
| 224 | 218 | PRO | PRO | H | Tic | betaHomoLys | L | D | T |
| 225 | 219 | PRO | PRO | H | dTic | betaHomoLys | L | D | T |
| 226 | 220 | PRO | PRO | H | dTic | dbetaHomoLys | L | D | T |
| 227 | 221 | PRO | PRO | H | Y | betaHomoIle | L | D | T |
| 228 | 222 | PRO | PRO | H | (4-aminomethyl-Phe) | betaHomoPro | L | D | T |
| 229 | 223 | PRO | PRO | H | Y | dbetaHomoPro | L | D | T |
| 230 | 224 | PRO | PRO | H | (4-aminomethyl-Phe) | dbetaHomoPro | L | D | T |
| 231 | 225 | PRO | PRO | H | R | betaHomoLys | L | D | T |
| 232 | 226 | PRO | PRO | H | F | MebetaHomoLys | L | D | T |
| 233 | 227 | PRO | PRO | H | Phe-reduced | betaHomoLys | L | D | T |
| 234 | 228 | PRO | PRO | H | (3-aminomethyl-dPhe) | betaHomoLys | L | D | T |
| 235 | 229 | PRO | PRO | H | [2-[3-(1-piperazinyl)phenyl]-Phe]-betaHomoLys | betaHomoLys | L | D | T |
| 236 | 230 | PRO | PRO | H | [3-(4-thiazolyl)-dAla] | betaHomoLys | L | D | T |
| 237 | 231 | PRO | PRO | H | (2-bromo-Phe) | betaHomoLys | L | D | T |
| 238 | 232 | PRO | PRO | H | (2-chloro-Phe) | betaHomoLys | L | D | T |
| 239 | 233 | PRO | PRO | H | (2-fluoro-Phe) | betaHomoLys | L | D | T |
| 240 | 234 | PRO | PRO | H | (2-CF3-Phe) | betaHomoLys | L | D | T |
| 241 | 235 | PRO | PRO | H | (2,4-dichloro-Phe) | betaHomoLys | L | D | T |
| 242 | 236 | PRO | PRO | H | (2-aminomethyl-Phe) | betaHomoLys | L | D | T |
| 243 | 237 | PRO | PRO | H | [2-(4-quinolinyl)-Phe] | betaHomoLys | L | D | T |
| 244 | 238 | PRO | PRO | H | [2-(5-quinolinyl)-Phe] | betaHomoLys | L | D | T |
| 245 | 239 | PRO | PRO | H | [2-(3-quinolinyl)-Phe] | betaHomoLys | L | D | T |
| 246 | 240 | PRO | PRO | H | dhomoPhe | betaHomoLys | L | D | T |
| 247 | 241 | PRO | PRO | H | (2-iodo-dPhe) | betaHomoLys | L | D | T |
| 248 | 242 | PRO | PRO | H | (2-phenyl-dPhe) | betaHomoLys | L | D | T |
| 249 | 243 | PRO | PRO | H | [(2-piperazinyl-2-Phenyl)-dPhe] | betaHomoLys | L | D | T |
| 250 | 244 | PRO | PRO | H | Y | betaHomoLys | L | D | I |
| 251 | 245 | PRO | PRO | H | Y | betaHomoLys | L | D | V |
| 252 | 246 | PRO | PRO | H | dTyr | betaHomoLys | L | D | I |
| 253 | 247 | PRO | PRO | H | (4-aminomethyl-dPhe) | betaHomoLys | L | D | I |
| 254 | 248 | PRO | PRO | H | (4-aminomethyl-Phe) | betaHomoLys | L | D | V |
| 255 | 249 | PRO | PRO | H | (3-iodo-Phe) | betaHomoLys | L | D | T |
| 256 | 250 | PRO | PRO | H | (3-phenyl-Phe) | betaHomoLys | L | D | T |
| 257 | 251 | PRO | PRO | H | [3-(2-methoxy-phenyl)-Phe] | betaHomoLys | L | D | T |
| 258 | 252 | PRO | PRO | H | [3-(2,6-dimethoxy-phenyl)-Phe] | betaHomoLys | L | D | T |
| 259 | 253 | PRO | PRO | H | [3-(2-trifluoromethoxy-phenyl)-Phe] | betaHomoLys | L | D | T |
| 260 | 254 | PRO | PRO | H | (4-iodo-Phe) | betaHomoLys | L | D | T |
| 261 | 255 | PRO | PRO | H | [4-(2-methoxy-phenyl)-Phe] | betaHomoLys | L | D | T |
| 262 | 256 | PRO | PRO | H | [4-(2-trifluoromethoxy-phenyl)-Phe] | betaHomoLys | L | D | T |
| 263 | 257 | PRO | PRO | H | alphaMePhe | betaHomoLys | L | D | T |
| 264 | 258 | PRO | PRO | H | MePhe | betaHomoLys | L | D | T |
| 265 | 259 | PRO | PRO | H | [3-(2,6-dimethyl-phenyl)-Phe] | betaHomoLys | L | D | T |
| 266 | 260 | PRO | PRO | H | [3-(quinolin-4-yl)-Phe] | betaHomoLys | L | D | T |
| 267 | 261 | PRO | PRO | H | [3-(3,4-difluoro-phenyl)-Phe] | betaHomoLys | L | D | T |
| 268 | 262 | PRO | PRO | H | [4-(2,6-dimethyl-phenyl)-Phe] | betaHomoLys | L | D | T |
| 269 | 263 | PRO | PRO | H | [4-(2-chloro-6-methoxy-phenyl)-Phe] | betaHomoLys | L | D | T |
| 270 | 264 | PRO | PRO | H | [3-(4-thiazolyl)-Ala]-reduced | betaHomoLys | L | D | T |
| 271 | 265 | PRO | PRO | H | [2-[4-(1-piperazinyl)phenyl]-Phe] | betaHomoLys | L | D | T |
| 272 | 266 | PRO | PRO | H | [2-(2,6-dimethylphenyl)-Phe] | betaHomoLys | L | D | T |
| 273 | 267 | PRO | PRO | H | [2-(benzothiazol-5-yl)-Phe] | betaHomoLys | L | D | T |
| 274 | 268 | PRO | PRO | H | HomoPhe | betaHomoLys | L | D | T |

TABLE 1B-continued

| Compound No. | Seq. ID. No. | R⁶ | R⁷ | R⁸ | Xʸ | Xᶻ | X¹ | X² | X³ |
|---|---|---|---|---|---|---|---|---|---|
| 275 | 269 | PRO | PRO | H | (piperidine-4-amino-4-carboxylic acid) | betaHomoLys | L | D | T |
| 276 | 270 | PRO | PRO | H | [2-(2,5-dimethyl-isoxazole)-dPhe] | betaHomoLys | L | D | T |
| 277 | 271 | PRO | PRO | H | dTyr | betaHomoLys | L | D | V |
| 278 | 272 | PRO | PRO | H | (4-aminomethyl-dPhe) | betaHomoLys | L | D | T |
| 279 | 273 | PRO | PRO | H | [2-(2-chloro-6-methoxyphenyl)-Phe] | betaHomoLys | L | D | T |
| 280 | 274 | PRO | PRO | H | 2Igl | betaHomoLys | L | D | T |
| 281 | 275 | PRO | PRO | H | d2Igl | betaHomoLys | L | D | T |
| 282 | 276 | PRO | PRO | H | Atc | betaHomoLys | L | D | T |
| 283 | 277 | PRO | PRO | H | Y | betaHomoLys | L | D | alloIle |
| 284 | 278 | PRO | PRO | H | dTyr | betaHomoLys | L | D | alloIle |
| 285 | 279 | PRO | PRO | H | (4-aminomethyl-Phe) | betaHomoLys | L | D | alloIle |
| 286 | 280 | PRO | PRO | H | [2-[2,5-Bis(trifluoromethyl)phenyl]-Phe] | betaHomoLys | L | D | T |
| 287 | 281 | PRO | PRO | H | [2-[2,5-Bis(trifluoromethyl)phenyl]-Phe] | betaHomoLys | L | D | T |
| 288 | 282 | PRO | PRO | H | Aic | betaHomoLys | L | D | T |
| 289 | 283 | PRO | PRO | H | P | betaHomoLys | L | D | T |
| 290 | 284 | PRO | PRO | H | dPro | betaHomoLys | L | D | T |
| 291 | 285 | PRO | PRO | H | Pip | betaHomoLys | L | D | T |
| 292 | 286 | PRO | PRO | H | [2-(3-Pyridyl)-Phe] | betaHomoLys | L | D | T |
| 293 | 287 | PRO | PRO | H | [2-(4-Pyridyl)-Phe] | betaHomoLys | L | D | T |
| 294 | 288 | PRO | PRO | H | [2-(3-bromo-2-Pyridyl)-Phe] | betaHomoLys | L | D | T |
| 295 | 289 | PRO | PRO | H | Y | dbetaHomoLys | L | D | T |
| 296 | 290 | PRO | PRO | H | (N-benzyl-Gly) | betaHomoLys | L | D | T |
| 297 | 291 | PRO | PRO | H | [2-(2-bromo-3-Pyridyl)-Phe] | betaHomoLys | L | D | T |
| 298 | 292 | PRO | PRO | H | [3-(2-chloro-6-methoxy-phenyl)-Phe] | betaHomoLys | L | D | T |
| 299 | 293 | PRO | PRO | H | [3-(benzothiazol-5-yl)-Phe] | betaHomoLys | L | D | T |
| 300 | 294 | PRO | PRO | H | (2-aminomethyl-Phe) | MebetaHomoLys | L | D | T |
| 301 | 295 | PRO | PRO | H | (2-aminomethyl-dPhe) | MebetaHomoLys | L | D | T |
| 302 | 296 | PRO | PRO | H | [3-(4-thiazolyl)-dAla] | MebetaHomoLys | L | D | T |
| 303 | 297 | PRO | PRO | H | [2-(2-trifluoromethoxy-phenyl)-dPhe] | MebetaHomoLys | L | D | T |
| 304 | 298 | PRO | PRO | H | Tic | MebetaHomoLys | L | D | T |
| 305 | 299 | PRO | PRO | H | dTic | MebetaHomoLys | L | D | T |
| 306 | 300 | PRO | PRO | H | [2-(5-quinolinyl)-dPhe] | betaHomoLys | L | D | T |
| 307 | 301 | PRO | PRO | H | Y | betaHomoLys | L | D | alloThr |
| 308 | 302 | PRO | PRO | H | Y | MebetaHomoLys | L | D | alloThr |
| 309 | 303 | PRO | PRO | H | MeTyr | MebetaHomoLys | L | D | T |
| 310 | 304 | PRO | PRO | H | MeTyr | MebetaHomoLys | L | D | alloThr |
| 311 | 305 | PRO | PRO | H | MePhe | MebetaHomoLys | L | D | T |
| 312 | 306 | PRO | PRO | H | (2-fluoro-Phe) | MebetaHomoLys | L | D | T |
| 313 | 307 | PRO | PRO | H | (2-fluoro-MePhe) | MebetaHomoLys | L | D | T |
| 314 | 308 | PRO | PRO | H | (2,4-dichloro-Phe) | MebetaHomoLys | L | D | T |
| 315 | 309 | PRO | PRO | H | (2,4-dichloro-MePhe) | MebetaHomoLys | L | D | T |
| 316 | 310 | PRO | PRO | H | (2-aminomethyl-MePhe) | MebetaHomoLys | L | D | T |
| 317 | 311 | PRO | PRO | H | [3-(2,6-dimethoxy-phenyl)-dPhe] | betaHomoLys | L | D | T |
| 318 | 312 | PRO | PRO | H | [3-(4-Quinolinyl)-dPhe] | betaHomoLys | L | D | T |
| 319 | 313 | PRO | PRO | H | betaHomoLys | Aze | L | D | T |
| 320 | 314 | PRO | PRO | H | (3-phenyl-dPhe) | betaHomoLys | L | D | T |
| 321 | 315 | PRO | PRO | H | [3-(2-trifluoromethoxy-phenyl)-dPhe] | betaHomoLys | L | D | T |
| 322 | 316 | PRO | PRO | H | [3-(2-methoxy-phenyl)-dPhe] | betaHomoLys | L | D | T |
| 323 | 317 | PRO | PRO | H | [2-(5-quinolinyl)-MePhe] | MebetaHomoLys | L | D | T |
| 324 | 318 | PRO | PRO | H | F | betaHomoNle | L | D | T |
| 325 | 319 | PRO | PRO | H | F | MebetaHomoLys(Me)2 | L | D | T |
| 326 | 320 | PRO | PRO | H | MePhe | MebetaHomoLys(Me)2 | L | D | T |
| 327 | 321 | PRO | PRO | H | M | MebetaHomoLys | L | D | T |
| 328 | 322 | PRO | PRO | H | Igl | MebetaHomoLys | L | D | T |
| 329 | 323 | PRO | PRO | H | HomoPhe | MebetaHomoLys | L | D | T |
| 330 | 324 | PRO | PRO | H | Hyp(OBn) | MebetaHomoLys | L | D | T |
| 331 | 325 | PRO | PRO | H | (1,2-cis-ACHC) | MebetaHomoLys | L | D | T |
| 332 | 326 | PRO | PRO | H | MeMet | MebetaHomoLys | L | D | T |
| 333 | 327 | PRO | PRO | H | betaHomoLys | betaHomoLys | L | D | T |
| 334 | 328 | PRO | PRO | H | BetaHomoPhe | MebetaHomoLys | L | D | T |
| 335 | 329 | PRO | PRO | H | betahomoMet | MebetaHomoLys | L | D | T |
| 336 | 330 | PRO | PRO | H | Y | (3-aminomethyl-4-bromo-benzoic acid) | L | D | T |
| 337 | 331 | PRO | PRO | H | Y | [3-aminomethyl-4-(4-aza-phenyl)-benzoic acid] | L | D | T |
| 338 | 332 | PRO | PRO | H | Y | [3-aminomethyl-4-(2,5-dimethyl-isoxazole)-benzoic acid] | L | D | T |
| 339 | 333 | PRO | PRO | H | Y | [3-aminomethyl-4-(3-aminomethyl-phenyl)-benzoic acid] | L | D | T |
| 340 | 334 | PRO | PRO | H | [3-aminomethyl-4-[4-(1-piperazinyl)-phenyl]-benzoic acid] | | L | D | T |

TABLE 1B-continued

| Compound No. | Seq. ID. No. | R⁶ | R⁷ | R⁸ | Xʸ | Xᶻ | X¹ | X² | X³ |
|---|---|---|---|---|---|---|---|---|---|
| 356 | 334 | PRO | PRO | H | [3-aminomethyl-4-[4-(1-piperazinyl-4-FITC)phenyl]-benzoic acid] | | L | D | T |
| 386 | 334 | PRO | PRO | H | [3-aminomethyl-4-[4-(1-piperazinyl-4-AlexaFluor 647)phenyl]-benzoic acid] | | L | D | T |
| 390 | 334 | PRO | PRO | H | [3-aminomethyl-4-[4-(1-piperazinyl)-phenyl]-benzoic acid] | | L | D | T |
| 391 | 334 | PRO | PRO | H | [3-aminomethyl-4-[4-(1-piperazinyl)-phenyl]-benzoic acid] | | L | D | T |
| 392 | 334 | PRO | PRO | H | [3-aminomethyl-4-[4-(1-piperazinyl)-phenyl]-benzoic acid] | | L | D | T |
| 341 | 335 | PRO | PRO | H | [3-aminomethyl-4-(4-quinolinyl)-benzoic acid] | | L | D | T |
| 342 | 336 | PRO | PRO | H | (3-aminomethyl-4-bromo-benzoic acid) | | L | D | T |
| 361 | 336 | PRO | PRO | H | (3-aminomethyl-4-bromo-benzoic acid) | | L | D | T |
| 343 | 337 | PRO | PRO | H | [3-aminomethyl-4-(2,5-dimethyl-isoxazole)-benzoic acid] | | L | D | T |
| 344 | 338 | dPRO | H | dPRO | [3-aminomethyl-4-(4-pyridyl)-benzoic acid] | | L | D | T |
| 345 | 339 | PRO | PRO | H | [3-aminomethyl-(4-methylpyrazole-3-yl)-benzoic acid] | | L | D | T |
| 346 | 340 | PRO | PRO | H | [3-aminomethyl-4-(3-quinolinyl)-benzoic acid] | | L | D | T |
| 347 | 341 | PRO | PRO | H | [3-aminomethyl-4-(5-quinolinyl)-benzoic acid] | | L | D | T |
| 348 | 342 | PRO | PRO | H | [3-aminomethyl-4-[2-(1-piperazinyl)phenyl]-benzoic acid] | | L | D | T |
| 349 | 343 | PRO | PRO | H | [3-aminomethyl-4-[3-(1-piperazinyl)phenyl]-benzoic acid] | | L | D | T |
| 350 | 344 | PRO | PRO | H | [3-aminomethyl-4-[2-(3-(piperidin-4-ylmethoxy)phenyl]-benzoic acid] | | L | D | T |
| 351 | 345 | PRO | PRO | H | [3-aminomethyl-4-(4-pyridyl)-benzoic acid] | | L | D | T |
| 352 | 346 | PRO | PRO | H | [3-aminomethyl-4-(4-pyridyl)-benzoic acid] | | L | D | Thr(OBn) |
| 353 | 347 | PRO | PRO | H | [3-aminomethyl-4-(4-quinolinyl)-benzoic acid] | | L | D | alloThr |
| 354 | 348 | PRO | PRO | H | [3-aminomethyl-4-[4-(1-piperazinyl)phenyl]-benzoic acid] | | L | D | T |
| 355 | 349 | PRO | PRO | H | [3-aminomethyl-4-(4-quinolinyl)]-benzoic acid | | tertbutylAla | D | T |
| 357 | 350 | PRO | PRO | H | (N-benzyl-3-aminomethyl-benzoic acid) | | L | D | T |
| 358 | 351 | PRO | PRO | H | (3-aminomethyl-benzoic acid | | L | D | T |
| 359 | 352 | PRO | PRO | H | (3-aminomethyl-5-bromo-benzoic acid) | | L | D | T |
| 360 | 353 | PRO | PRO | H | (3-aminomethyl-6-bromo-benzoic acid) | | L | D | T |
| 362 | 354 | PRO | PRO | H | [3-aminomethyl-5-(4-aza-phenyl)-benzoic acid] | | L | D | T |
| 363 | 355 | PRO | PRO | H | [3-aminomethyl-4-(3-thiophenyl)-benzoic acid] | | L | D | T |
| 364 | 356 | PRO | PRO | H | [3-aminomethyl-4-(4-N,N-dimethyl-carboxamide-phenyl)-benzoic acid] | | L | D | T |
| 365 | 357 | PRO | PRO | H | [3-aminomethyl-4-(4-aza-phenyl)-benzoic acid] | | L | D | T |
| 366 | 358 | PRO | PRO | H | [3-aminomethyl-4-(3-aza-phenyl)-benzoic acid] | | L | D | T |
| 367 | 359 | PRO | PRO | H | [3-aminomethyl-4-(4-hydroxy-phenyl)-benzoic acid] | | L | D | T |
| 368 | 360 | PRO | PRO | H | [3-aminomethyl-4-[5-(2,4-dimethyl)thiazole]-benzoic acid] | | L | D | T |
| 369 | 361 | PRO | PRO | H | [3-aminomethyl-4-(3-N,N-dimethylaniline)-benzoic acid] | | L | D | T |
| 370 | 362 | PRO | PRO | H | [3-aminomethyl-4-(2-fluoro-pyridyl)-benzoic acid] | | L | D | T |
| 371 | 363 | PRO | PRO | H | [3-aminomethyl-4-(5-pyrimidinyl)-benzoic acid] | | L | D | T |
| 372 | 364 | PRO | PRO | H | [3-aminomethyl-4-(3-N,N-dimethyl-diaryl ether)-benzoic acid] | | L | D | T |
| 373 | 365 | PRO | PRO | H | [3-aminomethyl-4-(3-CF3-phenyl)-benzoic acid] | | L | D | T |
| 374 | 366 | PRO | PRO | H | [3-aminomethyl-4-(2,5-dimethoxy-phenyl)-benzoic acid] | | L | D | T |
| 375 | 367 | PRO | PRO | H | [3-aminomethyl-4-[(2,3,4-tri-methoxy)-phenyl]-benzoic acid] | | L | D | T |
| 376 | 368 | PRO | PRO | H | [3-aminomethyl-4-(4-carboxy)-phenyl)-benzoic acid] | | L | D | T |
| 377 | 369 | PRO | PRO | H | [3-aminomethyl-4-(piperonyl)-benzoic acid] | | L | D | T |
| 378 | 370 | PRO | PRO | H | (3-aminomethyl-4-piperidinyl-benzoic acid) | | L | D | T |
| 379 | 371 | PRO | PRO | H | (3-aminomethyl-4-morpholinyl-benzoic acid) | | L | D | T |
| 380 | 372 | PRO | PRO | H | [3-aminomethyl-4-(N,N-dimethyl)-benzoic acid] | | L | D | T |

TABLE 1B-continued

| Compound No. | Seq. ID. No. | R⁶ | R⁷ | R⁸ | Xʸ | Xᶻ | X¹ | X² | X³ |
|---|---|---|---|---|---|---|---|---|---|
| 381 | 373 | PRO | PRO | H | [3-aminomethyl-4-(2-aminomethylphenyl)-benzoic acid] | | L | D | T |
| 382 | 374 | PRO | PRO | H | [3-aminomethyl-4-(3-aminomethylphenyl)-benzoic acid] | | L | D | T |
| 383 | 375 | PRO | PRO | H | [3-aminomethyl-4-(4-aminomethylphenyl)-benzoic acid] | | L | D | T |
| 384 | 376 | PRO | PRO | H | [3-aminomethyl-4-(4-quinolinyl)-benzoic acid] | | L | D | Abu |
| 385 | 377 | H | Nva | H | [3-aminomethyl-4-(4-quinolinyl)-benzoic acid] | | L | D | T |
| 387 | 378 | PRO | PRO | H | (N-methyl-3-aminomethyl-benzoic acid) | | L | D | T |
| 388 | 379 | PRO | PRO | H | [N-methyl-3-aminomethyl-4-(4-quinolinyl)-benzoic acid] | | L | D | T |
| 389 | 380 | PRO | PRO | H | [2-(5-quinolinyl)-Phe]-reduced | betaHomoLys | L | D | T |
| 456 | 427 | PRO | PRO | H | K | MebetaHomoLys | L | D | T |

TABLE 1C

| Compound No. | ELISA a4b7 Assay IC₅₀(μM) | ELISA a4b1 Assay IC₅₀(μM) | ELISA Assay Ratio b1/b7 | RPMI8866 Adhesion a4b7/MAdCAM IC50 (mM) |
|---|---|---|---|---|
| 1 | 0.164 | 0.162 | 0.988 | |
| 2 | 0.109 | 0.185 | 1.697 | |
| 3 | 0.192 | 0.475 | 2.474 | 25.000 |
| 4 | 0.129 | 0.357 | 2.8 | 11.782 |
| 5 | 0.087 | 0.062 | 0.7 | 7.916 |
| 6 | 0.103 | 0.200 | 1.9 | |
| 7 | 0.117 | 0.190 | 1.6 | 23.000 |
| 8 | 0.103 | 0.096 | 0.9 | |
| 9 | 0.061 | 0.106 | 1.7 | |
| 10 | 0.052 | 0.070 | 1.3 | |
| 11 | 0.051 | 0.094 | 1.8 | 3.602 |
| 12 | 0.063 | 0.113 | 1.8 | 8.885 |
| 13 | 0.097 | 0.171 | 1.8 | 19.520 |
| 14 | 0.026 | 0.025 | 1.0 | 2.664 |
| 15 | 0.040 | 0.026 | 0.7 | 3.071 |
| 16 | 0.086 | 0.053 | 0.6 | 1.624 |
| 17 | 0.173 | | | 26.92 |
| 18 | 0.120 | | | |
| 19 | 0.114 | | | 15.044 |
| 20 | 0.146 | | | 8.716 |
| 21 | 0.092 | | | 9.466 |
| 22 | 0.100 | | | 11.556 |
| 23 | 0.176 | 0.458 | 2.6 | 18.880 |
| 24 | 0.087 | 0.192 | 2.2 | 7.632 |
| 25 | 0.096 | 0.209 | 2.2 | 12.431 |
| 26 | 0.088 | 0.236 | 2.7 | 14.070 |
| 27 | 0.067 | 0.161 | 2.4 | 10.478 |
| 28 | 0.117 | 0.264 | 2.3 | 12.562 |
| 29 | 0.073 | 0.167 | 2.3 | 8.133 |
| 30 | 0.058 | 0.162 | 2.8 | 9.277 |
| 31 | 0.057 | 0.215 | 3.7 | 7.950 |
| 32 | 0.100 | 0.311 | 3.1 | 11.161 |
| 33 | 0.090 | 0.324 | 3.6 | 13.059 |
| 34 | 0.043 | 0.083 | 1.9 | 1.153 |
| 35 | 0.039 | 0.096 | 2.5 | 1.230 |
| 36 | 0.112 | 0.215 | 1.9 | 2.392 |
| 37 | 0.036 | 0.063 | 1.8 | 0.856 |
| 38 | 0.065 | 0.120 | 1.9 | 1.899 |
| 39 | 0.152 | 0.595 | 3.9 | 7.576 |
| 40 | 0.063 | 0.119 | 1.9 | |
| 41 | 0.042 | 0.106 | 2.5 | |
| 42 | 0.079 | 0.232 | 2.9 | |
| 43 | 0.026 | 0.072 | 2.8 | |
| 44 | 0.083 | 0.188 | 2.3 | |
| 45 | 0.074 | 0.238 | 3.2 | |
| 46 | 0.106 | 0.258 | 2.4 | |
| 47 | 0.061 | 0.135 | 2.2 | 6.777 |
| 48 | 0.094 | 0.332 | 3.5 | 20.686 |
| 49 | 0.137 | 0.326 | 2.4 | 17.374 |
| 50 | 0.023 | 0.290 | 12.6 | 3.709 |
| 51 | 0.031 | 0.102 | 3.3 | |
| 52 | 0.075 | 0.367 | 4.9 | 14.719 |

TABLE 1C-continued

| Compound No. | ELISA a4b7 Assay IC$_{50}$(μM) | ELISA a4b1 Assay IC$_{50}$(μM) | ELISA Assay Ratio b1/b7 | RPMI8866 Adhesion a4b7/MAdCAM IC50 (mM) |
|---|---|---|---|---|
| 53 | 0.182 | | | 21.956 |
| 54 | 0.190 | | | 23.916 |
| 55 | 0.113 | 0.119 | 1.1 | |
| 56 | 0.058 | 0.200 | 3.5 | 4.203 |
| 57 | 0.059 | 0.148 | 2.5 | |
| 58 | 0.156 | 0.445 | 2.9 | |
| 59 | 0.197 | 0.610 | 3.1 | |
| 60 | 0.066 | 0.214 | 3.3 | 6.554 |
| 61 | 0.063 | 0.223 | 3.6 | |
| 62 | 0.027 | 0.115 | 4.3 | 2.548 |
| 63 | 0.107 | 0.251 | 2.3 | |
| 64 | 0.046 | 0.268 | 5.8 | 5.367 |
| 65 | 0.005 | 0.095 | 18.1 | 1.033 |
| 66 | 0.093 | 0.326 | 3.5 | 6.348 |
| 67 | 0.075 | 0.341 | 4.5 | 5.093 |
| 68 | 0.067 | 0.280 | 4.2 | 4.158 |
| 69 | 0.022 | 0.060 | 2.7 | 2.646 |
| 70 | 0.035 | 0.099 | 2.9 | 1.163 |
| 71 | 0.184 | 0.816 | 4.4 | |
| 72 | 0.151 | 0.409 | 2.7 | 7.284 |
| 73 | 0.144 | 1.247 | 8.6 | 17.304 |
| 74 | 0.100 | 0.763 | 7.6 | 15.503 |
| 75 | 0.171 | 1.209 | 7.1 | 13.166 |
| 76 | 0.114 | 0.466 | 4.1 | 6.267 |
| 77 | 0.036 | 0.185 | 5.1 | 5.633 |
| 78 | 0.069 | 0.272 | 3.9 | 6.479 |
| 79 | 0.110 | 0.552 | 5.0 | 13.217 |
| 80 | 0.053 | 0.556 | 10.6 | 3.599 |
| 81 | 0.054 | 0.241 | 4.5 | 5.405 |
| 82 | 0.073 | 0.213 | 2.9 | 5.716 |
| 83 | 0.179 | 1.226 | 6.9 | 32.316 |
| 84 | 0.035 | 0.218 | 6.2 | 6.143 |
| 85 | 0.052 | 0.206 | 3.9 | 4.229 |
| 86 | 0.050 | 0.167 | 3.3 | 4.074 |
| 87 | 0.019 | 0.269 | 14.1 | |
| 88 | 0.011 | 0.166 | 14.9 | |
| 89 | 0.016 | 0.232 | 14.4 | |
| 90 | 0.009 | 0.317 | 35.0 | |
| 91 | 0.126 | 1.824 | 14.5 | |
| 92 | 0.053 | 1.063 | 19.9 | |
| 93 | 0.078 | 0.311 | 4.0 | 6.009 |
| 94 | 0.080 | 0.250 | 3.1 | 9.484 |
| 95 | 0.125 | 0.303 | 2.4 | |
| 96 | 0.138 | 0.321 | 2.3 | |
| 97 | 0.124 | 0.311 | 2.5 | |
| 98 | 0.021 | 0.058 | 2.7 | |
| 99 | 0.057 | 0.154 | 2.7 | |
| 100 | 0.132 | 0.453 | 3.4 | 4.446 |
| 101 | 0.129 | 0.609 | 4.7 | 16.092 |
| 102 | 0.021 | 0.136 | 6.6 | 1.464 |
| 103 | 0.108 | 1.631 | 15.1 | |
| 104 | 0.120 | 0.506 | 4.2 | |
| 105 | 0.110 | 1.734 | 15.8 | 9.731 |
| 106 | 0.059 | 1.109 | 18.7 | |
| 107 | 0.150 | 2.390 | 16.0 | |
| 108 | 0.077 | 0.814 | 10.5 | 13.867 |
| 109 | 0.133 | 3.312 | 24.9 | 15.287 |
| 110 | 0.185 | 3.923 | 21.3 | 21.753 |
| 111 | 0.100 | 3.923 | 39.3 | 12.926 |
| 112 | 0.138 | 3.008 | 21.7 | 17.420 |
| 113 | 0.052 | 0.709 | 13.7 | 7.634 |
| 114 | 0.083 | 1.889 | 22.8 | 6.866 |
| 115 | 0.125 | 1.121 | 9.0 | 15.436 |
| 116 | 0.166 | 1.385 | 8.4 | |
| 117 | 0.158 | 1.381 | 8.7 | |
| 118 | 0.112 | 0.132 | 1.2 | 14.202 |
| 119 | 0.079 | 1.688 | 21.5 | 14.057 |
| 120 | 0.157 | 3.000 | 19.1 | |
| 121 | 0.192 | 2.187 | 11.4 | |
| 122 | 0.090 | 1.666 | 18.6 | 16.615 |
| 123 | 0.007 | 0.019 | 2.5 | 1.138 |
| 124 | 0.013 | 0.104 | 8.3 | 1.172 |
| 125 | 0.025 | 0.458 | 18.4 | 1.925 |
| 126 | 0.024 | 0.135 | 5.6 | 1.232 |
| 127 | 0.025 | 0.196 | 7.8 | |
| 128 | 0.026 | 0.296 | 11.4 | |
| 129 | 0.065 | 0.636 | 9.7 | |

TABLE 1C-continued

| Compound No. | ELISA a4b7 Assay IC$_{50}$(μM) | ELISA a4b1 Assay IC$_{50}$(μM) | ELISA Assay Ratio b1/b7 | RPMI8866 Adhesion a4b7/MAdCAM IC50 (mM) |
|---|---|---|---|---|
| 130 | 0.022 | 0.125 | 5.6 | 1.327 |
| 131 | 0.026 | 0.080 | 3.1 | |
| 132 | 0.029 | 0.309 | 10.8 | 3.626 |
| 133 | 0.015 | 0.080 | 5.3 | |
| 134 | 0.023 | 0.178 | 7.6 | |
| 135 | 0.024 | 0.119 | 4.9 | |
| 136 | 0.032 | 0.209 | 6.6 | |
| 137 | 0.033 | 0.254 | 7.8 | |
| 138 | 0.024 | 0.118 | 5.0 | |
| 139 | 0.100 | 0.073 | 0.7 | |
| 140 | 0.053 | 0.512 | 9.6 | |
| 141 | 0.019 | 0.036 | 2.0 | |
| 142 | 0.164 | 0.084 | 0.5 | |
| 143 | 0.033 | 0.068 | 2.1 | |
| 144 | 0.043 | 0.027 | 0.6 | 6.083 |
| 145 | 0.023 | 0.045 | 2.0 | 3.268 |
| 146 | 0.016 | 0.012 | 0.7 | 0.672 |
| 147 | 0.052 | 0.039 | 0.8 | |
| 148 | 0.086 | 0.105 | 1.2 | |
| 149 | 0.046 | 0.546 | 12.0 | 12.600 |
| 150 | 0.054 | 0.447 | 8.2 | |
| 151 | 0.053 | 0.218 | 4.1 | |
| 152 | 0.102 | 1.347 | 13.2 | |
| 153 | 0.006 | 0.017 | 2.8 | 0.125 |
| 154 | 0.117 | 2.664 | 22.8 | |
| 155 | 0.054 | 1.085 | 20.3 | |
| 156 | 0.019 | 0.258 | 13.3 | 1.412 |
| 157 | 0.067 | 3.707 | 55.3 | |
| 158 | 0.110 | 1.537 | 14.0 | 15.746 |
| 159 | 0.053 | 0.467 | 8.9 | 41.275 |
| 160 | 0.141 | 1.349 | 9.5 | 8.794 |
| 161 | 0.135 | 2.035 | 15.1 | 6.662 |
| 162 | 0.107 | 1.875 | 17.5 | 16.696 |
| 163 | 0.126 | 1.389 | 11.0 | 22.489 |
| 164 | 0.127 | 3.288 | 25.8 | 30.192 |
| 165 | 0.128 | 2.918 | 22.8 | 30.337 |
| 166 | 0.179 | 1.382 | 7.7 | |
| 167 | 0.147 | 1.997 | 13.6 | |
| 168 | 0.077 | 1.051 | 13.6 | 17.847 |
| 169 | 0.176 | 0.488 | 2.8 | |
| 170 | 0.013 | 0.104 | 8.0 | 1.033 |
| 171 | 0.128 | 0.658 | 5.1 | 14.357 |
| 172 | 0.096 | 1.030 | 10.7 | 9.922 |
| 173 | 0.054 | 0.719 | 13.4 | 12.042 |
| 174 | 0.160 | 0.619 | 3.9 | |
| 175 | 0.018 | 0.130 | 7.2 | 0.986 |
| 176 | 0.189 | 1.202 | 6.3 | |
| 177 | 0.019 | 0.463 | 24.0 | 2.853 |
| 178 | 0.027 | 0.113 | 4.1 | 2.710 |
| 179 | 0.174 | 2.656 | 15.2 | |
| 180 | 0.013 | 0.068 | 5.1 | 0.841 |
| 181 | 0.180 | 2.272 | 12.6 | |
| 182 | 0.017 | 0.083 | 5.0 | 1.128 |
| 183 | 0.014 | 0.105 | 7.5 | 1.070 |
| 184 | 0.099 | 0.953 | 9.6 | |
| 185 | 0.018 | 0.095 | 5.4 | 0.662 |
| 186 | 0.062 | 0.027 | 0.4 | |
| 187 | 0.083 | 0.404 | 4.9 | |
| 188 | 0.027 | 0.189 | 7.0 | 7.308 |
| 189 | 0.018 | 0.019 | 1.0 | 2.251 |
| 190 | 0.021 | 0.145 | 7.0 | 2.470 |
| 191 | 0.083 | 4.020 | 48.4 | |
| 192 | 0.118 | 6.823 | 57.8 | 37.800 |
| 193 | 0.092 | 0.303 | 3.3 | 5.621 |
| 194 | 0.038 | 0.207 | 5.4 | 4.617 |
| 195 | 0.049 | 1.917 | 38.9 | 7.931 |
| 196 | 0.158 | 0.275 | 1.7 | |
| 197 | 0.044 | 1.327 | 30.2 | 7.441 |
| 198 | 0.041 | 1.223 | 29.9 | 5.089 |
| 199 | 0.069 | 3.138 | 45.2 | 19.350 |
| 200 | 0.134 | 0.352 | 2.6 | |
| 201 | 0.061 | 0.695 | 11.4 | |
| 202 | 0.086 | 0.680 | 8.0 | |
| 203 | 0.055 | 0.534 | 9.8 | |
| 204 | 0.063 | 0.429 | 6.8 | |
| 205 | 0.047 | 1.517 | 32.2 | 2.231 |
| 206 | 0.046 | 2.890 | 63.0 | 27.621 |

TABLE 1C-continued

| Compound No. | ELISA a4b7 Assay IC$_{50}$(μM) | ELISA a4b1 Assay IC$_{50}$(μM) | ELISA Assay Ratio b1/b7 | RPMI8866 Adhesion a4b7/MAdCAM IC50 (mM) |
|---|---|---|---|---|
| 207 | 0.025 | 0.460 | 18.5 | |
| 208 | 0.019 | 0.522 | 28.1 | 4.679 |
| 209 | 0.035 | 1.977 | 56.9 | 16.508 |
| 210 | 0.072 | 1.148 | 16.0 | |
| 211 | 0.060 | 2.511 | 42.2 | 8.101 |
| 212 | 0.068 | 2.190 | 32.1 | |
| 213 | 0.055 | 2.247 | 41.2 | 10.605 |
| 214 | 0.069 | 4.222 | 60.8 | 72.055 |
| 215 | 0.033 | 0.413 | 12.4 | |
| 216 | 0.123 | 2.509 | 20.4 | |
| 217 | 0.034 | 1.088 | 31.8 | |
| 218 | 0.190 | 3.135 | 16.5 | |
| 219 | 0.147 | 3.253 | 22.1 | |
| 220 | 0.096 | 1.740 | 18.2 | |
| 221 | 0.015 | 0.165 | 11.1 | 0.248 |
| 222 | 0.013 | 0.212 | 16.1 | 0.325 |
| 223 | 0.015 | 0.122 | 8.2 | 0.549 |
| 224 | 0.055 | 2.978 | 53.9 | 10.962 |
| 225 | 0.099 | 4.523 | 45.6 | 18.130 |
| 226 | 0.094 | 10.797 | 115.0 | 4.076 |
| 227 | 0.034 | 0.047 | 1.4 | 1.491 |
| 228 | 0.034 | 0.503 | 14.7 | |
| 229 | 0.058 | 0.075 | 1.3 | |
| 230 | 0.120 | 0.131 | 1.1 | |
| 231 | 0.031 | 0.993 | 32.0 | |
| 232 | 0.012 | 0.110 | 8.9 | 0.353 |
| 233 | 0.094 | 3.861 | 41.0 | 19.372 |
| 234 | 0.099 | 3.203 | 32.3 | |
| 235 | 0.025 | 1.553 | 62.6 | 4.614 |
| 236 | 0.060 | 6.203 | 104.2 | 7.320 |
| 237 | 0.020 | 0.870 | 43.9 | 5.131 |
| 238 | 0.025 | 1.049 | 42.3 | 8.425 |
| 239 | 0.020 | 0.641 | 32.3 | 4.407 |
| 240 | 0.027 | 0.905 | 33.2 | 12.040 |
| 241 | 0.031 | 3.207 | 103.4 | 6.006 |
| 242 | 0.067 | 5.307 | 79.0 | 8.335 |
| 243 | 0.026 | 0.767 | 29.4 | 2.007 |
| 244 | 0.016 | 0.753 | 46.7 | 0.719 |
| 245 | 0.024 | 0.414 | 17.5 | 3.067 |
| 246 | 0.120 | 17.702 | 147.1 | |
| 247 | 0.035 | 4.614 | 132.8 | 15.134 |
| 248 | 0.045 | 3.088 | 69.2 | 16.371 |
| 249 | 0.045 | 4.233 | 94.8 | 23.107 |
| 250 | 0.017 | 0.150 | 8.7 | 0.401 |
| 251 | 0.024 | 0.349 | 14.8 | 1.386 |
| 252 | 0.032 | 0.390 | 12.1 | 2.408 |
| 253 | 0.069 | 1.087 | 15.6 | |
| 254 | 0.055 | 1.803 | 33.0 | |
| 255 | 0.043 | 3.024 | 69.7 | |
| 256 | 0.072 | 3.246 | 45.1 | 9.562 |
| 257 | 0.058 | 1.604 | 27.5 | |
| 258 | 0.056 | 1.584 | 28.4 | |
| 259 | 0.058 | 5.995 | 102.8 | 4.279 |
| 260 | 0.165 | 9.562 | 58.1 | |
| 261 | 0.096 | 23.155 | 241.0 | 16.926 |
| 262 | 0.080 | 3.740 | 47.0 | |
| 263 | 0.102 | 2.345 | 23.1 | |
| 264 | 0.117 | 5.560 | 47.5 | |
| 265 | 0.039 | 1.818 | 46.2 | |
| 266 | 0.037 | 1.206 | 33.0 | 11.641 |
| 267 | 0.044 | 1.936 | 44.1 | 20.440 |
| 268 | 0.076 | 1.868 | 24.6 | |
| 269 | 0.056 | 1.764 | 31.6 | |
| 270 | 0.160 | 17.562 | 109.8 | 18.900 |
| 271 | 0.033 | 1.151 | 34.6 | |
| 272 | 0.041 | 2.383 | 58.1 | |
| 273 | 0.012 | 0.303 | 24.6 | 1.730 |
| 274 | 0.026 | 0.454 | 17.5 | 7.938 |
| 275 | 0.101 | 0.779 | 7.7 | |
| 276 | 0.134 | 14.235 | 106.2 | |
| 277 | 0.052 | 0.357 | 6.9 | |
| 278 | 0.104 | 1.062 | 10.2 | |
| 279 | 0.100 | 5.847 | 58.2 | |
| 280 | 0.010 | 0.400 | 39.7 | 2.150 |
| 281 | 0.144 | 3.161 | 21.9 | |
| 282 | 0.119 | 0.626 | 5.2 | |
| 283 | 0.128 | 1.495 | 11.7 | |

TABLE 1C-continued

| Compound No. | ELISA a4b7 Assay IC$_{50}$(μM) | ELISA a4b1 Assay IC$_{50}$(μM) | ELISA Assay Ratio b1/b7 | RPMI8866 Adhesion a4b7/MAdCAM IC50 (mM) |
|---|---|---|---|---|
| 284 | 0.046 | 0.228 | 5.0 | |
| 285 | 0.089 | 0.553 | 6.2 | |
| 286 | 0.064 | 5.236 | 81.9 | |
| 287 | 0.084 | 3.553 | 42.1 | |
| 288 | 0.136 | 1.664 | 12.2 | |
| 289 | 0.038 | 0.349 | 9.3 | 1.242 |
| 290 | 0.067 | 1.894 | 28.4 | |
| 291 | 0.035 | 0.777 | 22.4 | 8.742 |
| 292 | 0.030 | 0.374 | 12.4 | |
| 293 | 0.019 | 0.198 | 10.6 | 4.008 |
| 294 | 0.045 | 0.937 | 20.7 | |
| 295 | 0.094 | 20.950 | 222.7 | 18.900 |
| 296 | 0.155 | 14.698 | 94.8 | |
| 297 | 0.037 | 0.786 | 21.3 | |
| 298 | 0.076 | 4.349 | 57.2 | |
| 299 | 0.002 | 0.090 | 41.5 | 0.556 |
| 300 | 0.022 | 0.225 | 10.4 | 0.672 |
| 301 | 0.018 | 0.846 | 47.6 | 1.020 |
| 302 | 0.012 | 0.598 | 51.6 | 1.764 |
| 303 | 0.020 | 0.497 | 24.8 | 1.662 |
| 304 | 0.015 | 0.293 | 19.0 | 0.191 |
| 305 | 0.008 | 0.221 | 26.6 | 3.533 |
| 306 | 0.104 | 2.763 | 26.5 | |
| 307 | 0.091 | 4.343 | 47.8 | |
| 308 | 0.039 | 0.480 | 12.3 | 1.982 |
| 309 | 0.008 | 0.023 | 3.0 | 0.126 |
| 310 | 0.017 | 0.300 | 17.6 | 0.434 |
| 311 | 0.007 | 0.198 | 27.6 | 0.158 |
| 312 | 0.011 | 0.145 | 13.4 | 0.273 |
| 313 | 0.011 | 0.206 | 19.2 | 0.210 |
| 314 | 0.011 | 0.138 | 12.8 | 0.305 |
| 315 | 0.013 | 0.312 | 24.9 | 0.431 |
| 316 | 0.022 | 0.349 | 16.2 | 0.690 |
| 317 | 0.047 | 0.685 | 14.5 | 9.408 |
| 318 | 0.091 | 1.513 | 16.6 | |
| 319 | 0.065 | 0.309 | 4.8 | |
| 320 | 0.163 | 0.127 | 0.8 | |
| 321 | 0.101 | 7.368 | 72.7 | |
| 322 | 0.093 | 4.166 | 44.7 | |
| 323 | 0.025 | 0.297 | 11.8 | 1.056 |
| 324 | 0.110 | 1.058 | 9.6 | 11.844 |
| 325 | 0.020 | 0.170 | 8.6 | 0.714 |
| 326 | 0.017 | 0.476 | 28.4 | 0.280 |
| 327 | 0.010 | 0.128 | 13.2 | 0.308 |
| 328 | 0.010 | 0.234 | 24.1 | 0.368 |
| 329 | 0.005 | 0.050 | 10.6 | 0.326 |
| 330 | 0.005 | 0.179 | 32.9 | 0.185 |
| 331 | 0.016 | 0.093 | 6.0 | 0.399 |
| 332 | 0.010 | 0.120 | 12.5 | 0.140 |
| 333 | 0.046 | 0.757 | 16.5 | 12.922 |
| 334 | | | | 5.061 |
| 335 | | | | 4.956 |
| 336 | 0.162 | 0.917 | 5.6 | |
| 337 | 0.061 | 0.177 | 2.9 | |
| 338 | 0.041 | 0.177 | 4.4 | |
| 339 | 0.051 | 0.299 | 5.8 | |
| 340 | 0.019 | 0.048 | 2.5 | 0.263 |
| 341 | 0.012 | 0.026 | 2.1 | 0.306 |
| 342 | 0.041 | 0.139 | 3.4 | |
| 343 | 0.018 | 0.029 | 1.6 | 0.269 |
| 344 | 0.052 | 0.107 | 2.1 | |
| 345 | 0.039 | 0.052 | 1.3 | |
| 346 | 0.028 | 0.011 | 0.4 | 0.580 |
| 347 | 0.023 | 0.030 | 1.3 | |
| 348 | 0.027 | 0.041 | 1.5 | |
| 349 | 0.023 | 0.043 | 1.9 | 0.479 |
| 350 | 0.027 | 0.055 | 2.0 | |
| 351 | 0.160 | 0.184 | 1.2 | |
| 352 | 0.024 | 0.005 | 0.2 | 0.070 |
| 353 | 0.031 | 0.103 | 3.3 | |
| 354 | 0.050 | 0.175 | 3.5 | |
| 355 | 0.048 | 0.069 | 1.4 | |
| 356 | 0.017 | 0.027 | 1.6 | |
| 357 | 0.102 | 0.406 | 4.0 | |
| 358 | 0.127 | 1.108 | 8.7 | 34.923 |
| 359 | 0.053 | 0.450 | 8.5 | 7.880 |
| 360 | 0.125 | 0.779 | 6.2 | 18.937 |

TABLE 1C-continued

| Compound No. | ELISA a4b7 Assay IC$_{50}$(μM) | ELISA a4b1 Assay IC$_{50}$(μM) | ELISA Assay Ratio b1/b7 | RPMI8866 Adhesion a4b7/MAdCAM IC50 (mM) |
|---|---|---|---|---|
| 361 | 0.049 | 0.288 | 5.9 | 2.843 |
| 362 | 0.043 | 0.238 | 5.6 | |
| 363 | 0.022 | 0.105 | 4.8 | 1.571 |
| 364 | 0.018 | 0.074 | 4.0 | 0.602 |
| 365 | 0.017 | 0.064 | 3.7 | 0.638 |
| 366 | 0.023 | 0.059 | 2.6 | 0.384 |
| 367 | 0.018 | 0.053 | 3.0 | 0.535 |
| 368 | 0.010 | 0.024 | 2.4 | 0.342 |
| 369 | 0.024 | 0.069 | 2.9 | 0.974 |
| 370 | 0.015 | 0.047 | 3.1 | 0.661 |
| 371 | 0.016 | 0.055 | 3.4 | 0.482 |
| 372 | 0.024 | 0.104 | 4.3 | 2.133 |
| 373 | 0.018 | 0.074 | 4.1 | 0.879 |
| 374 | 0.018 | 0.081 | 4.5 | 1.246 |
| 375 | 0.015 | 0.067 | 4.5 | 1.164 |
| 376 | 0.019 | 0.078 | 4.1 | 1.135 |
| 377 | 0.013 | 0.045 | 3.6 | 0.839 |
| 378 | 0.042 | 0.182 | 4.3 | |
| 379 | 0.033 | 0.161 | 4.9 | |
| 380 | 0.041 | 0.217 | 5.3 | |
| 381 | 0.010 | 0.010 | 1.1 | 0.323 |
| 382 | 0.012 | 0.025 | 2.0 | |
| 383 | 0.006 | 0.017 | 2.7 | 0.403 |
| 384 | 0.020 | 0.049 | 2.5 | 2.260 |
| 385 | 0.039 | 0.023 | 0.6 | 1.548 |
| 386 | 0.044 | 0.034 | 0.8 | 2.604 |
| 387 | 0.063 | 6.133 | 96.7 | 16.142 |
| 388 | 0.009 | 0.102 | 12.0 | 0.336 |
| 389 | 0.042 | 0.234 | 5.535 | 6.664 |
| 456 | | | | 0.196 |

TABLE 1C'

| Compound No. | MADCAM FACS a4b7 Th mem (nM) | RPMI8866 Adhesion a4b7/MAdCAM IC50 (nM) | Ramos Adhesion a4b1/VCAM IC$_{50}$ (nM) | Ratio Ramos/RPMI | ELISA a4b7 Assay IC$_{50}$ (nM) | ELISA a4b7 Assay IC$_{50}$ (nM) | ELISA Assay Ratio b1/b7 | VCAM FACS a4 + b7 − Th mem (nM) |
|---|---|---|---|---|---|---|---|---|
| 32 | | 11161 | | | | | | |
| 132 | | 3626 | | | | | | |
| 146 | | 672 | | | | | | |
| 340 | Unclear | 175 | 2767 | 16 | | | | |
| 456 | 1000 | 199 | 8925 | 45 | 14 | 21 | 1.5 | |

TABLE 1X

| Compound No. | LC-MS (m/z) | Experimental Protocol |
|---|---|---|
| 1 | | A, E, Fb, I, M |
| 2 | | A, E, Fb, I, M |
| 3 | | A, E, Fb, I, M |
| 4 | | A, E, Fa, Jb, I, M |
| 4 | | A, E, Fa, Jb, I, M |
| 5 | | A, E, Fa, Jb, I, M |
| 5 | | A, E, Fa, Jb, I, M |
| 6 | | A, E, Fa, Jb, I, M |
| 7 | | A, E, Fa, Jb, I, M |
| 8 | | A, E, Fa, Jb, I, M |
| 9 | 780.4 | A, E, Fa, Jb, I, M |
| 10 | 780.4 | A, E, Fa, Jb, I, M |
| 11 | 859.4 | A, E, Fa, Jb, I, M |
| 12 | 806.4 | A, E, Fa, Jb, I, M |
| 13 | | A, E, Fa, Jb, H, I, M |
| 14 | 792.4 | A, E, Fa, Jb, I, M |
| 15 | 792.4 | A, E, Fa, Jb, I, M |
| 16 | | A, E, Fa, Jb, I, M |
| 17 | | A, E, Fa, Jb, I, M |
| 18 | | A, E, Fa, Jb, I, M |
| 19 | | A, E, Fa, Jb, H, I, M |
| 20 | | A, E, Fa, Jb, H, I, M |
| 21 | | A, E, Fa, Jb, H, I, M |
| 22 | | A, E, Fa, Jb, H, I, M |
| 23 | | A, E, Fa, Jb, H, I, M |
| 24 | | A, E, Fa, Jb, H, I, M |
| 25 | | A, E, Fa, Jb, H, I, M |
| 26 | | A, E, Fa, Jb, H, I, M |
| 27 | 836.4 | A, E, Fa, Jb, H, I, M |
| 28 | | A, E, Fa, Jb, H, I, M |
| 29 | 880.4 | A, E, Fa, Jb, H, I, M |
| 30 | 880.4 | A, E, Fa, Jb, H, I, M |
| 31 | 866.4 | A, E, Fa, Jb, H, I, M |
| 32 | | A, E, Fa, Jb, I, M |
| 33 | | A, E, Fa, Jb, H, I, M |
| 34 | 891.4 | A, E, Fa, Jb, K, I, M |
| 35 | 829.4 | A, E, Fa, Jb, K, I, M |
| 36 | | A, E, Fa, Jb, K, I, M |
| 37 | 859.4 | A, E, Fa, Jb, K, I, M |
| 38 | 871.4 | A, E, Fa, Jb, K, I, M |
| 39 | | A, E, Fa, Jb, I, M |
| 40 | 744.4 | A, E, Fa, Jb, I, M |

TABLE 1X-continued

| Compound No. | LC-MS (m/z) | Experimental Protocol |
|---|---|---|
| 41 | 758.4 | A, E, Fa, Jb, I, M |
| 42 | 746.4 | A, D, I, M |
| 43 | 742.4 | A, D, I, M |
| 44 |  | A, E, Fa, Jb, I, M |
| 45 | 748.4 | A, E, Fa, Jb, I, M |
| 46 |  | A, E, Fa, Jb, I, M |
| 47 | 749.3 | A, E, Fa, Jb, I, M |
| 48 |  | A, E, Fa, Jb, I, M |
| 49 |  | A, E, Fa, Jb, I, M |
| 50 | 739.4 | A, D, I, M |
| 51 |  | A, D, I, M |
| 52 |  | A, D, I, M |
| 53 |  | A, D, I, M |
| 54 |  | A, D, I, M |
| 55 |  | A, D, I, M |
| 56 |  | A, D, I, M |
| 57 |  | A, D, I, M |
| 58 |  | A, D, I, M |
| 59 |  | A, D, I, M |
| 60 |  | A, D, I, M |
| 61 |  | A, D, I, M |
| 62 |  | A, D, I, M |
| 63 |  | A, D, I, M |
| 64 |  | A, D, I, M |
| 65 |  | A, D, I, M |
| 66 |  | A, D, I, M |
| 67 |  | A, D, I, M |
| 68 |  | A, D, I, M |
| 69 |  | A, D, I, M |
| 70 |  | A, D, I, M |
| 71 |  | A, D, I, M |
| 72 |  | A, D, I, M |
| 73 |  | A, D, I, M |
| 74 |  | A, D, I, M |
| 75 |  | A, D, I, M |
| 76 |  | A, D, I, M |
| 77 |  | A, D, I, M |
| 78 |  | A, D, I, M |
| 79 |  | A, D, I, M |
| 80 |  | A, D, I, M |
| 81 |  | A, D, I, M |
| 82 |  | A, D, I, M |
| 83 |  | A, D, I, M |
| 84 |  | A, D, I, M |
| 85 |  | A, D, I, M |
| 86 |  | A, D, I, M |
| 87 |  | A, D, I, M |
| 88 |  | A, D, I, M |
| 89 |  | A, D, I, M |
| 90 |  | A, D, I, M |
| 91 |  | A, D, I, M |
| 92 |  | A, D, I, M |
| 93 |  | A, D, I, M |
| 94 |  | A, D, I, M |
| 95 |  | A, D, G, I, M |
| 96 |  | A, D, G, I, M |
| 97 |  | A, D, G, I, M |
| 98 |  | A, D, I, M |
| 99 |  | A, D, I, M |
| 100 | 847.4 | A, D, I, M |
| 101 | 843.6 | A, D, I, M |
| 102 | 843.6 | A, D, I, M |
| 103 | 817.4 | A, D, I, M |
| 104 | 857.4 | A, D, I, M |
| 105 | 817.4 | A, D, I, M |
| 106 | 927.2 | A, D, I, M |
| 107 | 927.2 | A, D, I, M |
| 108 | 877.4 | A, D, I, M |
| 109 | 858.4 | A, D, I, M |
| 110 | 934.4 | A, D, I, M |
| 111 | 865.4 | A, D, I, M |
| 112 | 934.4 | A, D, I, M |
| 113 | 886.4 | A, D, I, M |
| 114 | 902.4 | A, D, I, M |
| 115 | 833.4 | A, D, I, M |
| 116 | 877.4 | A, D, I, M |
| 117 | 851.4 | A, D, I, M |
| 118 | 857.4 | A, D, I, M |
| 119 | 927.2 | A, D, I, M |
| 120 | 908.4 | A, D, I, M |
| 121 | 888.4 | A, D, I, M |
| 122 | 801.4 | A, D, I, M |
| 123 | 905.4 | A, D, I, M |
| 124 | 843.4 | A, D, I, M |
| 125 | 857.4 | A, D, I, M |
| 125 | 857.4 | A, D, I, M |
| 126 | 827.4 | A, D, I, M |
| 127 | 887.4 | A, D, I, M |
| 128 | 881.4 | A, D, I, M |
| 129 | 1001.2 | A, D, I, M |
| 130 |  | A, D, I, M |
| 131 |  | A, D, I, M |
| 132 |  | A, D, I, M |
| 133 |  | A, D, I, M |
| 134 |  | A, D, G, I, M |
| 135 |  | A, D, G, I, M |
| 136 |  | A, D, G, I, M |
| 137 |  | A, D, G, I, M |
| 138 |  | A, D, I, M |
| 139 |  | A, D, I, M |
| 140 |  | A, D, I, M |
| 141 |  | A, D, I, M |
| 142 |  | A, D, I, M |
| 143 | 891.1 | A, D, I, M |
| 144 | 891.1 | A, D, I, M |
| 145 | 918.1 | A, D, I, M |
| 146 | 918.1 | A, D, I, M |
| 147 | 918.1 | A, D, I, M |
| 148 | 871.1 | A, D, I, M |
| 149 | 857.1 | A, D, I, M |
| 150 | 871.1 | A, D, I, M |
| 151 | 850.0 | A, D, I, M |
| 152 | 872.1 | A, D, I, M |
| 153 | 869.2 | A, D, I, M |
| 154 | 900.2 | A, D, I, M |
| 155 | 859.4 | A, D, I, M |
| 156 | 843.4 | A, D, I, M |
| 157 | 916.2 | A, D, I, M |
| 158 |  | A, D, I, M |
| 159 |  | A, D, I, M |
| 160 |  | A, D, I, M |
| 161 |  | A, D, I, M |
| 162 |  | A, D, I, M |
| 163 |  | A, D, I, M |
| 164 |  | A, D, I, M |
| 165 |  | A, D, I, M |
| 166 |  | A, D, I, M |
| 167 |  | A, D, I, M |
| 168 |  | A, D, I, M |
| 169 |  | A, D, I, M |
| 170 |  | A, D, I, M |
| 171 |  | A, D, I, M |
| 172 |  | A, D, I, M |
| 173 |  | A, D, I, M |
| 174 |  | A, D, I, M |
| 175 |  | A, D, I, M |
| 176 |  | A, D, I, M |
| 177 |  | A, D, I, M |
| 178 |  | A, D, I, M |
| 179 |  | A, D, G, I, M |
| 180 |  | A, D, G, I, M |
| 181 |  | A, D, G, I, M |
| 182 |  | A, D, G, I, M |
| 183 |  | A, D, G, I, M |
| 184 |  | A, D, G, I, M |
| 185 |  | A, D, G, I, M |
| 186 | 869.3 | A, D, I, M |
| 187 | 842.4 | A, D, I, M |
| 188 | 842.1 | A, D, I, M |
| 189 | 902.1 | A, D, I, M |
| 190 | 909.1 | A, D, I, M |
| 191 | 948.4 | A, D, G, I, M |
| 192 | 968.4 | A, D, G, I, M |
| 193 | 861.4 | A, D, I, M |

TABLE 1X-continued

| Compound No. | LC-MS (m/z) | Experimental Protocol |
|---|---|---|
| 194 | 857.4 | A, D, I, M |
| 195 | 888.4 | A, D, I, M |
| 196 | 702.4 | A, D, I, M |
| 197 |  | A, D, I, M |
| 198 |  | A, D, I, M |
| 199 |  | A, D, I, M |
| 200 |  | A, D, I, M |
| 201 |  | A, D, I, M |
| 202 |  | A, D, I, M |
| 203 |  | A, D, I, M |
| 204 |  | A, D, I, M |
| 205 |  | A, D, I, M |
| 206 | 967.2 | A, D, G, I, M |
| 207 | 948.2 | A, D, G, I, M |
| 208 | 948.2 | A, D, G, I, M |
| 209 |  | A, D, G, I, M |
| 210 |  | A, D, I, M |
| 211 |  | A, D, I, M |
| 212 |  | A, D, I, M |
| 213 |  | A, D, I, M |
| 214 |  | A, D, I, M |
| 215 |  | A, D, I, M |
| 216 | 900.4 | A, D, I, M |
| 217 |  | A, D, I, M |
| 218 |  | A, C, D, I, M |
| 219 |  | A, D, I, M |
| 220 |  | A, D, I, M |
| 221 | 893.1 | A, B, D, I, M |
| 222 | 915.2 | A, B, D, I, M |
| 223 | 891.1 | A, D, I, M |
| 224 |  | A, D, I, M |
| 225 |  | A, D, I, M |
| 226 |  | A, D, I, M |
| 227 |  | A, D, I, M |
| 228 |  | A, D, I, M |
| 229 | 857.4 | A, D, I, M |
| 230 | 870.4 | A, D, I, M |
| 231 |  | A, D, I, M |
| 232 | 886.2 | A, B, D, I, M |
| 232 | 886.2 | A, B, D, I, M |
| 233 |  | A, C, D, I, M |
| 234 |  | A, D, I, M |
| 235 |  | A, D, G, I, M |
| 236 |  | A, D, I, M |
| 237 | 952.0 | A, D, I, M |
| 238 |  | A, D, I, M |
| 239 | 890.2 | A, D, I, M |
| 240 |  | A, D, I, M |
| 241 |  | A, D, I, M |
| 242 |  | A, D, I, M |
| 243 |  | A, D, G, I, M |
| 244 | 999.3 | A, D, G, I, M |
| 245 |  | A, D, G, I, M |
| 246 |  | A, D, I, M |
| 247 |  | A, D, I, M |
| 248 |  | A, D, G, I, M |
| 249 |  | A, D, G, I, M |
| 250 | 900.2 | A, D, I, M |
| 251 | 886.1 | A, D, I, M |
| 252 |  | A, D, I, M |
| 253 |  | A, D, I, M |
| 254 |  | A, D, I, M |
| 255 | 998.4 | A, D, I, M |
| 256 | 948.6 | A, D, G, I, M |
| 257 | 978.6 | A, D, G, I, M |
| 258 | 1008.6 | A, D, G, I, M |
| 259 | 1032.6 | A, D, G, I, M |
| 260 | 998.4 | A, D, I, M |
| 261 | 978.4 | A, D, G, I, M |
| 262 | 1032.4 | A, D, G, I, M |
| 263 | 886.6 | A, D, I, M |
| 264 | 886.6 | A, D, I, M |
| 265 | 976.6 | A, D, G, I, M |
| 266 | 1000.6 | A, D, G, I, M |
| 267 | 984.5 | A, D, G, I, M |
| 268 | 976.6 | A, D, G, I, M |
| 269 | 1012.6 | A, D, G, I, M |
| 270 |  | A, C, D, G, I, M |
| 270 |  | A, C, D, I, M |
| 271 |  | A, D, G, I, M |
| 272 |  | A, D, G, I, M |
| 273 | 1005.3 | A, D, G, I, M |
| 274 |  | A, D, I, M |
| 275 |  | A, D, I, M |
| 276 |  | A, D, G, I, M |
| 277 |  | A, D, I, M |
| 278 |  | A, D, I, M |
| 279 |  | A, D, I, M |
| 280 | 898.1 | A, D, I, M |
| 281 |  | A, D, I, M |
| 282 |  | A, D, I, M |
| 283 |  | A, D, I, M |
| 284 |  | A, D, I, M |
| 285 |  | A, D, I, M |
| 286 |  | A, D, G, I, M |
| 287 |  | A, D, G, I, M |
| 288 |  | A, D, I, M |
| 289 |  | A, D, I, M |
| 290 |  | A, D, I, M |
| 291 |  | A, D, I, M |
| 292 |  | A, D, G, I, M |
| 293 | 949.2 | A, D, G, I, M |
| 294 |  | A, D, G, I, M |
| 295 |  | A, D, I, M |
| 296 |  | A, D, I, M |
| 297 |  | A, D, G, I, M |
| 298 | 1012.6 | A, D, G, I, M |
| 299 | 1005.4 | A, D, G, I, M |
| 300 | 915.2 | A, B, D, I, M |
| 301 | 915.2 | A, B, D, I, M |
| 302 | 893.2 | A, B, D, I, M |
| 303 | 1047.3 | A, B, D, I, M |
| 304 | 898.2 | A, B, D, I, M |
| 305 | 898.2 | A, B, D, I, M |
| 306 |  | A, D, G, I, M |
| 307 |  | A, D, I, M |
| 308 |  | A, B, D, I, M |
| 309 | 916.2 | A, B, D, I, M |
| 310 | 916.2 | A, B, D, I, M |
| 311 | 900.2 | A, B, D, I, M |
| 312 | 904.2 | A, B, D, I, M |
| 313 | 918.2 | A, B, D, I, M |
| 314 | 954.1 | A, B, D, I, M |
| 315 | 968.1 | A, B, D, I, M |
| 316 | 929.2 | A, B, D, I, M |
| 317 |  | A, D, G, I, M |
| 318 | 999.4 | A, D, G, I, M |
| 319 | 808.6 | A, D, I, M |
| 320 | 917.4 | A, D, G, I, M |
| 321 | 1032.4 | A, D, G, I, M |
| 322 | 978.5 | A, D, G, I, M |
| 323 |  | A, B, D, G, I, M |
| 324 |  | A, D, I, M |
| 325 | 914.3 | A, B, D, I, M |
| 326 | 928.2 | A, B, D, I, M |
| 327 | 870.2 | A, B, D, I, M |
| 328 | 912.2 | A, B, D, I, M |
| 329 | 900.4 | A, B, D, I, M |
| 330 | 942.5 | A, B, D, I, M |
| 331 | 852.5 | A, B, D, I, M |
| 332 | 884.6 | A, B, D, I, M |
| 333 | 867.2 | A, D, I, M |
| 334 | 900.4 | A, B, D, I, M |
| 335 | 884.5 | A, B, D, I, M |
| 336 |  | A, D, I, M |
| 337 |  | A, D, G, I, M |
| 338 |  | A, D, G, I, M |
| 339 |  | A, D, G, I, M |
| 340 |  | A, D, G, I, M |
| 341 |  | A, D, G, I, M |
| 341 |  | A, D, G, I, M |
| 342 |  | A, D, I, M |
| 343 |  | A, D, G, I, M |
| 344 |  | A, D, G, I, M |

TABLE 1X-continued

| Compound No. | LC-MS (m/z) | Experimental Protocol |
|---|---|---|
| 345 | | A, D, G, I, M |
| 346 | | A, D, G, I, M |
| 347 | | A, D, G, I, M |
| 348 | | A, D, G, I, M |
| 349 | | A, D, G, I, M |
| 350 | | A, D, G, I, M |
| 351 | | A, D, G, I, M |
| 352 | | A, D, G, I, M |
| 353 | | A, D, G, I, M |
| 354 | | A, D, G, I, M |
| 355 | | A, D, G, I, M |
| 356 | | A, D, G, I, M, L, M |
| 357 | | A, D, I, M |
| 358 | | A, D, I, M |
| 359 | | A, D, I, M |
| 360 | | A, D, I, M |
| 361 | | A, D, I, M |
| 362 | | A, D, G, I, M |
| 363 | | A, D, G, I, M |
| 364 | | A, D, G, I, M |
| 365 | | A, D, G, I, M |
| 366 | | A, D, G, I, M |
| 367 | | A, D, G, I, M |
| 368 | | A, D, G, I, M |
| 369 | | A, D, G, I, M |
| 370 | | A, D, G, I, M |
| 371 | | A, D, G, I, M |
| 372 | | A, D, G, I, M |
| 373 | | A, D, G, I, M |
| 374 | | A, D, G, I, M |
| 375 | | A, D, G, I, M |
| 376 | | A, D, G, I, M |
| 377 | | A, D, G, I, M |
| 378 | | A, D, G, I, M |
| 379 | | A, D, G, I, M |
| 380 | | A, D, G, I, M |
| 381 | | A, D, G, I, M |
| 382 | | A, D, G, I, M |
| 383 | | A, D, G, I, M |
| 384 | | A, D, G, I, M |
| 385 | | A, D, G, I, M |
| 386 | | A, D, G, I, M |
| 387 | | A, B, D, I, M |
| 388 | | A, B, D, G, I, M |
| 389 | 985.2 | A, C, D, G, I, M |
| 398 | | A, D, I, M |
| 399 | | A, D, I, M |
| 400 | | A, D, I, M |
| 401 | | A, D, I, M |
| 402 | | A, D, I, M |
| 403 | | A, D, I, M |
| 404 | | A, D, I, M |
| 405 | | A, E, Fa, Jb, I, M |
| 406 | | A, E, Fa, Jb, I, M |
| 407 | | A, D, I, M |
| 408 | | A, D, I, M |
| 409 | | A, D, I, M |
| 410 | | A, D, I, M |
| 411 | | A, E, Fa, Jb, I, M |
| 412 | | A, D, I, M |
| 413 | | A, E, Fa, Jb, I, M |
| 414 | | A, E, Fa, Jb, I, M |
| 415 | | A, D, I, M |
| 416 | | A, D, I, M |
| 417 | | A, D, I, M |
| 418 | | A, D, I, M |
| 419 | | A, D, I, M |
| 420 | | A, D, I, M |
| 421 | | A, D, I, M |
| 422 | | A, D, I, M |
| 423 | | A, D, I, M |
| 424 | | A, D, I, M |
| 425 | | A, D, I, M |
| 426 | | A, D, I, M |
| 427 | | A, D, I, M |
| 428 | | A, D, I, M |
| 429 | | A, D, I, M |
| 430 | | A, D, I, M |
| 431 | | A, D, I, M |
| 432 | | A, D, I, M |
| 433 | | A, D, G, I, M |
| 434 | | A, D, G, I, M |
| 435 | | A, D, G, I, M |
| 436 | | A, D, G, I, M |
| 437 | | A, D, G, I, M |
| 438 | | A, D, G, I, M |
| 439 | | A, D, I, M |
| 440 | | A, D, I, M |
| 441 | | A, D, I, M |
| 442 | | A, B, D, I, M |
| 443 | | A, D, I, M |
| 444 | | A, D, I, M |
| 445 | | A, D, I, M |
| 446 | | A, D, I, M |
| 447 | | A, D, I, M |
| 448 | | A, D, I, M |
| 449 | | A, D, I, M |
| 450 | | A, D, I, M |
| 451 | | A, C, D, I, M |
| 452 | | A, C, D, I, M |
| 453 | | A, C, D, I, M |
| 454 | | A, C, D, I, M |
| 455 | | A, C, D, I, M |

TABLE 2A

| Compound No. | $R^1$ | $R^2$ | $R^3$ | $R^4$ | $R^5$ |
|---|---|---|---|---|---|
| 390 | H | H | $CH_3$ | H | C(O)—NH-tert-Butyl |
| 391 | H | H | $CH_3$ | H | C(O)—NH-tert-Butyl |
| 392 | H | H | $CH_3$ | H | C(O)—NH-tert-Butyl |
| 393 | H | H | $CH_3$ | H | C(O)—NH-tert-Butyl |
| 394 | H | H | $CH_3$ | H | C(O)—NH-tert-Butyl |
| 395 | H | H | $CH_3$ | H | C(O)—NH-tert-Butyl |
| 396 | H | H | $CH_3$ | H | C(O)—NH-tert-Butyl |
| 397 | H | H | $CH_3$ | H | C(O)—NH-tert-Butyl |
| 457 | H | H | $CH_3$ | H | C(O)—NH-tert-Butyl |
| 458 | H | H | $CH_3$ | H | C(O)—NH-tert-Butyl |
| 459 | H | H | $CH_3$ | H | C(O)—NH-tert-Butyl |
| 460 | H | H | $CH_3$ | H | C(O)—NH-tert-Butyl |
| 461 | H | H | $CH_3$ | H | C(O)—NH-tert-Butyl |
| 462 | H | H | $CH_3$ | H | C(O)—NH-tert-Butyl |
| 463 | H | H | $CH_3$ | H | C(O)—NH-tert-Butyl |
| 464 | H | H | $CH_3$ | H | C(O)—NH-tert-Butyl |
| 465 | H | H | $CH_3$ | H | C(O)—NH-tert-Butyl |
| 466 | H | H | $CH_3$ | H | C(O)—NH-tert-Butyl |
| 467 | H | H | $CH_3$ | H | C(O)—NH-tert-Butyl |
| 468 | H | H | $CH_3$ | H | C(O)—NH-tert-Butyl |
| 469 | H | H | $CH_3$ | H | C(O)—NH-tert-Butyl |
| 470 | H | H | $CH_3$ | H | C(O)—NH-tert-Butyl |
| 471 | H | H | $CH_3$ | H | C(O)—NH-tert-Butyl |
| 472 | H | H | $CH_3$ | H | C(O)—NH-tert-Butyl |
| 473 | H | H | $CH_3$ | H | C(O)—NH-tert-Butyl |
| 474 | H | H | $CH_3$ | H | C(O)—NH-tert-Butyl |
| 475 | H | H | $CH_3$ | H | C(O)—NH-tert-Butyl |
| 476 | H | H | $CH_3$ | H | C(O)—NH-tert-Butyl |
| 477 | H | H | $CH_3$ | H | C(O)—NH-tert-Butyl |
| 478 | H | H | $CH_3$ | H | C(O)—NH-tert-Butyl |
| 479 | H | H | $CH_3$ | H | C(O)—NH-tert-Butyl |
| 480 | H | H | $CH_3$ | H | C(O)—NH-tert-Butyl |
| 481 | H | H | $CH_3$ | H | C(O)—NH-tert-Butyl |
| 482 | H | H | $CH_3$ | H | C(O)—NH-tert-Butyl |
| 483 | H | H | $CH_3$ | H | C(O)—NH-tert-Butyl |
| 484 | H | H | $CH_3$ | H | C(O)—NH-tert-Butyl |
| 485 | H | H | $CH_3$ | H | C(O)—NH-tert-Butyl |
| 486 | H | H | $CH_3$ | H | C(O)—NH-tert-Butyl |
| 487 | H | H | $CH_3$ | H | C(O)—NH-tert-Butyl |
| 488 | H | H | $CH_3$ | H | C(O)—NH-tert-Butyl |
| 489 | H | H | $CH_3$ | H | C(O)—NH-tert-Butyl |
| 490 | H | H | $CH_3$ | H | C(O)—NH-tert-Butyl |

TABLE 2A-continued

| Compound No. | R¹ | R² | R³ | R⁴ | R⁵ |
|---|---|---|---|---|---|
| 491 | H | H | CH₃ | H | C(O)—NH-tert-Butyl |
| 492 | H | H | CH₃ | H | C(O)—NH-tert-Butyl |
| 493 | H | H | CH₃ | H | C(O)—NH-tert-Butyl |
| 494 | H | H | CH₃ | H | C(O)—NH-tert-Butyl |
| 495 | H | H | CH₃ | H | C(O)—NH-tert-Butyl |
| 496 | H | H | CH₃ | H | C(O)—NH-tert-Butyl |
| 497 | H | H | CH₃ | H | C(O)—NH-tert-Butyl |
| 498 | H | H | CH₃ | H | C(O)—NH-tert-Butyl |
| 499 | H | H | CH₃ | H | C(O)—NH-tert-Butyl |
| 500 | H | H | CH₃ | H | C(O)—NH-tert-Butyl |
| 501 | H | H | CH₃ | H | C(O)—NH-tert-Butyl |
| 502 | H | H | CH₃ | H | C(O)—NH-tert-Butyl |
| 503 | H | H | CH₃ | H | C(O)—NH-tert-Butyl |
| 504 | H | H | CH₃ | H | C(O)—NH-tert-Butyl |
| 505 | H | H | CH₃ | H | C(O)—NH-tert-Butyl |
| 506 | H | H | CH₃ | H | C(O)—NH-tert-Butyl |
| 507 | H | H | CH₃ | H | C(O)—NH-tert-Butyl |
| 508 | H | H | CH₃ | H | C(O)—NH-tert-Butyl |
| 509 | H | H | CH₃ | H | C(O)—NH-tert-Butyl |
| 510 | H | H | CH₃ | H | C(O)—NH-tert-Butyl |
| 511 | H | H | CH₃ | H | C(O)—NH-tert-Butyl |
| 512 | H | H | CH₃ | H | C(O)—NH-tert-Butyl |
| 513 | H | H | CH₃ | H | C(O)—NH-tert-Butyl |
| 514 | H | H | CH₃ | H | C(O)—NH-tert-Butyl |
| 515 | H | H | CH₃ | H | C(O)—NH-tert-Butyl |
| 516 | H | H | CH₃ | H | C(O)—NH-tert-Butyl |
| 517 | H | H | CH₃ | H | C(O)—NH-tert-Butyl |
| 518 | H | H | CH₃ | H | C(O)—NH-tert-Butyl |
| 519 | H | H | CH₃ | H | C(O)—NH-tert-Butyl |
| 520 | H | H | CH₃ | H | C(O)—NH-tert-Butyl |
| 521 | H | H | CH₃ | H | C(O)—NH-tert-Butyl |
| 522 | H | H | CH₃ | H | C(O)—NH-tert-Butyl |
| 523 | H | H | CH₃ | H | C(O)—NH-tert-Butyl |
| 524 | H | H | CH₃ | H | C(O)—NH-tert-Butyl |
| 525 | H | H | CH₃ | H | C(O)—NH-tert-Butyl |
| 526 | H | H | CH₃ | H | C(O)—NH-tert-Butyl |
| 527 | H | H | CH₃ | H | C(O)—NH-tert-Butyl |
| 528 | H | H | CH₃ | H | C(O)—NH-tert-Butyl |
| 529 | H | H | CH₃ | H | C(O)—NH-tert-Butyl |
| 530 | H | H | CH₃ | H | C(O)—NH-tert-Butyl |
| 531 | H | H | CH₃ | H | C(O)—NH-tert-Butyl |
| 532 | H | H | CH₃ | H | C(O)—NH-tert-Butyl |
| 533 | H | H | CH₃ | H | C(O)—NH-tert-Butyl |
| 534 | H | H | CH₃ | H | C(O)—NH-tert-Butyl |
| 535 | H | H | CH₃ | H | C(O)—NH-tert-Butyl |
| 536 | H | H | CH₃ | H | C(O)—NH-tert-Butyl |
| 537 | H | H | CH₃ | H | C(O)—NH-tert-Butyl |
| 538 | H | H | CH₃ | H | C(O)—NH-tert-Butyl |

TABLE 2B

| Compound No. | Seq. ID. No. | R⁶ | R⁷ | R⁸ | Xʸ | Xᶻ | X¹ | X² | X³ |
|---|---|---|---|---|---|---|---|---|---|
| 390 | 334 | PRO | PRO | H | | [3-aminomethyl-4-[4-(1-piperazinyl)-phenyl]-benzoic acid] | L | D | T |
| 391 | 334 | PRO | PRO | H | | [3-aminomethyl-4-[4-(1-piperazinyl)-phenyl]-benzoic acid] | L | D | T |
| 392 | 334 | PRO | PRO | H | | [3-aminomethyl-4-[4-(1-piperazinyl)-phenyl]-benzoic acid] | L | D | T |
| 393 | 31 | HYP | HYP | H | F | | L | D | T |
| 394 | 31 | HYP | HYP | H | F | | L | D | T |
| 395 | 31 | HYP | HYP | H | F | | L | D | T |
| 396 | 31 | HYP | HYP | H | F | | L | D | T |
| 397 | 31 | HYP | HYP | H | F | | L | D | T |
| 457 | 31 | HYP | HYP | H | F | | L | D | T |
| 458 | 334 | PRO | PRO | H | | [3-aminomethyl-4-[4-(1-piperazinyl)-phenyl]-benzoic acid] | L | D | T |
| 459 | 334 | PRO | PRO | H | | [3-aminomethyl-4-[4-(1-piperazinyl)-phenyl]-benzoic acid] | L | D | T |
| 460 | 334 | PRO | PRO | H | | [3-aminomethyl-4-[4-(1-piperazinyl)-phenyl]-benzoic acid] | L | D | T |
| 461 | 334 | PRO | PRO | H | | [3-aminomethyl-4-[4-(1-piperazinyl)-phenyl]-benzoic acid] | L | D | T |
| 462 | 334 | PRO | PRO | H | | [3-aminomethyl-4-[4-(1-piperazinyl)-phenyl]-benzoic acid] | L | D | T |
| 463 | 334 | PRO | PRO | H | | [3-aminomethyl-4-[4-(1-piperazinyl)-phenyl]-benzoic acid] | L | D | T |
| 464 | 334 | PRO | PRO | H | | [3-aminomethyl-4-[4-(1-piperazinyl)-phenyl]-benzoic acid] | L | D | T |
| 465 | 334 | PRO | PRO | H | | [3-aminomethyl-4-[4-(1-piperazinyl)-phenyl]-benzoic acid] | L | D | T |
| 466 | 334 | PRO | PRO | H | | [3-aminomethyl-4-[4-(1-piperazinyl)-phenyl]-benzoic acid] | L | D | T |
| 467 | 334 | PRO | PRO | H | | [3-aminomethyl-4-[4-(1-piperazinyl)-phenyl]-benzoic acid] | L | D | T |
| 468 | 334 | PRO | PRO | H | | [3-aminomethyl-4-[4-(1-piperazinyl)-phenyl]-benzoic acid] | L | D | T |
| 469 | 334 | PRO | PRO | H | | [3-aminomethyl-4-[4-(1-piperazinyl)-phenyl]-benzoic acid] | L | D | T |
| 470 | 334 | PRO | PRO | H | | [3-aminomethyl-4-[4-(1-piperazinyl)-phenyl]-benzoic acid] | L | D | T |
| 471 | 334 | PRO | PRO | H | | [3-aminomethyl-4-[4-(1-piperazinyl)-phenyl]-benzoic acid] | L | D | T |
| 472 | 334 | PRO | PRO | H | | [3-aminomethyl-4-[4-(1-piperazinyl)-phenyl]-benzoic acid] | L | D | T |
| 473 | 334 | PRO | PRO | H | | [3-aminomethyl-4-[4-(1-piperazinyl)-phenyl]-benzoic acid] | L | D | T |
| 474 | 334 | PRO | PRO | H | | [3-aminomethyl-4-[4-(1-piperazinyl)-phenyl]-benzoic acid] | L | D | T |
| 475 | 334 | PRO | PRO | H | | [3-aminomethyl-4-[4-(1-piperazinyl)-phenyl]-benzoic acid] | L | D | T |
| 476 | 334 | PRO | PRO | H | | [3-aminomethyl-4-[4-(1-piperazinyl)-phenyl]-benzoic acid] | L | D | T |
| 477 | 334 | PRO | PRO | H | | [3-aminomethyl-4-[4-(1-piperazinyl)-phenyl]-benzoic acid] | L | D | T |
| 478 | 334 | PRO | PRO | H | | [3-aminomethyl-4-[4-(1-piperazinyl)-phenyl]-benzoic acid] | L | D | T |
| 479 | 334 | PRO | PRO | H | | [3-aminomethyl-4-[4-(1-piperazinyl)-phenyl]-benzoic acid] | L | D | T |
| 480 | 334 | PRO | PRO | H | | [3-aminomethyl-4-[4-(1-piperazinyl)-phenyl]-benzoic acid] | L | D | T |
| 481 | 334 | PRO | PRO | H | | [3-aminomethyl-4-[4-(1-piperazinyl)-phenyl]-benzoic acid] | L | D | T |
| 482 | 334 | PRO | PRO | H | | [3-aminomethyl-4-[4-(1-piperazinyl)-phenyl]-benzoic acid] | L | D | T |
| 483 | 334 | PRO | PRO | H | | [3-aminomethyl-4-[4-(1-piperazinyl)-phenyl]-benzoic acid] | L | D | T |
| 484 | 334 | PRO | PRO | H | | [3-aminomethyl-4-[4-(1-piperazinyl)-phenyl]-benzoic acid] | L | D | T |
| 485 | 334 | PRO | PRO | H | | [3-aminomethyl-4-[4-(1-piperazinyl)-phenyl]-benzoic acid] | L | D | T |
| 486 | 334 | PRO | PRO | H | | [3-aminomethyl-4-[4-(1-piperazinyl)-phenyl]-benzoic acid] | L | D | T |
| 487 | 334 | PRO | PRO | H | | [3-aminomethyl-4-[4-(1-piperazinyl)-phenyl]-benzoic acid] | L | D | T |
| 488 | 334 | PRO | PRO | H | | [3-aminomethyl-4-[4-(1-piperazinyl)-phenyl]-benzoic acid] | L | D | T |
| 489 | 334 | PRO | PRO | H | | [3-aminomethyl-4-[4-(1-piperazinyl)-phenyl]-benzoic acid] | L | D | T |
| 490 | 334 | PRO | PRO | H | | [3-aminomethyl-4-[4-(1-piperazinyl)-phenyl]-benzoic acid] | L | D | T |
| 491 | 334 | PRO | PRO | H | | [3-aminomethyl-4-[4-(1-piperazinyl)-phenyl]-benzoic acid] | L | D | T |

TABLE 2B-continued

| Compound No. | Seq. ID. No. | R6 | R7 | R8 | Xy | Xz | X1 | X2 | X3 |
|---|---|---|---|---|---|---|---|---|---|
| 492 | 334 | PRO | PRO | H | [3-aminomethyl-4-[4-(1-piperazinyl)-phenyl]-benzoic acid] | | L | D | T |
| 493 | 334 | PRO | PRO | H | [3-aminomethyl-4-[4-(1-piperazinyl)-phenyl]-benzoic acid] | | L | D | T |
| 494 | 334 | PRO | PRO | H | [3-aminomethyl-4-[4-(1-piperazinyl)-phenyl]-benzoic acid] | | L | D | T |
| 495 | 334 | PRO | PRO | H | [3-aminomethyl-4-[4-(1-piperazinyl)-phenyl]-benzoic acid] | | L | D | T |
| 496 | 334 | PRO | PRO | H | [3-aminomethyl-4-[4-(1-piperazinyl)-phenyl]-benzoic acid] | | L | D | T |
| 497 | 334 | PRO | PRO | H | [3-aminomethyl-4-[4-(1-piperazinyl)-phenyl]-benzoic acid] | | L | D | T |
| 498 | 334 | PRO | PRO | H | [3-aminomethyl-4-[4-(1-piperazinyl)-phenyl]-benzoic acid] | | L | D | T |
| 499 | 334 | PRO | PRO | H | [3-aminomethyl-4-[4-(1-piperazinyl)-phenyl]-benzoic acid] | | L | D | T |
| 500 | 334 | PRO | PRO | H | [3-aminomethyl-4-[4-(1-piperazinyl)-phenyl]-benzoic acid] | | L | D | T |
| 501 | 334 | PRO | PRO | H | [3-aminomethyl-4-[4-(1-piperazinyl)-phenyl]-benzoic acid] | | L | D | T |
| 502 | 334 | PRO | PRO | H | [3-aminomethyl-4-[4-(1-piperazinyl)-phenyl]-benzoic acid] | | L | D | T |
| 503 | 334 | PRO | PRO | H | [3-aminomethyl-4-[4-(1-piperazinyl)-phenyl]-benzoic acid] | | L | D | T |
| 504 | 334 | PRO | PRO | H | [3-aminomethyl-4-[4-(1-piperazinyl)-phenyl]-benzoic acid] | | L | D | T |
| 505 | 334 | PRO | PRO | H | [3-aminomethyl-4-[4-(1-piperazinyl)-phenyl]-benzoic acid] | | L | D | T |
| 506 | 334 | PRO | PRO | H | [3-aminomethyl-4-[4-(1-piperazinyl)-phenyl]-benzoic acid] | | L | D | T |
| 507 | 334 | PRO | PRO | H | [3-aminomethyl-4-[4-(1-piperazinyl)-phenyl]-benzoic acid] | | L | D | T |
| 508 | 334 | PRO | PRO | H | [3-aminomethyl-4-[4-(1-piperazinyl)-phenyl]-benzoic acid] | | L | D | T |
| 509 | 334 | PRO | PRO | H | [3-aminomethyl-4-[4-(1-piperazinyl)-phenyl]-benzoic acid] | | L | D | T |
| 510 | 334 | PRO | PRO | H | [3-aminomethyl-4-[4-(1-piperazinyl)-phenyl]-benzoic acid] | | L | D | T |
| 511 | 334 | PRO | PRO | H | [3-aminomethyl-4-[4-(1-piperazinyl)-phenyl]-benzoic acid] | | L | D | T |
| 512 | 334 | PRO | PRO | H | [3-aminomethyl-4-[4-(1-piperazinyl)-phenyl]-benzoic acid] | | L | D | T |
| 513 | 334 | PRO | PRO | H | [3-aminomethyl-4-[4-(1-piperazinyl)-phenyl]-benzoic acid] | | L | D | T |
| 514 | 334 | PRO | PRO | H | [3-aminomethyl-4-[4-(1-piperazinyl)-phenyl]-benzoic acid] | | L | D | T |
| 515 | 334 | PRO | PRO | H | [3-aminomethyl-4-[4-(1-piperazinyl)-phenyl]-benzoic acid] | | L | D | T |
| 516 | 334 | PRO | PRO | H | [3-aminomethyl-4-[4-(1-piperazinyl)-phenyl]-benzoic acid] | | L | D | T |
| 517 | 334 | PRO | PRO | H | [3-aminomethyl-4-[4-(1-piperazinyl)-phenyl]-benzoic acid] | | L | D | T |
| 518 | 334 | PRO | PRO | H | [3-aminomethyl-4-[4-(1-piperazinyl)-phenyl]-benzoic acid] | | L | D | T |
| 519 | 334 | PRO | PRO | H | [3-aminomethyl-4-[4-(1-piperazinyl)-phenyl]-benzoic acid] | | L | D | T |
| 520 | 334 | PRO | PRO | H | [3-aminomethyl-4-[4-(1-piperazinyl)-phenyl]-benzoic acid] | | L | D | T |
| 521 | 334 | PRO | PRO | H | [3-aminomethyl-4-[4-(1-piperazinyl)-phenyl]-benzoic acid] | | L | D | T |
| 522 | 127 | PRO | PRO | H | (4-aminomethyl-Phe) | dPip | L | D | T |
| 523 | 127 | PRO | PRO | H | (4-aminomethyl-Phe) | dPip | L | D | T |
| 524 | 127 | PRO | PRO | H | (4-aminomethyl-Phe) | dPip | L | D | T |
| 525 | 127 | PRO | PRO | H | (4-aminomethyl-Phe) | dPip | L | D | T |
| 526 | 127 | PRO | PRO | H | (4-aminomethyl-Phe) | dPip | L | D | T |
| 527 | 141 | PRO | PRO | H | (3-aminomethyl-Phe) | dTic | L | D | T |
| 528 | 141 | PRO | PRO | H | (3-aminomethyl-Phe) | dTic | L | D | T |
| 529 | 141 | PRO | PRO | H | (3-aminomethyl-Phe) | dTic | L | D | T |
| 530 | 427 | PRO | PRO | H | K | MebetaHomoLys | L | D | T |
| 531 | 427 | PRO | PRO | H | K | MebetaHomoLys | L | D | T |
| 532 | 427 | PRO | PRO | H | K | MebetaHomoLys | L | D | T |
| 533 | 427 | PRO | PRO | H | K | MebetaHomoLys | L | D | T |
| 534 | 427 | PRO | PRO | H | K | MebetaHomoLys | L | D | T |
| 535 | 427 | PRO | PRO | H | K | MebetaHomoLys | L | D | T |
| 536 | 427 | PRO | PRO | H | K | MebetaHomoLys | L | D | T |
| 537 | 427 | PRO | PRO | H | K | MebetaHomoLys | L | D | T |
| 538 | 427 | PRO | PRO | H | K | MebetaHomoLys | L | D | T |

TABLE 2C

| Compound No. | MADCAM FACS a4b7 Th mem (nM) | RPMI8866 Adhesion a4b7/MAdCAM IC50 (nM) | Ramos Adhesion a4b1/VCAM $IC_{50}$ (nM) | Ratio Ramos/RPMI | ELISA a4b7 Assay $IC_{50}$ (nM) | ELISA a4b1 Assay $IC_{50}$ (nM) | ELISA Assay Ratio b1/b7 | VCAM FACS a4 + b7 − Th mem (nM) |
|---|---|---|---|---|---|---|---|---|
| 390 | 90 | 13 | 857 | 66 | 8.3 | 2.0 | 0.2 | |
| 391 | | 22 | | | | | | |
| 392 | Unclear | 28 | 1845 | 65 | 18 | 6.3 | 0.3 | |
| 393 | | 635 | | | | | | |
| 394 | | 860 | | | | | | |
| 395 | | 1521 | | | | | | |
| 396 | | 1953 | | | | | | |
| 397 | | 2061 | | | | | | |
| 457 | | 2163 | | | | | | |
| 458 | 66 | 42 | 990 | 23 | 6.4 | 1.5 | 0.2 | |
| 459 | | 33 | | | | | | |
| 460 | 107 | 62 | 1848 | 30 | 14 | 1.0 | 0.1 | |
| 461 | 93 | 39 | 1224 | 31 | 18 | 7.9 | 0.4 | |
| 462 | 68 | 42 | 350 | 8 | | | | |
| 463 | | 21 | | | | | | |
| 464 | 232 | 19 | 1547 | 80 | 61 | 22 | 0.4 | |
| 465 | 132 | 22 | | | | | | |
| 466 | 164 | 97 | 3244 | 34 | 14 | 4.2 | 0.3 | |

TABLE 2C-continued

| Compound No. | MADCAM FACS a4b7 Th mem (nM) | RPMI8866 Adhesion a4b7/MAdCAM IC50 (nM) | Ramos Adhesion a4b1/VCAM IC$_{50}$ (nM) | Ratio Ramos/ RPMI | ELISA a4b7 Assay IC$_{50}$ (nM) | ELISA a4b1 Assay IC$_{50}$ (nM) | ELISA Assay Ratio b1/b7 | VCAM FACS a4 + b7 – Th mem (nM) |
|---|---|---|---|---|---|---|---|---|
| 467 | | 43 | 876 | 20 | 8.6 | 1.0 | 0.1 | |
| 468 | | 13 | 677 | 51 | 32 | 10 | 0.3 | |
| 469 | | 5 | 44 | | 36 | 10 | 0.3 | |
| 470 | 81 | 17 | 1110 | 66 | 5.4 | 1.0 | 0.2 | |
| 471 | 46 | 29 | | | | | | |
| 472 | | 80 | | | | | | |
| 473 | | 63 | | | | | | |
| 474 | 74 | 14 | 1297 | 95 | 19 | 7.1 | 0.4 | |
| 475 | 74 | 18 | 395 | 22 | 11 | 1.1 | 0.1 | |
| 476 | | 32 | | | | | | |
| 477 | 124 | 21 | | | | | | |
| 478 | | 34 | | | | | | |
| 479 | | | | | | | | |
| 480 | 92 | 21 | 1012 | 49 | 16 | 4.9 | 0.3 | |
| 481 | 67 | 36 | 940 | 26 | 7.1 | 1.6 | 0.2 | |
| 482 | 30 | 26 | 825 | 31 | 4.7 | 1.5 | 0.3 | 4000 |
| 483 | | 29 | | | | | | |
| 484 | 45 | 14 | 576 | 41 | 5.6 | 1.2 | 0.2 | |
| 485 | | 30 | | | | | | |
| 486 | | 42 | | | | | | |
| 487 | | 65 | | | | | | |
| 488 | | 34 | | | | | | |
| 489 | | 40 | | | | | | |
| 490 | | 41 | | | | | | |
| 491 | | 23 | | | | | | |
| 492 | 104 | 25 | | | | | | |
| 493 | 94 | 45 | 1254 | 28 | 12 | 3.5 | 0.3 | |
| 494 | 128 | 50 | 161 | 3 | 9.4 | 1.9 | 0.2 | |
| 495 | | 30 | | | | | | |
| 496 | | 41 | | | | | | |
| 497 | | 25 | | | | | | |
| 498 | 517 | 36 | 1360 | 38 | 12 | 3.0 | 0.3 | 4000 |
| 499 | 41 | 42 | 878 | 21 | 17 | 3.1 | 0.2 | |
| 500 | 55 | 32 | 1001 | 31 | 12 | 9.9 | 0.8 | |
| 501 | | 38 | | | | | | |
| 502 | Unclear, 148, 1000 | 102 | 779 | 8 | | | | |
| 503 | 250 | 45 | | | | | | |
| 504 | 301 | 42 | | | | | | |
| 505 | | 59 | 1775 | 30 | 19 | 6.6 | 0.3 | |
| 506 | | 289 | 11004 | 38 | | | | |
| 507 | 189 | 31 | 1928 | 62 | 18 | 4.4 | 0.2 | |
| 508 | | 46 | | | | | | |
| 509 | | 31 | | | | | | |
| 510 | | 87 | | | | | | |
| 511 | 182 | 30 | 3989 | 133 | 11 | 7.2 | 0.6 | 20000 |
| 512 | 64 | 25 | | | | | | |
| 513 | | 31 | | | | | | |
| 514 | | 95 | | | | | | |
| 515 | | 34 | | | | | | |
| 516 | | 98 | | | | | | |
| 517 | 43 | 10 | 211 | 21 | 7.5 | 2.1 | 0.3 | 607 |
| 518 | 189 | 18 | 947 | 53 | 36 | 8.7 | 0.2 | |
| 519 | | 27 | | | | | | |
| 520 | 1.2 | 6 | 82 | 14 | 6.3 | 1.2 | 0.2 | |
| 521 | 53 | 10 | 101 | 10 | 9.4 | 1.5 | 0.2 | |
| 522 | | 372 | | | | | | |
| 523 | | 434 | | | | | | |
| 524 | | 447 | | | | | | |
| 525 | | 472 | | | | | | |
| 526 | | 611 | | | | | | |
| 527 | 126 | 43 | 766 | 18 | 4.6 | 1.1 | 0.2 | |
| 528 | | 47 | | | | | | |
| 529 | | 47 | | | | | | |
| 530 | 33 | 15 | 10557 | 704 | 5.3 | 5.1 | 1.0 | >4000 |
| 531 | | 23 | | | | | | |
| 532 | 57 | 19 | 7145 | 370 | 6.1 | 6.9 | 1.1 | |
| 533 | 46 | 17 | 4235 | 257 | 5 | 6.2 | 1.2 | |
| 534 | 38 | 23 | 10839 | 471 | 12 | 10 | 0.9 | >4000 |
| 535 | 77 | 15 | 9507 | 634 | 8.6 | 9.7 | 0.9 | |
| 536 | 75 | 16 | 7817 | 479 | 9.5 | 8.9 | 0.9 | |
| 537 | | 19 | | | 6.5 | 2.5 | 0.4 | |
| 538 | | 13 | 7650 | | 10 | 13 | 1.3 | |

TABLE 2X

| Compound No. | LC-MS (m/z) | Reagent employed to form multimer | Linkage type(s) | Multimer type |
|---|---|---|---|---|
| 390 | 925.7 | Diglycolic acid | amide | homodimer |
| 391 | 939.0 | Pimelic acid | amide | homodimer |
| 392 | 973.6 | Dodecanedioic acid | amide | homodimer |
| 393 | 808.4 | Pimelic acid | ester | homodimer |
| 394 | 825.4 | 1,4-Phenylenediacetic acid | ester | homodimer |
| 395 | 822.4 | Azelaic acid | ester | homodimer |
| 396 | 815.4 | Suberic acid | ester | homodimer |
| 397 | 829.5 | Sebacic acid | ester | homodimer |
| 457 | 843.5 | Dodecanedioic acid | ester | homodimer |
| 458 | 938.0 | (±)-cis-Cyclopentane-1,2-dicarboxylic acid) | amide | homodimer |
| 459 | 923.6 | 1,1-Cyclopropanedicarboxylic acid | amide | homodimer |
| 460 | 971.2 | 1,3-Adamantanedicarboxylic acid | amide | homodimer |
| 461 | 961.6 | 1,3-Dihydroindene-2,2-dicarboxylic acid | amide | homodimer |
| 462 | 955.6 | 1,3-Phenylenediacetic acid | amide | homodimer |
| 463 | 967.0 | 1,4-Naphtalenedicarboxylic acid | amide | homodimer |
| 464 | 1004.2 | 2-Fluoro-5'-methoxybiphenyl-3',4-dicarboxylic acid | amide | homodimer |
| 465 | 980.6 | 2,2'-Bipyridine-4,4'-dicarboxylic | amide | homodimer |
| 466 | 980.6 | 2,2'-Bipyridine-5,6'-dicarboxylic acid | amide | homodimer |
| 467 | 943.2 | 2,3-Pyrazinedicarboxylic acid | amide | homodimer |
| 468 | 937.0 | 2,4-Dichloro-5-nitro-pyrimidine | amine | homodimer |
| 469 | 1017.6 | 2-5-Diphenylbenzene-1,4-dicarboxylic acid | amide | homodimer |
| 470 | 944.8 | 2,5-Thiophenedicarboxylic acid | amide | homodimer |
| 471 | 966.6 | 2,6-Naphthalenedicarboxylic acid | amide | homodimer |
| 472 | 942.6 | 2,6-Pyridinedicarboxylic acid | amide | homodimer |
| 473 | 947.8 | 3,3'-Thiodipropionic acid | amide | homodimer |
| 474 | 979.6 | 4,4-Dibenzoic acid | amide | homodimer |
| 475 | 997.8 | 4,4'-Difluorobiphenyl-2,2'-dicarboxylic acid | amide | homodimer |
| 476 | 944.2 | 4,5-Dicarboxy-1-methyl-1H-imidazole | amide | homodimer |
| 477 | 976.2 | 5-(Trifluoromethyl)benzene-1,3-dicarboxylic acid | amide | homodimer |
| 478 | 979.6 | Biphenyl-2,3'-dicarboxylic acid | amide | homodimer |
| 479 | 979.6 | Biphenyl-3,3'-dicarboxylic acid | amide | homodimer |
| 480 | 976.6 | Biphenyl-3,4'-dicarboxylic acid | amide | homodimer |
| 481 | 896.6 | Chloroacetyl chloride | amide/amine | homodimer |
| 482 | 903.6 | Acryloyl chloride | amide/amine | homodimer |
| 483 | 910.9 | Malonic acid | amide | homodimer |
| 484 | 917.9 | Succinic acid | amide | homodimer |
| 485 | 924.6 | Glutaric acid | amide | homodimer |
| 486 | 931.6 | Adipic | amide | homodimer |
| 487 | 945.9 | Suberic acid | amide | homodimer |
| 488 | 952.6 | Azelaic acid | amide | homodimer |
| 489 | 959.6 | Sebacic acid | amide | homodimer |
| 490 | 950.0 | Chelidamic acid | amide | homodimer |
| 491 | 945.0 | Cis-1,2-cyclohexanedicarboxylic acid | amide | homodimer |
| 492 | 925.6 | Aspartic acid | amide | homodimer |
| 493 | 925.6 | D-Aspartic acid | amide | homodimer |
| 494 | 932.2 | Glutamic acid | amide | homodimer |
| 495 | 932.2 | D-Glutamic acid | amide | homodimer |
| 496 | 949.0 | Homophthalic acid | amide | homodimer |
| 497 | 941.6 | Isophthalic acid | amide | homodimer |
| 498 | 1201.0 | Lys(Cbz)-C7-Lys(Cbz) | amide | homodimer |
| 499 | 927.8 | α,α'-Dibromo-m-xylene | amide | homodimer |
| 500 | 927.8 | α,α'-Dibromo-p-xylene | amide | homodimer |
| 501 | 932.6 | Methyliminodiacetic acid | amide | homodimer |
| 502 | 1053.2 | Pamoic acid | amide | homodimer |
| 503 | 1160.0 | PEG10-37 atoms | amide | homodimer |
| 504 | 1204.0 | PEG12-43 atoms | amide | homodimer |
| 505 | 1097.6 | PEG2-C7-PEG2 | amide | homodimer |
| 506 | 1084.6 | PEG2-diglycolic acid-PEG2 | amide | homodimer |
| 507 | 1038.6 | PEG2-diphenic acid-PEG2 | amide | homodimer |
| 508 | 969.6 | PEG3 linker | amide | homodimer |
| 509 | 1027.6 | PEG4 linker | amide | homodimer |
| 510 | 1072.0 | PEG6 linker | amide | homodimer |
| 511 | 1137.8 | PEG9 linker | amide | homodimer |
| 512 | 941.7 | Phthalic acid linker | amide | homodimer |
| 513 | 945.4 | trans-1,2-Cyclohexanedicarboxylic acid | amide | homodimer |
| 514 | 937.8 | trans-DL-1,2-Cyclopentanedicarboxylic acid | amide | homodimer |
| 515 | 963.6 | 1,3,5-Benzenetricarbonyl trichloride | amide | homodimer |
| 516 | 955.6 | 1,4-Phenylenediacetic acid | amide | homodimer |
| 517 | 979.6 | diphenic acid | amide | homodimer |
| 518 | 914.8 | 1,3,5-Tris(bromomethyl)benzene) | amine | homotrimer |
| 519 | 931.0 | 1,3,5-Cyclohexanetricarboxylic acid (all-cis) | amide | homotrimer |
| 520 | 928.6/1392.8 | 1,3,5-Benzenetricarbonyl trichloride | amide | homotrimer |
| 521 | 775.0/969.0/1291.7 | (+)-(18-Crown-6)-2,3,11,12-tetracarboxylic acid | amide | homotetramer |
| 522 | 918.7 | Glutaric acid | amide | homodimer |
| 523 | 925.6 | Adipic acid | amide | homodimer |
| 524 | 932.6 | Pimelic acid | amide | homodimer |
| 525 | 939.6 | Suberic acid | amide | homodimer |

TABLE 2X-continued

| | | | | |
|---|---|---|---|---|
| 526 | 946.6 | Azelaic acid | amide | homodimer |
| 527 | 980.6 | Pimelic acid | amide | homodimer |
| 528 | 987.6 | Suberic acid | amide | homodimer |
| 529 | 994.6 | Azelaic acid | amide | homodimer |
| 530 | 950.8 | Sebacic acid | amide | homodimer |
| 531 | 908.6 | Succinic acid | amide | homodimer |
| 532 | 929.8 | Pimelic acid | amide | homodimer |
| 533 | 944.2 | Azelaic acid | amide | homodimer |
| 534 | 983.4 | Diglycolic acid | amide | homodimer |
| 535 | 971.2 | Diphenic acid | amide | homodimer |
| 536 | 1063.2 | PEG6 | amide | homodimer |
| 537 | 955.2 | 1,2,3-Benzenetricarbonyl trichloride | amide | homodimer |
| 538 | 919.8 | 1,3,5-Benzenetricarbonyl trichforide | amide | homotrimer |

| Compound No. | Representative structures of Linker moieties (the nunther 1 represents an attachment point between Linker and monomeric macrocycle) | Experimental Protocol |
|---|---|---|
| 390 | | A,D,Gb,I,M,N,Oa |
| 391 | | A,D,Gb,I,M,N,Oa |
| 392 | | A,D,Gb,I,M,N,Oa |
| 393 | | A,E,Fa,Jb,M,Ob,I,M |
| 394 | | A,E,Fa,Jb,M,Ob,I,M |
| 395 | | A,E,Fa,Jb,M,Ob,I,M |
| 396 | | A,E,Fa,Jb,M,Ob,I,M |
| 397 | | A,E,Fa,Jb,M,Ob,I,M |
| 457 | | A,E,Fa,Jb,M,Ob,I,M |
| 458 | | A,D,Gb,I,M,Nb,Ob |
| 459 | | A,D,Gb,I,M,Nb,Ob |
| 460 | | A,D,Gb,I,M,Na,Oa |
| 461 | | A,D,Gb,I,M,Na,Oa |
| 462 | | A,D,Gb,I,M,Nb,Ob |
| 463 | | A,D,Gb,I,M,Na,Oa |
| 464 | | A,D,Gb,I,M,Na,Oa |
| 465 | | A,D,Gb,I,M,Na,Oa |
| 466 | | A,D,Gb,I,M,Na,Oa |
| 467 | | A,D,Gb,I,M,Nb,Ob |
| 468 | 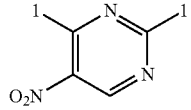 | A,D.Gb,I,M,Of |
| 469 | | A,D,Gb,I,M,Na,Oa |
| 470 | | A,D,Gb,I,M,Na,Oa |
| 471 | | A,D,Gb,I,M,Na,Oa |
| 472 | | A,D,Gb,I,M,Nb,Ob |
| 473 | | A,D,Gb,I,M,Nc,Ob |
| 474 | | A,D,Gb,I,M,Na,Oa |
| 475 | | A,D,Gb,I,M,Na,Oa |
| 476 | | A,D,Gb,I,M,Nb,Ob |
| 477 | | A,D,Gb,I,M,Na,Oa |
| 478 | | A,D,Gb,I,M,Nb,Ob |
| 479 | | A,D,Gb,I,M,Nb,Ob |
| 480 | | A,D,Gb,I,M,Nb,Ob |
| 481 | 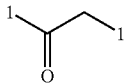 | A,D,Gb,I,M,Oc |
| 482 | 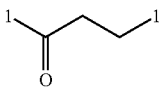 | A,D,Gb,I,M,Od |
| 483 | | A,D,Gb,I,M,Nb,Ob |
| 484 | | A,D,Gb,I,M,Nb,Ob |
| 485 | | A,D,Gb,I,M,Na,Oa |
| 486 | | A,D,Gb,I,M,Nb,Ob |
| 487 | | A,D,Gb,I,M,Na,Oa |
| 488 | | A,D,Gb,I,M,Na,Oa |
| 489 | | A,D,Gb,I,M,Na,Oa |
| 490 | | A,D,Gb,I,M,Na,Oa |
| 491 | | A,D,Gb,I,M,Nb,Ob |

TABLE 2X-continued

| # | Structure | Substituents |
|---|---|---|
| 492 | (L-aspartyl diacid, NH₂) | A,D,Gb,I,M,Nc,Ob |
| 493 | (D-aspartyl diacid, NH₂) | A,D,Gb,I,M,Nc,Ob |
| 494 | (L-glutamyl diacid, NH₂) | A,D,Gb,I,M,Nc,Ob |
| 495 | (D-glutamyl diacid, NH₂) | A,D,Gb,I,M,Nc,Ob |
| 496 | | A,D,Gb,I,M,Nb,Ob |
| 497 | | A,D,Gb,I,M,Nb,Ob |
| 498 | bis(Cbz-lysine)-adipamide diacid | A,D,Gb,I,M,Nd,Nc,Ob |
| 499 | 1,3-bis(methylene)benzene | A,D,Gb,I,M,Oh |
| 500 | 1,4-bis(methylene)benzene | A,D,Gb,I,M,Oh |
| 501 | | A,D,Gb,I,M,Nc,Ob |
| 502 | | A,D,Gb,I,M,Nc,Ob |
| 503 | bis(PEG6-propanoyl) | A,D,Gb,I,M,Nb,Ob |
| 504 | bis(PEG7-propanoyl) | A,D,Gb,I,M,Nb,Ob |
| 505 | bis(PEG2-ethylamido)-adipoyl | A,D,Gb,I,M,Ng,Nb,Ob |

TABLE 2X-continued

| # | Structure | Codes |
|---|---|---|
| 506 | [structure: 1-C(O)-CH2-O-CH2CH2-O-CH2CH2-NH-C(O)-O-CH2-C(O)-NH-CH2CH2-O-CH2CH2-O-CH2-C(O)-1] | A,D,Gb,I,M,Ne,Nb,Ob |
| 507 | [structure: 1-C(O)-CH2-O-CH2CH2-O-CH2CH2-NH-C(O)-biphenyl-C(O)-NH-CH2CH2-O-CH2CH2-O-CH2-C(O)-1] | A,D,Gb,I,M,Nf,Nb,Ob |
| 508 | [structure: 1-C(O)-CH2-O-CH2CH2-O-CH2CH2-O-CH2-C(O)-1] | A,D,Gb,I,M,Nb,Ob |
| 509 | [structure: PEG linker with 4 oxygens] | A,D,Gb,I,M,Na,Oa |
| 510 | [structure: branched PEG linker] | A,D,Gb,I,M,Na,Oa |
| 511 | [structure: larger branched PEG linker] | A,D,Gb,I,M,Nc,Ob |
| 512 | | A,D,Gb,I,M,Nb,Ob |
| 513 | | A,D,Gb,I,M,Na,Oa |
| 514 | | A,D,Gb,I,M,Nc,Ob |
| 515 | [structure: 5-carboxyisophthaloyl, benzene with COOH and two C(O)-1] | A,D,Gb,I,M,Oa |
| 516 | | A,D,Gb,I,M,Na,Oa |
| 517 | | A,D,Gb,I,M,Na,Oa |
| 518 | | A,D,Gb,I,M,Oa |
| 519 | | A,D,Gb,I,M,Nb,Ob |
| 520 | [structure: 1,3,5-benzenetricarbonyl, benzene with three C(O)-1] | A,D,Gb,I,M,Oa |
| 521 | | A,D,Gb,I,M,Nb,Ob |
| 522 | | A,D,I,M,Og,Ja |
| 523 | | A,D,I,M,Og,Ja |
| 524 | | A,D,I,M,Og,Ja |
| 525 | | A,D,I,M,Og,Ja |
| 526 | | A,D,I,M,Og,Ja |
| 527 | | A,D,I,M,Na,Oa |
| 528 | | A,D,I,M,Na,Oa |
| 529 | | A,D,I,M,Na,Oa |
| 530 | | B,A,D,M,Ja,Nc,Ob,I |
| 531 | | B,A,D,M,Ja,Nb,Ob,I |
| 532 | | B,A,D,M,Ja,Nc,Ob,I |

TABLE 2X-continued

| | | |
|---|---|---|
| 533 | | B,A,D,M,Ja,Nc,Ob,I |
| 534 | | B,A,D,M,Ja,Oa,I |
| 535 | | B,A,D,M,Ja,Nc,Ob,I |
| 536 | (structure: two PEG-like chains attached at position 1, each with ether linkages and carbonyl groups) | B,A,D,M,Ja,Nc,Ob,I |
| 537 | (structure: benzene ring with COOH and two acyl attachment points labeled 1) | B,A,D,M,Ja,Oa,I |
| 538 | (structure: benzene ring with three acyl attachment points labeled 1) | B,A,D,M,Ja,Nb,Ob,I |

TABLE 3

| Seq ID | Sequence | Features |
|---|---|---|
| 1 | Pro Tyr Leu Asp Val | |
| 2 | Pro His Leu Asp Val | |
| 3 | Pro Tyr Leu Asp Thr | |
| 4 | Pro Phe Leu Asp Thr | |
| 5 | Pro X Leu Asp Thr | X is homoPhe |
| 6 | Pro X Leu Asp Thr | X is beta-cyclohexyl alanine, (S)-2-amino-3-cyclohexylpropionic acid |
| 7 | Pro Trp Leu Asp Ile | |
| 8 | Pro X Leu Asp Thr | X is 1-napthylalanine |
| 9 | Pro X Leu Asp Thr | X is 2-napthylalanine |
| 10 | Pro Trp Leu Asp X | X is O-benzyl-threonine |
| 11 | Pro X Leu Asp Thr | X is biphenylalanine |
| 12 | Pro X Leu Asp Thr | X is O-phenyl-tyrosine |
| 13 | Pro X Leu Asp Ile | X is 1-napthylalanine |
| 14 | Pro X Leu Asp Ile | X is 2-napthylalanine |
| | Pro $X_1$ Leu Asp $X_2$ | $X_1$ is 2-napthylalanine; $X_2$ is O-benzyl-threonine |
| 16 | X Trp Leu Asp Thr | X is (4S)-fluoro-proline |
| | Pro $X_1$ Leu Asp $X_2$ | $X_1$ is biphenylalanine; $X_2$ is O-benzyl-threonine |
| 18 | Pro X Leu Asp Thr | X is O-2-methyl-phenyl-tyrosine |
| 19 | Pro X Leu Asp Thr | X is O-4-trifluoromethyl-phenyl-tyrosine |
| 20 | Pro X Leu Asp Thr | X is O-4-methoxy-phenyl-tyrosine |
| 21 | Pro X Leu Asp Thr | X is O-4-fluoro-phenyl-tyrosine |
| 22 | Pro X Leu Asp Thr | X is O-2-methoxy-phenyl-tyrosine |
| 23 | Pro X Leu Asp Thr | X is O-3-methoxy-phenyl-tyrosine |
| 24 | Pro X Leu Asp Thr | X is O-3-fluoro-phenyl-tyrosine |
| 25 | Pro X Leu Asp Thr | X is O-3,4-difluoro-phenyl-tyrosine |
| 26 | Pro X Leu Asp Thr | X is O-3-methyl-phenyl-tyrosine |
| 27 | Pro X Leu Asp Thr | X is O-3,4-dimethyl-phenyl-tyrosine |
| 28 | Pro X Leu Asp Thr | X is O-4-methylester-phenyl-tyrosine |
| 29 | Pro X Leu Asp Thr | X is O-3-methylester-phenyl-tyrosine |
| 30 | Pro X Leu Asp Thr | X is O-4-carboxylate-phenyl-tyrosine |
| 31 | X Phe Leu Asp Thr | X is trans-4-hydroxyproline, (2S,4R)-4-hydroxypyrrolidine-2-carboxylic acid |
| 32 | Pro X Leu Asp Thr | X is metaTyrosine |
| | Pro $X_1$ Leu Asp $X_2$ | $X_1$ is Ndelta-benzamide-ornithine; $X_2$ is O-benzyl-threonine |
| | Pro $X_1$ Leu Asp $X_2$ | $X_1$ is Ndelta-acetamide-ornithine; $X_2$ is O-benzyl-threonine |
| | Pro $X_1$ Leu Asp $X_2$ | $X_1$ is Ndelta-methanesulfonamide-ornithine; $X_2$ is O-benzyl-threonine |

TABLE 3-continued

| Seq ID | Sequence | Features |
|---|---|---|
| | Pro X$_1$ Leu Asp X$_2$ | X$_1$ is Ndelta-ethylcarbamate-ornithine<br>X$_2$ is O-benzyl-threonine |
| | Pro X$_1$ Leu Asp X$_2$ | X$_1$ is Ndelta-pentyl amide-ornithine<br>X$_2$ is O-benzyl-threonine |
| 38 | Pro Arg Leu Asp Thr | |
| 39 | Pro Phe Leu Asp X | X is O-methyl-threonine |
| 40 | Pro Phe Leu Asp X | X is O-ethyl-threonine |
| 41 | Pro X Leu Asp Thr | X is D-tyrosine |
| 42 | Pro X Leu Asp Thr | X is (3R)-1,2,3,4-tetrahydroisoquinoline-3-carboxylic acid |
| | X$_1$ X$_2$ Leu Asp Thr | X$_1$ is trans-4-hydroxyproline, (2S,4R)-4-hydroxypyrrolidine-2-carboxylic acid<br>X$_2$ is [3-(3'-pyridyl)-alanine] |
| 44 | X Phe Leu Asp Thr | X is (4R)-fluoro-proline |
| | X$_1$ X$_2$ Leu Asp Thr | X$_1$ is (4R)-fluoro-proline<br>X$_2$ is biphenylalanine |
| | X$_1$ X$_2$ Leu Asp Thr | X$_1$ is (4R)-fluoro-proline<br>X$_2$ is [3-(3'-pyridyl)-alanine] |
| 47 | X Tyr Leu Asp Thr | X is (4R)-fluoro-proline |
| 48 | X Tyr Leu Asp Thr | X is (4S)-fluoro-proline |
| 49 | Pro X Leu Asp Thr | X is D-arginine |
| 50 | Pro X Leu Asp Thr | X is D-pipecolic acid, D-homoPro |
| 51 | Pro X Leu Asp Thr | X is (3-(4-thiazolyl)-alanine) |
| 52 | Pro Tyr Leu Asp Ile | |
| 53 | Pro X Leu Asp Thr | X is 4-aza-phenylalanine |
| 54 | Pro Tyr Leu Asp X | X is penicillamine, beta,beta-dimethyl-cysteine |
| 55 | Pro X Leu Asp Thr | X is 2-amino-4-bromo-4-pentenoic acid |
| 56 | Pro X Leu Asp Thr | X is O-benzyl-trans-4-hydroxyproline |
| 57 | Pro X Leu Asp Thr | X is Nbeta-Z-2,3-diaminopropionic acid |
| 58 | Pro X Leu Asp Thr | X is N-tau-benzyl-histidine |
| 59 | Pro X Leu Asp Thr | X is 4-amino-phenylalanine |
| 60 | Pro X Leu Asp Thr | X is 4-aza-D-phenylalanine |
| 61 | Pro X Leu Asp Thr | X is trans-4-hydroxyproline, (2S,4R)-4-hydroxypyrrolidine-2-carboxylic acid |
| 62 | Pro X Leu Asp Thr | X is D-tryptophan |
| 63 | Pro Met Leu Asp Thr | |
| 64 | Pro X Leu Asp Thr | X is D-methionine |
| 65 | Pro X Leu Asp Thr | X is 4-guanidino-phenylalanine |
| 66 | Pro X Leu Asp Thr | X is 3-aza-phenylalanine |
| 67 | Pro X Leu Asp Thr | X is 3-aza-D-phenylalanine |
| 68 | Pro X Leu Asp Thr | X is norvaline |
| 69 | Pro X Leu Asp Thr | X is D-norleucine |
| 70 | Pro X Leu Asp Thr | X is D-lysine |
| 71 | Pro X Leu Asp Thr | X is D-proline |
| 72 | Pro X Leu Asp Thr | X is D-ornithine |
| 73 | Pro X Leu Asp Thr | X is 3-benzothienyl-alanine |
| 74 | Pro X Leu Asp Thr | X is O-allyl-D-tyrosine |
| 75 | Pro X Leu Asp Thr | X is O-benzyl-D-serine |
| 76 | Pro X Leu Asp Thr | X is 3-(4-thiazolyl)-D-alanine |
| 77 | Pro X Leu Asp Thr | X is 3-benzothienyl-D-alanine |
| 78 | Pro X Leu Asp Thr | X is 3-(2-thienyl)-D-alanine |
| 79 | Pro X Leu Asp Thr | X is 4-aminomethyl-phenylalanine |
| 80 | Pro X Leu Asp Thr | X is Ndelta-dimethyl-D-ornithine |
| 81 | Pro X Leu Asp Thr | X is 4-amino-D-phenylalanine |
| 82 | Pro X Leu Asp Thr | X is 4-aminomethyl-D-phenylalanine |
| 83 | Pro X Leu Asp Thr | X is O-benzyl-D-tyrosine |
| 84 | Pro Pro Leu Asp Thr | |
| 85 | Pro X Leu Asp Thr | X is cyclo leucine, 1-aminocyclopentane-1-carboxylic acid |
| 86 | Pro X Leu Asp Thr | X is aminoindan-2-carboxylic acid |
| 87 | Pro X Leu Asp Thr | X is O-allyl-tyrosine |
| 88 | Pro X Leu Asp Thr | X is cyclohexyl glycine |
| 89 | Pro Lys Leu Asp Thr | |
| 90 | Pro X Leu Asp Thr | X is 2-aza-D-phenylalanine |
| 91 | Pro X Leu Asp Thr | X is 2-aza-phenylalanine |
| 92 | Pro X Leu Asp Thr | X is 2-(2-pyridyl)-4-thiazolyl-alanine |
| 93 | Pro X Leu Asp Thr | X is 2-(3-pyridyl)-4-thiazolyl-alanine |
| 94 | Pro X Leu Asp Thr | X is 2-(4-pyridyl)-4-thiazolyl-alanine |
| 95 | Pro X Leu Asp Thr | X is D-1,2,3,4-tetrahydroisoquinoline-1-carboxylic acid |
| 96 | Pro X Leu Asp Thr | X is 1-(S)-isoindoline-carboxylic acid |
| 97 | Pro Tyr X Leu Asp Thr | X is D-threonine |
| 98 | Pro Tyr Pro Leu Asp Thr | |
| 99 | Pro Tyr X Leu Asp Thr | X is D-proline |
| 100 | Pro Tyr X Leu Asp Thr | X is sarcosine, N-methyl glycine |
| 101 | Pro Tyr X Leu Asp Thr | X is cyclo leucine, 1-Aminocyclopentane-1-carboxylic acid |
| 102 | Pro X$_1$ X$_2$ Leu Asp Thr | X$_1$ is 3-iodo-phenylalanine<br>X$_2$ is sarcosine, N-methyl glycine |
| 103 | Pro X$_1$ X$_2$ Leu Asp Thr | X$_1$ is 4-iodo-phenylalanine<br>X$_2$ is sarcosine, N-methyl glycine |
| 104 | Pro X$_1$ X$_2$ Leu Asp Thr | X$_1$ is 3,3-diphenyl-alanine<br>X$_2$ is sarcosine, N-methyl glycine |
| 105 | Pro Phe X Leu Asp Thr | X is D-lysine |

TABLE 3-continued

| Seq ID | Sequence | Features |
|---|---|---|
| 106 | Pro X$_1$ X$_2$ Leu Asp Thr | X$_1$ is biphenylalanine<br>X$_2$ is D-lysine |
| 107 | Pro X$_1$ X$_2$ Leu Asp Thr | X$_1$ is 3-(4-thiazolyl)-alanine<br>X$_2$ is D-lysine |
| 108 | Pro X$_1$ X$_2$ Leu Asp Thr | X$_1$ is 3,3-diphenyl-alanine<br>X$_2$ is D-lysine |
| 109 | Pro Tyr X Leu Asp Ile | X is D-lysine |
| 110 | Pro Tyr X Leu Asp Thr | X is D-arginine |
| 111 | Pro Tyr X Leu Asp Thr | X is D-serine |
| 112 | Pro X$_1$ X$_2$ Leu Asp Thr | X$_1$ is biphenylalanine<br>X$_2$ is sarcosine, N-methyl glycine |
| 113 | Pro X$_1$ X$_2$ Leu Asp Thr | X$_1$ is 1-napthylalanine<br>X$_2$ is sarcosine, N-methyl glycine |
| 114 | Pro Tyr X Leu Asp Thr | X is pipecolic acid, homoPro |
| 115 | Pro X$_1$ X$_2$ Leu Asp Thr | X$_1$ is 2-iodo-phenylalanine<br>X$_2$ is sarcosine, N-methyl glycine |
| 116 | Pro X$_1$ X$_2$ Leu Asp Thr | X$_1$ is 1-napthylalanine<br>X$_2$ is D-lysine |
| 117 | Pro Tyr X$_1$ Leu Asp X$_2$ | X$_1$ is D-lysine<br>X$_2$ is N-methyl threonine |
| 118 | Pro Phe X Leu Asp Thr | X is sarcosine, N-methyl glycine |
| 119 | Pro Tyr X Leu Asp Thr | X is (3R)-1,2,3,4-tetrahydroisoquinoline-3-carboxylic acid |
| 120 | Pro Tyr X Leu Asp Thr | X is D-pipecolic acid, D-homoPro |
| 121 | Pro Phe X Leu Asp Thr | X is D-proline |
| 122 | Pro X$_1$ X$_2$ Leu Asp Thr | X$_1$ is 3,4-dimethoxy-phenylalanine<br>X$_2$ is D-proline |
| 123 | Pro X$_1$ X$_2$ Leu Asp Thr | X$_1$ is 3,4,5-trifluoro-phenylalanine<br>X$_2$ is D-proline |
| 124 | Pro X$_1$ X$_2$ Leu Asp Thr | X$_1$ is 3,5-dibromo-tyrosine<br>X$_2$ is D-proline |
| 125 | Pro Phe X Leu Asp Thr | X is D-pipecolic acid, D-homoPro |
| 126 | Pro X$_1$ X$_2$ Leu Asp Thr | X$_1$ is 3-(4-thiazoly!)-alanine<br>X$_2$ is D-pipecolic acid, D-homoPro |
| 127 | Pro X$_1$ X$_2$ Leu Asp Thr | X$_1$ is 4-aminomethyl-phenylalanine<br>X$_2$ is D-pipecolic acid, D-homoPro |
| 128 | Pro X$_1$ X$_2$ Leu Asp Thr | X$_1$ is 2-iodo-phenylalanine<br>X$_2$ is D-pipecolic acid, D-homoPro |
| 129 | Pro X$_1$ X$_2$ Leu Asp Thr | X$_1$ is 2-phenyl-phenylalanine<br>X$_2$ is D-pipecolic acid, D-homoPro |
| 130 | Pro X$_1$ X$_2$ Leu Asp Thr | X$_1$ is 2-(2-methoxy-phenyl)-phenylalanine<br>X$_2$ is D-pipecolic acid, D-homoPro |
| 131 | Pro X$_1$ X$_2$ Leu Asp Thr | X$_1$ is 2-(3-methoxy-phenyl)-phenylalanine<br>X$_2$ is D-pipecolic acid, D-homoPro |
| 132 | Pro X$_1$ X$_2$ Leu Asp Thr | X$_1$ is 2-(4-methoxy-phenyl)-phenylalanine<br>X$_2$ is D-pipecolic acid, D-homoPro |
| 133 | Pro X$_1$ X$_2$ Leu Asp Thr | X$_1$ is biphenylalanine<br>X$_2$ is D-pipecolic acid, D-homoPro |
| 134 | Pro Tyr X Leu Asp Thr | X is trans-4-hydroxyproline, (2S,4R)-4-hydroxypyrrolidine-2-carboxylic acid |
| 135 | Pro Tyr X Leu Asp Thr | X is trans-D-4-hydroxyproline, (2R,4S)-4-hydroxypyrrolidine-2-carboxylic acid |
| 136 | Pro Tyr X Leu Asp Thr | X is cis-D-4-Hydroxyproline, (2R,4R)-4-Hydroxypyrrolidine-2-carboxylic acid |
| 137 | X$_1$ X$_2$ X$_3$ Leu Asp Thr | X$_1$ is D-proline<br>X$_2$ is D-tyrosine<br>X$_3$ is D-pipecolic acid, D-homoPro |
| 138 | Pro X$_1$ X$_2$ Leu Asp Thr | X$_1$ is 1-napthylalanine<br>X$_2$ is D-pipecolic acid, D-homoPro |
| 139 | Pro X$_1$ X$_2$ Leu Asp Thr | X$_1$ is 2-napthylalanine<br>X$_2$ is D-pipecolic acid, D-homoPro |
| 140 | Pro X$_1$ X$_2$ Leu Asp Thr | X$_1$ is 4-aminomethyl-phenylalanine<br>X$_2$ is (3R)-1,2,3,4-tetrahydroisoquinoline-3-carboxylic acid |
| 141 | Pro X$_1$ X$_2$ Leu Asp Thr | X$_1$ is 3-aminomethyl-phenylalanine<br>X$_2$ is (3R)-1,2,3,4-tetrahydroisoquinoline-3-carboxylic acid |
| 142 | Pro X$_1$ X$_2$ Leu Asp Thr | X$_1$ is 3-aminomethyl-D-phenylalanine<br>X$_2$ is (3R)-1,2,3,4-tetrahydroisoquinoline-3-carboxylic acid |
| 143 | Pro X$_1$ X$_2$ Leu Asp Thr | X$_1$ is N-methyl tyrosine<br>X$_2$ is D-pipecolic acid, D-homoPro |
| 144 | Pro Tyr X$_1$ Leu Asp X$_2$ | X$_1$ is D-pipecolic acid, D-homoPro<br>X$_2$ is allo-threonine, (2S,3S)-2-amino-3-hydroxybutyric acid |
| 145 | Pro Tyr X$_1$ X$_2$ Asp Thr | X$_1$ is D-pipecolic acid, D-homoPro<br>X$_2$ is beta-tert-butyl alanine, neopentylglycine |
| 146 | Pro X$_1$ X$_2$ Leu Asp Thr | X$_1$ is 3-(4-thiazolyl)-alanine<br>X$_2$ is trans-D-4-hydroxyproline, (2R,4S)-4-hydroxypyrrolidine-2-carboxylic acid |
| 147 | Pro X$_1$ X$_2$ Leu Asp Thr | X$_1$ is 4-aminomethyl-phenylalanine<br>X$_2$ is trans-D-4-hydroxyproline, (2R,4S)-4-hydroxypyrrolidine-2-carboxylic acid |
| 148 | Pro Tyr X Leu Asp Ile | X is D-pipecolic acid, D-homoPro |
| 149 | Pro Tyr X Leu Asp Ile | X is N-methyl-D-lysine |
| 150 | Pro Tyr X Leu Asp Thr | X is D-norleucine |
| 151 | Pro Phe X Leu Asp Thr | X is trans-D-4-hydroxyproline, (2R,4S)-4-hydroxypyrrolidine-2-carboxylic acid |
| 152 | Pro Tyr X Leu Asp Thr | X is N-methyl-D-arginine |

TABLE 3-continued

| Seq ID | Sequence | Features |
|---|---|---|
| 153 | Pro Tyr Gly Leu Asp Thr | |
| 154 | Pro Tyr Ala Leu Asp Thr | |
| 155 | Pro Tyr X Leu Asp Thr | X is D-alanine |
| 156 | Pro Met Gly Leu Asp Thr | |
| 157 | Pro $X_1$ $X_2$ Leu Asp Thr | $X_1$ is O-allyl-tyrosine<br>$X_2$ is sarcosine, N-methyl glycine |
| 158 | Pro X Gly Leu Asp Thr | X is O-allyl-tyrosine |
| 159 | Pro $X_1$ $X_2$ Leu Asp Thr | $X_1$ is 3-(4-thiazolyl)-alanine<br>$X_2$ is sarcosine, N-methyl glycine |
| 160 | Pro X Gly Leu Asp Thr | X is 4-aminomethyl-phenylalanine |
| 161 | Pro $X_1$ $X_2$ Leu Asp Thr | $X_1$ is O-allyl-tyrosine<br>$X_2$ is D-valine |
| 162 | Pro $X_1$ $X_2$ Leu Asp Thr | $X_1$ is O-allyl-tyrosine<br>$X_2$ is D-serine |
| 163 | Pro X1 X2 Leu Asp Thr | $X_1$ is O-allyl-tyrosine<br>$X_2$ is D-alanine |
| 164 | Pro X Pro Leu Asp Thr | X is O-allyl-tyrosine |
| 165 | Pro $X_1$ $X_2$ Leu Asp Thr | $X_1$ is O-allyl-tyrosine<br>$X_2$ is D-proline |
| 166 | Pro $X_1$ $X_2$ Leu Asp Thr | $X_1$ is 3-(4-thiazolyl)-alanine<br>$X_2$ is D-valine |
| 167 | Pro $X_1$ $X_2$ Leu Asp Thr | $X_1$ is 3-(4-thiazolyl)-alanine<br>$X_2$ is D-serine |
| 168 | Pro $X_1$ $X_2$ Leu Asp Thr | $X_1$ is 3-(4-thiazolyl)-alanine<br>$X_2$ is D-alanine |
| 169 | Pro X Pro Leu Asp Thr | X is 3-(4-thiazolyl)-alanine |
| 170 | Pro $X_1$ $X_2$ Leu Asp Thr | $X_1$ is 3-(4-thiazolyl)-alanine<br>$X_2$ is D-proline |
| 171 | Pro X Pro Leu Asp Thr | X is 4-aminomethyl-phenylalanine |
| 172 | Pro $X_1$ $X_2$ Leu Asp Thr | $X_1$ is 4-aminomethyl-phenylalanine<br>$X_2$ is D-proline |
| 173 | Pro X Pro Leu Asp Thr | X is cyclo leucine, 1-aminocyclopentane-1-carboxylic acid |
| 174 | Pro $X_1$ $X_2$ Leu Asp Thr | $X_1$ is 2-(2-pyridyl)-4-thiazolyl-alanine<br>$X_2$ is sarcosine, N-methyl glycine |
| 175 | Pro $X_1$ $X_2$ Leu Asp Thr | $X_1$ is 2-(2-pyridyl)-4-thiazolyl-alanine<br>$X_2$ is D-proline |
| 176 | Pro $X_1$ $X_2$ Leu Asp Thr | $X_1$ is 2-(3-pyridyl)-4-thiazolyl-alanine<br>$X_2$ is sarcosine, N-methyl glycine |
| 177 | Pro $X_1$ $X_2$ Leu Asp Thr | X1 is 2-(3-pyridyl)-4-thiazolyl-alanine<br>$X_2$ is D-proline |
| 178 | Pro $X_1$ $X_2$ Leu Asp Thr | $X_1$ is 2-(4-pyridyl)-4-thiazolyl-alanine<br>$X_2$ is D-proline |
| 179 | Pro $X_1$ $X_2$ Leu Asp Thr | $X_1$ is 3-(2-aminobenzyl-4-thiazolyl)-alanine<br>$X_2$ is sarcosine, N-methyl glycine |
| 180 | Pro $X_1$ $X_2$ Leu Asp Thr | $X_1$ is 2-(amino-benzyl)-4-thiazolyl-alanine<br>$X_2$ is D-proline |
| 181 | Pro $X_1$ $X_2$ Leu Asp Ile | $X_1$ is D-tyrosine<br>$X_2$ is D-pipecolic acid, D-homoPro |
| 182 | Pro $X_1$ $X_2$ Leu Asp Thr | $X_1$ is 2-aminomethyl-phenylalanine<br>$X_2$ is azetidine-2-carboxylic acid |
| 183 | Pro Tyr $X_1$ Leu Asp $X_2$ | $X_1$ is D-pipecolic acid, D-homoPro<br>$X_2$ is 2-aminobutyric acid |
| | Pro $X_1$ $X_2$ Leu Asp $X_3$ | $X_1$ is 3-aminomethyl-phenylalanine<br>$X_2$ is (3R)-1,2,3,4-tetrahydroisoquinoline-3-carboxylic acid<br>$X_3$ is 2-aminobutyric acid |
| 185 | Pro $X_1$ $X_2$ Leu Asp Thr | $X_1$ is 2,4-dichloro-phenylalanine<br>$X_2$ is D-pipecolic acid, D-homoPro |
| 186 | Pro $X_1$ $X_2$ Leu Asp Thr | $X_1$ is 3-phenyl-D-phenylalanine<br>$X_2$ is D-pipecolic acid, D-homoPro |
| 187 | Pro $X_1$ $X_2$ Leu Asp Thr | $X_1$ is 3-(5-quinoliny!)-D-phenylalanine<br>$X_2$ is D-pipecolic acid, D-homoPro |
| 188 | Pro Tyr X Leu Asp Thr | X is beta-homolysine |
| 189 | Pro Tyr X Leu Asp Thr | X is beta-homoproline |
| 190 | Pro Tyr X Leu Asp Thr | X is beta-homolysine |
| 191 | Pro Tyr X Leu Asp Thr | X is anthranilic acid, 2-aminobenzoic acid |
| 192 | Pro Phe X Leu Asp Thr | X is beta-homolysine |
| 193 | Pro $X_1$ $X_2$ Leu Asp Thr | $X_1$ is 3-(4-thiazolyl)-alanine<br>$X_2$ is beta-homolysine |
| 194 | Pro $X_1$ $X_2$ Leu Asp Thr | $X_1$ is 4-aminomethyl-phenylalanine<br>$X_2$ is beta-homolysine |
| 195 | Pro Tyr $X_1$ Leu Asp $X_2$ | $X_1$ is beta-homolysine<br>$X_2$ is O-benzyl-threonine |
| 196 | Pro $X_1$ $X_2$ Leu Asp Thr | $X_1$ is N-methyl tyrosine<br>$X_2$ is D-beta-homolysine |
| 197 | Pro $X_1$ $X_2$ Leu Asp Thr | $X_1$ is 1-napthylalanine<br>$X_2$ is beta-homolysine |
| 198 | Pro $X_1$ $X_2$ Leu Asp Thr | $X_1$ is 2-napthylalanine<br>$X_2$ is beta-homolysine |

TABLE 3-continued

| Seq ID | Sequence | Features |
|---|---|---|
| 199 | Pro X$_1$ X$_2$ Leu Asp Thr | X$_1$ is biphenylalanine<br>X$_2$ is beta-homolysine |
| 200 | Pro X$_1$ X$_2$ Leu Asp Thr | X$_1$ is 2-iodo-phenylalanine<br>X$_2$ is beta-homolysine |
| 201 | Pro X$_1$ X$_2$ Leu Asp Thr | X$_1$ is 2-(2,5-dimethyl-isoxazole)-phenylalanine<br>X$_2$ is beta-homolysine |
| 202 | Pro X$_1$ X$_2$ Leu Asp Thr | X$_1$ is 2-phenyl-phenylalanine<br>X$_2$ is beta-homolysine |
| 203 | Pro X$_1$ X$_2$ Leu Asp Thr | X$_1$ is (2-piperazinyl-2-phenyl)-phenylalanine<br>X$_2$ is beta-homolysine |
| 204 | Pro X$_1$ X$_2$ Leu Asp Thr | X$_1$ is beta-cyclohexyl alanine, (S)-2-amino-3-cyclohexylpropionic acid<br>X$_2$ is beta-homolysine |
| 205 | Pro Trp X Leu Asp Thr | X is beta-homolysine |
| 206 | Pro X$_1$ X$_2$ Leu Asp Thr | X$_1$ is D-tryptophan<br>X$_2$ is beta-homolysine |
| 207 | Pro X$_1$ X$_2$ Leu Asp Thr | X$_1$ is 3-aminomethyl-phenylalanine<br>X$_2$ is beta-homolysine |
| 208 | Pro X$_1$ X$_2$ Leu Asp Thr | X$_1$ is 4-aminomethyl-D-phenylalanine<br>X$_2$ is beta-homolysine |
| 209 | Pro X$_1$ X$_2$ Leu Asp Ile | X$_1$ is 4-aminomethyl-phenylalanine<br>X$_2$ is beta-homolysine |
| 210 | Pro Tyr X Leu Asp Ile | X is beta-D-homolysine |
| 211 | Pro X$_1$ X$_2$ Leu Asp Thr | X$_1$ is D-arginine<br>X$_2$ is beta-homolysine |
| 212 | Pro X$_1$ X$_2$ Leu Asp Thr | X$_1$ is 4-aminomethyl-phenylalanine-reduced<br>X$_2$ is beta-homolysine |
| 213 | Pro X$_1$ X$_2$ Leu Asp Ile | X$_1$ is 3-(4-thiazoly!)-alanine<br>X$_2$ is beta-D-homolysine |
| 214 | Pro Phe X Leu Asp Ile | X is beta-D-homolysine |
| 215 | Pro X$_1$ X$_2$ Leu Asp Thr | X$_1$ is 3-(4-thiazolyl)-alanine<br>X$_2$ is N-methyl beta-homolysine |
| 216 | Pro X$_1$ X$_2$ Leu Asp Thr | X$_1$ is 4-aminomethyl-phenylalanine<br>X$_2$ is N-methyl beta-homolysine |
| 217 | Pro X$_1$ X$_2$ Leu Asp Ile | X$_1$ is 3-(4-thiazolyl)-alanine<br>X$_2$ is beta-homolysine |
| 218 | Pro X$_1$ X$_2$ Leu Asp Thr | X$_1$ is (3S)-1,2,3,4-tetrahydroisoquinoline-3-carboxylic acid<br>X$_2$ is beta-homolysine |
| 219 | Pro X$_1$ X$_2$ Leu Asp Thr | X$_1$ is (3R)-1,2,3,4-tetrahydroisoquinoline-3-carboxylic acid<br>X$_2$ is beta-homolysine |
| 220 | Pro X$_1$ X$_2$ Leu Asp Thr | X$_1$ is (3R)-1,2,3,4-tetrahydroisoquinoline-3-carboxylic acid<br>X$_2$ is beta-D-homolysine |
| 221 | Pro Tyr X Leu Asp Thr | X is beta-homoisoleucine |
| 222 | Pro X$_1$ X$_2$ Leu Asp Thr | X$_1$ is 4-aminomethyl-phenylalanine<br>X$_2$ is beta-homoproline |
| 223 | Pro Tyr X Leu Asp Thr | X is beta-D-homoproline |
| 224 | Pro X$_1$ X$_2$ Leu Asp Thr | X$_1$ is 4-aminomethyl-phenylalanine<br>X$_2$ is beta-D-homoproline |
| 225 | Pro Arg X Leu Asp Thr | X is beta-homolysine |
| 226 | Pro Phe X Leu Asp Thr | X is N-methyl beta-homolysine |
| 227 | Pro X$_1$ X$_2$ Leu Asp Thr | X$_1$ is phenlyalanine-reduced<br>X$_2$ is beta-homolysine |
| 228 | Pro X$_1$ X$_2$ Leu Asp Thr | X$_1$ is 3-aminomethyl-D-phenylalanine<br>X$_2$ is beta-homolysine |
| 229 | Pro X$_1$ X$_2$ Leu Asp Thr | X$_1$ is {2-[3-(1-piperazinyl)phenyl]-phenylalanine}-beta-homolysine<br>X$_2$ is beta-homolysine |
| 230 | Pro X$_1$ X$_2$ Leu Asp Thr | X$_1$ is 3-(4-thiazolyl)-D-alanine<br>X$_2$ is beta-homolysine |
| 231 | Pro X$_1$ X$_2$ Leu Asp Thr | X$_1$ is 2-bromo-phenylalanine<br>X$_2$ is beta-homolysine |
| 232 | Pro X$_1$ X$_2$ Leu Asp Thr | X$_1$ is 2-chloro-phenylalanine<br>X$_2$ is beta-homolysine |
| 233 | Pro X$_1$ X$_2$ Leu Asp Thr | X$_1$ is 2-fluoro-phenylalanine<br>X$_2$ is beta-homolysine |
| 234 | Pro X$_1$ X$_2$ Leu Asp Thr | X$_1$ is 2-trifluoromethyl-phenlyalanine<br>X$_2$ is beta-homolysine |
| 235 | Pro X$_1$ X$_2$ Leu Asp Thr | X$_1$ is 2,4-dichloro-phenlyalanine<br>X$_2$ is beta-homolysine |
| 236 | Pro X$_1$ X$_2$ Leu Asp Thr | X$_1$ is 2-aminomethyl-phenylalanine<br>X$_2$ is beta-homolysine |
| 237 | Pro X$_1$ X$_2$ Leu Asp Thr | X$_1$ is 2-(4-quinolinyl)-phenylalanine<br>X$_2$ is beta-homolysine |
| 238 | Pro X$_1$ X$_2$ Leu Asp Thr | X$_1$ is 2-(5-quinolinyl)-phenylalanine<br>X$_2$ is beta-homolysine |
| 239 | Pro X$_1$ X$_2$ Leu Asp Thr | X$_1$ is 2-(3-quinolinyl)-phenylalanine<br>X$_2$ is beta-homolysine |
| 240 | Pro X$_1$ X$_2$ Leu Asp Thr | X$_1$ is D-homophenylalanine<br>X$_2$ is beta-homolysine |

TABLE 3-continued

| Seq ID | Sequence | Features |
|---|---|---|
| 241 | Pro X$_1$ X$_2$ Leu Asp Thr | X$_1$ is 2-iodo-D-phenylalanine<br>X$_2$ is beta-homolysine |
| 242 | Pro X$_1$ X$_2$ Leu AspThr | X$_1$ is 2-phenyl-D-phenylalanine<br>X$_2$ is beta-homolysine |
| 243 | Pro X$_1$ X$_2$ Leu Asp Thr | X$_1$ is (2-piperazinyl-2-phenyl)-D-phenylalanine<br>X$_2$ is beta-homolysine |
| 244 | Pro Tyr X Leu Asp Ile | X is beta-homolysine |
| 245 | Pro Tyr X Leu Asp Val | X is beta-homolysine |
| 246 | Pro X$_1$ X$_2$ Leu Asp Ile | X1 is D-tyrosine<br>X2 is beta-homolysine |
| 247 | Pro X$_1$ X$_2$ Leu Asp Ile | X$_1$ is 4-aminomethyl-D-phenylalanine<br>X$_2$ is beta-homolysine |
| 248 | Pro X$_1$ X$_2$ Leu Asp Val | X$_1$ is 4-aminomethyl-phenylalanine<br>X$_2$ is beta-homolysine |
| 249 | Pro X$_1$ X$_2$ Leu Asp Thr | X$_1$ is 3-iodo-phenylalanine<br>X$_2$ is beta-homolysine |
| 250 | Pro X$_1$ X$_2$ Leu Asp Thr | X$_1$ is 3-phenyl-phenylalanine<br>X$_2$ is beta-homolysine |
| 251 | Pro X$_1$ X$_2$ Leu Asp Thr | X$_1$ is 3-(2-methoxy-phenyl)-phenylalanine<br>X$_2$ is beta-homolysine |
| 252 | Pro X$_1$ X$_2$ Leu Asp Thr | X$_1$ is 3-(2,6-dimthoxy-phenyl)-phenylalanine<br>X$_2$ is beta-homolysine |
| 253 | Pro X$_1$ X$_2$ Leu Asp Thr | X$_1$ is 3-(2-trifluoromethoxy-phenyl)-phenylalanine<br>X$_2$ is beta-homolysine |
| 254 | Pro X$_1$ X$_2$ Leu Asp Thr | X$_1$ is 4-iodo-phenylalanine<br>X$_2$ is beta-homolysine |
| 255 | Pro X$_1$ X$_2$ Leu Asp Thr | X$_1$ is 4-(2-methoxy-phenyl)-phenylalanine<br>X$_2$ is beta-homolysine |
| 256 | Pro X$_1$ X$_2$ Leu Asp Thr | X$_1$ is 4-(2-trifluoromethoxy-phenyl)-phenylalanine<br>X$_2$ is beta-homolysine |
| 257 | Pro X$_1$ X$_2$ Leu Asp Thr | X$_1$ is alpha-methyl-phenylalanine, (S)-(-)-2-amino-2-methyl-3-phenylpropionic acid<br>X$_2$ is beta-homolysine |
| 258 | Pro X$_1$ X$_2$ Leu Asp Thr | X$_1$ is N-methyl phenylalanine<br>X$_2$ is beta-homolysine |
| 259 | Pro X$_1$ X$_2$ Leu Asp Thr | X$_1$ is 3-(2,6-dimethyl-phenyl)-phenylalanine<br>X$_2$ is beta-homolysine |
| 260 | Pro X$_1$ X$_2$ Leu Asp Thr | X$_1$ is 3-(quinolin-4-yl)-phenylalanine<br>X$_2$ is beta-homolysine |
| 261 | Pro X$_1$ X$_2$ Leu Asp Thr | X$_1$ is 3-(3,4-difluoro-phenyl)-phenylalanine<br>X$_2$ is beta-homolysine |
| 262 | Pro X$_1$ X$_2$ Leu Asp Thr | X$_1$ is 4-(2,6-dimethyl-phenyl)-phenylalanine<br>X$_2$ is beta-homolysine |
| 263 | Pro X$_1$ X$_2$ Leu Asp Thr | X$_1$ is 4-(2-chloro-6-methoxy-phenyl)-phenylalanine<br>X$_2$ is beta-homolysine |
| 264 | Pro X$_1$ X$_2$ Leu Asp Thr | X$_1$ is 3-(4-thiazolyl)-alanine<br>X$_2$ is beta-homolysine |
| 265 | Pro X$_1$ X$_2$ Leu Asp Thr | X$_1$ is 2-(4-[1-piperazinyl)phenyl)-phenylalanine<br>X$_2$ is beta-homolysine |
| 266 | Pro X$_1$ X$_2$ Leu Asp Thr | X$_1$ is 2-(2,6-dimethylphenyl)-phenylalanine<br>X$_2$ is beta-homolysine |
| 267 | Pro X$_1$ X$_2$ Leu Asp Thr | X$_1$ is 2-(benzolthiazol-5-yl)-phenylalanine<br>X$_2$ is beta-homolysine |
| 268 | Pro X$_1$ X$_2$ Leu Asp Thr | X$_1$ is homophenylalanine<br>X$_2$ is beta-homolysine |
| 269 | Pro X$_1$ X$_2$ Leu Asp Thr | X$_1$ is piperidine-4-amino-4-carboxylic acid<br>X$_2$ is beta-homolysine |
| 270 | Pro X$_1$ X$_2$ Leu Asp Thr | X$_1$ is 2-(2,5-dimethyl-isoxazole)-D-phenylalanine<br>X$_2$ is beta-homolysine |
| 271 | Pro X$_1$ X$_2$ Leu Asp Val | X$_1$ is D-tyrosine<br>X$_2$ is beta-homolysine |
| 272 | Pro X$_1$ X$_2$ Leu Asp Thr | X$_1$ is 4-aminomethyl-D-phenylalanine<br>X$_2$ is beta-homolysine |
| 273 | Pro X$_1$ X$_2$ Leu Asp Thr | X$_1$ is 2-(2-chloro-6-methoxyphenyl)-phenylalanine<br>X$_2$ is beta-homolysine |
| 274 | Pro X$_1$ X$_2$ Leu Asp Thr | X$_1$ is 2-indanylglycine<br>X$_2$ is beta-homolysine |
| 275 | Pro X$_1$ X$_2$ Leu Asp Thr | X$_1$ is 2-indanyl-D-glycine<br>X$_2$ is beta-homolysine |
| 276 | Pro X$_1$ X$_2$ Leu Asp Thr | X$_1$ is 2-aminotetraline-2-carboxylic acid<br>X$_2$ is beta-homolysine |
| 277 | Pro Tyr X$_1$ Leu Asp X$_2$ | X$_1$ is beta-homolysine<br>X$_2$ is allo-isoleucine, (2S,3R)-2-amino-3-methylpentanoic acid |
| 278 | Pro X$_1$ X$_2$ Leu Asp X$_3$ | X$_1$ is D-tyrosine<br>X$_2$ is beta-homolysine<br>X$_3$ is allo-isoleucine, (2S,3R)-2-amino-3-methylpentanoic acid |

TABLE 3-continued

| Seq ID | Sequence | Features |
|---|---|---|
|  | Pro X$_1$ X$_2$ Leu Asp X$_3$ | X$_1$ is 4-aminomethyl-phenylalanine<br>X$_2$ is beta-homolysine<br>X$_3$ is allo-isoleucine, (2S,3R)-2-amino-3-methylpentanoic acid |
| 280 | Pro X$_1$ X$_2$ Leu Asp Thr | X$_1$ is 2-(2,5-bis(trifluoromethyl)phenyl)-phenylalanine<br>X$_2$ is beta-homolysine |
| 281 | Pro X$_1$ X$_2$ Leu Asp Thr | X$_1$ is 2-(2,5-bis(trifluoromethyl)phenyl)-phenylalanine<br>X$_2$ is beta-homolysine |
| 282 | Pro X$_1$ X$_2$ Leu Asp Thr | X$_1$ is aminoindan-2-carboxylic acid<br>X$_2$ is beta-homolysine |
| 283 | Pro Pro X Leu Asp Thr | X is beta-homolysine |
| 284 | Pro X$_1$ X$_2$ Leu Asp Thr | X$_1$ is D-proline<br>X$_2$ is beta-homolysine |
| 285 | Pro X$_1$ X$_2$ Leu Asp Thr | X$_1$ is pipecolic acid, homoPro<br>X$_2$ is beta-homolysine |
| 286 | Pro X$_1$ X$_2$ Leu Asp Thr | X$_1$ is 2-(3-pyridyl)- phenylalanine<br>X$_2$ is beta-homolysine |
| 287 | Pro X$_1$ X$_2$ Leu Asp Thr | X$_1$ is 2-(4-pyridyl)-phenylalanine<br>X$_2$ is beta-homolysine |
| 288 | Pro X$_1$ X$_2$ Leu Asp Thr | X$_1$ is 2-(3-bromo-2-pyridyl)-phenylalanine<br>X$_2$ is beta-homolysine |
| 289 | Pro Tyr X Leu Asp Thr | X is beta-D-homolysine |
| 290 | Pro X$_1$ X$_2$ Leu Asp Thr | X$_1$ is N-benzyl-glycine<br>X$_2$ is beta-homolysine |
| 291 | Pro X$_1$ X$_2$ Leu Asp Thr | X$_1$ is 2-(2-bromo-3-pyridyl)-phenylalanine<br>X$_2$ is beta-homolysine |
| 292 | Pro X$_1$ X$_2$ Leu Asp Thr | X$_1$ is 3-(2-chloro-6-methoxy-phenyl)-phenylalanine<br>X$_2$ is beta-homolysine |
| 293 | Pro X$_1$ X$_2$ Leu Asp Thr | X$_1$ is 3-(benzothiazol-5-yl)-phenylalanine<br>X$_2$ is beta-homolysine |
| 294 | Pro X$_1$ X$_2$ Leu Asp Thr | X$_1$ is 2-aminomethyl-phenylalanine<br>X$_2$ is N-methyl beta-homolysine |
| 295 | Pro X$_1$ X$_2$ Leu Asp Thr | X$_1$ is 2-aminomethyl-D-phenylalanine<br>X$_2$ is N-methyl beta-homolysine |
| 296 | Pro X$_1$ X$_2$ Leu Asp Thr | X$_1$ is 3-(4-thiazolyl)-D-alanine<br>X$_2$ is N-methyl beta-homolysine |
| 297 | Pro X$_1$ X$_2$ Leu Asp Thr | X$_1$ is 2-(2-trifluoromethoxy-phenyl)-D-phenylalanine<br>X$_2$ is N-methyl beta-homolysine |
| 298 | Pro X$_1$ X$_2$ Leu Asp Thr | X$_1$ is (3S)-1,2,3,4-tetrahydroisoquinoline-3-carboxylic acid<br>X$_2$ is N-methyl beta-homolysine |
| 299 | Pro X$_1$ X$_2$ Leu Asp Thr | X$_1$ is (3R)-1,2,3,4-tetrahydroisoquinoline-3-carboxylic acid<br>X$_2$ is N-methyl beta-homolysine |
| 300 | Pro X$_1$ X$_2$ Leu Asp Thr | X$_1$ is 2-(5-quinolinyl)-D-phenylalanine<br>X$_2$ is beta-homolysine |
| 301 | Pro Tyr X$_1$ Leu Asp X$_2$ | X$_1$ is beta-homolysine<br>X$_2$ is allo-threonine, (2S,3S)-2-amino-3-hydroxybutyric acid |
| 302 | Pro Tyr X$_1$ Leu Asp X$_2$ | X$_1$ is N-methyl beta-homolysine<br>X$_2$ is allo-threonine, (2S,3S)-2-amino-3-hydroxybutyric acid |
| 303 | Pro X$_1$ X$_2$ Leu Asp Thr | X$_1$ is N-methyl tyrosine<br>X$_2$ is N-methyl beta-homolysine |
|  | Pro X$_1$ X$_2$ Leu Asp X$_3$ | X$_1$ is N-methyl tyrosine<br>X$_2$ is N-methyl beta-homolysine<br>X$_3$ is allo-threonine, (2S,3S)-2-amino-3-hydroxybutyric acid |
| 305 | Pro X$_1$ X$_2$ Leu Asp Thr | X$_1$ is N-methyl phenylalanine<br>X$_2$ is N-methyl beta-homolysine |
| 306 | Pro X$_1$ X$_2$ Leu Asp Thr | X$_1$ is 2-fluoro-phenylalanine<br>X$_2$ is N-methyl beta-homolysine |
| 307 | Pro X$_1$ X$_2$ Leu Asp Thr | X$_1$ is 2-fluoro-N-methyl phenylalanine<br>X$_2$ is N-methyl beta-homolysine |
| 308 | Pro X$_1$ X$_2$ Leu Asp Thr | X$_1$ is 2,4-dichloro-phenylalanine<br>X$_2$ is N-methyl beta-homolysine |
| 309 | Pro X$_1$ X$_2$ Leu Asp Thr | X$_1$ is 2,4-dichloro-N-methyl phenylalanine<br>X$_2$ is N-methyl beta-homolysine |
| 310 | Pro X$_1$ X$_2$ Leu Asp Thr | X$_1$ is 2-aminomethyl-N-methyl-phenylalanine<br>X$_2$ is N-methyl beta-homolysine |
| 311 | Pro X$_1$ X$_2$ Leu Asp Thr | X$_1$ is 3-(2,6-dimethoxy-phenyl)-D-phenylalanine<br>X$_2$ is beta-homolysine |
| 312 | Pro X$_1$ X$_2$ Leu Asp Thr | X$_1$ is 3-(4-quinolinyl)-D-phenylalanine<br>X$_2$ is beta-homolysine |
| 313 | Pro X$_1$ X$_2$ Leu Asp Thr | X$_1$ is beta-homolysine<br>X$_2$ is azetidine-2-carboxylic acid |
| 314 | Pro X$_1$ X$_2$ Leu Asp Thr | X$_1$ is 3-phenyl-D-phenylalanine<br>X$_2$ is beta-homolysine |
| 315 | Pro X$_1$ X$_2$ Leu Asp Thr | X$_1$ is 3-(2-trifluoromethoxy-phenyl)-D-phenylalanine<br>X$_2$ is beta-homolysine |
| 316 | Pro X$_1$ X$_2$ Leu Asp Thr | X$_1$ is 3-(2-methoxy-phenyl)-D-phenylalanine<br>X$_2$ is beta-homolysine |
| 317 | Pro X$_1$ X$_2$ Leu Asp Thr | X$_1$ is 2-(5-quinolinyl)-N-methyl-phenylalanine<br>X$_2$ is N-methyl beta-homolysine |

TABLE 3-continued

| Seq ID | Sequence | Features |
|---|---|---|
| 318 | Pro Phe X Leu Asp Thr | X is beta-homonorleucine |
| 319 | Pro Phe X Leu Asp Thr | X is N-alpha-methyl-N-epsilon-dimethyl-beta-homolysine |
| 320 | Pro $X_1$ $X_2$ Leu Asp Thr | $X_1$ is N-methyl phenylalanine<br>$X_2$ is N-alpha-methyl-N-epsilon-dimethyl-beta-homolysine |
| 321 | Pro Met X Leu Asp Thr | X is N-methyl beta-homolysine |
| 322 | Pro $X_1$ $X_2$ Leu Asp Thr | $X_1$ is 2-indanylglycine<br>$X_2$ is N-methyl beta-homolysine |
| 323 | Pro $X_1$ $X_2$ Leu Asp Thr | $X_1$ is homophenylalanine<br>$X_2$ is N-methyl beta-homolysine |
| 324 | Pro $X_1$ $X_2$ Leu Asp Thr | $X_1$ is O-benzyl-trans-4-hydroxyproline<br>$X_2$ is N-methyl beta-homolysine |
| 325 | Pro $X_1$ $X_2$ Leu Asp Thr | $X_1$ is cis-2-aminocyclohexanecarboxylic acid<br>$X_2$ is N-methyl beta-homolysine |
| 326 | Pro $X_1$ $X_2$ Leu Asp Thr | $X_1$ is N-methyl methionine<br>$X_2$ is N-methyl beta-homolysine |
| 327 | Pro $X_1$ $X_2$ Leu Asp Thr | $X_1$ is beta-homolysine<br>$X_2$ is beta-homolysine |
| 328 | Pro $X_1$ $X_2$ Leu Asp Thr | $X_1$ is beta-homophenylalanine<br>$X_2$ is N-methyl beta-homolysine |
| 329 | Pro $X_1$ $X_2$ Leu Asp Thr | $X_1$ is beta-homomethionine<br>$X_2$ is N-methyl beta-homolysine |
| 330 | Pro Tyr X Leu Asp Thr | X is 3-aminomethyl-4-bromo-benzoic acid |
| 331 | Pro Tyr X Leu Asp Thr | X is 3-aminomethyl-4-(4-aza-phenyl)-benzoic acid |
| 332 | Pro Tyr X Leu Asp Thr | X is 3-aminomethyl-4-(2,5-dimethyl-isoxazole)-benzoic acid |
| 333 | Pro Tyr X Leu Asp Thr | X is 3-aminomethyl-4-(3-aminomethyl-phenyl)-benzoic acid |
| 334 | Pro X Leu Asp Thr | X is 3-aminomethyl-4-(4-(1-piperazinyl)-phenyl)-benzoic acid |
| 335 | Pro X Leu Asp Thr | X is 3-aminomethyl-4-(4-quinolinyl)-benzoic acid |
| 336 | Pro X Leu Asp Thr | X is 3-aminomethyl-4-bromo-benzoic acid |
| 337 | Pro X Leu Asp Thr | X is 3-aminomethyl-4-(2,5-dimethyl-isoxazole)-benzoic acid |
| 338 | $X_1$ $X_2$ Leu Asp Thr | $X_1$ is D-proline<br>$X_2$ is 3-aminomethyl-4-(4-pyridyl)-benzoic acid |
| 339 | Pro X Leu Asp Thr | X is 3-aminomethyl-(4-methylpyrazole-3-yl)-benzoic acid |
| 340 | Pro X Leu Asp Thr | X is 3-aminomethyl-4-(3-quinolinyl)-benzoic acid |
| 341 | Pro X Leu Asp Thr | X is 3-aminomethyl-4-(5-quinolinyl)-benzoic acid |
| 342 | Pro X Leu Asp Thr | X is 3-aminomethyl-4-(2-(1-piperazinyl)phenyl)-benzoic acid |
| 343 | Pro X Leu Asp Thr | X is 3-aminomethyl-4-(3-(1-piperzainyl)phenyl)-benzoic acid |
| 344 | Pro X Leu Asp Thr | X is 3-aminomethyl-4-(2-(3-(piperidin-4-ylmethoxy)phenyl))-benzoic acid |
| 345 | Pro X Leu Asp Thr | X is 3-aminomethyl-4-(4-pyridyl)-benzoic acid |
|  | Pro $X_1$ Leu Asp $X_2$ | $X_1$ is 3-aminomethyl-4-(4-pyridyl)-benzoic acid<br>$X_2$ is O-benzyl-threonine |
|  | Pro $X_1$ Leu Asp $X_2$ | $X_1$ is 3-aminomethyl-4-(4-quinolinyl)-benzoic acid<br>$X_2$ is allo-threonine, (2S,3S)-2-amino-3-hydroxybutyric acid |
| 348 | Pro X Leu Asp Thr | X is 3-aminomethyl-4-(4-(1-piperazinyl)phenyl))-benzoic acid |
|  | Pro $X_1$ $X_2$ Asp Thr | $X_1$ is 3-aminomethyl-4-(4-quinolinyl))-benzoic acid<br>$X_2$ is beta-tert-butyl alanine, neopentylglycine |
| 350 | Pro X Leu Asp Thr | X is N-benzyl-3-aminomethyl-benzoic acid |
| 351 | Pro X Leu Asp Thr | X is 3-aminomethyl-benzoic acid |
| 352 | Pro X Leu Asp Thr | X is 3-aminomethyl-5-bromo-benzoic acid |
| 353 | Pro X Leu Asp Thr | X is 3-aminomethyl-6-bromo-benzoic acid |
| 354 | Pro X Leu Asp Thr | X is 3-aminomethyl-5-(4-aza-phenyl)-benzoic acid |
| 355 | Pro X Leu Asp Thr | X is 3-aminomethyl-4-(3-thiophenyl)-benzoic acid |
| 356 | Pro X Leu Asp Thr | X is 3-aminomethyl-4-(4-N,N-dimethyl-carboxamide-phenyl)-benzoic acid |
| 357 | Pro X Leu Asp Thr | X is 3-aminomethyl-4-(4-aza-phenyl)-benzoic acid |
| 358 | Pro X Leu Asp Thr | X is 3-aminomethyl-4-(3-aza-phenyl)-benzoic acid |
| 359 | Pro X Leu Asp Thr | X is 3-aminomethyl-4-(4-hydroxy-phenyl)-benzoic acid |
| 360 | Pro X Leu Asp Thr | X is 3-aminomethyl-4-(5-(2,4-dimethyl)thiazole)-benzoic acid |
| 361 | Pro X Leu Asp Thr | X is 3-aminomethyl-4-(3-N,N-dimethylaniline)-benzoic acid |
| 362 | Pro X Leu Asp Thr | X is 3-aminomethyl-4-(2-fluoro-pyridyl)-benzoic acid |
| 363 | Pro X Leu Asp Thr | X is 3-aminomethyl-4-(5-pyrimidinyl)-benzoic acid |
| 364 | Pro X Leu Asp Thr | X is 3-aminomethyl-4-(3-N,N-dimethyl-diarylether)-benzoic acid |
| 365 | Pro X Leu Asp Thr | X is 3-aminomethyl-4-(3-trifluoromethyl-phenyl)-benzoic acid |
| 366 | Pro X Leu Asp Thr | X is 3-aminomethyl-4-(2,5-dimethoxy-phenyl)-benzoic acid |
| 367 | Pro X Leu Asp Thr | X is 3-aminomethyl-4-((2,3,4-tri-methoxy)-phenyl)-benzoic acid |
| 368 | Pro X Leu Asp Thr | X is 3-aminomethyl-4-(4-carboxy)-phenyl-benzoic acid |
| 369 | Pro X Leu Asp Thr | X is 3-aminomethyl-4-piperonyl-benzoic acid |
| 370 | Pro X Leu Asp Thr | X is 3-aminomethyl-4-piperidinyl-benzoic acid |
| 371 | Pro X Leu Asp Thr | X is 3-aminomethyl-4-morpholinyl-benzoic acid |
| 372 | Pro X Leu Asp Thr | X is 3-aminomethyl-4-(N,N-dimethyl)-benzoic acid |
| 373 | Pro X Leu Asp Thr | X is 3-aminomethyl-4-(2-aminomethylphenyl)-benzoic acid |
| 374 | Pro X Leu Asp Thr | X is 3-aminomethyl-4-(3-aminomethylphenyl)-benzoic acid |
| 375 | Pro X Leu Asp Thr | X is 3-aminomethyl-4-(4-aminomethylphenyl)-benzoic acid |
|  | Pro $X_1$ Leu Asp $X_2$ | $X_1$ is 3-aminomethyl-4-(4-quinolinyl)-benzoic acid<br>$X_2$ is 2-aminobutyric acid |
|  | $X_1$ $X_2$ Leu Asp Thr | $X_1$ is norvaline<br>$X_2$ is 3-aminomethyl-4-(4-quinoliny!)-benzoic acid |

TABLE 3-continued

| Seq ID | Sequence | Features |
|---|---|---|
| 378 | Pro X Leu Asp Thr | X is N-methyl-3-aminomethyl-benzoic acid |
| 379 | Pro X Leu Asp Thr | X is N-methyl-3-aminomethyl-4-(4-quinolinyl)-benzoic acid |
| 380 | Pro X$_1$ X$_2$ Leu Asp Thr | X$_1$ is 2-(5-quinolinyl)-phenylalanine-reduced<br>X$_2$ is beta-homolysine |
| 381 | Lys X Leu Asp Thr | X is N-methyl beta-homolysine |

SEQUENCE LISTING

```
Sequence total quantity: 381
SEQ ID NO: 1                moltype = AA  length = 5
FEATURE                     Location/Qualifiers
REGION                      1..5
                            note = peptide motif
source                      1..5
                            mol_type = protein
                            organism = synthetic construct
SEQUENCE: 1
PYLDV                                                                     5

SEQ ID NO: 2                moltype = AA  length = 5
FEATURE                     Location/Qualifiers
REGION                      1..5
                            note = peptide motif
source                      1..5
                            mol_type = protein
                            organism = synthetic construct
SEQUENCE: 2
PHLDV                                                                     5

SEQ ID NO: 3                moltype = AA  length = 5
FEATURE                     Location/Qualifiers
REGION                      1..5
                            note = peptide motif
source                      1..5
                            mol_type = protein
                            organism = synthetic construct
SEQUENCE: 3
PYLDT                                                                     5

SEQ ID NO: 4                moltype = AA  length = 5
FEATURE                     Location/Qualifiers
REGION                      1..5
                            note = peptide motif
source                      1..5
                            mol_type = protein
                            organism = synthetic construct
SEQUENCE: 4
PFLDT                                                                     5

SEQ ID NO: 5                moltype = AA  length = 5
FEATURE                     Location/Qualifiers
REGION                      1..5
                            note = peptide motif
SITE                        2
                            note = MISC_FEATURE - X is homophenylalanine
source                      1..5
                            mol_type = protein
                            organism = synthetic construct
SEQUENCE: 5
PXLDT                                                                     5

SEQ ID NO: 6                moltype = AA  length = 5
FEATURE                     Location/Qualifiers
REGION                      1..5
                            note = peptide motif
SITE                        2
                            note = MISC_FEATURE - X is beta-cyclohexyl alanine,
                             (S)-2-amino-3-cyclohexylpropionic acid
source                      1..5
                            mol_type = protein
                            organism = synthetic construct
SEQUENCE: 6
PXLDT                                                                     5
```

```
SEQ ID NO: 7              moltype = AA  length = 5
FEATURE                   Location/Qualifiers
REGION                    1..5
                          note = peptide motif
source                    1..5
                          mol_type = protein
                          organism = synthetic construct
SEQUENCE: 7
PWLDI                                                                     5

SEQ ID NO: 8              moltype = AA  length = 5
FEATURE                   Location/Qualifiers
REGION                    1..5
                          note = peptide motif
SITE                      2
                          note = MISC_FEATURE - X is 1-napthylalanine
source                    1..5
                          mol_type = protein
                          organism = synthetic construct
SEQUENCE: 8
PXLDT                                                                     5

SEQ ID NO: 9              moltype = AA  length = 5
FEATURE                   Location/Qualifiers
REGION                    1..5
                          note = peptide motif
SITE                      2
                          note = MISC_FEATURE - X is 2-napthylalanine
source                    1..5
                          mol_type = protein
                          organism = synthetic construct
SEQUENCE: 9
PXLDT                                                                     5

SEQ ID NO: 10             moltype = AA  length = 5
FEATURE                   Location/Qualifiers
REGION                    1..5
                          note = peptide motif
SITE                      5
                          note = MISC_FEATURE - X is O-benzyl-threonine
source                    1..5
                          mol_type = protein
                          organism = synthetic construct
SEQUENCE: 10
PWLDX                                                                     5

SEQ ID NO: 11             moltype = AA  length = 5
FEATURE                   Location/Qualifiers
REGION                    1..5
                          note = peptide motif
SITE                      2
                          note = MISC_FEATURE - X is biphenylalanine
source                    1..5
                          mol_type = protein
                          organism = synthetic construct
SEQUENCE: 11
PXLDT                                                                     5

SEQ ID NO: 12             moltype = AA  length = 5
FEATURE                   Location/Qualifiers
REGION                    1..5
                          note = peptide motif
SITE                      2
                          note = MISC_FEATURE - X is O-phenyl-tyrosine
source                    1..5
                          mol_type = protein
                          organism = synthetic construct
SEQUENCE: 12
PXLDT                                                                     5

SEQ ID NO: 13             moltype = AA  length = 5
FEATURE                   Location/Qualifiers
REGION                    1..5
                          note = peptide motif
SITE                      2
                          note = MISC_FEATURE - X is 1-napthylalanine
source                    1..5
                          mol_type = protein
```

```
                            organism = synthetic construct
SEQUENCE: 13
PXLDI                                                               5

SEQ ID NO: 14               moltype = AA  length = 5
FEATURE                     Location/Qualifiers
REGION                      1..5
                            note = peptide motif
SITE                        2
                            note = MISC_FEATURE - X is 2-napthylalanine
source                      1..5
                            mol_type = protein
                            organism = synthetic construct
SEQUENCE: 14
PXLDI                                                               5

SEQ ID NO: 15               moltype =    length =
SEQUENCE: 15
000

SEQ ID NO: 16               moltype = AA  length = 5
FEATURE                     Location/Qualifiers
REGION                      1..5
                            note = peptide motif
SITE                        1
                            note = MISC_FEATURE - X is (4S)-fluoro-proline
source                      1..5
                            mol_type = protein
                            organism = synthetic construct
SEQUENCE: 16
XWLDT                                                               5

SEQ ID NO: 17               moltype =    length =
SEQUENCE: 17
000

SEQ ID NO: 18               moltype = AA  length = 5
FEATURE                     Location/Qualifiers
REGION                      1..5
                            note = peptide motif
SITE                        2
                            note = MISC_FEATURE - X is O-2-methyl-phenyl-tyrosine
source                      1..5
                            mol_type = protein
                            organism = synthetic construct
SEQUENCE: 18
PXLDT                                                               5

SEQ ID NO: 19               moltype = AA  length = 5
FEATURE                     Location/Qualifiers
REGION                      1..5
                            note = peptide motif
SITE                        2
                            note = MISC_FEATURE - X is
                             O-4-trifluoromethyl-phenyl-tyrosine
source                      1..5
                            mol_type = protein
                            organism = synthetic construct
SEQUENCE: 19
PXLDT                                                               5

SEQ ID NO: 20               moltype = AA  length = 5
FEATURE                     Location/Qualifiers
REGION                      1..5
                            note = peptide motif
SITE                        2
                            note = MISC_FEATURE - X is O-4-methoxy-phenyl-tyrosine
source                      1..5
                            mol_type = protein
                            organism = synthetic construct
SEQUENCE: 20
PXLDT                                                               5

SEQ ID NO: 21               moltype = AA  length = 5
FEATURE                     Location/Qualifiers
REGION                      1..5
                            note = peptide motif
SITE                        2
                            note = MISC_FEATURE - X is O-4-fluoro-phenyl-tyrosine
```

-continued

| | | |
|---|---|---|
| source | 1..5<br>mol_type = protein<br>organism = synthetic construct | |
| SEQUENCE: 21<br>PXLDT | | 5 |
| SEQ ID NO: 22<br>FEATURE<br>REGION | moltype = AA  length = 5<br>Location/Qualifiers<br>1..5<br>note = peptide motif | |
| SITE | 2<br>note = MISC_FEATURE - X is O-2-methoxy-phenyl-tyrosine | |
| source | 1..5<br>mol_type = protein<br>organism = synthetic construct | |
| SEQUENCE: 22<br>PXLDT | | 5 |
| SEQ ID NO: 23<br>FEATURE<br>REGION | moltype = AA  length = 5<br>Location/Qualifiers<br>1..5<br>note = peptide motif | |
| SITE | 2<br>note = MISC_FEATURE - X is O-3-methoxy-phenyl-tyrosine | |
| source | 1..5<br>mol_type = protein<br>organism = synthetic construct | |
| SEQUENCE: 23<br>PXLDT | | 5 |
| SEQ ID NO: 24<br>FEATURE<br>REGION | moltype = AA  length = 5<br>Location/Qualifiers<br>1..5<br>note = peptide motif | |
| SITE | 2<br>note = MISC_FEATURE - X is O-3-fluoro-phenyl-tyrosine | |
| source | 1..5<br>mol_type = protein<br>organism = synthetic construct | |
| SEQUENCE: 24<br>PXLDT | | 5 |
| SEQ ID NO: 25<br>FEATURE<br>REGION | moltype = AA  length = 5<br>Location/Qualifiers<br>1..5<br>note = peptide motif | |
| SITE | 2<br>note = MISC_FEATURE - X is O-3,4-difluoro-phenyl-tyrosine | |
| source | 1..5<br>mol_type = protein<br>organism = synthetic construct | |
| SEQUENCE: 25<br>PXLDT | | 5 |
| SEQ ID NO: 26<br>FEATURE<br>REGION | moltype = AA  length = 5<br>Location/Qualifiers<br>1..5<br>note = peptide motif | |
| SITE | 2<br>note = MISC_FEATURE - X is O-3-methyl-phenyl-tyrosine | |
| source | 1..5<br>mol_type = protein<br>organism = synthetic construct | |
| SEQUENCE: 26<br>PXLDT | | 5 |
| SEQ ID NO: 27<br>FEATURE<br>REGION | moltype = AA  length = 5<br>Location/Qualifiers<br>1..5<br>note = peptide motif | |
| SITE | 2<br>note = MISC_FEATURE - X is O-3,4-dimethyl-phenyl-tyrosine | |
| source | 1..5<br>mol_type = protein<br>organism = synthetic construct | |
| SEQUENCE: 27<br>PXLDT | | 5 |
| SEQ ID NO: 28 | moltype = AA  length = 5 | |

```
FEATURE                 Location/Qualifiers
REGION                  1..5
                        note = peptide motif
SITE                    2
                        note = MISC_FEATURE - X is O-4-methylester-phenyl-tyrosine
source                  1..5
                        mol_type = protein
                        organism = synthetic construct
SEQUENCE: 28
PXLDT                                                                           5

SEQ ID NO: 29           moltype = AA  length = 5
FEATURE                 Location/Qualifiers
REGION                  1..5
                        note = peptide motif
SITE                    2
                        note = MISC_FEATURE - X is O-3-methylester-phenyl-tyrosine
source                  1..5
                        mol_type = protein
                        organism = synthetic construct
SEQUENCE: 29
PXLDT                                                                           5

SEQ ID NO: 30           moltype = AA  length = 5
FEATURE                 Location/Qualifiers
REGION                  1..5
                        note = peptide motif
SITE                    2
                        note = MISC_FEATURE - X is O-4-carboxylate-phenyl-tyrosine
source                  1..5
                        mol_type = protein
                        organism = synthetic construct
SEQUENCE: 30
PXLDT                                                                           5

SEQ ID NO: 31           moltype = AA  length = 5
FEATURE                 Location/Qualifiers
REGION                  1..5
                        note = peptide motif
SITE                    1
                        note = MISC_FEATURE - X is trans-4-hydroxyproline,
                        (2S,4R)-4-hydroxypyrrolidine-2-carboxylic acid
source                  1..5
                        mol_type = protein
                        organism = synthetic construct
SEQUENCE: 31
XFLDT                                                                           5

SEQ ID NO: 32           moltype = AA  length = 5
FEATURE                 Location/Qualifiers
REGION                  1..5
                        note = peptide motif
SITE                    2
                        note = MISC_FEATURE - X is metaTyrosine
source                  1..5
                        mol_type = protein
                        organism = synthetic construct
SEQUENCE: 32
PXLDT                                                                           5

SEQ ID NO: 33           moltype =   length =
SEQUENCE: 33
000

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000
```

```
SEQ ID NO: 38           moltype = AA  length = 5
FEATURE                 Location/Qualifiers
REGION                  1..5
                        note = peptide motif
source                  1..5
                        mol_type = protein
                        organism = synthetic construct
SEQUENCE: 38
PRLDT                                                                    5

SEQ ID NO: 39           moltype = AA  length = 5
FEATURE                 Location/Qualifiers
REGION                  1..5
                        note = peptide motif
SITE                    5
                        note = MISC_FEATURE - X is O-methyl-threonine
source                  1..5
                        mol_type = protein
                        organism = synthetic construct
SEQUENCE: 39
PFLDX                                                                    5

SEQ ID NO: 40           moltype = AA  length = 5
FEATURE                 Location/Qualifiers
REGION                  1..5
                        note = peptide motif
SITE                    5
                        note = MISC_FEATURE - X is O-ethyl-threonine
source                  1..5
                        mol_type = protein
                        organism = synthetic construct
SEQUENCE: 40
PFLDX                                                                    5

SEQ ID NO: 41           moltype = AA  length = 5
FEATURE                 Location/Qualifiers
REGION                  1..5
                        note = peptide motif
SITE                    2
                        note = MISC_FEATURE - D-tyrosine
source                  1..5
                        mol_type = protein
                        organism = synthetic construct
SEQUENCE: 41
PYLDT                                                                    5

SEQ ID NO: 42           moltype = AA  length = 5
FEATURE                 Location/Qualifiers
REGION                  1..5
                        note = peptide motif
SITE                    2
                        note = MISC_FEATURE - X is
                         (3R)-1,2,3,4-tetrahydroisoquinoline-3-carboxylic acid
source                  1..5
                        mol_type = protein
                        organism = synthetic construct
SEQUENCE: 42
PXLDT                                                                    5

SEQ ID NO: 43           moltype =   length =
SEQUENCE: 43
000

SEQ ID NO: 44           moltype = AA  length = 5
FEATURE                 Location/Qualifiers
REGION                  1..5
                        note = peptide motif
SITE                    1
                        note = MISC_FEATURE - X is (4R)-fluoro-proline
source                  1..5
                        mol_type = protein
                        organism = synthetic construct
SEQUENCE: 44
XFLDT                                                                    5

SEQ ID NO: 45           moltype =   length =
SEQUENCE: 45
000
```

```
SEQ ID NO: 46           moltype =    length =
SEQUENCE: 46
000

SEQ ID NO: 47           moltype = AA   length = 5
FEATURE                 Location/Qualifiers
REGION                  1..5
                        note = peptide motif
SITE                    1
                        note = MISC_FEATURE - X is (4R)-fluoro-proline
source                  1..5
                        mol_type = protein
                        organism = synthetic construct
SEQUENCE: 47
XYLDT                                                                   5

SEQ ID NO: 48           moltype = AA   length = 5
FEATURE                 Location/Qualifiers
REGION                  1..5
                        note = peptide motif
SITE                    1
                        note = MISC_FEATURE - X is (4S)-fluoro-proline
source                  1..5
                        mol_type = protein
                        organism = synthetic construct
SEQUENCE: 48
XYLDT                                                                   5

SEQ ID NO: 49           moltype = AA   length = 5
FEATURE                 Location/Qualifiers
REGION                  1..5
                        note = peptide motif
SITE                    2
                        note = MISC_FEATURE - D-arginine
source                  1..5
                        mol_type = protein
                        organism = synthetic construct
SEQUENCE: 49
PRLDT                                                                   5

SEQ ID NO: 50           moltype = AA   length = 5
FEATURE                 Location/Qualifiers
REGION                  1..5
                        note = peptide motif
SITE                    2
                        note = MISC_FEATURE - X is D-pipecolic acid, D-homoproline
source                  1..5
                        mol_type = protein
                        organism = synthetic construct
SEQUENCE: 50
PXLDT                                                                   5

SEQ ID NO: 51           moltype = AA   length = 5
FEATURE                 Location/Qualifiers
REGION                  1..5
                        note = peptide motif
SITE                    2
                        note = MISC_FEATURE - X is (3-(4-thiazolyl)-alanine)
source                  1..5
                        mol_type = protein
                        organism = synthetic construct
SEQUENCE: 51
PXLDT                                                                   5

SEQ ID NO: 52           moltype = AA   length = 5
FEATURE                 Location/Qualifiers
REGION                  1..5
                        note = peptide motif
source                  1..5
                        mol_type = protein
                        organism = synthetic construct
SEQUENCE: 52
PYLDI                                                                   5

SEQ ID NO: 53           moltype = AA   length = 5
FEATURE                 Location/Qualifiers
REGION                  1..5
                        note = peptide motif
```

```
SITE                    2
                        note = MISC_FEATURE - X is 4-aza-phenylalanine
source                  1..5
                        mol_type = protein
                        organism = synthetic construct
SEQUENCE: 53
PXLDT                                                                   5

SEQ ID NO: 54           moltype = AA  length = 5
FEATURE                 Location/Qualifiers
REGION                  1..5
                        note = peptide motif
SITE                    5
                        note = MISC_FEATURE - X is penicillamine,
                         beta,beta-dimethyl-cysteine
source                  1..5
                        mol_type = protein
                        organism = synthetic construct
SEQUENCE: 54
PYLDX                                                                   5

SEQ ID NO: 55           moltype = AA  length = 5
FEATURE                 Location/Qualifiers
REGION                  1..5
                        note = peptide motif
SITE                    2
                        note = MISC_FEATURE - X is 2-amino-4-bromo-4-pentenoic acid
source                  1..5
                        mol_type = protein
                        organism = synthetic construct
SEQUENCE: 55
PXLDT                                                                   5

SEQ ID NO: 56           moltype = AA  length = 5
FEATURE                 Location/Qualifiers
REGION                  1..5
                        note = peptide motif
SITE                    2
                        note = MISC_FEATURE - X is O-benzyl-trans-4-hydroxyproline
source                  1..5
                        mol_type = protein
                        organism = synthetic construct
SEQUENCE: 56
PXLDT                                                                   5

SEQ ID NO: 57           moltype = AA  length = 5
FEATURE                 Location/Qualifiers
REGION                  1..5
                        note = peptide motif
SITE                    2
                        note = MISC_FEATURE - X is Nbeta-Z-2,3-diaminopropionic acid
source                  1..5
                        mol_type = protein
                        organism = synthetic construct
SEQUENCE: 57
PXLDT                                                                   5

SEQ ID NO: 58           moltype = AA  length = 5
FEATURE                 Location/Qualifiers
REGION                  1..5
                        note = peptide motif
SITE                    2
                        note = MISC_FEATURE - X is N-tau-benzyl-histidine
source                  1..5
                        mol_type = protein
                        organism = synthetic construct
SEQUENCE: 58
PXLDT                                                                   5

SEQ ID NO: 59           moltype = AA  length = 5
FEATURE                 Location/Qualifiers
REGION                  1..5
                        note = peptide motif
SITE                    2
                        note = MISC_FEATURE - X is 4-amino-phenylalanine
source                  1..5
                        mol_type = protein
                        organism = synthetic construct
SEQUENCE: 59
```

```
                                                      -continued

PXLDT                                                                              5

SEQ ID NO: 60           moltype = AA  length = 5
FEATURE                 Location/Qualifiers
REGION                  1..5
                        note = peptide motif
SITE                    2
                        note = MISC_FEATURE - X is 4-aza-D-phenylalanine
source                  1..5
                        mol_type = protein
                        organism = synthetic construct
SEQUENCE: 60
PXLDT                                                                              5

SEQ ID NO: 61           moltype = AA  length = 5
FEATURE                 Location/Qualifiers
REGION                  1..5
                        note = peptide motif
SITE                    2
                        note = MISC_FEATURE - X is trans-4-hydroxyproline,
                         (2S,4R)-4-hydroxypyrrolidine-2-carboxylic acid
source                  1..5
                        mol_type = protein
                        organism = synthetic construct
SEQUENCE: 61
PXLDT                                                                              5

SEQ ID NO: 62           moltype = AA  length = 5
FEATURE                 Location/Qualifiers
REGION                  1..5
                        note = peptide motif
SITE                    2
                        note = MISC_FEATURE - D-tryptophan
source                  1..5
                        mol_type = protein
                        organism = synthetic construct
SEQUENCE: 62
PWLDT                                                                              5

SEQ ID NO: 63           moltype = AA  length = 5
FEATURE                 Location/Qualifiers
REGION                  1..5
                        note = peptide motif
source                  1..5
                        mol_type = protein
                        organism = synthetic construct
SEQUENCE: 63
PMLDT                                                                              5

SEQ ID NO: 64           moltype = AA  length = 5
FEATURE                 Location/Qualifiers
REGION                  1..5
                        note = peptide motif
SITE                    2
                        note = MISC_FEATURE - D-methionine
source                  1..5
                        mol_type = protein
                        organism = synthetic construct
SEQUENCE: 64
PMLDT                                                                              5

SEQ ID NO: 65           moltype = AA  length = 5
FEATURE                 Location/Qualifiers
REGION                  1..5
                        note = peptide motif
SITE                    2
                        note = MISC_FEATURE - X is 4-guanidino-phenylalanine
source                  1..5
                        mol_type = protein
                        organism = synthetic construct
SEQUENCE: 65
PXLDT                                                                              5

SEQ ID NO: 66           moltype = AA  length = 5
FEATURE                 Location/Qualifiers
REGION                  1..5
                        note = peptide motif
SITE                    2
                        note = MISC_FEATURE - X is 3-aza-phenylalanine
```

```
source                  1..5
                        mol_type = protein
                        organism = synthetic construct
SEQUENCE: 66
PXLDT                                                                    5

SEQ ID NO: 67           moltype = AA  length = 5
FEATURE                 Location/Qualifiers
REGION                  1..5
                        note = peptide motif
SITE                    2
                        note = MISC_FEATURE - X is 3-aza-D-phenylalanine
source                  1..5
                        mol_type = protein
                        organism = synthetic construct
SEQUENCE: 67
PXLDT                                                                    5

SEQ ID NO: 68           moltype = AA  length = 5
FEATURE                 Location/Qualifiers
REGION                  1..5
                        note = peptide motif
SITE                    2
                        note = MISC_FEATURE - X is norvaline
source                  1..5
                        mol_type = protein
                        organism = synthetic construct
SEQUENCE: 68
PXLDT                                                                    5

SEQ ID NO: 69           moltype = AA  length = 5
FEATURE                 Location/Qualifiers
REGION                  1..5
                        note = peptide motif
SITE                    2
                        note = MISC_FEATURE - X is D-norleucine
source                  1..5
                        mol_type = protein
                        organism = synthetic construct
SEQUENCE: 69
PXLDT                                                                    5

SEQ ID NO: 70           moltype = AA  length = 5
FEATURE                 Location/Qualifiers
REGION                  1..5
                        note = peptide motif
SITE                    2
                        note = MISC_FEATURE - D-lysine
source                  1..5
                        mol_type = protein
                        organism = synthetic construct
SEQUENCE: 70
PKLDT                                                                    5

SEQ ID NO: 71           moltype = AA  length = 5
FEATURE                 Location/Qualifiers
REGION                  1..5
                        note = peptide motif
SITE                    2
                        note = MISC_FEATURE - D-proline
source                  1..5
                        mol_type = protein
                        organism = synthetic construct
SEQUENCE: 71
PPLDT                                                                    5

SEQ ID NO: 72           moltype = AA  length = 5
FEATURE                 Location/Qualifiers
REGION                  1..5
                        note = peptide motif
SITE                    2
                        note = MISC_FEATURE - X is D-ornithine
source                  1..5
                        mol_type = protein
                        organism = synthetic construct
SEQUENCE: 72
PXLDT                                                                    5

SEQ ID NO: 73           moltype = AA  length = 5
```

```
FEATURE                 Location/Qualifiers
REGION                  1..5
                        note = peptide motif
SITE                    2
                        note = MISC_FEATURE - X is 3-benzothienyl-alanine
source                  1..5
                        mol_type = protein
                        organism = synthetic construct SEQUENCE: 73
PXLDT                                                                        5

SEQ ID NO: 74           moltype = AA  length = 5
FEATURE                 Location/Qualifiers
REGION                  1..5
                        note = peptide motif
SITE                    2
                        note = MISC_FEATURE - X is O-allyl-D-tyrosine
source                  1..5
                        mol_type = protein
                        organism = synthetic construct SEQUENCE: 74
PXLDT                                                                        5

SEQ ID NO: 75           moltype = AA  length = 5
FEATURE                 Location/Qualifiers
REGION                  1..5
                        note = peptide motif
SITE                    2
                        note = MISC_FEATURE - X is O-benzyl-D-serine
source                  1..5
                        mol_type = protein
                        organism = synthetic construct SEQUENCE: 75
PXLDT                                                                        5

SEQ ID NO: 76           moltype = AA  length = 5
FEATURE                 Location/Qualifiers
REGION                  1..5
                        note = peptide motif
SITE                    2
                        note = MISC_FEATURE - X is 3-(4-thiazolyl)-D-alanine
source                  1..5
                        mol_type = protein
                        organism = synthetic construct SEQUENCE: 76
PXLDT                                                                        5

SEQ ID NO: 77           moltype = AA  length = 5
FEATURE                 Location/Qualifiers
REGION                  1..5
                        note = peptide motif
SITE                    2
                        note = MISC_FEATURE - X is 3-benzothienyl-D-alanine
source                  1..5
                        mol_type = protein
                        organism = synthetic construct SEQUENCE: 77
PXLDT                                                                        5

SEQ ID NO: 78           moltype = AA  length = 5
FEATURE                 Location/Qualifiers
REGION                  1..5
                        note = peptide motif
SITE                    2
                        note = MISC_FEATURE - X is 3-(2-thienyl)-D-alanine
source                  1..5
                        mol_type = protein
                        organism = synthetic construct SEQUENCE: 78
PXLDT                                                                        5

SEQ ID NO: 79           moltype = AA  length = 5
FEATURE                 Location/Qualifiers
REGION                  1..5
                        note = peptide motif
SITE                    2
                        note = MISC_FEATURE - X is 4-aminomethyl-phenylalanine
source                  1..5
                        mol_type = protein
```

```
                          organism = synthetic construct
SEQUENCE: 79
PXLDT                                                                        5

SEQ ID NO: 80             moltype = AA  length = 5
FEATURE                   Location/Qualifiers
REGION                    1..5
                          note = peptide motif
SITE                      2
                          note = MISC_FEATURE - X is Ndelta-dimethyl-D-ornithine
source                    1..5
                          mol_type = protein
                          organism = synthetic construct
SEQUENCE: 80
PXLDT                                                                        5

SEQ ID NO: 81             moltype = AA  length = 5
FEATURE                   Location/Qualifiers
REGION                    1..5
                          note = peptide motif
SITE                      2
                          note = MISC_FEATURE - X is 4-amino-D-phenylalanine
source                    1..5
                          mol_type = protein
                          organism = synthetic construct
SEQUENCE: 81
PXLDT                                                                        5

SEQ ID NO: 82             moltype = AA  length = 5
FEATURE                   Location/Qualifiers
REGION                    1..5
                          note = peptide motif
SITE                      2
                          note = MISC_FEATURE - X is 4-aminomethyl-D-phenylalanine
source                    1..5
                          mol_type = protein
                          organism = synthetic construct
SEQUENCE: 82
PXLDT                                                                        5

SEQ ID NO: 83             moltype = AA  length = 5
FEATURE                   Location/Qualifiers
REGION                    1..5
                          note = peptide motif
SITE                      2
                          note = MISC_FEATURE - O-benzyl-D-tyrosine
source                    1..5
                          mol_type = protein
                          organism = synthetic construct
SEQUENCE: 83
PXLDT                                                                        5

SEQ ID NO: 84             moltype = AA  length = 5
FEATURE                   Location/Qualifiers
REGION                    1..5
                          note = peptide motif
source                    1..5
                          mol_type = protein
                          organism = synthetic construct
SEQUENCE: 84
PPLDT                                                                        5

SEQ ID NO: 85             moltype = AA  length = 5
FEATURE                   Location/Qualifiers
REGION                    1..5
                          note = peptide motif
SITE                      2
                          note = MISC_FEATURE - X is cyclo leucine,
                           1-Aminocyclopentane-1-carboxylic acid
source                    1..5
                          mol_type = protein
                          organism = synthetic construct
SEQUENCE: 85
PXLDT                                                                        5

SEQ ID NO: 86             moltype = AA  length = 5
FEATURE                   Location/Qualifiers
REGION                    1..5
                          note = peptide motif
```

```
SITE                    2
                        note = MISC_FEATURE - X is aminoindan-2-carboxylic acid
source                  1..5
                        mol_type = protein
                        organism = synthetic construct
SEQUENCE: 86
PXLDT                                                                        5

SEQ ID NO: 87           moltype = AA   length = 5
FEATURE                 Location/Qualifiers
REGION                  1..5
                        note = peptide motif
SITE                    2
                        note = MISC_FEATURE - X is O-allyl-tyrosine
source                  1..5
                        mol_type = protein
                        organism = synthetic construct
SEQUENCE: 87
PXLDT                                                                        5

SEQ ID NO: 88           moltype = AA   length = 5
FEATURE                 Location/Qualifiers
REGION                  1..5
                        note = peptide motif
SITE                    2
                        note = MISC_FEATURE - X is cyclohexyl glycine
source                  1..5
                        mol_type = protein
                        organism = synthetic construct
SEQUENCE: 88
PXLDT                                                                        5

SEQ ID NO: 89           moltype = AA   length = 5
FEATURE                 Location/Qualifiers
REGION                  1..5
                        note = peptide motif
source                  1..5
                        mol_type = protein
                        organism = synthetic construct
SEQUENCE: 89
PKLDT                                                                        5

SEQ ID NO: 90           moltype = AA   length = 5
FEATURE                 Location/Qualifiers
REGION                  1..5
                        note = peptide motif
SITE                    2
                        note = MISC_FEATURE - X is 2-aza-D-phenylalanine
source                  1..5
                        mol_type = protein
                        organism = synthetic construct
SEQUENCE: 90
PXLDT                                                                        5

SEQ ID NO: 91           moltype = AA   length = 5
FEATURE                 Location/Qualifiers
REGION                  1..5
                        note = peptide motif
SITE                    2
                        note = MISC_FEATURE - X is 2- aza-phenylalanine
source                  1..5
                        mol_type = protein
                        organism = synthetic construct
SEQUENCE: 91
PXLDT                                                                        5

SEQ ID NO: 92           moltype = AA   length = 5
FEATURE                 Location/Qualifiers
REGION                  1..5
                        note = peptide motif
SITE                    2
                        note = MISC_FEATURE - X is 2-(2-pyridyl)-4-thiazolyl-alanine
source                  1..5
                        mol_type = protein
                        organism = synthetic construct
SEQUENCE: 92
PXLDT                                                                        5

SEQ ID NO: 93           moltype = AA   length = 5
```

```
FEATURE              Location/Qualifiers
REGION               1..5
                     note = peptide motif
SITE                 2
                     note = MISC_FEATURE - X is 2-(3-pyridyl)-4-thiazolyl-alanine
source               1..5
                     mol_type = protein
                     organism = synthetic construct
SEQUENCE: 93
PXLDT                                                                          5

SEQ ID NO: 94        moltype = AA   length = 5
FEATURE              Location/Qualifiers
REGION               1..5
                     note = peptide motif
SITE                 2
                     note = MISC_FEATURE - X is 2-(4-pyridyl)-4-thiazolyl-alanine
source               1..5
                     mol_type = protein
                     organism = synthetic construct
SEQUENCE: 94
PXLDT                                                                          5

SEQ ID NO: 95        moltype = AA   length = 5
FEATURE              Location/Qualifiers
REGION               1..5
                     note = peptide motif
SITE                 2
                     note = MISC_FEATURE - X is
                     D-1,2,3,4-tetrahydroisoquinoline-1-carboxylic acid
source               1..5
                     mol_type = protein
                     organism = synthetic construct
SEQUENCE: 95
PXLDT                                                                          5

SEQ ID NO: 96        moltype = AA   length = 5
FEATURE              Location/Qualifiers
REGION               1..5
                     note = peptide motif
SITE                 2
                     note = MISC_FEATURE - X is 1-(S)-isoindoline-carboxylic acid
source               1..5
                     mol_type = protein
                     organism = synthetic construct
SEQUENCE: 96
PXLDT                                                                          5

SEQ ID NO: 97        moltype = AA   length = 6
FEATURE              Location/Qualifiers
REGION               1..6
                     note = peptide motif
SITE                 3
                     note = MISC_FEATURE - D-threonine
source               1..6
                     mol_type = protein
                     organism = synthetic construct
SEQUENCE: 97
PYTLDT                                                                         6

SEQ ID NO: 98        moltype = AA   length = 6
FEATURE              Location/Qualifiers
REGION               1..6
                     note = peptide motif
source               1..6
                     mol_type = protein
                     organism = synthetic construct
SEQUENCE: 98
PYPLDT                                                                         6

SEQ ID NO: 99        moltype = AA   length = 6
FEATURE              Location/Qualifiers
REGION               1..6
                     note = peptide motif
SITE                 3
                     note = MISC_FEATURE - D-proline
source               1..6
                     mol_type = protein
                     organism = synthetic construct
```

```
SEQUENCE: 99
PYPLDT                                                                          6

SEQ ID NO: 100          moltype = AA  length = 6
FEATURE                 Location/Qualifiers
REGION                  1..6
                        note = peptide motif
SITE                    3
                        note = MISC_FEATURE - X is sarcosine, N-methyl glycine
source                  1..6
                        mol_type = protein
                        organism = synthetic construct
SEQUENCE: 100
PYXLDT                                                                          6

SEQ ID NO: 101          moltype = AA  length = 6
FEATURE                 Location/Qualifiers
REGION                  1..6
                        note = peptide motif
SITE                    3
                        note = MISC_FEATURE - X is cyclo leucine,
                        1-Aminocyclopentane-1-carboxylic acid
source                  1..6
                        mol_type = protein
                        organism = synthetic construct
SEQUENCE: 101
PYXLDT                                                                          6

SEQ ID NO: 102          moltype = AA  length = 6
FEATURE                 Location/Qualifiers
REGION                  1..6
                        note = peptide motif
SITE                    2
                        note = MISC_FEATURE - X is 3-iodo-phenylalanine
SITE                    3
                        note = MISC_FEATURE - X is sarcosine, N-methyl glycine
source                  1..6
                        mol_type = protein
                        organism = synthetic construct
SEQUENCE: 102
PXXLDT                                                                          6

SEQ ID NO: 103          moltype = AA  length = 6
FEATURE                 Location/Qualifiers
REGION                  1..6
                        note = peptide motif
SITE                    2
                        note = MISC_FEATURE - X is 4-iodo-phenylalanine
SITE                    3
                        note = MISC_FEATURE - X is sarcosine, N-methyl glycine
source                  1..6
                        mol_type = protein
                        organism = synthetic construct
SEQUENCE: 103
PXXLDT                                                                          6

SEQ ID NO: 104          moltype = AA  length = 6
FEATURE                 Location/Qualifiers
REGION                  1..6
                        note = peptide motif
SITE                    2
                        note = MISC_FEATURE - X is 3,3-diphenyl-alanine
SITE                    3
                        note = MISC_FEATURE - X is sarcosine, N-methyl glycine
source                  1..6
                        mol_type = protein
                        organism = synthetic construct
SEQUENCE: 104
PXXLDT                                                                          6

SEQ ID NO: 105          moltype = AA  length = 6
FEATURE                 Location/Qualifiers
REGION                  1..6
                        note = peptide motif
SITE                    3
                        note = MISC_FEATURE - D-lysine
source                  1..6
                        mol_type = protein
                        organism = synthetic construct
```

```
SEQUENCE: 105
PFKLDT                                                                          6

SEQ ID NO: 106          moltype = AA  length = 6
FEATURE                 Location/Qualifiers
REGION                  1..6
                        note = peptide motif
SITE                    2
                        note = MISC_FEATURE - X is biphenylalanine
SITE                    3
                        note = MISC_FEATURE - D-lysine
source                  1..6
                        mol_type = protein
                        organism = synthetic construct
SEQUENCE: 106
PXKLDT                                                                          6

SEQ ID NO: 107          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - D-lysine
source                  1..6
                        mol_type = protein
                        organism = synthetic construct
SEQUENCE: 107
PXKLDT                                                                          6

SEQ ID NO: 108          moltype = AA  length = 6
FEATURE                 Location/Qualifiers
REGION                  1..6
                        note = peptide motif
SITE                    2
                        note = MISC_FEATURE - X is 3,3-diphenyl-alanine
SITE                    3
                        note = MISC_FEATURE - D-lysine
source                  1..6
                        mol_type = protein
                        organism = synthetic construct
SEQUENCE: 108
PXKLDT                                                                          6

SEQ ID NO: 109          moltype = AA  length = 6
FEATURE                 Location/Qualifiers
REGION                  1..6
                        note = peptide motif
SITE                    3
                        note = MISC_FEATURE - D-lysine
source                  1..6
                        mol_type = protein
                        organism = synthetic construct
SEQUENCE: 109
PYKLDI                                                                          6

SEQ ID NO: 110          moltype = AA  length = 6
FEATURE                 Location/Qualifiers
REGION                  1..6
                        note = peptide motif
SITE                    3
                        note = MISC_FEATURE - D-arginine
source                  1..6
                        mol_type = protein
                        organism = synthetic construct
SEQUENCE: 110
PYRLDT                                                                          6

SEQ ID NO: 111          moltype = AA  length = 6
FEATURE                 Location/Qualifiers
REGION                  1..6
                        note = peptide motif
SITE                    3
                        note = MISC_FEATURE - D-serine
source                  1..6
                        mol_type = protein
                        organism = synthetic construct
SEQUENCE: 111
```

```
PYSLDT                                                                             6

SEQ ID NO: 112            moltype = AA  length = 6
FEATURE                   Location/Qualifiers
REGION                    1..6
                          note = peptide motif
SITE                      2
                          note = MISC_FEATURE - X is biphenylalanine
SITE                      3
                          note = MISC_FEATURE - X is sarcosine, N-methyl glycine
source                    1..6
                          mol_type = protein
                          organism = synthetic construct
SEQUENCE: 112
PXXLDT                                                                             6

SEQ ID NO: 113            moltype = AA  length = 6
FEATURE                   Location/Qualifiers
REGION                    1..6
                          note = peptide motif
SITE                      2
                          note = MISC_FEATURE - X is 1-napthylalanine
SITE                      3
                          note = MISC_FEATURE - X is sarcosine, N-methyl glycine
source                    1..6
                          mol_type = protein
                          organism = synthetic construct
SEQUENCE: 113
PXXLDT                                                                             6

SEQ ID NO: 114            moltype = AA  length = 6
FEATURE                   Location/Qualifiers
REGION                    1..6
                          note = peptide motif
SITE                      3
                          note = MISC_FEATURE - X is pipecolic acid, homoproline
source                    1..6
                          mol_type = protein
                          organism = synthetic construct
SEQUENCE: 114
PYXLDT                                                                             6

SEQ ID NO: 115            moltype = AA  length = 6
FEATURE                   Location/Qualifiers
REGION                    1..6
                          note = peptide motif
SITE                      2
                          note = MISC_FEATURE - X is 2-iodo-phenylalanine
SITE                      3
                          note = MISC_FEATURE - X is sarcosine, N-methyl glycine
source                    1..6
                          mol_type = protein
                          organism = synthetic construct
SEQUENCE: 115
PXXLDT                                                                             6

SEQ ID NO: 116            moltype = AA  length = 6
FEATURE                   Location/Qualifiers
REGION                    1..6
                          note = peptide motif
SITE                      2
                          note = MISC_FEATURE - X is 1-napthylalanine
SITE                      3
                          note = MISC_FEATURE - D-lysine
source                    1..6
                          mol_type = protein
                          organism = synthetic construct
SEQUENCE: 116
PXKLDT                                                                             6

SEQ ID NO: 117            moltype = AA  length = 6
FEATURE                   Location/Qualifiers
REGION                    1..6
                          note = peptide motif
SITE                      3
                          note = MISC_FEATURE - D-lysine
SITE                      6
                          note = MISC_FEATURE - X is N-methyl threonine
source                    1..6
```

```
                            mol_type = protein
                            organism = synthetic construct
SEQUENCE: 117
PYKLDX                                                                       6

SEQ ID NO: 118              moltype = AA  length = 6
FEATURE                     Location/Qualifiers
REGION                      1..6
                            note = peptide motif
SITE                        3
                            note = MISC_FEATURE - X is sarcosine, N-methyl glycine
source                      1..6
                            mol_type = protein
                            organism = synthetic construct
SEQUENCE: 118
PFXLDT                                                                       6

SEQ ID NO: 119              moltype = AA  length = 6
FEATURE                     Location/Qualifiers
REGION                      1..6
                            note = peptide motif
SITE                        3
                            note = MISC_FEATURE - X is
                             (3R)-1,2,3,4-tetrahydroisoquinoline-3-carboxylic acid
source                      1..6
                            mol_type = protein
                            organism = synthetic construct
SEQUENCE: 119
PYXLDT                                                                       6

SEQ ID NO: 120              moltype = AA  length = 6
FEATURE                     Location/Qualifiers
REGION                      1..6
                            note = peptide motif
SITE                        3
                            note = MISC_FEATURE - X is D-pipecolic acid, D-homoproline
source                      1..6
                            mol_type = protein
                            organism = synthetic construct
SEQUENCE: 120
PYXLDT                                                                       6

SEQ ID NO: 121              moltype = AA  length = 6
FEATURE                     Location/Qualifiers
REGION                      1..6
                            note = peptide motif
SITE                        3
                            note = MISC_FEATURE - D-proline
source                      1..6
                            mol_type = protein
                            organism = synthetic construct
SEQUENCE: 121
PFPLDT                                                                       6

SEQ ID NO: 122              moltype = AA  length = 6
FEATURE                     Location/Qualifiers
REGION                      1..6
                            note = peptide motif
SITE                        2
                            note = MISC_FEATURE - X is 3,4-dimethoxy-phenylalanine
SITE                        3
                            note = MISC_FEATURE - D-proline
source                      1..6
                            mol_type = protein
                            organism = synthetic construct
SEQUENCE: 122
PXPLDT                                                                       6

SEQ ID NO: 123              moltype = AA  length = 6
FEATURE                     Location/Qualifiers
REGION                      1..6
                            note = peptide motif
SITE                        2
                            note = MISC_FEATURE - X is 3,4,5-trifluoro-phenylalanine
SITE                        3
                            note = MISC_FEATURE - D-proline
source                      1..6
                            mol_type = protein
                            organism = synthetic construct
```

```
SEQUENCE: 123
PXPLDT                                                                              6

SEQ ID NO: 124          moltype = AA  length = 6
FEATURE                 Location/Qualifiers
REGION                  1..6
                        note = peptide motif
SITE                    2
                        note = MISC_FEATURE - X is 3,5-dibromo-tyrosine
SITE                    3
                        note = MISC_FEATURE - D-proline
source                  1..6
                        mol_type = protein
                        organism = synthetic construct
SEQUENCE: 124
PXPLDT                                                                              6

SEQ ID NO: 125          moltype = AA  length = 6
FEATURE                 Location/Qualifiers
REGION                  1..6
                        note = peptide motif
SITE                    3
                        note = MISC_FEATURE - X is D-pipecolic acid, D-homoproline
source                  1..6
                        mol_type = protein
                        organism = synthetic construct
SEQUENCE: 125
PFXLDT                                                                              6

SEQ ID NO: 126          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - X is D-pipecolic acid, D-homoproline
source                  1..6
                        mol_type = protein
                        organism = synthetic construct
SEQUENCE: 126
PXXLDT                                                                              6

SEQ ID NO: 127          moltype = AA  length = 6
FEATURE                 Location/Qualifiers
REGION                  1..6
                        note = peptide motif
SITE                    2
                        note = MISC_FEATURE - X is 4-aminomethyl-phenylalanine
SITE                    3
                        note = MISC_FEATURE - X is D-pipecolic acid, D-homoproline
source                  1..6
                        mol_type = protein
                        organism = synthetic construct
SEQUENCE: 127
PXXLDT                                                                              6

SEQ ID NO: 128          moltype = AA  length = 6
FEATURE                 Location/Qualifiers
REGION                  1..6
                        note = peptide motif
SITE                    2
                        note = MISC_FEATURE - X is 2-iodo-phenylalanine
SITE                    3
                        note = MISC_FEATURE - X is D-pipecolic acid, D-homoproline
source                  1..6
                        mol_type = protein
                        organism = synthetic construct
SEQUENCE: 128
PXXLDT                                                                              6

SEQ ID NO: 129          moltype = AA  length = 6
FEATURE                 Location/Qualifiers
REGION                  1..6
                        note = peptide motif
SITE                    2
                        note = MISC_FEATURE - X is 2-phenyl-phenylalanine
SITE                    3
                        note = MISC_FEATURE - X is D-pipecolic acid, D-homoproline
```

```
source                  1..6
                        mol_type = protein
                        organism = synthetic construct
SEQUENCE: 129
PXXLDT                                                                    6

SEQ ID NO: 130          moltype = AA  length = 6
FEATURE                 Location/Qualifiers
REGION                  1..6
                        note = peptide motif
SITE                    2
                        note = MISC_FEATURE - X is
                        2-(2-methoxy-phenyl)-phenylalanine
SITE                    3
                        note = MISC_FEATURE - X is D-pipecolic acid, D-homoproline
source                  1..6
                        mol_type = protein
                        organism = synthetic construct
SEQUENCE: 130
PXXLDT                                                                    6

SEQ ID NO: 131          moltype = AA  length = 6
FEATURE                 Location/Qualifiers
REGION                  1..6
                        note = peptide motif
SITE                    2
                        note = MISC_FEATURE - X is
                        2-(3-methoxy-phenyl)-phenylalanine
SITE                    3
                        note = MISC_FEATURE - X is D-pipecolic acid, D-homoproline
source                  1..6
                        mol_type = protein
                        organism = synthetic construct
SEQUENCE: 131
PXXLDT                                                                    6

SEQ ID NO: 132          moltype = AA  length = 6
FEATURE                 Location/Qualifiers
REGION                  1..6
                        note = peptide motif
SITE                    2
                        note = MISC_FEATURE - X is
                        2-(4-methoxy-phenyl)-phenylalanine
SITE                    3
                        note = MISC_FEATURE - X is D-pipecolic acid, D-homoproline
source                  1..6
                        mol_type = protein
                        organism = synthetic construct
SEQUENCE: 132
PXXLDT                                                                    6

SEQ ID NO: 133          moltype = AA  length = 6
FEATURE                 Location/Qualifiers
REGION                  1..6
                        note = peptide motif
SITE                    2
                        note = MISC_FEATURE - X is biphenylalanine
SITE                    3
                        note = MISC_FEATURE - X is D-pipecolic acid, D-homoproline
source                  1..6
                        mol_type = protein
                        organism = synthetic construct
SEQUENCE: 133
PXXLDT                                                                    6

SEQ ID NO: 134          moltype = AA  length = 6
FEATURE                 Location/Qualifiers
REGION                  1..6
                        note = peptide motif
SITE                    3
                        note = MISC_FEATURE - X is trans-4-hydroxyproline,
                        (2S,4R)-4-hydroxypyrrolidine-2-carboxylic acid
source                  1..6
                        mol_type = protein
                        organism = synthetic construct
SEQUENCE: 134
PYXLDT                                                                    6

SEQ ID NO: 135          moltype = AA  length = 6
```

```
FEATURE              Location/Qualifiers
REGION               1..6
                     note = peptide motif
SITE                 3
                     note = MISC_FEATURE - X is trans-D-4-hydroxyproline,
                     (2R,4S)-4-hydroxypyrrolidine-2-carboxylic acid
source               1..6
                     mol_type = protein
                     organism = synthetic construct
SEQUENCE: 135
PYXLDT                                                                   6

SEQ ID NO: 136       moltype = AA  length = 6
FEATURE              Location/Qualifiers
REGION               1..6
                     note = peptide motif
SITE                 3
                     note = MISC_FEATURE - X is cis-D-4-Hydroxyproline,
                     (2R,4R)-4-Hydroxypyrrolidine-2-carboxylic acid
source               1..6
                     mol_type = protein
                     organism = synthetic construct
SEQUENCE: 136
PYXLDT                                                                   6

SEQ ID NO: 137       moltype = AA  length = 6
FEATURE              Location/Qualifiers
REGION               1..6
                     note = peptide motif
SITE                 1
                     note = MISC_FEATURE - D-proline
SITE                 2
                     note = MISC_FEATURE - D-tyrosine
SITE                 3
                     note = MISC_FEATURE - X is D-pipecolic acid, D-homoproline
source               1..6
                     mol_type = protein
                     organism = synthetic construct
SEQUENCE: 137
PYXLDT                                                                   6

SEQ ID NO: 138       moltype = AA  length = 6
FEATURE              Location/Qualifiers
REGION               1..6
                     note = peptide motif
SITE                 2
                     note = MISC_FEATURE - X is 1-napthylalanine
SITE                 3
                     note = MISC_FEATURE - X is D-pipecolic acid, D-homoproline
source               1..6
                     mol_type = protein
                     organism = synthetic construct
SEQUENCE: 138
PXXLDT                                                                   6

SEQ ID NO: 139       moltype = AA  length = 6
FEATURE              Location/Qualifiers
REGION               1..6
                     note = peptide motif
SITE                 2
                     note = MISC_FEATURE - X is 2-napthylalanine
SITE                 3
                     note = MISC_FEATURE - X is D-pipecolic acid, D-homoproline
source               1..6
                     mol_type = protein
                     organism = synthetic construct
SEQUENCE: 139
PXXLDT                                                                   6

SEQ ID NO: 140       moltype = AA  length = 6
FEATURE              Location/Qualifiers
REGION               1..6
                     note = peptide motif
SITE                 2
                     note = MISC_FEATURE - X is 4-aminomethyl-phenylalanine
SITE                 3
                     note = MISC_FEATURE - X is
                     (3R)-1,2,3,4-tetrahydroisoquinoline-3-carboxylic acid
source               1..6
```

```
                           mol_type = protein
                           organism = synthetic construct
SEQUENCE: 140
PXXLDT                                                                       6

SEQ ID NO: 141             moltype = AA   length = 6
FEATURE                    Location/Qualifiers
REGION                     1..6
                           note = peptide motif
SITE                       2
                           note = MISC_FEATURE - X is 3-aminomethyl-phenylalanine
SITE                       3
                           note = MISC_FEATURE - X is
                           (3R)-1,2,3,4-tetrahydroisoquinoline-3-carboxylic acid
source                     1..6
                           mol_type = protein
                           organism = synthetic construct
SEQUENCE: 141
PXXLDT                                                                       6

SEQ ID NO: 142             moltype = AA   length = 6
FEATURE                    Location/Qualifiers
REGION                     1..6
                           note = peptide motif
SITE                       2
                           note = MISC_FEATURE - X is 3-aminomethyl-D-phenylalanine
SITE                       3
                           note = MISC_FEATURE - X is
                           (3R)-1,2,3,4-tetrahydroisoquinoline-3-carboxylic acid
source                     1..6
                           mol_type = protein
                           organism = synthetic construct
SEQUENCE: 142
PXXLDT                                                                       6

SEQ ID NO: 143             moltype = AA   length = 6
FEATURE                    Location/Qualifiers
REGION                     1..6
                           note = peptide motif
SITE                       2
                           note = MISC_FEATURE - X is N-methyl tyrosine
SITE                       3
                           note = MISC_FEATURE - X is D-pipecolic acid, D-homoproline
source                     1..6
                           mol_type = protein
                           organism = synthetic construct
SEQUENCE: 143
PXXLDT                                                                       6

SEQ ID NO: 144             moltype = AA   length = 6
FEATURE                    Location/Qualifiers
REGION                     1..6
                           note = peptide motif
SITE                       3
                           note = MISC_FEATURE - X is D-pipecolic acid, D-homoproline
SITE                       6
                           note = MISC_FEATURE - X is allo-threonine,
                           (2S,3S)-2-amino-3-hydroxybutyric acid
source                     1..6
                           mol_type = protein
                           organism = synthetic construct
SEQUENCE: 144
PYXLDX                                                                       6

SEQ ID NO: 145             moltype = AA   length = 6
FEATURE                    Location/Qualifiers
REGION                     1..6
                           note = peptide motif
SITE                       3
                           note = MISC_FEATURE - X is D-pipecolic acid, D-homoproline
SITE                       4
                           note = MISC_FEATURE - X is beta-tert-butyl alanine,
                           neopentylglycine
source                     1..6
                           mol_type = protein
                           organism = synthetic construct
SEQUENCE: 145
PYXXDT                                                                       6
```

```
SEQ ID NO: 146             moltype = AA   length = 6
FEATURE                    Location/Qualifiers
REGION                     1..6
                           note = peptide motif
SITE                       2
                           note = MISC_FEATURE - X is 3-(4-thiazolyl)-alanine
SITE                       3
                           note = MISC_FEATURE - X is trans-D-4-hydroxyproline,
                           (2R,4S)-4-hydroxypyrrolidine-2-carboxylic acid
source                     1..6
                           mol_type = protein
                           organism = synthetic construct
SEQUENCE: 146
PXXLDT                                                                      6

SEQ ID NO: 147             moltype = AA   length = 6
FEATURE                    Location/Qualifiers
REGION                     1..6
                           note = peptide motif
SITE                       2
                           note = MISC_FEATURE - X is 4-aminomethyl-phenylalanine
SITE                       3
                           note = MISC_FEATURE - X is trans-D-4-hydroxyproline,
                           (2R,4S)-4-hydroxypyrrolidine-2-carboxylic acid
source                     1..6
                           mol_type = protein
                           organism = synthetic construct
SEQUENCE: 147
PXXLDT                                                                      6

SEQ ID NO: 148             moltype = AA   length = 6
FEATURE                    Location/Qualifiers
REGION                     1..6
                           note = peptide motif
SITE                       3
                           note = MISC_FEATURE - X is D-pipecolic acid, D-homoproline
source                     1..6
                           mol_type = protein
                           organism = synthetic construct
SEQUENCE: 148
PYXLDI                                                                      6

SEQ ID NO: 149             moltype = AA   length = 6
FEATURE                    Location/Qualifiers
REGION                     1..6
                           note = peptide motif
SITE                       3
                           note = MISC_FEATURE - X is N-methyl-D-Lysine
source                     1..6
                           mol_type = protein
                           organism = synthetic construct
SEQUENCE: 149
PYXLDI                                                                      6

SEQ ID NO: 150             moltype = AA   length = 6
FEATURE                    Location/Qualifiers
REGION                     1..6
                           note = peptide motif
SITE                       3
                           note = MISC_FEATURE - X is D-norleucine
source                     1..6
                           mol_type = protein
                           organism = synthetic construct
SEQUENCE: 150
PYXLDT                                                                      6

SEQ ID NO: 151             moltype = AA   length = 6
FEATURE                    Location/Qualifiers
REGION                     1..6
                           note = peptide motif
SITE                       3
                           note = MISC_FEATURE - X is trans-D-4-hydroxyproline,
                           (2R,4S)-4-hydroxypyrrolidine-2-carboxylic acid
source                     1..6
                           mol_type = protein
                           organism = synthetic construct
SEQUENCE: 151
PFXLDT                                                                      6
```

```
SEQ ID NO: 152          moltype = AA   length = 6
FEATURE                 Location/Qualifiers
REGION                  1..6
                        note = peptide motif
SITE                    3
                        note = MISC_FEATURE - X is N-methyl-D-arginine
source                  1..6
                        mol_type = protein
                        organism = synthetic construct
SEQUENCE: 152
PYXLDT                                                                    6

SEQ ID NO: 153          moltype = AA   length = 6
FEATURE                 Location/Qualifiers
REGION                  1..6
                        note = peptide motif
source                  1..6
                        mol_type = protein
                        organism = synthetic construct
SEQUENCE: 153
PYGLDT                                                                    6

SEQ ID NO: 154          moltype = AA   length = 6
FEATURE                 Location/Qualifiers
REGION                  1..6
                        note = peptide motif
source                  1..6
                        mol_type = protein
                        organism = synthetic construct
SEQUENCE: 154
PYALDT                                                                    6

SEQ ID NO: 155          moltype = AA   length = 6
FEATURE                 Location/Qualifiers
REGION                  1..6
                        note = peptide motif
SITE                    3
                        note = MISC_FEATURE - D-alanine
source                  1..6
                        mol_type = protein
                        organism = synthetic construct
SEQUENCE: 155
PYALDT                                                                    6

SEQ ID NO: 156          moltype = AA   length = 6
FEATURE                 Location/Qualifiers
REGION                  1..6
                        note = peptide motif
source                  1..6
                        mol_type = protein
                        organism = synthetic construct
SEQUENCE: 156
PMGLDT                                                                    6

SEQ ID NO: 157          moltype = AA   length = 6
FEATURE                 Location/Qualifiers
REGION                  1..6
                        note = peptide motif
SITE                    2
                        note = MISC_FEATURE - X is O-allyl-tyrosine
SITE                    3
                        note = MISC_FEATURE - X is sarcosine, N-methyl glycine
source                  1..6
                        mol_type = protein
                        organism = synthetic construct
SEQUENCE: 157
PXXLDT                                                                    6

SEQ ID NO: 158          moltype = AA   length = 6
FEATURE                 Location/Qualifiers
REGION                  1..6
                        note = peptide motif
SITE                    2
                        note = MISC_FEATURE - X is O-allyl-tyrosine
source                  1..6
                        mol_type = protein
                        organism = synthetic construct
SEQUENCE: 158
PXGLDT                                                                    6
```

```
SEQ ID NO: 159          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - X is sarcosine, N-methyl glycine
source                  1..6
                        mol_type = protein
                        organism = synthetic construct
SEQUENCE: 159
PXXLDT                                                                      6

SEQ ID NO: 160          moltype = AA  length = 6
FEATURE                 Location/Qualifiers
REGION                  1..6
                        note = peptide motif
SITE                    2
                        note = MISC_FEATURE - X is 4-aminomethyl-phenylalanine
source                  1..6
                        mol_type = protein
                        organism = synthetic construct
SEQUENCE: 160
PXGLDT                                                                      6

SEQ ID NO: 161          moltype = AA  length = 6
FEATURE                 Location/Qualifiers
REGION                  1..6
                        note = peptide motif
SITE                    2
                        note = MISC_FEATURE - X is O-allyl-tyrosine
SITE                    3
                        note = MISC_FEATURE - D-valine
source                  1..6
                        mol_type = protein
                        organism = synthetic construct
SEQUENCE: 161
PXVLDT                                                                      6

SEQ ID NO: 162          moltype = AA  length = 6
FEATURE                 Location/Qualifiers
REGION                  1..6
                        note = peptide motif
SITE                    2
                        note = MISC_FEATURE - X is O-allyl-tyrosine
SITE                    3
                        note = MISC_FEATURE - D-serine
source                  1..6
                        mol_type = protein
                        organism = synthetic construct
SEQUENCE: 162
PXSLDT                                                                      6

SEQ ID NO: 163          moltype = AA  length = 6
FEATURE                 Location/Qualifiers
REGION                  1..6
                        note = peptide motif
SITE                    2
                        note = MISC_FEATURE - X is O-allyl-tyrosine
SITE                    3
                        note = MISC_FEATURE - D-alanine
source                  1..6
                        mol_type = protein
                        organism = synthetic construct
SEQUENCE: 163
PXALDT                                                                      6

SEQ ID NO: 164          moltype = AA  length = 6
FEATURE                 Location/Qualifiers
REGION                  1..6
                        note = peptide motif
SITE                    2
                        note = MISC_FEATURE - X is O-allyl-tyrosine
source                  1..6
                        mol_type = protein
                        organism = synthetic construct
SEQUENCE: 164
```

```
PXPLDT                                                                           6

SEQ ID NO: 165          moltype = AA  length = 6
FEATURE                 Location/Qualifiers
REGION                  1..6
                        note = peptide motif
SITE                    2
                        note = MISC_FEATURE - X is O-allyl-tyrosine
SITE                    3
                        note = MISC_FEATURE - D-proline
source                  1..6
                        mol_type = protein
                        organism = synthetic construct
SEQUENCE: 165
PXPLDT                                                                           6

SEQ ID NO: 166          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - D-valine
source                  1..6
                        mol_type = protein
                        organism = synthetic construct
SEQUENCE: 166
PXVLDT                                                                           6

SEQ ID NO: 167          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - D-serine
source                  1..6
                        mol_type = protein
                        organism = synthetic construct
SEQUENCE: 167
PXSLDT                                                                           6

SEQ ID NO: 168          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - D-alanine
source                  1..6
                        mol_type = protein
                        organism = synthetic construct
SEQUENCE: 168
PXALDT                                                                           6

SEQ ID NO: 169          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
source                  1..6
                        mol_type = protein
                        organism = synthetic construct
SEQUENCE: 169
PXPLDT                                                                           6

SEQ ID NO: 170          moltype = AA  length = 6
FEATURE                 Location/Qualifiers
REGION                  1..6
                        note = peptide motif
SITE                    2
                        note = MISC_FEATURE - X is 3-(4-thiazolyl)-alanine
SITE                    3
                        note = MISC_FEATURE - D-proline
source                  1..6
```

```
                        mol_type = protein
                        organism = synthetic construct
SEQUENCE: 170
PXPLDT                                                                    6

SEQ ID NO: 171          moltype = AA  length = 6
FEATURE                 Location/Qualifiers
REGION                  1..6
                        note = peptide motif
SITE                    2
                        note = MISC_FEATURE - X is 4-aminomethyl-phenylalanine
source                  1..6
                        mol_type = protein
                        organism = synthetic construct
SEQUENCE: 171
PXPLDT                                                                    6

SEQ ID NO: 172          moltype = AA  length = 6
FEATURE                 Location/Qualifiers
REGION                  1..6
                        note = peptide motif
SITE                    2
                        note = MISC_FEATURE - X is 4-aminomethyl-phenylalanine
SITE                    3
                        note = MISC_FEATURE - D-proline
source                  1..6
                        mol_type = protein
                        organism = synthetic construct
SEQUENCE: 172
PXPLDT                                                                    6

SEQ ID NO: 173          moltype = AA  length = 6
FEATURE                 Location/Qualifiers
REGION                  1..6
                        note = peptide motif
SITE                    2
                        note = MISC_FEATURE - X is cyclo leucine,
                         1-Aminocyclopentane-1-carboxylic acid
source                  1..6
                        mol_type = protein
                        organism = synthetic construct
SEQUENCE: 173
PXPLDT                                                                    6

SEQ ID NO: 174          moltype = AA  length = 6
FEATURE                 Location/Qualifiers
REGION                  1..6
                        note = peptide motif
SITE                    2
                        note = MISC_FEATURE - X is 2-(2-pyridyl)-4-thiazolyl-alanine
SITE                    3
                        note = MISC_FEATURE - X is sarcosine, N-methyl glycine
source                  1..6
                        mol_type = protein
                        organism = synthetic construct
SEQUENCE: 174
PXXLDT                                                                    6

SEQ ID NO: 175          moltype = AA  length = 6
FEATURE                 Location/Qualifiers
REGION                  1..6
                        note = peptide motif
SITE                    2
                        note = MISC_FEATURE - X is 2-(2-pyridyl)-4-thiazolyl-alanine
SITE                    3
                        note = MISC_FEATURE - D-proline
source                  1..6
                        mol_type = protein
                        organism = synthetic construct
SEQUENCE: 175
PXPLDT                                                                    6

SEQ ID NO: 176          moltype = AA  length = 6
FEATURE                 Location/Qualifiers
REGION                  1..6
                        note = peptide motif
SITE                    2
                        note = MISC_FEATURE - X is 2-(3-pyridyl)-4-thiazolyl-alanine
SITE                    3
```

```
                        note = MISC_FEATURE - X is sarcosine, N-methyl glycine
source                  1..6
                        mol_type = protein
                        organism = synthetic construct
SEQUENCE: 176
PXXLDT                                                                         6

SEQ ID NO: 177          moltype = AA  length = 6
FEATURE                 Location/Qualifiers
REGION                  1..6
                        note = peptide motif
SITE                    2
                        note = MISC_FEATURE - X is 2-(3-pyridyl)-4-thiazolyl-alanine
SITE                    3
                        note = MISC_FEATURE - D-proline
source                  1..6
                        mol_type = protein
                        organism = synthetic construct
SEQUENCE: 177
PXPLDT                                                                         6

SEQ ID NO: 178          moltype = AA  length = 6
FEATURE                 Location/Qualifiers
REGION                  1..6
                        note = peptide motif
SITE                    2
                        note = MISC_FEATURE - X is 2-(4-pyridyl)-4-thiazolyl-alanine
SITE                    3
                        note = MISC_FEATURE - D-proline
source                  1..6
                        mol_type = protein
                        organism = synthetic construct
SEQUENCE: 178
PXPLDT                                                                         6

SEQ ID NO: 179          moltype = AA  length = 6
FEATURE                 Location/Qualifiers
REGION                  1..6
                        note = peptide motif
SITE                    2
                        note = MISC_FEATURE - X is
                        3-(2-aminobenzyl-4-thiazolyl)-alanine
SITE                    3
                        note = MISC_FEATURE - X is sarcosine, N-methyl glycine
source                  1..6
                        mol_type = protein
                        organism = synthetic construct
SEQUENCE: 179
PXXLDT                                                                         6

SEQ ID NO: 180          moltype = AA  length = 6
FEATURE                 Location/Qualifiers
REGION                  1..6
                        note = peptide motif
SITE                    2
                        note = MISC_FEATURE - X is
                        2-(amino-benzyl)-4-thiazolyl-alanine
SITE                    3
                        note = MISC_FEATURE - D-proline
source                  1..6
                        mol_type = protein
                        organism = synthetic construct
SEQUENCE: 180
PXPLDT                                                                         6

SEQ ID NO: 181          moltype = AA  length = 6
FEATURE                 Location/Qualifiers
REGION                  1..6
                        note = peptide motif
SITE                    2
                        note = MISC_FEATURE - D-tyrosine
SITE                    3
                        note = MISC_FEATURE - X is D-pipecolic acid, D-homoproline
source                  1..6
                        mol_type = protein
                        organism = synthetic construct
SEQUENCE: 181
PYXLDI                                                                         6
```

| | | |
|---|---|---|
| SEQ ID NO: 182<br>FEATURE<br>REGION<br><br>SITE<br><br>SITE<br><br>source<br><br>SEQUENCE: 182<br>PXXLDT | moltype = AA  length = 6<br>Location/Qualifiers<br>1..6<br>note = peptide motif<br>2<br>note = MISC_FEATURE - X is 2-aminomethyl-phenylalanine<br>3<br>note = MISC_FEATURE - X is azetidine-2-carboxylic acid<br>1..6<br>mol_type = protein<br>organism = synthetic construct<br><br> | <br><br><br><br><br><br><br><br><br><br><br><br>6 |
| SEQ ID NO: 183<br>FEATURE<br>REGION<br><br>SITE<br><br>SITE<br><br>source<br><br>SEQUENCE: 183<br>PYXLDX | moltype = AA  length = 6<br>Location/Qualifiers<br>1..6<br>note = peptide motif<br>3<br>note = MISC_FEATURE - X is D-pipecolic acid, D-homoproline<br>6<br>note = MISC_FEATURE - X is 2-aminobutyric acid<br>1..6<br>mol_type = protein<br>organism = synthetic construct<br><br> | <br><br><br><br><br><br><br><br><br><br><br><br>6 |
| SEQ ID NO: 184<br>SEQUENCE: 184<br>000 | moltype =   length = | |
| SEQ ID NO: 185<br>FEATURE<br>REGION<br><br>SITE<br><br>SITE<br><br>source<br><br>SEQUENCE: 185<br>PXXLDT | moltype = AA  length = 6<br>Location/Qualifiers<br>1..6<br>note = peptide motif<br>2<br>note = MISC_FEATURE - X is 2,4-dichloro-phenylalanine<br>3<br>note = MISC_FEATURE - X is D-pipecolic acid, D-homoproline<br>1..6<br>mol_type = protein<br>organism = synthetic construct<br><br> | <br><br><br><br><br><br><br><br><br><br><br><br>6 |
| SEQ ID NO: 186<br>FEATURE<br>REGION<br><br>SITE<br><br>SITE<br><br>source<br><br>SEQUENCE: 186<br>PXXLDT | moltype = AA  length = 6<br>Location/Qualifiers<br>1..6<br>note = peptide motif<br>2<br>note = MISC_FEATURE - X is 3-phenyl-D-phenylalanine<br>3<br>note = MISC_FEATURE - X is D-pipecolic acid, D-homoproline<br>1..6<br>mol_type = protein<br>organism = synthetic construct<br><br> | <br><br><br><br><br><br><br><br><br><br><br><br>6 |
| SEQ ID NO: 187<br>FEATURE<br>REGION<br><br>SITE<br><br>SITE<br><br>source<br><br>SEQUENCE: 187<br>PXXLDT | moltype = AA  length = 6<br>Location/Qualifiers<br>1..6<br>note = peptide motif<br>2<br>note = MISC_FEATURE - X is 3-(5-quinolinyl)-D-phenylalanine<br>3<br>note = MISC_FEATURE - X is D-pipecolic acid, D-homoproline<br>1..6<br>mol_type = protein<br>organism = synthetic construct<br><br> | <br><br><br><br><br><br><br><br><br><br><br><br>6 |
| SEQ ID NO: 188<br>FEATURE<br>REGION<br><br>SITE | moltype = AA  length = 6<br>Location/Qualifiers<br>1..6<br>note = peptide motif<br>3 | |

|  |  |  |
|---|---|---|
| source | 1..6<br>mol_type = protein<br>organism = synthetic construct | |
| SEQUENCE: 188<br>PYXLDT | | 6 |
| SEQ ID NO: 189<br>FEATURE<br>REGION | moltype = AA length = 6<br>Location/Qualifiers<br>1..6<br>note = peptide motif | |
| SITE | 3<br>note = MISC_FEATURE - X is beta-homoproline | |
| source | 1..6<br>mol_type = protein<br>organism = synthetic construct | |
| SEQUENCE: 189<br>PYXLDT | | 6 |
| SEQ ID NO: 190<br>FEATURE<br>REGION | moltype = AA length = 6<br>Location/Qualifiers<br>1..6<br>note = peptide motif | |
| SITE | 3<br>note = MISC_FEATURE - X is beta-homolysine | |
| source | 1..6<br>mol_type = protein<br>organism = synthetic construct | |
| SEQUENCE: 190<br>PYXLDT | | 6 |
| SEQ ID NO: 191<br>FEATURE<br>REGION | moltype = AA length = 6<br>Location/Qualifiers<br>1..6<br>note = peptide motif | |
| SITE | 3<br>note = MISC_FEATURE - X is anthranilic acid, 2-aminobenzoic<br>acid | |
| source | 1..6<br>mol_type = protein<br>organism = synthetic construct | |
| SEQUENCE: 191<br>PYXLDT | | 6 |
| SEQ ID NO: 192<br>FEATURE<br>REGION | moltype = AA length = 6<br>Location/Qualifiers<br>1..6<br>note = peptide motif | |
| SITE | 3<br>note = MISC_FEATURE - X is beta-homolysine | |
| source | 1..6<br>mol_type = protein<br>organism = synthetic construct | |
| SEQUENCE: 192<br>PFXLDT | | 6 |
| SEQ ID NO: 193<br>FEATURE<br>REGION | moltype = AA length = 6<br>Location/Qualifiers<br>1..6<br>note = peptide motif | |
| SITE | 2<br>note = MISC_FEATURE - X is 3-(4-thiazolyl)-alanine | |
| SITE | 3<br>note = MISC_FEATURE - X is beta-homolysine | |
| source | 1..6<br>mol_type = protein<br>organism = synthetic construct | |
| SEQUENCE: 193<br>PXXLDT | | 6 |
| SEQ ID NO: 194<br>FEATURE<br>REGION | moltype = AA length = 6<br>Location/Qualifiers<br>1..6<br>note = peptide motif | |
| SITE | 2<br>note = MISC_FEATURE - X is 4-aminomethyl-phenylalanine | |
| SITE | 3<br>note = MISC_FEATURE - X is beta-homolysine | |
| source | 1..6 | |

```
                            mol_type = protein
                            organism = synthetic construct
SEQUENCE: 194
PXXLDT                                                                  6

SEQ ID NO: 195              moltype = AA   length = 6
FEATURE                     Location/Qualifiers
REGION                      1..6
                            note = peptide motif
SITE                        3
                            note = MISC_FEATURE - X is beta-homolysine
SITE                        6
                            note = MISC_FEATURE - X is O-benzyl-threonine
source                      1..6
                            mol_type = protein
                            organism = synthetic construct
SEQUENCE: 195
PYXLDX                                                                  6

SEQ ID NO: 196              moltype = AA   length = 6
FEATURE                     Location/Qualifiers
REGION                      1..6
                            note = peptide motif
SITE                        2
                            note = MISC_FEATURE - X is N-methyl tyrosine
SITE                        3
                            note = MISC_FEATURE - X is D-beta-homolysine
source                      1..6
                            mol_type = protein
                            organism = synthetic construct
SEQUENCE: 196
PXXLDT                                                                  6

SEQ ID NO: 197              moltype = AA   length = 6
FEATURE                     Location/Qualifiers
REGION                      1..6
                            note = peptide motif
SITE                        2
                            note = MISC_FEATURE - X is 1-napthylalanine
SITE                        3
                            note = MISC_FEATURE - X is beta-homolysine
source                      1..6
                            mol_type = protein
                            organism = synthetic construct
SEQUENCE: 197
PXXLDT                                                                  6

SEQ ID NO: 198              moltype = AA   length = 6
FEATURE                     Location/Qualifiers
REGION                      1..6
                            note = peptide motif
SITE                        2
                            note = MISC_FEATURE - X is 2-napthylalanine
SITE                        3
                            note = MISC_FEATURE - X is beta-homolysine
source                      1..6
                            mol_type = protein
                            organism = synthetic construct
SEQUENCE: 198
PXXLDT                                                                  6

SEQ ID NO: 199              moltype = AA   length = 6
FEATURE                     Location/Qualifiers
REGION                      1..6
                            note = peptide motif
SITE                        2
                            note = MISC_FEATURE - X is biphenylalanine
SITE                        3
                            note = MISC_FEATURE - X is beta-homolysine
source                      1..6
                            mol_type = protein
                            organism = synthetic construct
SEQUENCE: 199
PXXLDT                                                                  6

SEQ ID NO: 200              moltype = AA   length = 6
FEATURE                     Location/Qualifiers
REGION                      1..6
                            note = peptide motif
```

```
SITE                         2
                             note = MISC_FEATURE - X is 2-iodo-phenylalanine
SITE                         3
                             note = MISC_FEATURE - X is beta-homolysine
source                       1..6
                             mol_type = protein
                             organism = synthetic construct
SEQUENCE: 200
PXXLDT                                                                        6

SEQ ID NO: 201               moltype = AA  length = 6
FEATURE                      Location/Qualifiers
REGION                       1..6
                             note = peptide motif
SITE                         2
                             note = MISC_FEATURE - X is
                             2-(2,5-dimethyl-isoxazole)-phenylalanine
SITE                         3
                             note = MISC_FEATURE - X is beta-homolysine
source                       1..6
                             mol_type = protein
                             organism = synthetic construct
SEQUENCE: 201
PXXLDT                                                                        6

SEQ ID NO: 202               moltype = AA  length = 6
FEATURE                      Location/Qualifiers
REGION                       1..6
                             note = peptide motif
SITE                         2
                             note = MISC_FEATURE - X is 2-phenyl-phenylalanine
SITE                         3
                             note = MISC_FEATURE - X is beta-homolysine
source                       1..6
                             mol_type = protein
                             organism = synthetic construct
SEQUENCE: 202
PXXLDT                                                                        6

SEQ ID NO: 203               moltype = AA  length = 6
FEATURE                      Location/Qualifiers
REGION                       1..6
                             note = peptide motif
SITE                         2
                             note = MISC_FEATURE - X is
                             (2-piperazinyl-2-phenyl)-phenylalanine
SITE                         3
                             note = MISC_FEATURE - X is beta-homolysine
source                       1..6
                             mol_type = protein
                             organism = synthetic construct
SEQUENCE: 203
PXXLDT                                                                        6

SEQ ID NO: 204               moltype = AA  length = 6
FEATURE                      Location/Qualifiers
REGION                       1..6
                             note = peptide motif
SITE                         2
                             note = MISC_FEATURE - X is beta-cyclohexyl alanine,
                             (S)-2-amino-3-cyclohexylpropionic acid
SITE                         3
                             note = MISC_FEATURE - X is beta-homolysine
source                       1..6
                             mol_type = protein
                             organism = synthetic construct
SEQUENCE: 204
PXXLDT                                                                        6

SEQ ID NO: 205               moltype = AA  length = 6
FEATURE                      Location/Qualifiers
REGION                       1..6
                             note = peptide motif
SITE                         3
                             note = MISC_FEATURE - X is beta-homolysine
source                       1..6
                             mol_type = protein
                             organism = synthetic construct
SEQUENCE: 205
```

```
PWXLDT                                                                      6

SEQ ID NO: 206          moltype = AA   length = 6
FEATURE                 Location/Qualifiers
REGION                  1..6
                        note = peptide motif
SITE                    2
                        note = MISC_FEATURE - D-tryptophan
SITE                    3
                        note = MISC_FEATURE - X is beta-homolysine
source                  1..6
                        mol_type = protein
                        organism = synthetic construct
SEQUENCE: 206
PWXLDT                                                                      6

SEQ ID NO: 207          moltype = AA   length = 6
FEATURE                 Location/Qualifiers
REGION                  1..6
                        note = peptide motif
SITE                    2
                        note = MISC_FEATURE - X is 3-aminomethyl-phenylalanine
SITE                    3
                        note = MISC_FEATURE - X is beta-homolysine
source                  1..6
                        mol_type = protein
                        organism = synthetic construct
SEQUENCE: 207
PXXLDT                                                                      6

SEQ ID NO: 208          moltype = AA   length = 6
FEATURE                 Location/Qualifiers
REGION                  1..6
                        note = peptide motif
SITE                    2
                        note = MISC_FEATURE - X is 4-aminomethyl-D-phenylalanine
SITE                    3
                        note = MISC_FEATURE - X is beta-homolysine
source                  1..6
                        mol_type = protein
                        organism = synthetic construct
SEQUENCE: 208
PXXLDT                                                                      6

SEQ ID NO: 209          moltype = AA   length = 6
FEATURE                 Location/Qualifiers
REGION                  1..6
                        note = peptide motif
SITE                    2
                        note = MISC_FEATURE - X is 4-aminomethyl-phenylalanine
SITE                    3
                        note = MISC_FEATURE - X is beta-homolysine
source                  1..6
                        mol_type = protein
                        organism = synthetic construct
SEQUENCE: 209
PXXLDI                                                                      6

SEQ ID NO: 210          moltype = AA   length = 6
FEATURE                 Location/Qualifiers
REGION                  1..6
                        note = peptide motif
SITE                    3
                        note = MISC_FEATURE - X is beta-D-homolysine
source                  1..6
                        mol_type = protein
                        organism = synthetic construct
SEQUENCE: 210
PYXLDI                                                                      6

SEQ ID NO: 211          moltype = AA   length = 6
FEATURE                 Location/Qualifiers
REGION                  1..6
                        note = peptide motif
SITE                    2
                        note = MISC_FEATURE - D-arginine
SITE                    3
                        note = MISC_FEATURE - X is beta-homolysine
source                  1..6
```

```
                            mol_type = protein
                            organism = synthetic construct
SEQUENCE: 211
PRXLDT                                                                      6

SEQ ID NO: 212              moltype = AA  length = 6
FEATURE                     Location/Qualifiers
REGION                      1..6
                            note = peptide motif
SITE                        2
                            note = MISC_FEATURE - X is
                             4-aminomethyl-phenylalanine-reduced
SITE                        3
                            note = MISC_FEATURE - X is beta-homolysine
source                      1..6
                            mol_type = protein
                            organism = synthetic construct
SEQUENCE: 212
PXXLDT                                                                      6

SEQ ID NO: 213              moltype = AA  length = 6
FEATURE                     Location/Qualifiers
REGION                      1..6
                            note = peptide motif
SITE                        2
                            note = MISC_FEATURE - X is 3-(4-thiazolyl)-alanine
SITE                        3
                            note = MISC_FEATURE - X is beta-D-homolysine
source                      1..6
                            mol_type = protein
                            organism = synthetic construct
SEQUENCE: 213
PXXLDI                                                                      6

SEQ ID NO: 214              moltype = AA  length = 6
FEATURE                     Location/Qualifiers
REGION                      1..6
                            note = peptide motif
SITE                        3
                            note = MISC_FEATURE - X is beta-D-homolysine
source                      1..6
                            mol_type = protein
                            organism = synthetic construct
SEQUENCE: 214
PFXLDI                                                                      6

SEQ ID NO: 215              moltype = AA  length = 6
FEATURE                     Location/Qualifiers
REGION                      1..6
                            note = peptide motif
SITE                        2
                            note = MISC_FEATURE - X is 3-(4-thiazolyl)-alanine
SITE                        3
                            note = MISC_FEATURE - X is N-methyl beta-homoLysine
source                      1..6
                            mol_type = protein
                            organism = synthetic construct
SEQUENCE: 215
PXXLDT                                                                      6

SEQ ID NO: 216              moltype = AA  length = 6
FEATURE                     Location/Qualifiers
REGION                      1..6
                            note = peptide motif
SITE                        2
                            note = MISC_FEATURE - X is 4-aminomethyl-phenylalanine
SITE                        3
                            note = MISC_FEATURE - X is N-methyl beta-homoLysine
source                      1..6
                            mol_type = protein
                            organism = synthetic construct
SEQUENCE: 216
PXXLDT                                                                      6

SEQ ID NO: 217              moltype = AA  length = 6
FEATURE                     Location/Qualifiers
REGION                      1..6
                            note = peptide motif
SITE                        2
```

```
                        note = MISC_FEATURE - X is 3-(4-thiazolyl)-alanine
SITE                    3
                        note = MISC_FEATURE - X is beta-homolysine
source                  1..6
                        mol_type = protein
                        organism = synthetic construct
SEQUENCE: 217
PXXLDI                                                                       6

SEQ ID NO: 218          moltype = AA   length = 6
FEATURE                 Location/Qualifiers
REGION                  1..6
                        note = peptide motif
SITE                    2
                        note = MISC_FEATURE - X is
                         (3S)-1,2,3,4-tetrahydroisoquinoline-3-carboxylic acid
SITE                    3
                        note = MISC_FEATURE - X is beta-homolysine
source                  1..6
                        mol_type = protein
                        organism = synthetic construct
SEQUENCE: 218
PXXLDT                                                                       6

SEQ ID NO: 219          moltype = AA   length = 6
FEATURE                 Location/Qualifiers
REGION                  1..6
                        note = peptide motif
SITE                    2
                        note = MISC_FEATURE - X is
                         (3R)-1,2,3,4-tetrahydroisoquinoline-3-carboxylic acid
SITE                    3
                        note = MISC_FEATURE - X is beta-homolysine
source                  1..6
                        mol_type = protein
                        organism = synthetic construct
SEQUENCE: 219
PXXLDT                                                                       6

SEQ ID NO: 220          moltype = AA   length = 6
FEATURE                 Location/Qualifiers
REGION                  1..6
                        note = peptide motif
SITE                    2
                        note = MISC_FEATURE - X is
                         (3R)-1,2,3,4-tetrahydroisoquinoline-3-carboxylic acid
SITE                    3
                        note = MISC_FEATURE - X is beta-D-homolysine
source                  1..6
                        mol_type = protein
                        organism = synthetic construct
SEQUENCE: 220
PXXLDT                                                                       6

SEQ ID NO: 221          moltype = AA   length = 6
FEATURE                 Location/Qualifiers
REGION                  1..6
                        note = peptide motif
SITE                    3
                        note = MISC_FEATURE - X is beta-homoisoleucine
source                  1..6
                        mol_type = protein
                        organism = synthetic construct
SEQUENCE: 221
PYXLDT                                                                       6

SEQ ID NO: 222          moltype = AA   length = 6
FEATURE                 Location/Qualifiers
REGION                  1..6
                        note = peptide motif
SITE                    2
                        note = MISC_FEATURE - X is 4-aminomethyl-phenylalanine
SITE                    3
                        note = MISC_FEATURE - X is beta-homoproline
source                  1..6
                        mol_type = protein
                        organism = synthetic construct
SEQUENCE: 222
PXXLDT                                                                       6
```

```
SEQ ID NO: 223          moltype = AA   length = 6
FEATURE                 Location/Qualifiers
REGION                  1..6
                        note = peptide motif
SITE                    3
                        note = MISC_FEATURE - X is beta-D-homoproline
source                  1..6
                        mol_type = protein
                        organism = synthetic construct
SEQUENCE: 223
PYXLDT                                                                    6

SEQ ID NO: 224          moltype = AA   length = 6
FEATURE                 Location/Qualifiers
REGION                  1..6
                        note = peptide motif
SITE                    2
                        note = MISC_FEATURE - X is 4-aminomethyl-phenylalanine
SITE                    3
                        note = MISC_FEATURE - X is beta-D-homoproline
source                  1..6
                        mol_type = protein
                        organism = synthetic construct
SEQUENCE: 224
PXXLDT                                                                    6

SEQ ID NO: 225          moltype = AA   length = 6
FEATURE                 Location/Qualifiers
REGION                  1..6
                        note = peptide motif
SITE                    3
                        note = MISC_FEATURE - X is beta-homolysine
source                  1..6
                        mol_type = protein
                        organism = synthetic construct
SEQUENCE: 225
PRXLDT                                                                    6

SEQ ID NO: 226          moltype = AA   length = 6
FEATURE                 Location/Qualifiers
REGION                  1..6
                        note = peptide motif
SITE                    3
                        note = MISC_FEATURE - X is N-methyl beta-homoLysine
source                  1..6
                        mol_type = protein
                        organism = synthetic construct
SEQUENCE: 226
PFXLDT                                                                    6

SEQ ID NO: 227          moltype = AA   length = 6
FEATURE                 Location/Qualifiers
REGION                  1..6
                        note = peptide motif
SITE                    2
                        note = MISC_FEATURE - X is phenlyalanine-reduced
SITE                    3
                        note = MISC_FEATURE - X is beta-homolysine
source                  1..6
                        mol_type = protein
                        organism = synthetic construct
SEQUENCE: 227
PXXLDT                                                                    6

SEQ ID NO: 228          moltype = AA   length = 6
FEATURE                 Location/Qualifiers
REGION                  1..6
                        note = peptide motif
SITE                    2
                        note = MISC_FEATURE - X is 3-aminomethyl-D-phenylalanine
SITE                    3
                        note = MISC_FEATURE - X is beta-homolysine
source                  1..6
                        mol_type = protein
                        organism = synthetic construct
SEQUENCE: 228
PXXLDT                                                                    6
```

```
SEQ ID NO: 229          moltype = AA  length = 6
FEATURE                 Location/Qualifiers
REGION                  1..6
                        note = peptide motif
SITE                    2
                        note = MISC_FEATURE - X is
-beta-homolysine
SITE                    3
                        note = MISC_FEATURE - X is beta-homolysine
source                  1..6
                        mol_type = protein
                        organism = synthetic construct
SEQUENCE: 229
PXXLDT                                                                   6

SEQ ID NO: 230          moltype = AA  length = 6
FEATURE                 Location/Qualifiers
REGION                  1..6
                        note = peptide motif
SITE                    2
                        note = MISC_FEATURE - X is 3-(4-thiazolyl)-D-alanine
SITE                    3
                        note = MISC_FEATURE - X is beta-homolysine
source                  1..6
                        mol_type = protein
                        organism = synthetic construct
SEQUENCE: 230
PXXLDT                                                                   6

SEQ ID NO: 231          moltype = AA  length = 6
FEATURE                 Location/Qualifiers
REGION                  1..6
                        note = peptide motif
SITE                    2
                        note = MISC_FEATURE - X is 2-bromo-phenylalanine
SITE                    3
                        note = MISC_FEATURE - X is beta-homolysine
source                  1..6
                        mol_type = protein
                        organism = synthetic construct
SEQUENCE: 231
PXXLDT                                                                   6

SEQ ID NO: 232          moltype = AA  length = 6
FEATURE                 Location/Qualifiers
REGION                  1..6
                        note = peptide motif
SITE                    2
                        note = MISC_FEATURE - X is 2-chloro-phenylalanine
SITE                    3
                        note = MISC_FEATURE - X is beta-homolysine
source                  1..6
                        mol_type = protein
                        organism = synthetic construct
SEQUENCE: 232
PXXLDT                                                                   6

SEQ ID NO: 233          moltype = AA  length = 6
FEATURE                 Location/Qualifiers
REGION                  1..6
                        note = peptide motif
SITE                    2
                        note = MISC_FEATURE - X is 2-fluoro-phenylalanine
SITE                    3
                        note = MISC_FEATURE - X is beta-homolysine
source                  1..6
                        mol_type = protein
                        organism = synthetic construct
SEQUENCE: 233
PXXLDT                                                                   6

SEQ ID NO: 234          moltype = AA  length = 6
FEATURE                 Location/Qualifiers
REGION                  1..6
                        note = peptide motif
SITE                    2
                        note = MISC_FEATURE - X is 2-trifluoromethyl-phenlyalanine
SITE                    3
                        note = MISC_FEATURE - X is beta-homolysine
```

| | | |
|---|---|---|
| source | 1..6<br>mol_type = protein<br>organism = synthetic construct | |
| SEQUENCE: 234<br>PXXLDT | | 6 |
| SEQ ID NO: 235<br>FEATURE<br>REGION | moltype = AA  length = 6<br>Location/Qualifiers<br>1..6<br>note = peptide motif | |
| SITE | 2<br>note = MISC_FEATURE - X is 2,4-dichloro-phenlyalanine | |
| SITE | 3<br>note = MISC_FEATURE - X is beta-homolysine | |
| source | 1..6<br>mol_type = protein<br>organism = synthetic construct | |
| SEQUENCE: 235<br>PXXLDT | | 6 |
| SEQ ID NO: 236<br>FEATURE<br>REGION | moltype = AA  length = 6<br>Location/Qualifiers<br>1..6<br>note = peptide motif | |
| SITE | 2<br>note = MISC_FEATURE - X is 2-aminomethyl-phenylalanine | |
| SITE | 3<br>note = MISC_FEATURE - X is beta-homolysine | |
| source | 1..6<br>mol_type = protein<br>organism = synthetic construct | |
| SEQUENCE: 236<br>PXXLDT | | 6 |
| SEQ ID NO: 237<br>FEATURE<br>REGION | moltype = AA  length = 6<br>Location/Qualifiers<br>1..6<br>note = peptide motif | |
| SITE | 2<br>note = MISC_FEATURE - X is 2-(4-quinolinyl)-phenylalanine | |
| SITE | 3<br>note = MISC_FEATURE - X is beta-homolysine | |
| source | 1..6<br>mol_type = protein<br>organism = synthetic construct | |
| SEQUENCE: 237<br>PXXLDT | | 6 |
| SEQ ID NO: 238<br>FEATURE<br>REGION | moltype = AA  length = 6<br>Location/Qualifiers<br>1..6<br>note = peptide motif | |
| SITE | 2<br>note = MISC_FEATURE - X is 2-(5-quinolinyl)-phenylalanine | |
| SITE | 3<br>note = MISC_FEATURE - X is beta-homolysine | |
| source | 1..6<br>mol_type = protein<br>organism = synthetic construct | |
| SEQUENCE: 238<br>PXXLDT | | 6 |
| SEQ ID NO: 239<br>FEATURE<br>REGION | moltype = AA  length = 6<br>Location/Qualifiers<br>1..6<br>note = peptide motif | |
| SITE | 2<br>note = MISC_FEATURE - X is 2-(3-quinolinyl)-phenylalanine | |
| SITE | 3<br>note = MISC_FEATURE - X is beta-homolysine | |
| source | 1..6<br>mol_type = protein<br>organism = synthetic construct | |
| SEQUENCE: 239<br>PXXLDT | | 6 |
| SEQ ID NO: 240<br>FEATURE<br>REGION | moltype = AA  length = 6<br>Location/Qualifiers<br>1..6 | |

```
                    note = peptide motif
SITE                2
                    note = MISC_FEATURE - X is D-homophenylalanine
SITE                3
                    note = MISC_FEATURE - X is beta-homolysine
source              1..6
                    mol_type = protein
                    organism = synthetic construct
SEQUENCE: 240
PXXLDT                                                                    6

SEQ ID NO: 241      moltype = AA  length = 6
FEATURE             Location/Qualifiers
REGION              1..6
                    note = peptide motif
SITE                2
                    note = MISC_FEATURE - X is 2-iodo-D-phenylalanine
SITE                3
                    note = MISC_FEATURE - X is beta-homolysine
source              1..6
                    mol_type = protein
                    organism = synthetic construct
SEQUENCE: 241
PXXLDT                                                                    6

SEQ ID NO: 242      moltype = AA  length = 6
FEATURE             Location/Qualifiers
REGION              1..6
                    note = peptide motif
SITE                2
                    note = MISC_FEATURE - X is 2-phenyl-D-phenylalanine
SITE                3
                    note = MISC_FEATURE - X is beta-homolysine
source              1..6
                    mol_type = protein
                    organism = synthetic construct
SEQUENCE: 242
PXXLDT                                                                    6

SEQ ID NO: 243      moltype = AA  length = 6
FEATURE             Location/Qualifiers
REGION              1..6
                    note = peptide motif
SITE                2
                    note = MISC_FEATURE - X is
                     (2-piperazinyl-2-phenyl)-D-phenylalanine
SITE                3
                    note = MISC_FEATURE - X is beta-homolysine
source              1..6
                    mol_type = protein
                    organism = synthetic construct
SEQUENCE: 243
PXXLDT                                                                    6

SEQ ID NO: 244      moltype = AA  length = 6
FEATURE             Location/Qualifiers
REGION              1..6
                    note = peptide motif
SITE                3
                    note = MISC_FEATURE - X is beta-homolysine
source              1..6
                    mol_type = protein
                    organism = synthetic construct
SEQUENCE: 244
PYXLDI                                                                    6

SEQ ID NO: 245      moltype = AA  length = 6
FEATURE             Location/Qualifiers
REGION              1..6
                    note = peptide motif
SITE                3
                    note = MISC_FEATURE - X is beta-homolysine
source              1..6
                    mol_type = protein
                    organism = synthetic construct
SEQUENCE: 245
PYXLDV                                                                    6

SEQ ID NO: 246      moltype = AA  length = 6
```

```
FEATURE                     Location/Qualifiers
REGION                      1..6
                            note = peptide motif
SITE                        2
                            note = MISC_FEATURE - D-tyrosine
SITE                        3
                            note = MISC_FEATURE - X is beta-homolysine
source                      1..6
                            mol_type = protein
                            organism = synthetic construct
SEQUENCE: 246
PYXLDI                                                                      6

SEQ ID NO: 247              moltype = AA  length = 6
FEATURE                     Location/Qualifiers
REGION                      1..6
                            note = peptide motif
SITE                        2
                            note = MISC_FEATURE - X is 4-aminomethyl-D-phenylalanine
SITE                        3
                            note = MISC_FEATURE - X is beta-homolysine
source                      1..6
                            mol_type = protein
                            organism = synthetic construct
SEQUENCE: 247
PXXLDI                                                                      6

SEQ ID NO: 248              moltype = AA  length = 6
FEATURE                     Location/Qualifiers
REGION                      1..6
                            note = peptide motif
SITE                        2
                            note = MISC_FEATURE - X is 4-aminomethyl-phenylalanine
SITE                        3
                            note = MISC_FEATURE - X is beta-homolysine
source                      1..6
                            mol_type = protein
                            organism = synthetic construct
SEQUENCE: 248
PXXLDV                                                                      6

SEQ ID NO: 249              moltype = AA  length = 6
FEATURE                     Location/Qualifiers
REGION                      1..6
                            note = peptide motif
SITE                        2
                            note = MISC_FEATURE - X is 3-iodo-phenylalanine
SITE                        3
                            note = MISC_FEATURE - X is beta-homolysine
source                      1..6
                            mol_type = protein
                            organism = synthetic construct
SEQUENCE: 249
PXXLDT                                                                      6

SEQ ID NO: 250              moltype = AA  length = 6
FEATURE                     Location/Qualifiers
REGION                      1..6
                            note = peptide motif
SITE                        2
                            note = MISC_FEATURE - X is 3-phenyl-phenylalanine
SITE                        3
                            note = MISC_FEATURE - X is beta-homolysine
source                      1..6
                            mol_type = protein
                            organism = synthetic construct
SEQUENCE: 250
PXXLDT                                                                      6

SEQ ID NO: 251              moltype = AA  length = 6
FEATURE                     Location/Qualifiers
REGION                      1..6
                            note = peptide motif
SITE                        2
                            note = MISC_FEATURE - X is
                              3-(2-methoxy-phenyl)-phenylalanine
SITE                        3
                            note = MISC_FEATURE - X is beta-homolysine
source                      1..6
```

```
                        mol_type = protein
                        organism = synthetic construct
SEQUENCE: 251
PXXLDT                                                                      6

SEQ ID NO: 252          moltype = AA   length = 6
FEATURE                 Location/Qualifiers
REGION                  1..6
                        note = peptide motif
SITE                    2
                        note = MISC_FEATURE - X is
                        3-(2,6-dimthoxy-phenyl)-phenylalanine
SITE                    3
                        note = MISC_FEATURE - X is beta-homolysine
source                  1..6
                        mol_type = protein
                        organism = synthetic construct
SEQUENCE: 252
PXXLDT                                                                      6

SEQ ID NO: 253          moltype = AA   length = 6
FEATURE                 Location/Qualifiers
REGION                  1..6
                        note = peptide motif
SITE                    2
                        note = MISC_FEATURE - X is
                        3-(2-trifluoromethoxy-phenyl)-phenylalanine
SITE                    3
                        note = MISC_FEATURE - X is beta-homolysine
source                  1..6
                        mol_type = protein
                        organism = synthetic construct
SEQUENCE: 253
PXXLDT                                                                      6

SEQ ID NO: 254          moltype = AA   length = 6
FEATURE                 Location/Qualifiers
REGION                  1..6
                        note = peptide motif
SITE                    2
                        note = MISC_FEATURE - X is 4-iodo-phenylalanine
SITE                    3
                        note = MISC_FEATURE - X is beta-homolysine
source                  1..6
                        mol_type = protein
                        organism = synthetic construct
SEQUENCE: 254
PXXLDT                                                                      6

SEQ ID NO: 255          moltype = AA   length = 6
FEATURE                 Location/Qualifiers
REGION                  1..6
                        note = peptide motif
SITE                    2
                        note = MISC_FEATURE - X is
                        4-(2-methoxy-phenyl)-phenylalanine
SITE                    3
                        note = MISC_FEATURE - X is beta-homolysine
source                  1..6
                        mol_type = protein
                        organism = synthetic construct
SEQUENCE: 255
PXXLDT                                                                      6

SEQ ID NO: 256          moltype = AA   length = 6
FEATURE                 Location/Qualifiers
REGION                  1..6
                        note = peptide motif
SITE                    2
                        note = MISC_FEATURE - X is
                        4-(2-trifluoromethoxy-phenyl)-phenylalanine
SITE                    3
                        note = MISC_FEATURE - X is beta-homolysine
source                  1..6
                        mol_type = protein
                        organism = synthetic construct
SEQUENCE: 256
PXXLDT                                                                      6
```

```
SEQ ID NO: 257         moltype = AA   length = 6
FEATURE                Location/Qualifiers
REGION                 1..6
                       note = peptide motif
SITE                   2
                       note = MISC_FEATURE - X is alpha-methyl-phenylalanine,
                        (S)-(-)-2-amino-2-methyl-3-phenylpropionic acid
SITE                   3
                       note = MISC_FEATURE - X is beta-homolysine
source                 1..6
                       mol_type = protein
                       organism = synthetic construct
SEQUENCE: 257
PXXLDT                                                                    6

SEQ ID NO: 258         moltype = AA   length = 6
FEATURE                Location/Qualifiers
REGION                 1..6
                       note = peptide motif
SITE                   2
                       note = MISC_FEATURE - X is N-methyl phenylalanine
SITE                   3
                       note = MISC_FEATURE - X is beta-homolysine
source                 1..6
                       mol_type = protein
                       organism = synthetic construct
SEQUENCE: 258
PXXLDT                                                                    6

SEQ ID NO: 259         moltype = AA   length = 6
FEATURE                Location/Qualifiers
REGION                 1..6
                       note = peptide motif
SITE                   2
                       note = MISC_FEATURE - X is
                        3-(2,6-dimethyl-phenyl)-phenylalanine
SITE                   3
                       note = MISC_FEATURE - X is beta-homolysine
source                 1..6
                       mol_type = protein
                       organism = synthetic construct
SEQUENCE: 259
PXXLDT                                                                    6

SEQ ID NO: 260         moltype = AA   length = 6
FEATURE                Location/Qualifiers
REGION                 1..6
                       note = peptide motif
SITE                   2
                       note = MISC_FEATURE - X is 3-(quinolin-4-yl)-phenylalanine
SITE                   3
                       note = MISC_FEATURE - X is beta-homolysine
source                 1..6
                       mol_type = protein
                       organism = synthetic construct
SEQUENCE: 260
PXXLDT                                                                    6

SEQ ID NO: 261         moltype = AA   length = 6
FEATURE                Location/Qualifiers
REGION                 1..6
                       note = peptide motif
SITE                   2
                       note = MISC_FEATURE - X is
                        3-(3,4-difluoro-phenyl)-phenylalanine
SITE                   3
                       note = MISC_FEATURE - X is beta-homolysine
source                 1..6
                       mol_type = protein
                       organism = synthetic construct
SEQUENCE: 261
PXXLDT                                                                    6

SEQ ID NO: 262         moltype = AA   length = 6
FEATURE                Location/Qualifiers
REGION                 1..6
                       note = peptide motif
SITE                   2
                       note = MISC_FEATURE - X is
```

```
                           4-(2,6-dimethyl-phenyl)-phenylalanine
SITE                       3
                           note = MISC_FEATURE - X is beta-homolysine
source                     1..6
                           mol_type = protein
                           organism = synthetic construct
SEQUENCE: 262
PXXLDT                                                                         6

SEQ ID NO: 263             moltype = AA  length = 6
FEATURE                    Location/Qualifiers
REGION                     1..6
                           note = peptide motif
SITE                       2
                           note = MISC_FEATURE - X is
                           4-(2-chloro-6-methoxy-phenyl)-phenylalanine
SITE                       3
                           note = MISC_FEATURE - X is beta-homolysine
source                     1..6
                           mol_type = protein
                           organism = synthetic construct
SEQUENCE: 263
PXXLDT                                                                         6

SEQ ID NO: 264             moltype = AA  length = 6
FEATURE                    Location/Qualifiers
REGION                     1..6
                           note = peptide motif
SITE                       2
                           note = MISC_FEATURE - X is 3-(4-thiazolyl)-alanine
SITE                       3
                           note = MISC_FEATURE - X is beta-homolysine
source                     1..6
                           mol_type = protein
                           organism = synthetic construct
SEQUENCE: 264
PXXLDT                                                                         6

SEQ ID NO: 265             moltype = AA  length = 6
FEATURE                    Location/Qualifiers
REGION                     1..6
                           note = peptide motif
SITE                       2
                           note = MISC_FEATURE - X is
                           2-(4-[1-piperazinyl)phenyl)-phenylalanine
SITE                       3
                           note = MISC_FEATURE - X is beta-homolysine
source                     1..6
                           mol_type = protein
                           organism = synthetic construct
SEQUENCE: 265
PXXLDT                                                                         6

SEQ ID NO: 266             moltype = AA  length = 6
FEATURE                    Location/Qualifiers
REGION                     1..6
                           note = peptide motif
SITE                       2
                           note = MISC_FEATURE - X is
                           2-(2,6-dimethylphenyl)-phenylalanine
SITE                       3
                           note = MISC_FEATURE - X is beta-homolysine
source                     1..6
                           mol_type = protein
                           organism = synthetic construct
SEQUENCE: 266
PXXLDT                                                                         6

SEQ ID NO: 267             moltype = AA  length = 6
FEATURE                    Location/Qualifiers
REGION                     1..6
                           note = peptide motif
SITE                       2
                           note = MISC_FEATURE - X is
                           2-(benzolthiazol-5-yl)-phenylalanine
SITE                       3
                           note = MISC_FEATURE - X is beta-homolysine
source                     1..6
                           mol_type = protein
```

```
                            -continued

SEQUENCE: 267           organism = synthetic construct
PXXLDT                                                                  6

SEQ ID NO: 268          moltype = AA   length = 6
FEATURE                 Location/Qualifiers
REGION                  1..6
                        note = peptide motif
SITE                    2
                        note = MISC_FEATURE - X is homophenylalanine
SITE                    3
                        note = MISC_FEATURE - X is beta-homolysine
source                  1..6
                        mol_type = protein
                        organism = synthetic construct
SEQUENCE: 268
PXXLDT                                                                  6

SEQ ID NO: 269          moltype = AA   length = 6
FEATURE                 Location/Qualifiers
REGION                  1..6
                        note = peptide motif
SITE                    2
                        note = MISC_FEATURE - X is piperidine-4-amino-4-carboxylic
                         acid
SITE                    3
                        note = MISC_FEATURE - X is beta-homolysine
source                  1..6
                        mol_type = protein
                        organism = synthetic construct
SEQUENCE: 269
PXXLDT                                                                  6

SEQ ID NO: 270          moltype = AA   length = 6
FEATURE                 Location/Qualifiers
REGION                  1..6
                        note = peptide motif
SITE                    2
                        note = MISC_FEATURE - X is
                         2-(2,5-dimethyl-isoxazole)-D-phenylalanine
SITE                    3
                        note = MISC_FEATURE - X is beta-homolysine
source                  1..6
                        mol_type = protein
                        organism = synthetic construct
SEQUENCE: 270
PXXLDT                                                                  6

SEQ ID NO: 271          moltype = AA   length = 6
FEATURE                 Location/Qualifiers
REGION                  1..6
                        note = peptide motif
SITE                    2
                        note = MISC_FEATURE - D-tyrosine
SITE                    3
                        note = MISC_FEATURE - X is beta-homolysine
source                  1..6
                        mol_type = protein
                        organism = synthetic construct
SEQUENCE: 271
PYXLDV                                                                  6

SEQ ID NO: 272          moltype = AA   length = 6
FEATURE                 Location/Qualifiers
REGION                  1..6
                        note = peptide motif
SITE                    2
                        note = MISC_FEATURE - X is 4-aminomethyl-D-phenylalanine
SITE                    3
                        note = MISC_FEATURE - X is beta-homolysine
source                  1..6
                        mol_type = protein
                        organism = synthetic construct
SEQUENCE: 272
PXXLDT                                                                  6

SEQ ID NO: 273          moltype = AA   length = 6
FEATURE                 Location/Qualifiers
REGION                  1..6
```

```
                        note = peptide motif
SITE                    2
                        note = MISC_FEATURE - X is
                         2-(2-chloro-6-methoxyphenyl)-phenylalanine
SITE                    3
                        note = MISC_FEATURE - X is beta-homolysine
source                  1..6
                        mol_type = protein
                        organism = synthetic construct
SEQUENCE: 273
PXXLDT                                                                        6

SEQ ID NO: 274          moltype = AA  length = 6
FEATURE                 Location/Qualifiers
REGION                  1..6
                        note = peptide motif
SITE                    2
                        note = MISC_FEATURE - X is 2-indanylglycine
SITE                    3
                        note = MISC_FEATURE - X is beta-homolysine
source                  1..6
                        mol_type = protein
                        organism = synthetic construct
SEQUENCE: 274
PXXLDT                                                                        6

SEQ ID NO: 275          moltype = AA  length = 6
FEATURE                 Location/Qualifiers
REGION                  1..6
                        note = peptide motif
SITE                    2
                        note = MISC_FEATURE - X is 2-indanyl-D-glycine
SITE                    3
                        note = MISC_FEATURE - X is beta-homolysine
source                  1..6
                        mol_type = protein
                        organism = synthetic construct
SEQUENCE: 275
PXXLDT                                                                        6

SEQ ID NO: 276          moltype = AA  length = 6
FEATURE                 Location/Qualifiers
REGION                  1..6
                        note = peptide motif
SITE                    2
                        note = MISC_FEATURE - X is 2-aminotetraline-2-carboxylic
                         acid
SITE                    3
                        note = MISC_FEATURE - X is beta-homolysine
source                  1..6
                        mol_type = protein
                        organism = synthetic construct
SEQUENCE: 276
PXXLDT                                                                        6

SEQ ID NO: 277          moltype = AA  length = 6
FEATURE                 Location/Qualifiers
REGION                  1..6
                        note = peptide motif
SITE                    3
                        note = MISC_FEATURE - X is beta-homolysine
SITE                    6
                        note = MISC_FEATURE - X is allo-isoleucine,
                         (2S,3R)-2-amino-3-methylpentanoic acid
source                  1..6
                        mol_type = protein
                        organism = synthetic construct
SEQUENCE: 277
PYXLDX                                                                        6

SEQ ID NO: 278          moltype = AA  length = 6
FEATURE                 Location/Qualifiers
REGION                  1..6
                        note = peptide motif
SITE                    2
                        note = MISC_FEATURE - D-tyrosine
SITE                    3
                        note = MISC_FEATURE - X is beta-homolysine
SITE                    6
```

```
                        note = MISC_FEATURE - X is allo-isoleucine,
                        (2S,3R)-2-amino-3-methylpentanoic acid
source                  1..6
                        mol_type = protein
                        organism = synthetic construct
SEQUENCE: 278
PYXLDX                                                                    6

SEQ ID NO: 279          moltype =    length =
SEQUENCE: 279
000

SEQ ID NO: 280          moltype = AA   length = 6
FEATURE                 Location/Qualifiers
REGION                  1..6
                        note = peptide motif
SITE                    2
                        note = MISC_FEATURE - X is
                        2-(2,5-bis(trifluoromethyl)phenyl)-phenylalanine
SITE                    3
                        note = MISC_FEATURE - X is beta-homolysine
source                  1..6
                        mol_type = protein
                        organism = synthetic construct
SEQUENCE: 280
PXXLDT                                                                    6

SEQ ID NO: 281          moltype = AA   length = 6
FEATURE                 Location/Qualifiers
REGION                  1..6
                        note = peptide motif
SITE                    2
                        note = MISC_FEATURE - X is
                        2-(2,5-bis(trifluoromethyl)phenyl)-phenylalanine
SITE                    3
                        note = MISC_FEATURE - X is beta-homolysine
source                  1..6
                        mol_type = protein
                        organism = synthetic construct
SEQUENCE: 281
PXXLDT                                                                    6

SEQ ID NO: 282          moltype = AA   length = 6
FEATURE                 Location/Qualifiers
REGION                  1..6
                        note = peptide motif
SITE                    2
                        note = MISC_FEATURE - X is aminoindan-2-carboxylic acid
SITE                    3
                        note = MISC_FEATURE - beta-homolysine
source                  1..6
                        mol_type = protein
                        organism = synthetic construct
SEQUENCE: 282
PXXLDT                                                                    6

SEQ ID NO: 283          moltype = AA   length = 6
FEATURE                 Location/Qualifiers
REGION                  1..6
                        note = peptide motif
SITE                    3
                        note = MISC_FEATURE - X is beta-homolysine
source                  1..6
                        mol_type = protein
                        organism = synthetic construct
SEQUENCE: 283
PPXLDT                                                                    6

SEQ ID NO: 284          moltype = AA   length = 6
FEATURE                 Location/Qualifiers
REGION                  1..6
                        note = peptide motif
SITE                    2
                        note = MISC_FEATURE - D-proline
SITE                    3
                        note = MISC_FEATURE - X is beta-homolysine
source                  1..6
                        mol_type = protein
                        organism = synthetic construct
```

```
SEQUENCE: 284
PPXLDT                                                                              6

SEQ ID NO: 285           moltype = AA  length = 6
FEATURE                  Location/Qualifiers
REGION                   1..6
                         note = peptide motif
SITE                     2
                         note = MISC_FEATURE - X is pipecolic acid, homoproline
SITE                     3
                         note = MISC_FEATURE - X is beta-homolysine
source                   1..6
                         mol_type = protein
                         organism = synthetic construct
SEQUENCE: 285
PXXLDT                                                                              6

SEQ ID NO: 286           moltype = AA  length = 6
FEATURE                  Location/Qualifiers
REGION                   1..6
                         note = peptide motif
SITE                     2
                         note = MISC_FEATURE - X is 2-(3-pyridyl)-phenylalanine
SITE                     3
                         note = MISC_FEATURE - X is beta-homolysine
source                   1..6
                         mol_type = protein
                         organism = synthetic construct
SEQUENCE: 286
PXXLDT                                                                              6

SEQ ID NO: 287           moltype = AA  length = 6
FEATURE                  Location/Qualifiers
REGION                   1..6
                         note = peptide motif
SITE                     2
                         note = MISC_FEATURE - X is 2-(4-pyridyl)-phenylalanine
SITE                     3
                         note = MISC_FEATURE - X is beta-homolysine
source                   1..6
                         mol_type = protein
                         organism = synthetic construct
SEQUENCE: 287
PXXLDT                                                                              6

SEQ ID NO: 288           moltype = AA  length = 6
FEATURE                  Location/Qualifiers
REGION                   1..6
                         note = peptide motif
SITE                     2
                         note = MISC_FEATURE - 2-(3-bromo-2-pyridyl)-phenylalanine
SITE                     3
                         note = MISC_FEATURE - beta-homolysine
source                   1..6
                         mol_type = protein
                         organism = synthetic construct
SEQUENCE: 288
PXXLDT                                                                              6

SEQ ID NO: 289           moltype = AA  length = 6
FEATURE                  Location/Qualifiers
REGION                   1..6
                         note = peptide motif
SITE                     3
                         note = MISC_FEATURE - X is beta-D-homolysine
source                   1..6
                         mol_type = protein
                         organism = synthetic construct
SEQUENCE: 289
PYXLDT                                                                              6

SEQ ID NO: 290           moltype = AA  length = 6
FEATURE                  Location/Qualifiers
REGION                   1..6
                         note = peptide motif
SITE                     2
                         note = MISC_FEATURE - X is N-benzyl-glycine
SITE                     3
                         note = MISC_FEATURE - X is beta-homolysine
```

```
source                  1..6
                        mol_type = protein
                        organism = synthetic construct
SEQUENCE: 290
PXXLDT                                                                                  6

SEQ ID NO: 291          moltype = AA  length = 6
FEATURE                 Location/Qualifiers
REGION                  1..6
                        note = peptide motif
SITE                    2
                        note = MISC_FEATURE - X is
                        2-(2-bromo-3-pyridyl)-phenylalanine
SITE                    3
                        note = MISC_FEATURE - X is beta-homolysine
source                  1..6
                        mol_type = protein
                        organism = synthetic construct
SEQUENCE: 291
PXXLDT                                                                                  6

SEQ ID NO: 292          moltype = AA  length = 6
FEATURE                 Location/Qualifiers
REGION                  1..6
                        note = peptide motif
SITE                    2
                        note = MISC_FEATURE - X is
                        3-(2-chloro-6-methoxy-phenyl)-phenylalanine
SITE                    3
                        note = MISC_FEATURE - X is beta-homolysine
source                  1..6
                        mol_type = protein
                        organism = synthetic construct
SEQUENCE: 292
PXXLDT                                                                                  6

SEQ ID NO: 293          moltype = AA  length = 6
FEATURE                 Location/Qualifiers
REGION                  1..6
                        note = peptide motif
SITE                    2
                        note = MISC_FEATURE - X is
                        3-(benzothiazol-5-yl)-phenylalanine
SITE                    3
                        note = MISC_FEATURE - X is beta-homolysine
source                  1..6
                        mol_type = protein
                        organism = synthetic construct
SEQUENCE: 293
PXXLDT                                                                                  6

SEQ ID NO: 294          moltype = AA  length = 6
FEATURE                 Location/Qualifiers
REGION                  1..6
                        note = peptide motif
SITE                    2
                        note = MISC_FEATURE - X is 2-aminomethyl-phenylalanine
SITE                    3
                        note = MISC_FEATURE - X is N-methyl beta-homoLysine
source                  1..6
                        mol_type = protein
                        organism = synthetic construct
SEQUENCE: 294
PXXLDT                                                                                  6

SEQ ID NO: 295          moltype = AA  length = 6
FEATURE                 Location/Qualifiers
REGION                  1..6
                        note = peptide motif
SITE                    2
                        note = MISC_FEATURE - X is 2-aminomethyl-D-phenylalanine
SITE                    3
                        note = MISC_FEATURE - X is N-methyl beta-homoLysine
source                  1..6
                        mol_type = protein
                        organism = synthetic construct
SEQUENCE: 295
PXXLDT                                                                                  6
```

```
SEQ ID NO: 296         moltype = AA  length = 6
FEATURE                Location/Qualifiers
REGION                 1..6
                       note = peptide motif
SITE                   2
                       note = MISC_FEATURE - X is 3-(4-thiazolyl)-D-alanine
SITE                   3
                       note = MISC_FEATURE - X is N-methyl beta-homoLysine
source                 1..6
                       mol_type = protein
                       organism = synthetic construct
SEQUENCE: 296
PXXLDT                                                                      6

SEQ ID NO: 297         moltype = AA  length = 6
FEATURE                Location/Qualifiers
REGION                 1..6
                       note = peptide motif
SITE                   2
                       note = MISC_FEATURE - X is
                        2-(2-trifluoromethoxy-phenyl)-D-phenylalanine
SITE                   3
                       note = MISC_FEATURE - X is N-methyl beta-homoLysine
source                 1..6
                       mol_type = protein
                       organism = synthetic construct
SEQUENCE: 297
PXXLDT                                                                      6

SEQ ID NO: 298         moltype = AA  length = 6
FEATURE                Location/Qualifiers
REGION                 1..6
                       note = peptide motif
SITE                   2
                       note = MISC_FEATURE - X is
                        (3S)-1,2,3,4-tetrahydroisoquinoline-3-carboxylic acid
SITE                   3
                       note = MISC_FEATURE - X is N-methyl beta-homoLysine
source                 1..6
                       mol_type = protein
                       organism = synthetic construct
SEQUENCE: 298
PXXLDT                                                                      6

SEQ ID NO: 299         moltype = AA  length = 6
FEATURE                Location/Qualifiers
REGION                 1..6
                       note = peptide motif
SITE                   2
                       note = MISC_FEATURE - X is
                        (3R)-1,2,3,4-tetrahydroisoquinoline-3-carboxylic acid
SITE                   3
                       note = MISC_FEATURE - X is N-methyl beta-homoLysine
source                 1..6
                       mol_type = protein
                       organism = synthetic construct
SEQUENCE: 299
PXXLDT                                                                      6

SEQ ID NO: 300         moltype = AA  length = 6
FEATURE                Location/Qualifiers
REGION                 1..6
                       note = peptide motif
SITE                   2
                       note = MISC_FEATURE - X is 2-(5-quinolinyl)-D-phenylalanine
SITE                   3
                       note = MISC_FEATURE - X is beta-homolysine
source                 1..6
                       mol_type = protein
                       organism = synthetic construct
SEQUENCE: 300
PXXLDT                                                                      6

SEQ ID NO: 301         moltype = AA  length = 6
FEATURE                Location/Qualifiers
REGION                 1..6
                       note = peptide motif
SITE                   3
                       note = MISC_FEATURE - X is beta-homolysine
```

```
SITE                    6
                        note = MISC_FEATURE - X is allo-threonine,
                        (2S,3S)-2-amino-3-hydroxybutyric acid
source                  1..6
                        mol_type = protein
                        organism = synthetic construct
SEQUENCE: 301
PYXLDX                                                                      6

SEQ ID NO: 302          moltype = AA  length = 6
FEATURE                 Location/Qualifiers
REGION                  1..6
                        note = peptide motif
SITE                    3
                        note = MISC_FEATURE - X is N-methyl beta-homoLysine
SITE                    6
                        note = MISC_FEATURE - X is allo-threonine,
                        (2S,3S)-2-amino-3-hydroxybutyric acid
source                  1..6
                        mol_type = protein
                        organism = synthetic construct
SEQUENCE: 302
PYXLDX                                                                      6

SEQ ID NO: 303          moltype = AA  length = 6
FEATURE                 Location/Qualifiers
REGION                  1..6
                        note = peptide motif
SITE                    2
                        note = MISC_FEATURE - X is N-methyl tyrosine
SITE                    3
                        note = MISC_FEATURE - X is N-methyl beta-homoLysine
source                  1..6
                        mol_type = protein
                        organism = synthetic construct
SEQUENCE: 303
PXXLDT                                                                      6

SEQ ID NO: 304          moltype =     length =
SEQUENCE: 304
000

SEQ ID NO: 305          moltype = AA  length = 6
FEATURE                 Location/Qualifiers
REGION                  1..6
                        note = peptide motif
SITE                    2
                        note = MISC_FEATURE - X is N-methyl phenylalanine
SITE                    3
                        note = MISC_FEATURE - X is N-methyl beta-homoLysine
source                  1..6
                        mol_type = protein
                        organism = synthetic construct
SEQUENCE: 305
PXXLDT                                                                      6

SEQ ID NO: 306          moltype = AA  length = 6
FEATURE                 Location/Qualifiers
REGION                  1..6
                        note = peptide motif
SITE                    2
                        note = MISC_FEATURE - X is 2-fluoro-phenylalanine
SITE                    3
                        note = MISC_FEATURE - X is N-methyl beta-homoLysine
source                  1..6
                        mol_type = protein
                        organism = synthetic construct
SEQUENCE: 306
PXXLDT                                                                      6

SEQ ID NO: 307          moltype = AA  length = 6
FEATURE                 Location/Qualifiers
REGION                  1..6
                        note = peptide motif
SITE                    2
                        note = MISC_FEATURE - X is 2-fluoro-N-methyl phenylalanine
SITE                    3
                        note = MISC_FEATURE - X is N-methyl beta-homoLysine
source                  1..6
```

```
SEQUENCE: 307
PXXLDT                                                                                   6

SEQ ID NO: 308           moltype = AA  length = 6
FEATURE                  Location/Qualifiers
REGION                   1..6
                         note = peptide motif
SITE                     2
                         note = MISC_FEATURE - X is 2,4-dichloro-phenylalanine
SITE                     3
                         note = MISC_FEATURE - X is N-methyl beta-homoLysine
source                   1..6
                         mol_type = protein
                         organism = synthetic construct
SEQUENCE: 308
PXXLDT                                                                                   6

SEQ ID NO: 309           moltype = AA  length = 6
FEATURE                  Location/Qualifiers
REGION                   1..6
                         note = peptide motif
SITE                     2
                         note = MISC_FEATURE - X is 2,4-dichloro-N-methyl
                          phenylalanine
SITE                     3
                         note = MISC_FEATURE - X is N-methyl beta-homoLysine
source                   1..6
                         mol_type = protein
                         organism = synthetic construct
SEQUENCE: 309
PXXLDT                                                                                   6

SEQ ID NO: 310           moltype = AA  length = 6
FEATURE                  Location/Qualifiers
REGION                   1..6
                         note = peptide motif
SITE                     2
                         note = MISC_FEATURE - X is
                          2-aminomethyl-N-methyl-phenylalanine
SITE                     3
                         note = MISC_FEATURE - X is N-methyl beta-homoLysine
source                   1..6
                         mol_type = protein
                         organism = synthetic construct
SEQUENCE: 310
PXXLDT                                                                                   6

SEQ ID NO: 311           moltype = AA  length = 6
FEATURE                  Location/Qualifiers
REGION                   1..6
                         note = peptide motif
SITE                     2
                         note = MISC_FEATURE - X is
                          3-(2,6-dimethoxy-phenyl)-D-phenylalanine
SITE                     3
                         note = MISC_FEATURE - X is beta-homolysine
source                   1..6
                         mol_type = protein
                         organism = synthetic construct
SEQUENCE: 311
PXXLDT                                                                                   6

SEQ ID NO: 312           moltype = AA  length = 6
FEATURE                  Location/Qualifiers
REGION                   1..6
                         note = peptide motif
SITE                     2
                         note = MISC_FEATURE - X is 3-(4-quinolinyl)-D-phenylalanine
SITE                     3
                         note = MISC_FEATURE - X is beta-homolysine
source                   1..6
                         mol_type = protein
                         organism = synthetic construct
SEQUENCE: 312
PXXLDT                                                                                   6

SEQ ID NO: 313           moltype = AA  length = 6
```

```
FEATURE              Location/Qualifiers
REGION               1..6
                     note = peptide motif
SITE                 2
                     note = MISC_FEATURE - X is beta-homolysine
SITE                 3
                     note = MISC_FEATURE - X is azetidine-2-carboxylic acid
source               1..6
                     mol_type = protein
                     organism = synthetic construct
SEQUENCE: 313
PXXLDT                                                                  6

SEQ ID NO: 314       moltype = AA  length = 6
FEATURE              Location/Qualifiers
REGION               1..6
                     note = peptide motif
SITE                 2
                     note = MISC_FEATURE - X is 3-phenyl-D-phenylalanine
SITE                 3
                     note = MISC_FEATURE - X is beta-homolysine
source               1..6
                     mol_type = protein
                     organism = synthetic construct
SEQUENCE: 314
PXXLDT                                                                  6

SEQ ID NO: 315       moltype = AA  length = 6
FEATURE              Location/Qualifiers
REGION               1..6
                     note = peptide motif
SITE                 2
                     note = MISC_FEATURE - X is
                     3-(2-trifluoromethoxy-phenyl)-D-phenylalanine
SITE                 3
                     note = MISC_FEATURE - X is beta-homolysine
source               1..6
                     mol_type = protein
                     organism = synthetic construct
SEQUENCE: 315
PXXLDT                                                                  6

SEQ ID NO: 316       moltype = AA  length = 6
FEATURE              Location/Qualifiers
REGION               1..6
                     note = peptide motif
SITE                 2
                     note = MISC_FEATURE - X is
                     3-(2-methoxy-phenyl)-D-phenylalanine
SITE                 3
                     note = MISC_FEATURE - X is beta-homolysine
source               1..6
                     mol_type = protein
                     organism = synthetic construct
SEQUENCE: 316
PXXLDT                                                                  6

SEQ ID NO: 317       moltype = AA  length = 6
FEATURE              Location/Qualifiers
REGION               1..6
                     note = peptide motif
SITE                 2
                     note = MISC_FEATURE - X is
                     2-(5-quinolinyl)-N-methyl-phenylalanine
SITE                 3
                     note = MISC_FEATURE - X is N-methyl beta-homoLysine
source               1..6
                     mol_type = protein
                     organism = synthetic construct
SEQUENCE: 317
PXXLDT                                                                  6

SEQ ID NO: 318       moltype = AA  length = 6
FEATURE              Location/Qualifiers
REGION               1..6
                     note = peptide motif
SITE                 3
                     note = MISC_FEATURE - X is beta-homonorleucine
source               1..6
```

```
                              mol_type = protein
                              organism = synthetic construct
SEQUENCE: 318
PFXLDT                                                                          6

SEQ ID NO: 319                moltype = AA   length = 6
FEATURE                       Location/Qualifiers
REGION                        1..6
                              note = peptide motif
SITE                          3
                              note = MISC_FEATURE - X is
                              N-alpha-methyl-N-epsilon-dimethyl-beta-homoLysine
source                        1..6
                              mol_type = protein
                              organism = synthetic construct
SEQUENCE: 319
PFXLDT                                                                          6

SEQ ID NO: 320                moltype = AA   length = 6
FEATURE                       Location/Qualifiers
REGION                        1..6
                              note = peptide motif
SITE                          2
                              note = MISC_FEATURE - X is N-methyl phenylalanine
SITE                          3
                              note = MISC_FEATURE - X is
                              N-alpha-methyl-N-epsilon-dimethyl-beta-homoLysine
source                        1..6
                              mol_type = protein
                              organism = synthetic construct
SEQUENCE: 320
PXXLDT                                                                          6

SEQ ID NO: 321                moltype = AA   length = 6
FEATURE                       Location/Qualifiers
REGION                        1..6
                              note = peptide motif
SITE                          3
                              note = MISC_FEATURE - X is N-methyl beta-homoLysine
source                        1..6
                              mol_type = protein
                              organism = synthetic construct
SEQUENCE: 321
PMXLDT                                                                          6

SEQ ID NO: 322                moltype = AA   length = 6
FEATURE                       Location/Qualifiers
REGION                        1..6
                              note = peptide motif
SITE                          2
                              note = MISC_FEATURE - X is 2-indanylglycine
SITE                          3
                              note = MISC_FEATURE - X is N-methyl beta-homoLysine
source                        1..6
                              mol_type = protein
                              organism = synthetic construct
SEQUENCE: 322
PXXLDT                                                                          6

SEQ ID NO: 323                moltype = AA   length = 6
FEATURE                       Location/Qualifiers
REGION                        1..6
                              note = peptide motif
SITE                          2
                              note = MISC_FEATURE - X is homophenylalanine
SITE                          3
                              note = MISC_FEATURE - X is N-methyl beta-homoLysine
source                        1..6
                              mol_type = protein
                              organism = synthetic construct
SEQUENCE: 323
PXXLDT                                                                          6

SEQ ID NO: 324                moltype = AA   length = 6
FEATURE                       Location/Qualifiers
REGION                        1..6
                              note = peptide motif
SITE                          2
                              note = MISC_FEATURE - X is O-benzyl-trans-4-hydroxyproline
```

```
SITE                    3
                        note = MISC_FEATURE - X is N-methyl beta-homoLysine
source                  1..6
                        mol_type = protein
                        organism = synthetic construct
SEQUENCE: 324
PXXLDT                                                                            6

SEQ ID NO: 325          moltype = AA  length = 6
FEATURE                 Location/Qualifiers
REGION                  1..6
                        note = peptide motif
SITE                    2
                        note = MISC_FEATURE - X is cis-2-aminocyclohexanecarboxylic
                         acid
SITE                    3
                        note = MISC_FEATURE - X is N-methyl beta-homoLysine
source                  1..6
                        mol_type = protein
                        organism = synthetic construct
SEQUENCE: 325
PXXLDT                                                                            6

SEQ ID NO: 326          moltype = AA  length = 6
FEATURE                 Location/Qualifiers
REGION                  1..6
                        note = peptide motif
SITE                    2
                        note = MISC_FEATURE - X is N-methyl methionine
SITE                    3
                        note = MISC_FEATURE - X is N-methyl beta-homoLysine
source                  1..6
                        mol_type = protein
                        organism = synthetic construct
SEQUENCE: 326
PXXLDT                                                                            6

SEQ ID NO: 327          moltype = AA  length = 6
FEATURE                 Location/Qualifiers
REGION                  1..6
                        note = peptide motif
SITE                    2
                        note = MISC_FEATURE - X is beta-homolysine
SITE                    3
                        note = MISC_FEATURE - X is beta-homolysine
source                  1..6
                        mol_type = protein
                        organism = synthetic construct
SEQUENCE: 327
PXXLDT                                                                            6

SEQ ID NO: 328          moltype = AA  length = 6
FEATURE                 Location/Qualifiers
REGION                  1..6
                        note = peptide motif
SITE                    2
                        note = MISC_FEATURE - X is beta-homophenylalanine
SITE                    3
                        note = MISC_FEATURE - X is N-methyl beta-homoLysine
source                  1..6
                        mol_type = protein
                        organism = synthetic construct
SEQUENCE: 328
PXXLDT                                                                            6

SEQ ID NO: 329          moltype = AA  length = 6
FEATURE                 Location/Qualifiers
REGION                  1..6
                        note = peptide motif
SITE                    2
                        note = MISC_FEATURE - X is beta-homomethionine
SITE                    3
                        note = MISC_FEATURE - X is N-methyl beta-homoLysine
source                  1..6
                        mol_type = protein
                        organism = synthetic construct
SEQUENCE: 329
PXXLDT                                                                            6
```

| | | |
|---|---|---|
| SEQ ID NO: 330<br>FEATURE<br>REGION<br><br>SITE<br><br><br>source<br><br><br>SEQUENCE: 330<br>PYXLDT | moltype = AA   length = 6<br>Location/Qualifiers<br>1..6<br>note = peptide motif<br>3<br>note = MISC_FEATURE - X is 3-aminomethyl-4-bromo-benzoic<br>  acid<br>1..6<br>mol_type = protein<br>organism = synthetic construct<br><br> | <br><br><br><br><br><br><br><br><br><br>6 |
| SEQ ID NO: 331<br>FEATURE<br>REGION<br><br>SITE<br><br><br>source<br><br><br>SEQUENCE: 331<br>PYXLDT | moltype = AA   length = 6<br>Location/Qualifiers<br>1..6<br>note = peptide motif<br>3<br>note = MISC_FEATURE - X is<br>  3-aminomethyl-4-(4-aza-phenyl)-benzoic acid<br>1..6<br>mol_type = protein<br>organism = synthetic construct<br><br> | <br><br><br><br><br><br><br><br><br><br>6 |
| SEQ ID NO: 332<br>FEATURE<br>REGION<br><br>SITE<br><br><br>source<br><br><br>SEQUENCE: 332<br>PYXLDT | moltype = AA   length = 6<br>Location/Qualifiers<br>1..6<br>note = peptide motif<br>3<br>note = MISC_FEATURE - X is<br>  3-aminomethyl-4-(2,5-dimethyl-isoxazole)-benzoic acid<br>1..6<br>mol_type = protein<br>organism = synthetic construct<br><br> | <br><br><br><br><br><br><br><br><br><br>6 |
| SEQ ID NO: 333<br>FEATURE<br>REGION<br><br>SITE<br><br><br>source<br><br><br>SEQUENCE: 333<br>PYXLDT | moltype = AA   length = 6<br>Location/Qualifiers<br>1..6<br>note = peptide motif<br>3<br>note = MISC_FEATURE - X is<br>  3-aminomethyl-4-(3-aminomethyl-phenyl)-benzoic acid<br>1..6<br>mol_type = protein<br>organism = synthetic construct<br><br> | <br><br><br><br><br><br><br><br><br><br>6 |
| SEQ ID NO: 334<br>FEATURE<br>REGION<br><br>SITE<br><br><br>source<br><br><br>SEQUENCE: 334<br>PXLDT | moltype = AA   length = 5<br>Location/Qualifiers<br>1..5<br>note = peptide motif<br>2<br>note = MISC_FEATURE - X is<br>  3-aminomethyl-4-(4-(1-piperazinyl)-phenyl)-benzoic acid<br>1..5<br>mol_type = protein<br>organism = synthetic construct<br><br> | <br><br><br><br><br><br><br><br><br><br>5 |
| SEQ ID NO: 335<br>FEATURE<br>REGION<br><br>SITE<br><br><br>source<br><br><br>SEQUENCE: 335<br>PXLDT | moltype = AA   length = 5<br>Location/Qualifiers<br>1..5<br>note = peptide motif<br>2<br>note = MISC_FEATURE - X is<br>  3-aminomethyl-4-(4-quinolinyl)-benzoic acid<br>1..5<br>mol_type = protein<br>organism = synthetic construct<br><br> | <br><br><br><br><br><br><br><br><br><br>5 |
| SEQ ID NO: 336 | moltype = AA   length = 5 | |

```
FEATURE              Location/Qualifiers
REGION               1..5
                     note = peptide motif
SITE                 2
                     note = MISC_FEATURE - X is 3-aminomethyl-4-bromo-benzoic
                      acid
source               1..5
                     mol_type = protein
                     organism = synthetic construct
SEQUENCE: 336
PXLDT                                                                    5

SEQ ID NO: 337       moltype = AA  length = 5
FEATURE              Location/Qualifiers
REGION               1..5
                     note = peptide motif
SITE                 2
                     note = MISC_FEATURE - X is
                      3-aminomethyl-4-(2,5-dimethyl-isoxazole)-benzoic acid
source               1..5
                     mol_type = protein
                     organism = synthetic construct
SEQUENCE: 337
PXLDT                                                                    5

SEQ ID NO: 338       moltype = AA  length = 5
FEATURE              Location/Qualifiers
REGION               1..5
                     note = peptide motif
SITE                 1
                     note = MISC_FEATURE - D-proline
SITE                 2
                     note = MISC_FEATURE - X is
                      3-aminomethyl-4-(4-pyridyl)-benzoic acid
source               1..5
                     mol_type = protein
                     organism = synthetic construct
SEQUENCE: 338
PXLDT                                                                    5

SEQ ID NO: 339       moltype = AA  length = 5
FEATURE              Location/Qualifiers
REGION               1..5
                     note = peptide motif
SITE                 2
                     note = MISC_FEATURE - X is
                      3-aminomethyl-(4-methylpyrazole-3-yl)-benzoic acid
source               1..5
                     mol_type = protein
                     organism = synthetic construct
SEQUENCE: 339
PXLDT                                                                    5

SEQ ID NO: 340       moltype = AA  length = 5
FEATURE              Location/Qualifiers
REGION               1..5
                     note = peptide motif
SITE                 2
                     note = MISC_FEATURE - X is
                      3-aminomethyl-4-(3-quinolinyl)-benzoic acid
source               1..5
                     mol_type = protein
                     organism = synthetic construct
SEQUENCE: 340
PXLDT                                                                    5

SEQ ID NO: 341       moltype = AA  length = 5
FEATURE              Location/Qualifiers
REGION               1..5
                     note = peptide motif
SITE                 2
                     note = MISC_FEATURE - X is
                      3-aminomethyl-4-(5-quinolinyl)-benzoic acid
source               1..5
                     mol_type = protein
                     organism = synthetic construct
SEQUENCE: 341
PXLDT                                                                    5
```

```
SEQ ID NO: 342          moltype = AA   length = 5
FEATURE                 Location/Qualifiers
REGION                  1..5
                        note = peptide motif
SITE                    2
                        note = MISC_FEATURE - X is
                         3-aminomethyl-4-(2-(1-piperazinyl)phenyl)-benzoic acid
source                  1..5
                        mol_type = protein
                        organism = synthetic construct
SEQUENCE: 342
PXLDT                                                                      5

SEQ ID NO: 343          moltype = AA   length = 5
FEATURE                 Location/Qualifiers
REGION                  1..5
                        note = peptide motif
SITE                    2
                        note = MISC_FEATURE - X is
                         3-aminomethyl-4-(3-(1-piperzainyl)phenyl)-benzoic acid
source                  1..5
                        mol_type = protein
                        organism = synthetic construct
SEQUENCE: 343
PXLDT                                                                      5

SEQ ID NO: 344          moltype = AA   length = 5
FEATURE                 Location/Qualifiers
REGION                  1..5
                        note = peptide motif
SITE                    2
                        note = MISC_FEATURE - X is
                         3-aminomethyl-4-(2-(3-(piperidin-4-ylmethoxy)phenyl))-benzo
                         ic acid
source                  1..5
                        mol_type = protein
                        organism = synthetic construct
SEQUENCE: 344
PXLDT                                                                      5

SEQ ID NO: 345          moltype = AA   length = 5
FEATURE                 Location/Qualifiers
REGION                  1..5
                        note = peptide motif
SITE                    2
                        note = MISC_FEATURE - X is
                         3-aminomethyl-4-(4-pyridyl)-benzoic acid
source                  1..5
                        mol_type = protein
                        organism = synthetic construct
SEQUENCE: 345
PXLDT                                                                      5

SEQ ID NO: 346          moltype =    length =
SEQUENCE: 346
000

SEQ ID NO: 347          moltype =    length =
SEQUENCE: 347
000

SEQ ID NO: 348          moltype = AA   length = 5
FEATURE                 Location/Qualifiers
REGION                  1..5
                        note = peptide motif
SITE                    2
                        note = MISC_FEATURE - X is
                         3-aminomethyl-4-(4-(1-piperazinyl)phenyl))-benzoic acid
source                  1..5
                        mol_type = protein
                        organism = synthetic construct
SEQUENCE: 348
PXLDT                                                                      5

SEQ ID NO: 349          moltype =    length =
SEQUENCE: 349
000

SEQ ID NO: 350          moltype = AA   length = 5
```

| | | |
|---|---|---|
| FEATURE | Location/Qualifiers | |
| REGION | 1..5 | |
| | note = peptide motif | |
| SITE | 2 | |
| | note = MISC_FEATURE - X is N-benzyl-3-aminomethyl-benzoic acid | |
| source | 1..5 | |
| | mol_type = protein | |
| | organism = synthetic construct | |
| SEQUENCE: 350 | | |
| PXLDT | | 5 |
| | | |
| SEQ ID NO: 351 | moltype = AA   length = 5 | |
| FEATURE | Location/Qualifiers | |
| REGION | 1..5 | |
| | note = peptide motif | |
| SITE | 2 | |
| | note = MISC_FEATURE - X is 3-aminomethyl-benzoic acid | |
| source | 1..5 | |
| | mol_type = protein | |
| | organism = synthetic construct | |
| SEQUENCE: 351 | | |
| PXLDT | | 5 |
| | | |
| SEQ ID NO: 352 | moltype = AA   length = 5 | |
| FEATURE | Location/Qualifiers | |
| REGION | 1..5 | |
| | note = peptide motif | |
| SITE | 2 | |
| | note = MISC_FEATURE - X is 3-aminomethyl-5-bromo-benzoic acid | |
| source | 1..5 | |
| | mol_type = protein | |
| | organism = synthetic construct | |
| SEQUENCE: 352 | | |
| PXLDT | | 5 |
| | | |
| SEQ ID NO: 353 | moltype = AA   length = 5 | |
| FEATURE | Location/Qualifiers | |
| REGION | 1..5 | |
| | note = peptide motif | |
| SITE | 2 | |
| | note = MISC_FEATURE - X is 3-aminomethyl-6-bromo-benzoic acid | |
| source | 1..5 | |
| | mol_type = protein | |
| | organism = synthetic construct | |
| SEQUENCE: 353 | | |
| PXLDT | | 5 |
| | | |
| SEQ ID NO: 354 | moltype = AA   length = 5 | |
| FEATURE | Location/Qualifiers | |
| REGION | 1..5 | |
| | note = peptide motif | |
| SITE | 2 | |
| | note = MISC_FEATURE - X is 3-aminomethyl-5-(4-aza-phenyl)-benzoic acid | |
| source | 1..5 | |
| | mol_type = protein | |
| | organism = synthetic construct | |
| SEQUENCE: 354 | | |
| PXLDT | | 5 |
| | | |
| SEQ ID NO: 355 | moltype = AA   length = 5 | |
| FEATURE | Location/Qualifiers | |
| REGION | 1..5 | |
| | note = peptide motif | |
| SITE | 2 | |
| | note = MISC_FEATURE - X is 3-aminomethyl-4-(3-thiophenyl)-benzoic acid | |
| source | 1..5 | |
| | mol_type = protein | |
| | organism = synthetic construct | |
| SEQUENCE: 355 | | |
| PXLDT | | 5 |
| | | |
| SEQ ID NO: 356 | moltype = AA   length = 5 | |
| FEATURE | Location/Qualifiers | |
| REGION | 1..5 | |

```
                    note = peptide motif
SITE                2
                    note = MISC_FEATURE - X is
                     3-aminomethyl-4-(4-N,N-dimethyl-carboxamide-phenyl)-benzoic
                     acid
source              1..5
                    mol_type = protein
                    organism = synthetic construct
SEQUENCE: 356
PXLDT                                                                        5

SEQ ID NO: 357      moltype = AA   length = 5
FEATURE             Location/Qualifiers
REGION              1..5
                    note = peptide motif
SITE                2
                    note = MISC_FEATURE - X is
                     3-aminomethyl-4-(4-aza-phenyl)-benzoic acid
source              1..5
                    mol_type = protein
                    organism = synthetic construct
SEQUENCE: 357
PXLDT                                                                        5

SEQ ID NO: 358      moltype = AA   length = 5
FEATURE             Location/Qualifiers
REGION              1..5
                    note = peptide motif
SITE                2
                    note = MISC_FEATURE - X is
                     3-aminomethyl-4-(3-aza-phenyl)-benzoic acid
source              1..5
                    mol_type = protein
                    organism = synthetic construct
SEQUENCE: 358
PXLDT                                                                        5

SEQ ID NO: 359      moltype = AA   length = 5
FEATURE             Location/Qualifiers
REGION              1..5
                    note = peptide motif
SITE                2
                    note = MISC_FEATURE - X is
                     3-aminomethyl-4-(4-hydroxy-phenyl)-benzoic acid
source              1..5
                    mol_type = protein
                    organism = synthetic construct
SEQUENCE: 359
PXLDT                                                                        5

SEQ ID NO: 360      moltype = AA   length = 5
FEATURE             Location/Qualifiers
REGION              1..5
                    note = peptide motif
SITE                2
                    note = MISC_FEATURE - X is
                     3-aminomethyl-4-(5-(2,4-dimethyl)thiazole)-benzoic acid
source              1..5
                    mol_type = protein
                    organism = synthetic construct
SEQUENCE: 360
PXLDT                                                                        5

SEQ ID NO: 361      moltype = AA   length = 5
FEATURE             Location/Qualifiers
REGION              1..5
                    note = peptide motif
SITE                2
                    note = MISC_FEATURE - X is
                     3-aminomethyl-4-(3-N,N-dimethylaniline)-benzoic acid
source              1..5
                    mol_type = protein
                    organism = synthetic construct
SEQUENCE: 361
PXLDT                                                                        5

SEQ ID NO: 362      moltype = AA   length = 5
FEATURE             Location/Qualifiers
REGION              1..5
```

| | | |
|---|---|---|
| SITE | | note = peptide motif |
| | | 2 |
| | | note = MISC_FEATURE - X is |
| | | 3-aminomethyl-4-(2-fluoro-pyridyl)-benzoic acid |
| source | | 1..5 |
| | | mol_type = protein |
| | | organism = synthetic construct |
| SEQUENCE: 362 | | |
| PXLDT | | 5 |
| | | |
| SEQ ID NO: 363 | | moltype = AA  length = 5 |
| FEATURE | | Location/Qualifiers |
| REGION | | 1..5 |
| | | note = peptide motif |
| SITE | | 2 |
| | | note = MISC_FEATURE - X is |
| | | 3-aminomethyl-4-(5-pyrimidinyl)-benzoic acid |
| source | | 1..5 |
| | | mol_type = protein |
| | | organism = synthetic construct |
| SEQUENCE: 363 | | |
| PXLDT | | 5 |
| | | |
| SEQ ID NO: 364 | | moltype = AA  length = 5 |
| FEATURE | | Location/Qualifiers |
| REGION | | 1..5 |
| | | note = peptide motif |
| SITE | | 2 |
| | | note = MISC_FEATURE - X is |
| | | 3-aminomethyl-4-(3-N,N-dimethyl-diarylether)-benzoic acid |
| source | | 1..5 |
| | | mol_type = protein |
| | | organism = synthetic construct |
| SEQUENCE: 364 | | |
| PXLDT | | 5 |
| | | |
| SEQ ID NO: 365 | | moltype = AA  length = 5 |
| FEATURE | | Location/Qualifiers |
| REGION | | 1..5 |
| | | note = peptide motif |
| SITE | | 2 |
| | | note = MISC_FEATURE - X is |
| | | 3-aminomethyl-4-(3-trifluoromethyl-phenyl)-benzoic acid |
| source | | 1..5 |
| | | mol_type = protein |
| | | organism = synthetic construct |
| SEQUENCE: 365 | | |
| PXLDT | | 5 |
| | | |
| SEQ ID NO: 366 | | moltype = AA  length = 5 |
| FEATURE | | Location/Qualifiers |
| REGION | | 1..5 |
| | | note = peptide motif |
| SITE | | 2 |
| | | note = MISC_FEATURE - X is |
| | | 3-aminomethyl-4-(2,5-dimethoxy-phenyl)-benzoic acid |
| source | | 1..5 |
| | | mol_type = protein |
| | | organism = synthetic construct |
| SEQUENCE: 366 | | |
| PXLDT | | 5 |
| | | |
| SEQ ID NO: 367 | | moltype = AA  length = 5 |
| FEATURE | | Location/Qualifiers |
| REGION | | 1..5 |
| | | note = peptide motif |
| SITE | | 2 |
| | | note = MISC_FEATURE - X is |
| | | 3-aminomethyl-4-((2,3,4-tri-methoxy)-phenyl)-benzoic acid |
| source | | 1..5 |
| | | mol_type = protein |
| | | organism = synthetic construct |
| SEQUENCE: 367 | | |
| PXLDT | | 5 |
| | | |
| SEQ ID NO: 368 | | moltype = AA  length = 5 |
| FEATURE | | Location/Qualifiers |
| REGION | | 1..5 |
| | | note = peptide motif |

| | |
|---|---|
| SITE | 2<br>note = MISC_FEATURE - X is<br> 3-aminomethyl-4-(4-carboxy)-phenyl-benzoic acid |
| source | 1..5<br>mol_type = protein<br>organism = synthetic construct |

SEQUENCE: 368
PXLDT                                                                        5

| | |
|---|---|
| SEQ ID NO: 369<br>FEATURE<br>REGION | moltype = AA   length = 5<br>Location/Qualifiers<br>1..5<br>note = peptide motif |
| SITE | 2<br>note = MISC_FEATURE - X is<br> 3-aminomethyl-4-piperonyl-benzoic acid |
| source | 1..5<br>mol_type = protein<br>organism = synthetic construct |

SEQUENCE: 369
PXLDT                                                                        5

| | |
|---|---|
| SEQ ID NO: 370<br>FEATURE<br>REGION | moltype = AA   length = 5<br>Location/Qualifiers<br>1..5<br>note = peptide motif |
| SITE | 2<br>note = MISC_FEATURE - X is<br> 3-aminomethyl-4-piperidinyl-benzoic acid |
| source | 1..5<br>mol_type = protein<br>organism = synthetic construct |

SEQUENCE: 370
PXLDT                                                                        5

| | |
|---|---|
| SEQ ID NO: 371<br>FEATURE<br>REGION | moltype = AA   length = 5<br>Location/Qualifiers<br>1..5<br>note = peptide motif |
| SITE | 2<br>note = MISC_FEATURE - X is<br> 3-aminomethyl-4-morpholinyl-benzoic acid |
| source | 1..5<br>mol_type = protein<br>organism = synthetic construct |

SEQUENCE: 371
PXLDT                                                                        5

| | |
|---|---|
| SEQ ID NO: 372<br>FEATURE<br>REGION | moltype = AA   length = 5<br>Location/Qualifiers<br>1..5<br>note = peptide motif |
| SITE | 2<br>note = MISC_FEATURE - X is<br> 3-aminomethyl-4-(N,N-dimethyl)-benzoic acid |
| source | 1..5<br>mol_type = protein<br>organism = synthetic construct |

SEQUENCE: 372
PXLDT                                                                        5

| | |
|---|---|
| SEQ ID NO: 373<br>FEATURE<br>REGION | moltype = AA   length = 5<br>Location/Qualifiers<br>1..5<br>note = peptide motif |
| SITE | 2<br>note = MISC_FEATURE - X is<br> 3-aminomethyl-4-(2-aminomethylphenyl)-benzoic acid |
| source | 1..5<br>mol_type = protein<br>organism = synthetic construct |

SEQUENCE: 373
PXLDT                                                                        5

| | |
|---|---|
| SEQ ID NO: 374<br>FEATURE<br>REGION | moltype = AA   length = 5<br>Location/Qualifiers<br>1..5<br>note = peptide motif |
| SITE | 2 |

| | | |
|---|---|---|
| | | note = MISC_FEATURE - X is
3-aminomethyl-4-(3-aminomethylphenyl)-benzoic acid |
| source | 1..5 | |
| | mol_type = protein | |
| | organism = synthetic construct | |
| SEQUENCE: 374 | | |
| PXLDT | | 5 |

| | | |
|---|---|---|
| SEQ ID NO: 375 | moltype = AA  length = 5 | |
| FEATURE | Location/Qualifiers | |
| REGION | 1..5 | |
| | note = peptide motif | |
| SITE | 2 | |
| | note = MISC_FEATURE - X is
3-aminomethyl-4-(4-aminomethylphenyl)-benzoic acid | |
| source | 1..5 | |
| | mol_type = protein | |
| | organism = synthetic construct | |
| SEQUENCE: 375 | | |
| PXLDT | | 5 |

| | | |
|---|---|---|
| SEQ ID NO: 376 | moltype =   length = | |
| SEQUENCE: 376 | | |
| 000 | | |

| | | |
|---|---|---|
| SEQ ID NO: 377 | moltype =   length = | |
| SEQUENCE: 377 | | |
| 000 | | |

| | | |
|---|---|---|
| SEQ ID NO: 378 | moltype = AA  length = 5 | |
| FEATURE | Location/Qualifiers | |
| REGION | 1..5 | |
| | note = peptide motif | |
| SITE | 2 | |
| | note = MISC_FEATURE - X is N-methyl-3-aminomethyl-benzoic
 acid | |
| source | 1..5 | |
| | mol_type = protein | |
| | organism = synthetic construct | |
| SEQUENCE: 378 | | |
| PXLDT | | 5 |

| | | |
|---|---|---|
| SEQ ID NO: 379 | moltype = AA  length = 5 | |
| FEATURE | Location/Qualifiers | |
| REGION | 1..5 | |
| | note = peptide motif | |
| SITE | 2 | |
| | note = MISC_FEATURE - X is
N-methyl-3-aminomethyl-4-(4-quinolinyl)-benzoic acid | |
| source | 1..5 | |
| | mol_type = protein | |
| | organism = synthetic construct | |
| SEQUENCE: 379 | | |
| PXLDT | | 5 |

| | | |
|---|---|---|
| SEQ ID NO: 380 | moltype = AA  length = 6 | |
| FEATURE | Location/Qualifiers | |
| REGION | 1..6 | |
| | note = peptide motif | |
| SITE | 2 | |
| | note = MISC_FEATURE - X is
2-(5-quinolinyl)-phenylalanine-reduced | |
| SITE | 3 | |
| | note = MISC_FEATURE - X is beta-homolysine | |
| source | 1..6 | |
| | mol_type = protein | |
| | organism = synthetic construct | |
| SEQUENCE: 380 | | |
| PXXLDT | | 6 |

```
SEQ ID NO: 381         moltype = AA  length = 5
FEATURE                Location/Qualifiers
REGION                 1..5
                       note = peptide motif
SITE                   2
                       note = MISC_FEATURE - X is N-methyl beta-homoLysine
source                 1..5
                       mol_type = protein
                       organism = synthetic construct
SEQUENCE: 381
KXLDT                                                                      5
```

The invention claimed is:

1. A method of treating ulcerative colitis or Crohn's disease in a patient, comprising administering to the patient a therapeutically effective amount of a multimer selected from the group consisting of a homodimer, a homotrimer and a homotetramer, the multimer comprising two, three or four compounds covalently linked together by a linker selected from the group consisting of an amide linker, an amine linker and a mixed amide/amine linker, the compounds being identical and having the formula (I):

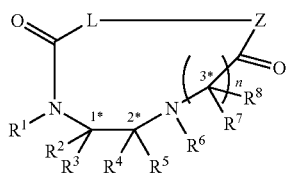

or a pharmaceutically acceptable salt thereof, wherein
$R^1$ is H, $C_1$-$C_6$ alkyl, aryl, heteroaryl, alkenyl, or heterocycle, all of which are optionally substituted at one or more substitutable positions with one or more substituents selected from the group consisting of hydroxyl, cyano, alkoxy, aryloxy, vinyl, alkenyl, alkynyl, formyl, haloalkyl, halide, aryl, heteroaryl, amide, acyl, ether, thioether, thioalkoxy, phosphino, and —$NR_aR_b$, where $R_a$ and $R_b$ are independently selected from $C_1$-$C_6$ alkyl, aryl or benzyl,
and where the one or more substituents is not alkyl when $R^1$ is $C_1$-$C_6$ alkyl;
$R^2$ and $R^3$ are each independently an amino acid side chain of a proteinogenic or a non-proteinogenic alpha-amino acid,
or $R^2$ and $R^3$ are covalently linked to each other to form a ring;
$R^4$ and $R^5$ are each independently H, $C_1$-$C_6$ alkyl, aryl, heteroaryl, alkenyl, heterocycle, acids of the formula —C(O)OH, esters of the formula —C(O)OR* wherein R* is selected from alkyl and aryl, amides of the formula —C(O)NR R*, wherein R and R* are independently selected from H, alkyl and aryl; —$CH_2$C(O)R, wherein R is selected from —OH, —$C_1$-$C_6$ alkyl, aryl, —$C_1$-$C_6$ alkyl-aryl, or —$NR_aR_b$, where $R_a$ and $R_b$ are independently selected from H, $C_1$-$C_6$ alkyl, aryl or —$C_1$-$C_6$ alkyl-aryl; or —C(O)Rc, wherein Rc is selected from $C_1$-$C_6$ alkyl, aryl or —$C_1$-$C_6$ alkyl-aryl, or —$C_1$-$C_6$ alkyl-ORd, wherein Rd is a suitable protecting group or OH group; all of which are optionally substituted at one or more substitutable positions with one or more substituents selected from the group consisting of hydroxyl, cyano, alkoxy, aryloxy, vinyl, alkenyl, alkynyl, formyl, haloalkyl, halide, aryl, heteroaryl, amide, acyl, ether, thioether, thioalkoxy, phosphino, and —$NR_aR_b$, where $R_a$ and $R_b$ are independently selected from $C_1$-$C_6$ alkyl, aryl or benzyl;
and where the one or more substituents is not alkyl when $R^4$ and/or $R^5$ is $C_1$-$C_6$ alkyl;
or $R^2$ or $R^3$ are covalently linked to $R^1$ to form a cyclic secondary amine, and/or to $R^4$ or $R^5$ to form a ring, or $R^4$ and $R^5$ are covalently linked to each other to form a ring;
$R^6$ is H, $C_1$-$C_6$ alkyl, benzyl, alkenyl, $C_1$-$C_6$ alkyloxy, aryl, heteroaryl, heterocycle, —C(O)R **, wherein R * is independently selected from alkyl, aryl, heteroaryl, amino, aminoalkyl, aminoaryl, aminoheteroaryl, alkoxy, aryloxy, heteroaryloxy; —$CH_2$C(O)R, or —C(O) Rc; all of which are optionally substituted at one or more substitutable positions with one or more substituents selected from the group consisting of hydroxyl, cyano, alkoxy, aryloxy, vinyl, alkenyl, alkynyl, formyl, haloalkyl, halide, aryl, heteroaryl, amide, acyl, ether, thioether, thioalkoxy, phosphino, and —$NR_aR_b$, where $R_a$ and $R_b$ are independently selected from $C_1$-$C_6$ alkyl, aryl or benzyl;
and where the one or more substituents is not alkyl when $R^6$ is $C_1$-$C_6$ alkyl;
or along with $R^7$ or $R^8$, a cyclic side chain of a proteinogenic or a non-proteinogenic amino acid having, the N-terminus thereof being the N-$R^6$, wherein the proteinogenic or non-proteinogenic amino acid is optionally substituted with a substituent selected from the group consisting of hydroxyl, cyano, alkoxy, aryloxy, vinyl, alkenyl, alkynyl, formyl, haloalkyl, halide, aryl, heteroaryl, amide, acyl, ether, thioether, thioalkoxy, phosphino, and —$NR_aR_b$, where $R_a$ and $R_b$ are independently selected from $C_1$-$C_6$ alkyl, aryl or benzyl;
$R^7$ and $R^8$ are independently selected from the amino acid side chains of a proteinogenic or a non-proteinogenic alpha-amino acid having the N-terminus thereof being the N-$R^6$, or form a cyclic side chain with $R^6$;
stereocentres 1*, 2* and 3* are each independently selected from R and S;
n is 1, 2, 3, or 4 and where n is 2-4, each $R^7$ and each $R^8$ are independent of each other; and
wherein Z is an amino terminus of an amino acid; —C=O— adjacent L is the carboxy terminus of an amino acid; and L along with Z and —C=O— is a peptide having the following formula:

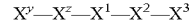

wherein $X^y$ and $X^z$ are each independently a proteinogenic or non-proteinogenic amino acid, or $X^z$ is absent;

$X^1$ is Leucine or tert-butyl-Ala;

$X^2$ is Asp; and $X^3$ is an amino acid selected from the group consisting of Val, Thr, Ile, Thr(OBn), Thr(OMe), Thr (OEt), Pen, MeThr, alloThr, Abu, and alloIle;

wherein the compounds are linked together at a nitrogen atom associated with $X^y$;

or a pharmaceutically acceptable salt thereof.

2. The method of claim 1, wherein $R^1$ is H.

3. The method of claim 1, wherein $R^2$ and $R^3$ are each independently selected from the group consisting of amino acid side chains of a proteinogenic or a non-proteinogenic alpha-amino acid.

4. The method of claim 1, wherein $R^2$ and $R^3$ are H and $CH_3$ respectively or vice versa.

5. The method of claim 1, wherein $R^4$ and $R^5$ are not both H.

6. The method of claim 1, wherein R  and R * are not both H.

7. The method of claim 1, wherein $R^4$ and $R^5$ are each independently H, or C(O)—$NHR^r$, wherein $R^r$ is H or a $C_1$-$C_6$ alkyl.

8. The method of claim 7, wherein $R^r$ is tert-butyl.

9. The method of claim 1, wherein $R^6$ and either $R^8$ or $R^9$ form a ring resulting in a proline residue having N-$R^6$ as its N-terminus.

10. The method of claim 1, wherein n is 1.

11. The method of claim 1, wherein $X^1$ is Leu.

12. The method of claim 1, wherein $X^2$ is Asp.

13. The method of claim 1, wherein $X^3$ is Thr.

14. The method of claim 1, wherein $X^3$ is Val.

15. The method of claim 1, wherein $X^3$ is Ile.

16. The method of claim 1, wherein $X^y$ and $X^z$ are each independently a proteinogenic or non-proteinogenic alpha-amino acid.

17. The method of claim 1, wherein $X^y$ and $X^z$ are each any amino acid selected from the group consisting of:

| $X^y$ | $X^z$ |
|---|---|
| Y | absent |
| H | absent |
| F | absent |
| HomoPhe | absent |
| Cha | absent |
| W | absent |
| 1Nal | absent |
| 2Nal | absent |
| W | absent |
| Bip | absent |
| Tyr(OPh) | absent |
| Tyr(2-tolyl diaryl ether) | absent |
| Tyr(4-CF3 diaryl ether) | absent |
| Tyr(4-methoxy diaryl ether) | absent |
| Tyr(4-fluoro diaryl ether) | absent |
| Tyr(2-methoxy diaryl ether) | absent |
| Tyr(3-methoxy diaryl ether) | absent |
| Tyr(3-fluoro diaryl ether) | absent |
| Tyr(3,4-difluoro diaryl ether) | absent |
| Tyr(3-methyl diaryl ether) | absent |
| Tyr(3,4-dimethyl diaryl ether) | absent |
| Tyr(4-CO2Me diaryl ether) | absent |
| Tyr(3-CO2Me diaryl ether) | absent |
| Tyr(4-CO2H diaryl ether) | absent |
| metaY(Opr) | absent |
| Orn(benzamide) | absent |
| Orn(acetamide) | absent |
| Orn(methanesulfonamide) | absent |
| Orn(ethylcarbamate) | absent |
| Orn(pentyl amide) | absent |
| R | absent |
| dTyr | absent |
| dTic | absent |
| [3-(3'-pyridyl)-Ala] | absent |
| dArg | absent |
| dPip | absent |
| [3-(4-thiazolyl)-Ala] | absent |
| (4-aza-Phe) | absent |
| (vinyl-Br-Leu) | absent |
| Hyp(OBn) | absent |
| Dap(Cbz) | absent |
| His(Bn) | absent |
| (4-amino-Phe) | absent |
| (4-aza-dPhe) | absent |
| Hyp | absent |
| dTrp | absent |
| M | absent |
| dMet | absent |
| (4-guanidino-Phe) | absent |
| (3-aza-Phe) | absent |
| (3-aza-dPhe) | absent |
| Nva | absent |
| dNle | absent |
| dLys | absent |
| dPro | absent |
| dOrn | absent |
| (3-benzothienyl-Ala) | absent |
| dTyr(OAllyl) | absent |
| dSer(OBn) | absent |
| [3-(4-thiazolyl)-dAla] | absent |
| (3-benzothienyl-dAla) | absent |
| [3-(2-thienyl)-dAla] | absent |
| (4-aminomethyl-Phe) | absent |
| dOrn(dimethyl) | absent |
| (4-amino-dPhe) | absent |
| (4-aminomethyl-dPhe) | absent |
| dTyr(OBn) | absent |
| P | absent |
| cycloLeu | absent |
| Aic | absent |
| Tyr(OAllyl) | absent |
| Chg | absent |
| K | absent |
| (2-aza-dPhe) | absent |
| (2-aza-Phe) | absent |
| [2-(2-pyridyl)-4-thiazolyl-Ala] | absent |
| [2-(3-pyridyl)-4-thiazolyl-Ala] | absent |
| [2-(4-pyridyl)-4-thiazolyl-Ala] | absent |
| dTiq | absent |
| [1-(S)-isoindoline-carboxylic acid] | absent |
| Y | dThr |
| Y | P |
| Y | dPro |
| Y | Sar |
| Y | cycloLeu |
| (3-iodo-Phe) | Sar |
| (4-iodo-Phe) | Sar |
| (3,3-diphenyl-Ala) | Sar |
| F | dLys |
| Bip | dLys |
| [3-(4-thiazolyl)-Ala] | dLys |
| (3,3-diphenyl-Ala) | dLys |
| Y | dLys |
| Y | dArg |
| Y | dSer |
| Bip | Sar |
| 1Nal | Sar |
| Y | Pip |
| (2-iodo-Phe) | Sar |
| 1Nal | dLys |
| F | Sar |
| Y | dTic |
| Y | dPip |
| F | dPro |
| (3,4-dimethoxy-Phe) | dPro |

| X^y | X^z |
| --- | --- |
| (3,4,5-trifluoro-Phe) | dPro |
| (3,5-dibromo-Tyr) | dPro |
| F | dPip |
| [3-(4-thiazolyl)-Ala] | dPip |
| (4-aminomethyl-Phe) | dPip |
| [2-iodo-Phe] | dPip |
| (2-phenyl-Phe) | dPip |
| [2-(2-methoxy-phenyl)-Phe] | dPip |
| [2-(3-methoxy-phenyl)-Phe] | dPip |
| [2-(4-methoxy-phenyl)-Phe] | dPip |
| Bip | dPip |
| Y | Hyp |
| Y | dHyp |
| Y | (cis-dHyp) |
| dTyr | dPip |
| 1Nal | dPip |
| 2Nal | dPip |
| (4-aminomethyl-Phe) | dTic |
| (3-aminomethyl-Phe) | dTic |
| (3-aminomethyl-dPhe) | dTic |
| MeTyr | dPip |
| Y | dPip |
| [3-(4-thiazolyl)-Ala] | dHyp |
| (4-aminomethyl-Phe) | dHyp |
| Y | dMeLys |
| Y | dNle |
| F | dHyp |
| Y | dMeArg |
| Y | G |
| Y | A |
| Y | dAla |
| M | G |
| Tyr(OAllyl) | Sar |
| Tyr(OAllyl) | G |
| [3-(4-thiazolyl)-Ala] | Sar |
| (4-aminomethyl-Phe) | G |
| Tyr(OAllyl) | dVal |
| Tyr(OAllyl) | dSer |
| Tyr(OAllyl) | dAla |
| Tyr(OAllyl) | P |
| Tyr(OAllyl) | dPro |
| [3-(4-thiazolyl)-Ala] | dVal |
| [3-(4-thiazolyl)-Ala] | dSer |
| [3-(4-thiazolyl)-Ala] | dAla |
| [3-(4-thiazolyl)-Ala] | P |
| [3-(4-thiazolyl)-Ala] | dPro |
| (4-aminomethyl-Phe) | P |
| (4-aminomethyl-Phe) | dPro |
| cycloLeu | P |
| [2-(2-pyridyl)-4-thiazolyl-Ala] | Sar |
| [2-(2-pyridyl)-4-thiazolyl-Ala] | dPro |
| [2-(3-pyridyl)-4-thiazolyl-Ala] | Sar |
| [2-(3-pyridyl)-4-thiazolyl-Ala] | dPro |
| [2-(4-pyridyl)-4-thiazolyl-Ala] | dPro |
| [3-(2-aminobenzyl-4-thiazolyl)-Ala] | Sar |
| [2-(amino-benzyl)-4-thiazolyl-Ala] | dPro |
| dTyr | dPip |
| (2-aminomethyl-Phe) | Aze |
| (3-aminomethyl-Phe) | dTic |
| (2,4-dichloro-Phe) | dPip |
| (3-phenyl-dPhe) | dPip |
| [3-(5-quinolinyl)-dPhe] | dPip |
| Y | betaHomoLys |
| Y | betaHomoPro |
| Y | 2Abz |
| F | betaHomoLys |
| [3-(4-thiazolyl)-Ala] | betaHomoLys |
| (4-aminomethyl-Phe) | betaHomoLys |
| MeTyr | dbetaHomoLys |
| 1Nal | betaHomoLys |
| 2Nal | betaHomoLys |
| Bip | betaHomoLys |
| (2-iodo-Phe) | betaHomoLys |
| [2-(2,5-dimethyl-isoxazole)-Phe] | betaHomoLys |
| (2-phenyl-Phe) | betaHomoLys |
| [(2-piperazinyl-2-Phenyl)-Phe] | betaHomoLys |
| Cha | betaHomoLys |
| W | betaHomoLys |
| dTrp | betaHomoLys |
| (3-aminomethyl-Phe) | betaHomoLys |
| (4-aminomethyl-dPhe) | betaHomoLys |
| (4-aminomethyl-Phe) | betaHomoLys |
| Y | dbetaHomoLys |
| dArg | betaHomoLys |
| (4-aminomethyl-Phe)-reduced | betaHomoLys |
| [3-(4-thiazolyl)-Ala] | dbetaHomoLys |
| F | dbetaHomoLys |
| [3-(4-thiazolyl)-Ala] | MebetaHomoLys |
| (4-aminomethyl-Phe) | MebetaHomoLys |
| [3-(4-thiazolyl)-Ala] | betaHomoLys |
| Tic | betaHomoLys |
| dTic | betaHomoLys |
| dTic | dbetaHomoLys |
| Y | betaHomoIle |
| (4-aminomethyl-Phe) | betaHomoPro |
| Y | dbetaHomoPro |
| (4-aminomethyl-Phe) | dbetaHomoPro |
| R | betaHomoLys |
| F | MebetaHomoLys |
| Phe-reduced | betaHomoLys |
| (3-aminomethyl-dPhe) | betaHomoLys |
| [2-[3-(1-piperazinyl)phenyl]-Phe]-betaHomoLys | |
| [3-(4-thiazolyl)-dAla] | betaHomoLys |
| (2-bromo-Phe) | betaHomoLys |
| (2-chloro-Phe) | betaHomoLys |
| (2-fluoro-Phe) | betaHomoLys |
| (2-CF3-Phe) | betaHomoLys |
| (2,4-dichloro-Phe) | betaHomoLys |
| (2-aminomethyl-Phe) | betaHomoLys |
| [2-(4-quinolinyl)-Phe] | betaHomoLys |
| [2-(5-quinolinyl)-Phe] | betaHomoLys |
| [2-(3-quinolinyl)-Phe] | betaHomoLys |
| dhomoPhe | betaHomoLys |
| (2-iodo-dPhe) | betaHomoLys |
| (2-phenyl-dPhe) | betaHomoLys |
| [(2-piperazinyl-2-Phenyl)-dPhe] | betaHomoLys |
| Y | betaHomoLys |
| dTyr | betaHomoLys |
| (4-aminomethyl-dPhe) | betaHomoLys |
| (4-aminomethyl-Phe) | betaHomoLys |
| (3-iodo-Phe) | betaHomoLys |
| (3-phenyl-Phe) | betaHomoLys |
| [3-(2-methoxy-phenyl)-Phe] | betaHomoLys |
| [3-(2,6-dimethoxy-phenyl)-Phe] | betaHomoLys |
| [3-(2-trifluoromethoxy-phenyl)-Phe] | betaHomoLys |
| (4-iodo-Phe) | betaHomoLys |
| [4-(2-methoxy-phenyl)-Phe] | betaHomoLys |
| [4-(2-trifluoromethoxy-phenyl)-Phe] | betaHomoLys |
| alphaMePhe | betaHomoLys |
| MePhe | betaHomoLys |
| [3-(2,6-dimethyl-phenyl)-Phe] | betaHomoLys |
| [3-(quinolin-4-yl)-Phe] | betaHomoLys |
| [3-(3,4-difluoro-phenyl)-Phe] | betaHomoLys |
| [4-(2,6-dimethyl-phenyl)-Phe] | betaHomoLys |
| [4-(2-chloro-6-methoxy-phenyl)-Phe] | betaHomoLys |
| [3-(4-thiazolyl)-Ala]-reduced | betaHomoLys |
| [2-4-(1-piperazinyl)phenyl]-Phe] | betaHomoLys |
| [2-(2,6-dimethylphenyl)-Phe] | betaHomoLys |
| [2-(benzothiazol-5-yl)-Phe] | betaHomoLys |
| HomoPhe | betaHomoLys |
| (piperidine-4-amino-4-carboxylic acid) | betaHomoLys |
| [2-(2,5-dimethyl-isoxazole)-dPhe] | betaHomoLys |
| [2-(2-chloro-6-methoxyphenyl)-Phe] | betaHomoLys |
| 2Igl | betaHomoLys |
| d2Igl | betaHomoLys |
| Atc | betaHomoLys |
| [2-[2,5-Bis(trifluoromethyl)phenyl]-Phe] | betaHomoLys |
| Aic | betaHomoLys |
| P | betaHomoLys |
| dPro | betaHomoLys |
| Pip | betaHomoLys |
| [2-(3-Pyridyl)-Phe] | betaHomoLys |
| [2-(4-Pyridyl)-Phe] | betaHomoLys |

-continued

| X^y | X^z |
|---|---|
| [2-(3-bromo-2-Pyridyl)-Phe] | betaHomoLys |
| (N-benzyl-Gly) | betaHomoLys |
| [2-(2-bromo-3-Pyridyl)-Phe] | betaHomoLys |
| [3-(2-chloro-6-methoxy-phenyl)-Phe] | betaHomoLys |
| [3-(benzothiazol-5-yl)-Phe] | betaHomoLys |
| (2-aminomethyl-Phe) | MebetaHomoLys |
| (2-aminomethyl-dPhe) | MebetaHomoLys |
| [3-(4-thiazolyl)-dAla] | MebetaHomoLys |
| [2-(2-trifluoromethoxy-phenyl)-dPhe] | MebetaHomoLys |
| Tic | MebetaHomoLys |
| dTic | MebetaHomoLys |
| [2-(5-quinolinyl)-dPhe] | betaHomoLys |
| Y | MebetaHomoLys |
| MeTyr | MebetaHomoLys |
| MePhe | MebetaHomoLys |
| (2-fluoro-Phe) | MebetaHomoLys |
| (2-fluoro-MePhe) | MebetaHomoLys |
| (2,4-dichloro-Phe) | MebetaHomoLys |
| (2,4-dichloro-MePhe) | MebetaHomoLys |
| (2-aminomethyl-MePhe) | MebetaHomoLys |
| [3-(2,6-dimethoxy-phenyl)-dPhe] | betaHomoLys |
| [3-(4-Quinolinyl)-dPhe] | betaHomoLys |
| betaHomoLys | Aze |
| (3-phenyl-dPhe) | betaHomoLys |
| [3-(2-trifluoromethoxy-phenyl)-dPhe] | betaHomoLys |
| [3-(2-methoxy-phenyl)-dPhe] | betaHomoLys |
| [2-(5-quinolinyl)-MePhe] | MebetaHomoLys |
| F | betaHomoNle |
| F | MebetaHomoLys(Me)2 |
| MePhe | MebetaHomoLys(Me)2 |
| M | MebetaHomoLys |
| Igl | MebetaHomoLys |
| HomoPhe | MebetaHomoLys |
| Hyp(OBn) | MebetaHomoLys |
| (1,2-cis-ACHC) | MebetaHomoLys |
| MeMet | MebetaHomoLys |
| betaHomoLys | betaHomoLys |
| BetaHomoPhe | MebetaHomoLys |
| betahomoMet | MebetaHomoLys |
| Y | (3-aminomethyl-4-bromo-benzoic acid) |
| Y | [3-aminomethyl-4-(4-aza-phenyl)-benzoic acid] |
| Y | [3-aminomethyl-4-(2,5-dimethyl-isoxazole)-benzoic acid] |
| Y | [3-aminomethyl-4-(3-aminomethyl-phenyl)-benzoic acid] |
| [3-aminomethyl-4-[4-(1-piperazinyl)-phenyl]-benzoic acid] | absent |
| [3-aminomethyl-4-[4-(1-piperazinyl-4-FITC)phenyl]-benzoic acid] | absent |
| [3-aminomethyl-4-[4-(1-piperazinyl-4-AlexaFluor 647)phenyl]-benzoic acid] | absent |
| [3-aminomethyl-4-(4-quinolinyl)-benzoic acid] | absent |
| (3-aminomethyl-4-bromo-benzoic acid) | absent |
| [3-aminomethyl-4-(2,5-dimethyl-isoxazole)-benzoic acid] | absent |
| [3-aminomethyl-4-(4-pyridyl)-benzoic acid] | absent |
| [3-aminomethyl-(4-methylpyrazole-3-yl)-benzoic acid] | absent |
| [3-aminomethyl-4-(3-quinolinyl)-benzoic acid] | absent |
| [3-aminomethyl-4-(5-quinolinyl)-benzoic acid] | absent |
| [3-aminomethyl-4-[2-(1-piperazinyl)phenyl]-benzoic acid] | absent |
| [3-aminomethyl-4-[3-(1-piperazinyl)phenyl]-benzoic acid] | absent |
| [3-aminomethyl-4-[2-(3-(piperidin-4-ylmethoxy)phenyl]-benzoic acid] | absent |
| [3-aminomethyl-4-[4-(1-piperazinyl)phenyl]-benzoic acid] | absent |

-continued

| X^y | X^z |
|---|---|
| [3-aminomethyl-4-(4-quinolinyl)]-benzoic acid | absent |
| (N-benzyl-3-aminomethyl-benzoic acid) | absent |
| (3-aminomethyl-benzoic acid | absent |
| (3-aminomethyl-5-bromo-benzoic acid) | absent |
| (3-aminomethyl-6-bromo-benzoic acid) | absent |
| [3-aminomethyl-5-(4-aza-phenyl)-benzoic acid] | absent |
| [3-aminomethyl-4-(3-thiophenyl)-benzoic acid] | absent |
| [3-aminomethyl-4-(4-N,N-dimethyl-carboxamide-phenyl)-benzoic acid] | absent |
| [3-aminomethyl-4-(4-aza-phenyl)-benzoic acid] | absent |
| [3-aminomethyl-4-(3-aza-phenyl)-benzoic acid] | absent |
| [3-aminomethyl-4-(4-hydroxy-phenyl)-benzoic acid] | absent |
| [3-aminomethyl-4-[5-(2,4-dimethyl)thiazole]-benzoic acid] | absent |
| [3-aminomethyl-4-(3-N,N-dimethylaniline)-benzoic acid] | absent |
| [3-aminomethyl-4-(2-fluoro-pyridyl)-benzoic acid] | absent |
| [3-aminomethyl-4-(5-pyrimidinyl)-benzoic acid] | absent |
| [3-aminomethyl-4-(3-N,N-dimethyl-diaryl ether)-benzoic acid] | absent |
| [3-aminomethyl-4-(3-CF3-phenyl)-benzoic acid] | absent |
| [3-aminomethyl-4-(2,5-dimethoxy-phenyl)-benzoic acid] | absent |
| [3-aminomethyl-4-[(2,3,4-tri-methoxy)-phenyl]-benzoic acid] | absent |
| [3-aminomethyl-4-(4-carboxy)-phenyl)-benzoic acid] | absent |
| [3-aminomethyl-4-(piperonyl)-benzoic acid] | absent |
| (3-aminomethyl-4-piperidinyl-benzoic acid) | absent |
| (3-aminomethyl-4-morpholinyl-benzoic acid) | absent |
| [3-aminomethyl-4-(N,N-dimethyl)-benzoic acid] | absent |
| [3-aminomethyl-4-(2-aminomethylphenyl)-benzoic acid] | absent |
| [3-aminomethyl-4-(3-aminomethylphenyl)-benzoic acid] | absent |
| [3-aminomethyl-4-(4-aminomethylphenyl)-benzoic acid] | absent |
| (N-methyl-3-aminomethyl-benzoic acid) | absent |
| [N-methyl-3-aminomethyl-4-(4-quinolinyl)-benzoic acid] | absent |
| [2-(5-quinolinyl)-Phe]-reduced | betaHomoLys |
| K | MebetaHomoLys. |

18. The method of claim 1, wherein the compound is any one of compounds 4-16, 18-31, 33-42, 50-141, 143-294, 296-343, 345-350, 352-384, 387-389, or 456 wherein $R^1$ is H;

$R^2$ is H;

$R^3$ is $CH_3$;

$R^4$ is H;

$R^5$ is C(O)—NH-tert-Butyl;

$R^6$ and $R^7$ are PRO;

$R^8$ is H; and $X^y$, $X^z$, $X^1$, $X^2$ and $X^3$ are defined as follows:

| Cpd. No. | X^y | X^z | X^1 | X^2 | X^3 |
|---|---|---|---|---|---|
| 4 | Y | absent | L | D | T |
| 5 | F | absent | L | D | T |
| 6 | HomoPhe | absent | L | D | T |
| 7 | Cha | absent | L | D | T |
| 8 | W | absent | L | D | I |
| 9 | 1Nal | absent | L | D | T |
| 10 | 2Nal | absent | L | D | T |
| 11 | W | absent | L | D | Thr(OBn) |
| 12 | Bip | absent | L | D | T |
| 13 | Tyr(OPh) | absent | L | D | T |
| 14 | 1Nal | absent | L | D | I |
| 15 | 2Nal | absent | L | D | I |
| 16 | 2Nal | absent | L | D | Thr(OBn) |
| 18 | Bip | absent | L | D | Thr(OBn) |
| 19 | Tyr(2-tolyl diaryl ether) | absent | L | D | T |
| 20 | Tyr(4-CF3 diaryl ether) | absent | L | D | T |
| 21 | Tyr(4-methoxy diaryl ether) | absent | L | D | T |
| 22 | Tyr(4-fluoro diaryl ether) | absent | L | D | T |
| 23 | Tyr(2-methoxy diaryl ether) | absent | L | D | T |
| 24 | Tyr(3-methoxy diaryl ether) | absent | L | D | T |
| 25 | Tyr(3-fluoro diaryl ether) | absent | L | D | T |
| 26 | Tyr(3,4-difluoro diaryl ether) | absent | L | D | T |
| 27 | Tyr(3-methyl diaryl ether) | absent | L | D | T |
| 28 | Tyr(3,4-dimethyl diaryl ether) | absent | L | D | T |
| 29 | Tyr(4-CO$_2$Me diaryl ether) | absent | L | D | T |
| 30 | Tyr(3-CO$_2$Me diaryl ether) | absent | L | D | T |
| 31 | Tyr(4-CO$_2$H diaryl ether) | absent | L | D | T |
| 33 | metaY(Opr) | absent | L | D | T |
| 34 | Orn(benzamide) | absent | L | D | Thr(OBn) |
| 35 | Orn(acetamide) | absent | L | D | Thr(OBn) |
| 36 | Orn(methanesulfonamide) | absent | L | D | Thr(OBn) |
| 37 | Orn(ethylcarbamate) | absent | L | D | Thr(OBn) |
| 38 | Orn(pentyl amide) | absent | L | D | Thr(OBn) |
| 39 | R | absent | L | D | T |
| 40 | F | absent | L | D | Thr(OMe) |
| 41 | F | absent | L | D | Thr(OEt) |
| 42 | dTyr | absent | L | D | T |
| 50 | dArg | absent | L | D | T |
| 51 | dPip | absent | L | D | T |
| 52 | [3-(4-thiazolyl)-Ala] | absent | L | D | T |
| 53 | Y | absent | L | D | I |
| 54 | (4-aza-Phe) | absent | L | D | T |
| 55 | Y | absent | L | D | Pen |
| 56 | (vinyl-Br-Leu) | absent | L | D | T |
| 57 | Hyp(OBn) | absent | L | D | T |
| 58 | Hyp(OBn) | absent | L | D | T |
| 59 | Dap(Cbz) | absent | L | D | T |
| 60 | His(Bn) | absent | L | D | T |
| 61 | (4-amino-Phe) | absent | L | D | T |
| 62 | (4-aza-dPhe) | absent | L | D | T |
| 63 | Hyp | absent | L | D | T |
| 64 | dTrp | absent | L | D | T |
| 65 | M | absent | L | D | T |
| 66 | dMet | absent | L | D | T |
| 67 | (4-guanidino-Phe) | absent | L | D | T |
| 68 | (3-aza-Phe) | absent | L | D | T |
| 69 | dTic | absent | L | D | T |
| 70 | (3-aza-dPhe) | absent | L | D | T |
| 71 | Nva | absent | L | D | T |
| 72 | dNle | absent | L | D | T |
| 73 | dLys | absent | L | D | T |
| 74 | dPro | absent | L | D | T |
| 75 | dOrn | absent | L | D | T |
| 76 | (3-benzothienyl-Ala) | absent | L | D | T |
| 77 | dTyr(OAllyl) | absent | L | D | T |
| 78 | dSer(OBn) | absent | L | D | T |
| 79 | [3-(4-thiazolyl)-dAla] | absent | L | D | T |
| 80 | (3-benzothienyl-dAla) | absent | L | D | T |
| 81 | [3-(2-thienyl)-dAla] | absent | L | D | T |
| 82 | (4-aminomethyl-Phe) | absent | L | D | T |
| 83 | dOrn(dimethyl) | absent | L | D | T |
| 84 | (4-amino-dPhe) | absent | L | D | T |
| 85 | (4-aminomethyl-dPhe) | absent | L | D | T |
| 86 | dTyr(OBn) | absent | L | D | T |
| 87 | P | absent | L | D | T |
| 88 | cycloLeu | absent | L | D | T |
| 89 | Aic | absent | L | D | T |
| 90 | Tyr(OAllyl) | absent | L | D | T |

-continued

| Cpd. No. | $X^y$ | $X^z$ | $X^1$ | $X^2$ | $X^3$ |
|---|---|---|---|---|---|
| 91 | Chg | absent | L | D | T |
| 92 | K | absent | L | D | T |
| 93 | (2-aza-dPhe) | absent | L | D | T |
| 94 | (2-aza-Phe) | absent | L | D | T |
| 95 | [2-(2-pyridyl)-4-thiazolyl-Ala] | absent | L | D | T |
| 96 | [2-(3-pyridyl)-4-thiazolyl-Ala] | absent | L | D | T |
| 97 | [2-(4-pyridyl)-4-thiazolyl-Ala] | absent | L | D | T |
| 98 | dTiq | absent | L | D | T |
| 99 | [1-(S)-isoindoline-carboxylic acid] | absent | L | D | T |
| 100 | Y | dThr | L | D | T |
| 101 | Y | P | L | D | T |
| 102 | Y | dPro | L | D | T |
| 104 | Y | cycloLeu | L | D | T |
| 105 | Y | Sar | L | D | T |
| 106 | (3-iodo-Phe) | Sar | L | D | T |
| 107 | (4-iodo-Phe) | Sar | L | D | T |
| 108 | (3,3-diphenyl-Ala) | Sar | L | D | T |
| 109 | F | dLys | L | D | T |
| 110 | Bip | dLys | L | D | T |
| 111 | [3-(4-thiazolyl)-Ala] | dLys | L | D | T |
| 112 | (3,3-diphenyl-Ala) | dLys | L | D | T |
| 113 | Y | dLys | L | D | I |
| 114 | Y | dArg | L | D | T |
| 115 | Y | dSer | L | D | T |
| 116 | Bip | Sar | L | D | T |
| 117 | 1Nal | Sar | L | D | T |
| 118 | Y | Pip | L | D | T |
| 119 | (2-iodo-Phe) | Sar | L | D | T |
| 120 | 1Nal | dLys | L | D | T |
| 121 | Y | dLys | L | D | MeThr |
| 122 | F | Sar | L | D | T |
| 123 | Y | dTic | L | D | T |
| 125 | Y | dPip | L | D | T |
| 126 | F | dPro | L | D | T |
| 127 | (3,4-dimethoxy-Phe) | dPro | L | D | T |
| 128 | (3,4,5-trifluoro-Phe) | dPro | L | D | T |
| 129 | (3,5-dibromo-Tyr) | dPro | L | D | T |
| 130 | F | dPip | L | D | T |
| 131 | [3-(4-thiazolyl)-Ala] | dPip | L | D | T |
| 132 | (4-aminomethyl-Phe) | dPip | L | D | T |
| 133 | [2-iodo-Phe] | dPip | L | D | T |
| 134 | (2-phenyl-Phe) | dPip | L | D | T |
| 135 | [2-(2-methoxy-phenyl)-Phe] | dPip | L | D | T |
| 136 | [2-(3-methoxy-phenyl)-Phe] | dPip | L | D | T |
| 137 | [2-(4-methoxy-phenyl)-Phe] | dPip | L | D | T |
| 138 | Bip | dPip | L | D | T |
| 139 | Y | Hyp | L | D | T |
| 140 | Y | dHyp | L | D | T |
| 141 | Y | (cis-dHyp) | L | D | T |
| 142 | dTyr | dPip | L | D | T |
| 143 | 1Nal | dPip | L | D | T |
| 144 | 2Nal | dPip | L | D | T |
| 143 | (4-aminomethyl-Phe) | dTic | L | D | T |
| 144 | (3-aminomethyl-Phe) | dTic | L | D | T |
| 145 | (3-aminomethyl-dPhe) | dTic | L | D | T |
| 146 | MeTyr | dPip | L | D | T |
| 147 | Y | dPip | L | D | alloThr |
| 148 | Y | dPip | tertbutylAla | D | T |
| 149 | [3-(4-thiazolyl)-Ala] | dHyp | L | D | T |
| 150 | (4-aminomethyl-Phe) | dHyp | L | D | T |
| 151 | Y | dPip | L | D | I |
| 152 | Y | dMeLys | L | D | I |
| 153 | Y | dNle | L | D | T |
| 154 | F | dHyp | L | D | T |
| 155 | Y | dMeArg | L | D | T |
| 156 | Y | G | L | D | T |
| 157 | Y | A | L | D | T |
| 158 | Y | dAla | L | D | T |
| 159 | M | G | L | D | T |
| 160 | Tyr(OAllyl) | Sar | L | D | T |
| 161 | Tyr(OAllyl) | G | L | D | T |
| 162 | [3-(4-thiazolyl)-Ala] | Sar | L | D | T |
| 163 | (4-aminomethyl-Phe) | G | L | D | T |
| 164 | Tyr(OAllyl) | dVal | L | D | T |
| 165 | Tyr(OAllyl) | dSer | L | D | T |
| 166 | Tyr(OAllyl) | dAla | L | D | T |

-continued

| Cpd. No. | X^y | X^z | X^1 | X^2 | X^3 |
|---|---|---|---|---|---|
| 167 | Tyr(OAllyl) | P | L | D | T |
| 168 | Tyr(OAllyl) | dPro | L | D | T |
| 169 | [3-(4-thiazolyl)-Ala] | dVal | L | D | T |
| 170 | [3-(4-thiazolyl)-Ala] | dSer | L | D | T |
| 171 | [3-(4-thiazolyl)-Ala] | dAla | L | D | T |
| 172 | [3-(4-thiazolyl)-Ala] | P | L | D | T |
| 173 | [3-(4-thiazolyl)-Ala] | dPro | L | D | T |
| 174 | (4-aminomethyl-Phe) | P | L | D | T |
| 175 | (4-aminomethyl-Phe) | dPro | L | D | T |
| 176 | cycloLeu | P | L | D | T |
| 177 | [2-(2-pyridyl)-4-thiazolyl-Ala] | Sar | L | D | T |
| 178 | [2-(2-pyridyl)-4-thiazolyl-Ala] | dPro | L | D | T |
| 179 | [2-(3-pyridyl)-4-thiazolyl-Ala] | Sar | L | D | T |
| 180 | [2-(3-pyridyl)-4-thiazolyl-Ala] | dPro | L | D | T |
| 181 | [2-(4-pyridyl)-4-thiazolyl-Ala] | dPro | L | D | T |
| 182 | [3-(2-aminobenzyl-4-thiazolyl)-Ala] | Sar | L | D | T |
| 183 | [2-(amino-benzyl)-4-thiazolyl-Ala] | dPro | L | D | T |
| 184 | dTyr | dPip | L | D | I |
| 185 | (2-aminomethyl-Phe) | Aze | L | D | T |
| 186 | Y | dPip | L | D | Abu |
| 187 | (3-aminomethyl-Phe) | dTic | L | D | Abu |
| 188 | (2,4-dichloro-Phe) | dPip | L | D | T |
| 189 | (3-phenyl-dPhe) | dPip | L | D | T |
| 190 | [3-(5-quinolinyl)-dPhe] | dPip | L | D | T |
| 191 | Y | betaHomoLys | L | D | T |
| 192 | Y | betaHomoPro | L | D | T |
| 193 | Y | betaHomoLys | L | D | T |
| 194 | Y | 2Abz | L | D | T |
| 195 | F | betaHomoLys | L | D | T |
| 196 | [3-(4-thiazolyl)-Ala] | betaHomoLys | L | D | T |
| 197 | (4-aminomethyl-Phe) | betaHomoLys | L | D | T |
| 198 | Y | betaHomoLys | L | D | Thr(OBn) |
| 199 | MeTyr | dbetaHomoLys | L | D | T |
| 200 | 1Nal | betaHomoLys | L | D | T |
| 201 | 2Nal | betaHomoLys | L | D | T |
| 202 | Bip | betaHomoLys | L | D | T |
| 203 | (2-iodo-Phe) | betaHomoLys | L | D | T |
| 204 | [2-(2,5-dimethyl-isoxazole)-Phe] | betaHomoLys | L | D | T |
| 205 | (2-phenyl-Phe) | betaHomoLys | L | D | T |
| 206 | (2-phenyl-Phe) | betaHomoLys | L | D | T |
| 207 | [(2-piperazinyl-2-Phenyl)-Phe] | betaHomoLys | L | D | T |
| 208 | Cha | betaHomoLys | L | D | T |
| 209 | W | betaHomoLys | L | D | T |
| 210 | dTrp | betaHomoLys | L | D | T |
| 211 | (3-aminomethyl-Phe) | betaHomoLys | L | D | T |
| 212 | (4-aminomethyl-dPhe) | betaHomoLys | L | D | T |
| 213 | (4-aminomethyl-Phe) | betaHomoLys | L | D | I |
| 214 | Y | dbetaHomoLys | L | D | I |
| 215 | dArg | betaHomoLys | L | D | T |
| 216 | (4-aminomethyl-Phe)-reduced | betaHomoLys | L | D | T |
| 217 | [3-(4-thiazolyl)-Ala] | dbetaHomoLys | L | D | I |
| 218 | F | dbetaHomoLys | L | D | I |
| 219 | [3-(4-thiazolyl)-Ala] | MebetaHomoLys | L | D | T |
| 220 | (4-aminomethyl-Phe) | MebetaHomoLys | L | D | T |
| 221 | [3-(4-thiazolyl)-Ala] | betaHomoLys | L | D | I |
| 222 | Tic | betaHomoLys | L | D | T |
| 223 | dTic | betaHomoLys | L | D | T |
| 224 | dTic | dbetaHomoLys | L | D | T |
| 225 | Y | betaHomoIle | L | D | T |
| 226 | (4-aminomethyl-Phe) | betaHomoPro | L | D | T |
| 227 | Y | dbetaHomoPro | L | D | T |
| 228 | (4-aminomethyl-Phe) | dbetaHomoPro | L | D | T |
| 229 | R | betaHomoLys | L | D | T |
| 230 | F | MebetaHomoLys | L | D | T |
| 231 | Phe-reduced | betaHomoLys | L | D | T |
| 232 | (3-aminomethyl-dPhe) | betaHomoLys | L | D | T |
| 233 | [2-[3-(1-piperazinyl)phenyl]-Phe]-betaHomoLys | | L | D | T |
| 234 | [3-(4-thiazolyl)-dAla] | betaHomoLys | L | D | T |
| 235 | (2-bromo-Phe) | betaHomoLys | L | D | T |
| 236 | (2-chloro-Phe) | betaHomoLys | L | D | T |
| 237 | (2-fluoro-Phe) | betaHomoLys | L | D | T |
| 238 | (2-CF3-Phe) | betaHomoLys | L | D | T |
| 239 | (2,4-dichloro-Phe) | betaHomoLys | L | D | T |
| 240 | (2-aminomethyl-Phe) | betaHomoLys | L | D | T |
| 241 | [2-(4-quinolinyl)-Phe] | betaHomoLys | L | D | T |

-continued

| Cpd. No. | $X^y$ | $X^z$ | $X^1$ | $X^2$ | $X^3$ |
|---|---|---|---|---|---|
| 242 | [2-(5-quinolinyl)-Phe] | betaHomoLys | L | D | T |
| 243 | [2-(3-quinolinyl)-Phe] | betaHomoLys | L | D | T |
| 244 | dhomoPhe | betaHomoLys | L | D | T |
| 245 | (2-iodo-dPhe) | betaHomoLys | L | D | T |
| 246 | (2-phenyl-dPhe) | betaHomoLys | L | D | T |
| 247 | [(2-piperazinyl-2-Phenyl)-dPhe] | betaHomoLys | L | D | T |
| 248 | Y | betaHomoLys | L | D | I |
| 249 | Y | betaHomoLys | L | D | V |
| 250 | dTyr | betaHomoLys | L | D | I |
| 251 | (4-aminomethyl-dPhe) | betaHomoLys | L | D | I |
| 252 | (4-aminomethyl-Phe) | betaHomoLys | L | D | V |
| 253 | (3-iodo-Phe) | betaHomoLys | L | D | T |
| 254 | (3-phenyl-Phe) | betaHomoLys | L | D | T |
| 255 | [3-(2-methoxy-phenyl)-Phe] | betaHomoLys | L | D | T |
| 256 | [3-(2,6-dimethoxy-phenyl)-Phe] | betaHomoLys | L | D | T |
| 257 | [3-(2-trifluoromethoxy-phenyl)-Phe] | betaHomoLys | L | D | T |
| 258 | (4-iodo-Phe) | betaHomoLys | L | D | T |
| 259 | [4-(2-methoxy-phenyl)-Phe] | betaHomoLys | L | D | T |
| 260 | [4-(2-trifluoromethoxy-phenyl)-Phe] | betaHomoLys | L | D | T |
| 261 | alphaMePhe | betaHomoLys | L | D | T |
| 262 | MePhe | betaHomoLys | L | D | T |
| 263 | [3-(2,6-dimethyl-phenyl)-Phe] | betaHomoLys | L | D | T |
| 264 | [3-(quinolin-4-yl)-Phe] | betaHomoLys | L | D | T |
| 265 | [3-(3,4-difluoro-phenyl)-Phe] | betaHomoLys | L | D | T |
| 266 | [4-(2,6-dimethyl-phenyl)-Phe] | betaHomoLys | L | D | T |
| 267 | [4-(2-chloro-6-methoxy-phenyl)-Phe] | betaHomoLys | L | D | T |
| 268 | [3-(4-thiazolyl)-Ala]-reduced | betaHomoLys | L | D | T |
| 269 | [2-[4-(1-piperazinyl)phenyl]-Phe] | betaHomoLys | L | D | T |
| 270 | [2-(2,6-dimethylphenyl)-Phe] | betaHomoLys | L | D | T |
| 271 | [2-(benzothiazol-5-yl)-Phe] | betaHomoLys | L | D | T |
| 272 | HomoPhe | betaHomoLys | L | D | T |
| 273 | (piperidine-4-amino-4-carboxylic acid) | betaHomoLys | L | D | T |
| 274 | [2-(2,5-dimethyl-isoxazole)-dPhe] | betaHomoLys | L | D | T |
| 275 | dTyr | betaHomoLys | L | D | V |
| 276 | (4-aminomethyl-dPhe) | betaHomoLys | L | D | T |
| 277 | [2-(2-chloro-6-methoxyphenyl)-Phe] | betaHomoLys | L | D | T |
| 278 | 2Igl | betaHomoLys | L | D | T |
| 279 | d2Igl | betaHomoLys | L | D | T |
| 280 | Atc | betaHomoLys | L | D | T |
| 281 | Y | betaHomoLys | L | D | alloIle |
| 282 | dTyr | betaHomoLys | L | D | alloIle |
| 283 | (4-aminomethyl-Phe) | betaHomoLys | L | D | alloIle |
| 284 | [2-[2,5-Bis(trifluoromethyl)phenyl]-Phe] | betaHomoLys | L | D | T |
| 285 | [2-[2,5-Bis(trifluoromethyl)phenyl]-Phe] | betaHomoLys | L | D | T |
| 286 | Aic | betaHomoLys | L | D | T |
| 287 | P | betaHomoLys | L | D | T |
| 288 | dPro | betaHomoLys | L | D | T |
| 289 | Pip | betaHomoLys | L | D | T |
| 290 | [2-(3-Pyridyl)-Phe] | betaHomoLys | L | D | T |
| 291 | [2-(4-Pyridyl)-Phe] | betaHomoLys | L | D | T |
| 292 | [2-(3-bromo-2-Pyridyl)-Phe] | betaHomoLys | L | D | T |
| 293 | 2Nal | dPip | L | D | T |
| 294 | (4-aminomethyl-Phe) | dTic | L | D | T |

19. The method of claim 1, wherein the compound is any one of compounds 390-392, or 458-538 wherein $R^1$ is H;
$R^2$ is H;
$R^3$ is $CH_3$;
$R^4$ is H;
$R^5$ is C(O)—NH-tert-Butyl;
$R^6$ and $R^7$ are PRO;
$R^8$ is H; and
$X^y$, $X^z$, $X^1$, $X^2$ and $X^3$ are defined as follows:

TABLE 2B

| Cpd. No. | $X^y$ | $X^z$ | $X^1$ | $X^2$ | $X^3$ |
|---|---|---|---|---|---|
| 390 | [3-aminomethyl-4-[4-(1-piperazinyl)-phenyl]-benzoic acid] | absent | L | D | T |

TABLE 2B-continued

| Cpd. No. | $X^y$ | $X^z$ | $X^1$ | $X^2$ | $X^3$ |
|---|---|---|---|---|---|
| 391 | [3-aminomethyl-4-[4-(1-piperazinyl)-phenyl]-benzoic acid] | absent | L | D | T |
| 392 | [3-aminomethyl-4-[4-(1-piperazinyl)-phenyl]-benzoic acid] | absent | L | D | T |
| 458 | [3-aminomethyl-4-[4-(1-piperazinyl)-phenyl]-benzoic acid] | absent | L | D | T |
| 458 | [3-aminomethyl-4-[4-(1-piperazinyl)-phenyl]-benzoic acid] | absent | L | D | T |
| 459 | [3-aminomethyl-4-[4-(1-piperazinyl)-phenyl]-benzoic acid] | absent | L | D | T |
| 460 | [3-aminomethyl-4-[4-(1-piperazinyl)-phenyl]-benzoic acid] | absent | L | D | T |
| 461 | [3-aminomethyl-4-[4-(1-piperazinyl)-phenyl]-benzoic acid] | absent | L | D | T |

TABLE 2B-continued

| Cpd. No. | X$^y$ | X$^z$ | X$^1$ | X$^2$ | X$^3$ |
|---|---|---|---|---|---|
| 462 | [3-aminomethyl-4-[4-(1-piperazinyl)-phenyl]-benzoic acid] | absent | L | D | T |
| 463 | [3-aminomethyl-4-[4-(1-piperazinyl)-phenyl]-benzoic acid] | absent | L | D | T |
| 464 | [3-aminomethyl-4-[4-(1-piperazinyl)-phenyl]-benzoic acid] | absent | L | D | T |
| 465 | [3-aminomethyl-4-[4-(1-piperazinyl)-phenyl]-benzoic acid] | absent | L | D | T |
| 466 | [3-aminomethyl-4-[4-(1-piperazinyl)-phenyl]-benzoic acid] | absent | L | D | T |
| 467 | [3-aminomethyl-4-[4-(1-piperazinyl)-phenyl]-benzoic acid] | absent | L | D | T |
| 468 | [3-aminomethyl-4-[4-(1-piperazinyl)-phenyl]-benzoic acid] | absent | L | D | T |
| 469 | [3-aminomethyl-4-[4-(1-piperazinyl)-phenyl]-benzoic acid] | absent | L | D | T |
| 470 | [3-aminomethyl-4-[4-(1-piperazinyl)-phenyl]-benzoic acid] | absent | L | D | T |
| 471 | [3-aminomethyl-4-[4-(1-piperazinyl)-phenyl]-benzoic acid] | absent | L | D | T |
| 472 | [3-aminomethyl-4-[4-(1-piperazinyl)-phenyl]-benzoic acid] | absent | L | D | T |
| 473 | [3-aminomethyl-4-[4-(1-piperazinyl)-phenyl]-benzoic acid] | absent | L | D | T |
| 474 | [3-aminomethyl-4-[4-(1-piperazinyl)-phenyl]-benzoic acid] | absent | L | D | T |
| 475 | [3-aminomethyl-4-[4-(1-piperazinyl)-phenyl]-benzoic acid] | absent | L | D | T |
| 476 | [3-aminomethyl-4-[4-(1-piperazinyl)-phenyl]-benzoic acid] | absent | L | D | T |
| 477 | [3-aminomethyl-4-[4-(1-piperazinyl)-phenyl]-benzoic acid] | absent | L | D | T |
| 478 | [3-aminomethyl-4-[4-(1-piperazinyl)-phenyl]-benzoic acid] | absent | L | D | T |
| 479 | [3-aminomethyl-4-[4-(1-piperazinyl)-phenyl]-benzoic acid] | absent | L | D | T |
| 480 | [3-aminomethyl-4-[4-(1-piperazinyl)-phenyl]-benzoic acid] | absent | L | D | T |
| 481 | [3-aminomethyl-4-[4-(1-piperazinyl)-phenyl]-benzoic acid] | absent | L | D | T |
| 482 | [3-aminomethyl-4-[4-(1-piperazinyl)-phenyl]-benzoic acid] | absent | L | D | T |
| 483 | [3-aminomethyl-4-[4-(1-piperazinyl)-phenyl]-benzoic acid] | absent | L | D | T |
| 484 | [3-aminomethyl-4-[4-(1-piperazinyl)-phenyl]-benzoic acid] | absent | L | D | T |
| 485 | [3-aminomethyl-4-[4-(1-piperazinyl)-phenyl]-benzoic acid] | absent | L | D | T |
| 486 | [3-aminomethyl-4-[4-(1-piperazinyl)-phenyl]-benzoic acid] | absent | L | D | T |
| 487 | [3-aminomethyl-4-[4-(1-piperazinyl)-phenyl]-benzoic acid] | absent | L | D | T |
| 488 | [3-aminomethyl-4-[4-(1-piperazinyl)-phenyl]-benzoic acid] | absent | L | D | T |
| 489 | [3-aminomethyl-4-[4-(1-piperazinyl)-phenyl]-benzoic acid] | absent | L | D | T |
| 490 | [3-aminomethyl-4-[4-(1-piperazinyl)-phenyl]-benzoic acid] | absent | L | D | T |
| 491 | [3-aminomethyl-4-[4-(1-piperazinyl)-phenyl]-benzoic acid] | absent | L | D | T |
| 492 | [3-aminomethyl-4-[4-(1-piperazinyl)-phenyl]-benzoic acid] | absent | L | D | T |
| 493 | [3-aminomethyl-4-[4-(1-piperazinyl)-phenyl]-benzoic acid] | absent | L | D | T |
| 494 | [3-aminomethyl-4-[4-(1-piperazinyl)-phenyl]-benzoic acid] | absent | L | D | T |
| 495 | [3-aminomethyl-4-[4-(1-piperazinyl)-phenyl]-benzoic acid] | absent | L | D | T |
| 496 | [3-aminomethyl-4-[4-(1-piperazinyl)-phenyl]-benzoic acid] | absent | L | D | T |
| 497 | [3-aminomethyl-4-[4-(1-piperazinyl)-phenyl]-benzoic acid] | absent | L | D | T |
| 498 | [3-aminomethyl-4-[4-(1-piperazinyl)-phenyl]-benzoic acid] | absent | L | D | T |
| 499 | [3-aminomethyl-4-[4-(1-piperazinyl)-phenyl]-benzoic acid] | absent | L | D | T |
| 500 | [3-aminomethyl-4-[4-(1-piperazinyl)-phenyl]-benzoic acid] | absent | L | D | T |
| 501 | [3-aminomethyl-4-[4-(1-piperazinyl)-phenyl]-benzoic acid] | absent | L | D | T |
| 502 | [3-aminomethyl-4-[4-(1-piperazinyl)-phenyl]-benzoic acid] | absent | L | D | T |
| 503 | [3-aminomethyl-4-[4-(1-piperazinyl)-phenyl]-benzoic acid] | absent | L | D | T |
| 504 | [3-aminomethyl-4-[4-(1-piperazinyl)-phenyl]-benzoic acid] | absent | L | D | T |
| 505 | [3-aminomethyl-4-[4-(1-piperazinyl)-phenyl]-benzoic acid] | absent | L | D | T |
| 506 | [3-aminomethyl-4-[4-(1-piperazinyl)-phenyl]-benzoic acid] | absent | L | D | T |
| 507 | [3-aminomethyl-4-[4-(1-piperazinyl)-phenyl]-benzoic acid] | absent | L | D | T |
| 508 | [3-aminomethyl-4-[4-(1-piperazinyl)-phenyl]-benzoic acid] | absent | L | D | T |
| 509 | [3-aminomethyl-4-[4-(1-piperazinyl)-phenyl]-benzoic acid] | absent | L | D | T |
| 510 | [3-aminomethyl-4-[4-(1-piperazinyl)-phenyl]-benzoic acid] | absent | L | D | T |
| 511 | [3-aminomethyl-4-[4-(1-piperazinyl)-phenyl]-benzoic acid] | absent | L | D | T |
| 512 | [3-aminomethyl-4-[4-(1-piperazinyl)-phenyl]-benzoic acid] | absent | L | D | T |
| 513 | [3-aminomethyl-4-[4-(1-piperazinyl)-phenyl]-benzoic acid] | absent | L | D | T |
| 514 | [3-aminomethyl-4-[4-(1-piperazinyl)-phenyl]-benzoic acid] | absent | L | D | T |
| 515 | [3-aminomethyl-4-[4-(1-piperazinyl)-phenyl]-benzoic acid] | absent | L | D | T |
| 516 | [3-aminomethyl-4-[4-(1-piperazinyl)-phenyl]-benzoic acid] | absent | L | D | T |
| 517 | [3-aminomethyl-4-[4-(1-piperazinyl)-phenyl]-benzoic acid] | absent | L | D | T |
| 518 | [3-aminomethyl-4-[4-(1-piperazinyl)-phenyl]-benzoic acid] | absent | L | D | T |
| 519 | [3-aminomethyl-4-[4-(1-piperazinyl)-phenyl]-benzoic acid] | absent | L | D | T |
| 520 | [3-aminomethyl-4-[4-(1-piperazinyl)-phenyl]-benzoic acid] | absent | L | D | T |
| 521 | [3-aminomethyl-4-[4-(1-piperazinyl)-phenyl]-benzoic acid] | absent | L | D | T |
| 522 | (4-aminomethyl-Phe) | absent | L | D | T |
| 523 | (4-aminomethyl-Phe) | absent | L | D | T |
| 524 | (4-aminomethyl-Phe) | absent | L | D | T |
| 525 | (4-aminomethyl-Phe) | absent | L | D | T |
| 526 | (4-aminomethyl-Phe) | absent | L | D | T |
| 527 | (3-aminomethyl-Phe) | absent | L | D | T |
| 528 | (3-aminomethyl-Phe) | absent | L | D | T |
| 529 | (3-aminomethyl-Phe) | absent | L | D | T |
| 530 | K | absent | L | D | T |
| 531 | K | absent | L | D | T |
| 532 | K | absent | L | D | T |
| 533 | K | absent | L | D | T |
| 534 | K | absent | L | D | T |
| 535 | K | absent | L | D | T |
| 536 | K | absent | L | D | T |
| 537 | K | absent | L | D | T |
| 538 | [3-aminomethyl-4-[4-(1-piperazinyl)-phenyl]-benzoic acid] | absent | L | D | T. |

* * * * *